US010364433B2

(12) United States Patent
Lusis et al.

(10) Patent No.: US 10,364,433 B2
(45) Date of Patent: Jul. 30, 2019

(54) MODULATION OF AGPAT5 EXPRESSION

(71) Applicants: The Regents of the University of California, Oakland, CA (US); Ionis Pharmaceuticals, Inc., Calrsbad, CA (US)

(72) Inventors: Aldons J. Lusis, Tarzana, CA (US); Brian Parks, Los Angeles, CA (US); Richard Lee, Oceanside, CA (US)

(73) Assignees: The Regents of the University of California, Oakland, CA (US); Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 15/526,471

(22) PCT Filed: Nov. 13, 2015

(86) PCT No.: PCT/US2015/060591
§ 371 (c)(1),
(2) Date: May 12, 2017

(87) PCT Pub. No.: WO2016/077704
PCT Pub. Date: May 19, 2016

(65) Prior Publication Data
US 2017/0321216 A1    Nov. 9, 2017

Related U.S. Application Data
(60) Provisional application No. 62/079,983, filed on Nov. 14, 2014.

(51) Int. Cl.
| | | |
|---|---|---|
| *C12N 15/11* | (2006.01) | |
| *C12N 15/113* | (2010.01) | |
| *C12N 9/10* | (2006.01) | |
| *A61K 31/397* | (2006.01) | |
| *A61K 31/713* | (2006.01) | |
| *A61K 45/06* | (2006.01) | |

(52) U.S. Cl.
CPC ........ *C12N 15/1137* (2013.01); *A61K 31/397* (2013.01); *A61K 31/713* (2013.01); *A61K 45/06* (2013.01); *C12N 9/1029* (2013.01); *C12Y 203/01051* (2013.01); *C12N 2310/11* (2013.01); *C12N 2310/315* (2013.01); *C12N 2310/321* (2013.01); *C12N 2310/3231* (2013.01); *C12N 2310/3341* (2013.01); *C12N 2310/341* (2013.01); *C12N 2320/31* (2013.01)

(58) Field of Classification Search
None
See application file for complete search history.

(56) References Cited

U.S. PATENT DOCUMENTS

| | | |
|---|---|---|
| 5,801,154 A | 9/1998 | Baracchini et al. |
| 6,268,490 B1 | 7/2001 | Imanishi et al. |
| 6,525,191 B1 | 2/2003 | Ramasamy |
| 6,582,908 B2 | 6/2003 | Fodor et al. |
| 6,670,461 B1 | 12/2003 | Wengel et al. |
| 6,770,748 B2 | 8/2004 | Imanishi et al. |
| 6,794,499 B2 | 9/2004 | Wengel et al. |
| 7,034,133 B2 | 4/2006 | Wengel et al. |
| 7,053,207 B2 | 5/2006 | Wengel |
| 7,399,845 B2 | 7/2008 | Swayze et al. |
| 7,427,672 B2 | 9/2008 | Imanishi et al. |
| 7,741,457 B2 | 6/2010 | Seth et al. |
| 8,501,805 B2 | 8/2013 | Seth et al. |
| 8,530,640 B2 | 9/2013 | Seth et al. |
| 8,546,556 B2 | 10/2013 | Seth et al. |
| 9,012,421 B2 | 4/2015 | Migawa et al. |
| 2001/0053519 A1 | 12/2001 | Fodor et al. |
| 2003/0064439 A1 | 4/2003 | Bandaru et al. |
| 2003/0228597 A1 | 12/2003 | Cowsert et al. |
| 2004/0171570 A1 | 9/2004 | Allerson et al. |
| 2004/0198733 A1 | 10/2004 | Schwink et al. |
| 2007/0031844 A1 | 2/2007 | Khvorova et al. |
| 2007/0287831 A1 | 12/2007 | Seth et al. |
| 2008/0039618 A1 | 2/2008 | Allerson et al. |
| 2009/0063355 A1 | 2/2009 | Bhanot et al. |
| 2010/0048545 A1 | 2/2010 | Jette et al. |

FOREIGN PATENT DOCUMENTS

| | | | |
|---|---|---|---|
| WO | WO 1994/014226 | 6/1994 | |
| WO | WO 2000/063364 | 10/2000 | |
| WO | WO2003099215 A2 * | 12/2003 | ........... A61K 31/712 |
| WO | WO 2004/063329 | 7/2004 | |
| WO | WO 2004/106356 | 12/2004 | |

(Continued)

OTHER PUBLICATIONS

Allshire "RNAi and Heterochromatin—a Hushed-Up Affair" Science (2002) 297: 1818-1819.
Baker et al. "2'-O-(2-Methoxy)ethyl-modified Anti-intercellular Adhesion Molecule 1 (ICAM-1) Oligonucleotides Selectively Increase the ICAM-1 mRNA Level and Inhibit Formation of the ICAM-1 Translation Initiation Complex in Human Umbilical Wein Endothelial Cells" J. Biol. Chem. (1997) 272: 11944-12000.
Braasch et al. "Locked nucleic acid (LNA): fine-tuning the recognition of DNA and RNA" Chem. Biol. (2001) 8: 1-7.
Branch et al., "A good antisense molecule is hard to find," TIBS (1998) 23:45-50.
Browning et al. "Molecular mediators of hepatic steatosis and liver injury" J Clin Invest (2004) 114: 147-152.

(Continued)

*Primary Examiner* — Ekaterina Poliakova-Georgantas
(74) *Attorney, Agent, or Firm* — Grant IP, Inc.

(57) ABSTRACT

Provided herein are methods, compounds, and compositions for reducing expression of an AGPAT5 mRNA and protein in an animal. Also provided herein are methods, compounds, and compositions for reducing lipids, insulin resistance and/or glucose in an animal. Such methods, compounds, and compositions are useful to treat, prevent, delay, or ameliorate a cardiometabolic disease, disorder or condition, or a physiological marker thereof, in an individual in need.

14 Claims, No Drawings

Specification includes a Sequence Listing.

(56) References Cited

FOREIGN PATENT DOCUMENTS

| WO | WO 2005/021570 | 3/2005 |
|----|----------------|--------|
| WO | WO 2007/134181 | 11/2007 |
| WO | WO 2008/150729 | 12/2008 |
| WO | WO 2008/154401 | 12/2008 |
| WO | WO 2009/006478 | 1/2009 |
| WO | WO 2011/139702 | 11/2011 |

OTHER PUBLICATIONS

Zhou et al. "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74: 118-132.
Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.
Crooke et al., "Basic Principles of Antisense Therapeutics" Antisense Research and Application (1998) Chapter 1:1-50.
Elayadi et al. "Application of PNA and LNA oligomers to chemotherapy" Curr. Opinion Invens. Drugs (2001) 2: 558-561.
Frieden et al. "Expanding the design horizon of antisense oligonucleotides with alpha-L-LNA" Nucleic Acids Research (2003) 21: 6365-6372.
GenBank accession No. JN959516.
Goodman et al. "Report of the National Cholesterol Education Program Expert Panel on Detection, Evaluation, and Treatment of High Blood Cholesterol in Adults. The Expert Panel" Arch. Int. Med. (1988) 148: 36-39.
Hall et al. "Establishment and Maintenance of a Heterochromatin Domain" Science (2002) 297: 2232-2237.
International serach report for PCT/US15/60591 dated Apr. 14, 2016.
JAMA "Executive Summary of the Third Report of the National Cholesterol Education Program (NCEP) Expert Panel on Detection, Evaluation, and Treatment of High Blood Cholesterol in Adults (Adult Treatment Panel III" (2001) 285: 2486-2497.
Jenuwein "An RNA-Guided Pathway for the Epigenome" Science (2002) 297: 2215-2218.
Koshkin et al. "LNA (Locked Nucleic Acids): Synthesis of the Adenine, Cytosine, Guanine, 5-Methylcytosine, Thymine and Uracil Bicyclonucleoside Monomers, Oligomerisation, nad Unprecedented Nucleic Acid Recognition" Tetrahedron (1998) 54: 3607-3630.
Kumar et al. "The First Analogues of LNA (Locked Nucleic Acids): Phosphorothioate-LNA and 2'-Thio-LNA" Bioorg. Med. Chem. Lett. (1998) 8: 2219-2222.
Leumann "DNA Analogues: From Supramolecular Principles to Biological Properties" J. Bioorg & Med. Chem. (2002) 10: 841-854.
New England Biolabs 1998/99 Catalog (cover page and pp. 121 and 284).

GenBank accession No. NM_026792.3.
Orum et al. "Locked nucleic acids: A promising molecular family for gene-function analysis and antisense drug development" Curr. Opinion Mol. Ther. (2001) 3: 239-243.
Pal-Bhadra et al. "Heterochromatic Silencing and HP1 Localization in *Drosophila* Are Dependent on the RNAi Machinery" Science (2004) 303: 669-672.
Prasad et al. "Enzymatic activities of the human AGPAT isoform 3 and isoform 5: localization of AGPAT5 to mitochondria" J Lipid Res (2011) 52: 451-462.
Reynolds et al., "Rational siRNA design for RNA interference" Nature Biotechnology (2004) 22(3):326-330.
Sanghvi et al., "Heterocyclic Base Modifications in Nucleic Acids and Their Applications in Antisense Oligonucleotides" Antisense Research and Applications (1993) pp. 273-288.
Shimamura et al. "Leptin and insulin down-regulate angiopoietin-like protein 3, a plasma triglyceride-increasing factor" Biochem Biophys Res Commun (2004) 322: 1080-1085.
Sindelka et al. "Association of Obesity, Diabetes, Serum Lipids and Blood Pressure Regulates Insulin Action" Physiol Res. (2002) 51: 85-91.
Singh et al. "LNA (locked nucleic acids): synthesis and high-affinity nucleic acid recognition" Chem. Commun. (1998) 4: 455-456.
Singh et al. "Synthesis of 2'-Amino-LNA: A Novel Conformationally Restricted High-Affinity Oligonucleotide Analogue with a Handle" J. Org. Chem. (1998) 63: 10035-10039.
Srivastava et al. "Five- and Six-Membered Conformationally Locked 2',4'-Carbocyclic ribo-Thymidines: Synthesis, Structure, and Bio Chemical Studies" J. Am. Chem. Soc. (2007) 129(26): 8362-8379.
Takeuchi et al. "Biochemistry, physiology, and genetics of GPAT, AGPAT, and lipin enzymes in triglyceride synthesis" Am. J. Physiol Endocrinol Metlab (2009) 296(6): E1195-1209.
Valdivielso et al. "Association of moderate and severe hypertriglyceridemia with obesity, diabetes mellitus and vascular disease in the Spanish working population: Results of the ICARIA study" Atherosclerosis (2009).
Verdel et al. "RNAi-Mediated Targeting of Heterochromatin by the RITS Complex" Science (2004) 303: 672-676.
Volpe et al. "Regulation of Heterochromatic Silencing and Histone H3 Lysine-9 Methylation by RNAi" Science (2002) 297: 1833-1837.
Wahlestedt et al. "Potent and nontoxic antisense oligonucleotides containing locked nucleic acids" Proc. Natl. Acad. Sci. U.S.A. (2000) 97: 5633-5638.
Zhang et al. "Spontaneous Atherosclerosis in Aged Lipoprotein Lipase-Deficient Mice with Severe Hypertriglyceridemia on a Normal Chow Diet" Circ Res. (2008) 102(2): 250-256.
Parks et al., "Genetic architecture of insulin resistance in the mouse" (2015) Cell Metabolism (2015) 21:334-346 (and supplementary material).
Zhang et al., "Lipid signals and insulin resistance" Clin Lipidol (2013) 8(6):659-667.

* cited by examiner

SEQUENCE LISTING

<160> NUMBER OF SEQ ID NOS: 27

<210> SEQ ID NO 1
<211> LENGTH: 3829
<212> TYPE: DNA
<213> ORGANISM: Mus musculus

<400> SEQUENCE: 1

```
cgcctccccg ctgacaagca cgggtcgcgc ggagcaaagc gagcaccccg aggcgagtgc      60
gcccggcaag ccgaggcgtg cccttccaa ggcggcgagc agaggccgtc actgtccccg     120
ccgggtcccg ggcccccgcg gcccatgctg ggggcggagc cagggcggag ggcggcggcg     180
cggccggccc cgcgcagtga ttggcgggcg gccggcggtg gctgaggtcc tggtggccgc     240
gcgggcaacg caggcggagt cgcggctggc gagccgagag gatgctgctg tccctggtgc     300
tccacacgta ctctatgcgc tacctgctcc ccagcgtcct gttgctgggc tcggcgccca     360
cctacctgct ggcctggacg ctgtggcggg tgctctccgc gctgatgccc gcccgcctgt     420
accagcgcgt ggacgaccgg ctttactgcg tctaccagaa catggtgctc ttcttcttcg     480
agaactacac cggggtccag atattgctat atggagattt gccaaaaaat aaagaaaatg     540
taatatatct agcgaatcat caaagcacag ttgactggat tgttgcggac atgctggctg     600
ccagacagga tgccctagga catgtgcgct acgtactgaa agacaagtta aaatggcttc     660
cgctgtatgg gttctacttt gctcagcatg gaggaattta tgtaaaacga agtgccaaat     720
ttaatgataa agaaatgaga agcaagctgc agagctatgt gaacgcagga acaccgatgt     780
atcttgtgat tttcccagag ggaacaaggt ataatgcaac atacacaaaa ctcctttcag     840
ccagtcaggc atttgctgct cagcggggcc ttgcagtatt aaaacacgta ctgacaccaa     900
gaataaaggc cactcacgtt gcttttgatt ctatgaagag tcatttagat gcaatttatg     960
atgtcacagt ggtttatgaa gggaatgaga aaggttcagg aaaatactca aatccaccat    1020
ccatgactga gtttctctgc aaacagtgcc caaaacttca tattcacttt gatcgtatag    1080
acagaaatga agttccagag gaacaagaac acatgaaaaa gtggcttcat gagcgctttg    1140
agataaaaga taggttgctc atagagttct atgattcacc agatccagaa agaagaaaca    1200
```

```
aatttcctgg gaaaagtgtt cattccagac taagtgtgaa gaagacttta ccttcagtgt   1260
tgatcttggg gagtttgact gctgtcatgc tgatgacgga gtccggaagg aaactgtaca   1320
tgggcacctg gttgtatgga accctccttg gctgcctgtg gtttgttatt aaagcataag   1380
caagtagcag gctgcagtca cagtctctta ttgatggcta cacgttgtat cacattgttt   1440
cctgaattaa ataaggagtt ttcttgttgt tgttttttg ttttgttttg ttctgtttta   1500
agccttgatg attgaacact ggataaagta gagtttgtga ccacagccaa catgcatttg   1560
atttggggca acacatgtg gcttttcagg tgctgggtt gctggagaca tggaagctaa    1620
gtggagttta tgctgttttt tttttttaa tgttttcatg aattaatctc cacttgtaaa    1680
gattattgga tactttctgt aattcagaag gttgtatttt aacactagtt tgcagtatgt   1740
ttcgctatat tggttatctt ccatttgact acttggcagc tcagactctt aatactaaag   1800
tattttacat tttgaagcta tgtgatactg gttttttgtt gttgttgttg ttagtttctg   1860
aaagtcaatg aaagacactg taatgatgcg ttaagatgtt ccaagaaaaa ggtgagaatt   1920
attcatggca aaaagatctc gtctagtgta tattttatt atattgctct atttagctaa    1980
ttttctttat atttgcaaaa taatgaacat tttaatatt tattaaaatg cttgatttgc    2040 ataccccga ttctacagag aataatgtgt aaagtgtcag aatagacttg aagctctgct    2100
gtgactcagt ctcctttgtc agagcttcta gtagcccagc tactgagctg ctttgttagt   2160
acctccagca cctgagccgt taagtactta taaatgcaag ggacccgtta tcttcatatc   2220
ggaatagaca tgaacagagc tctaaggcga tgaaagtctg ccagcatcct ctctgtcctc   2280
gcacgtgcct tctgcctggc tccatttgct ttggcactgc gttcgatcta gagtgtaggt   2340
gctcactgct tatttcagcc ctggctctgt ggttttgtgt cctccagtgg tgctgttcac   2400
tgttggggtg caggtggtgc tgccctgact cagaggggca gctccctggc tcctgagggt   2460
gagccttctt ggctactaca gaagtattgt gcgtttgttt atggcaagaa ccatcaggat   2520
tggataaatg tgttatttct ctttgatttc catggagcca cactgttggt acatgtcccc   2580
tgtgaacaga gctacctttc aggagcacat catactgtcg tgagtcacgg cacggtgtgt   2640
cctgtgagaa gaggctttct aacgtgtgat ttgccgtgtt tctatgttgt gatttaagcg   2700
tgattgccta ctagtcattc aaggtaacat ttctgcaaat ttcatacaga ttttttgtcac  2760 aaaattacta taccaatgat ctagttgaaa tagaccaatt gaatcacaat aaataatttt   2820
ttttaattga gggaaaattt gcttcttgtt ttttcaaagc cagaaaacga gccatttcaa   2880
acatctttga agagtcatgt gctgtcactt gttttctatg tgttagtgtc tatattcatg   2940
tatggataca catgaacatg tatattcata cacacacgcc aatagaatat aacagcctaa   3000
aaacaatcca gcttgtgtat catgttactg tgctgaattg taatggtttt tacttacaaa   3060
gtgaggctaa aatcgatttc atgtctttgt taaatacgtt ttttcagcaa tcctattaga   3120
gcttattttg accagatcaa aataagtaca agttcagaga ctttaaatat ggctgaggtc   3180
tagagcgata gctcagtagt taggaacaca tgccactctt tcaagggctt cagttcccag   3240
cactcatatg gaggctcaca gaaggctgga attccagctt catggaattg gacacatcct   3300
ctagcttcca tggatctgtc tgtctgtctc tcccttctct ctctctctct ctctctctct   3360
ctctctctct ctctctctct cactcactct ttaaatatca tggatatgct gtgcatttaa   3420
attttaagac acagaaccat tggaattaca tggattatag ctgattctct ttgaacaggg   3480
cacagtgttc tgcgtaagat ctcttgatca ttagcactgg actcactctc ctcacaagta   3540
```

```
gcctatcaaa tgtggtatta gaaaatacat tgtgtcaaaa tctttgaaag atgagaagaa      3600
tctcctaaac atgtttattt tgacttgaca tcactatttc ctgaaaatta actgtctatg      3660
attcttttca catagtgtaa gatcttactt gtatcaccat cagcttgcag cttagggct       3720 gcagttgttc tccttcataa gactgccatc cgtgtgcatg cttttatgtt tttcagaaag      3780
gatgttggga tgaaagtaag aaaacaaata aagtctcttc ttgtctctc                  3829

<210> SEQ ID NO 2
<211> LENGTH: 41406
<212> TYPE: DNA
<213> ORGANISM: Mus musculus

<400> SEQUENCE: 2
ggagttcccc tggattttag ggacttcagc tcgggctaaa ccaggattag tggatttgat        60
gttgaaaaga atttatagtg aaacatagct gggaatttta ttacaggtat tttaatgtaa       120
gcttaagcat aaagggtttt tgtttttttt tttttttttt tggttaaaaa aaacacacag       180
gctcacattg ttagtattat ccagataagc tatagtggtt ctcagattgt gcatctaaga       240
gtcaccagaa caccttccta tttgtctagt tttacagcta tctgtgtgta tgggtgcatg       300
ccatggacac ctgtagaggt cacaggacaa tctccaattc actttctcct tccaccacat       360
gggctctgta atcactaagg tttgtcaatc ctgagtacag atgttcagaa ccatcttact       420
gtctcctctc ttctgataaa acatgaggtg gccccagaga cgtttagac agggttataa        480 tctgataagg gaaaagccac atgtcctttc cttacaaatg taatttctac agacattcct       540
agaaaattga aactttatgg ttgggaaagg agaggggggcc ctcaggtacc ttgttttttct     600 gttgacaaaa gttgactctt aacattgtca agtaaatgct cccacaaatg gatcatctga      660
ctatttgcag aatgtcatag gccaacagag agagaacccc tgaatttcca gagaccttca      720
ggttggctca gtcccttctt ttttgatgtg tacctcaatt cctgtcttcc tgaactcttg      780
tttgccaatc tgaatctaca gtctatctgt caaacaattc ctttgtctgg actggtctgc     840
tgaactgaca gtgaattgtc ttgacagttc ctttgcctgc ccttttacct ctgcatcttc     900
attaaactgg acagtttgtc atatctgtga cccaccaaca gctgcttttc ccctaaagct     960
gggtttgtgg ttcatgttat cgtgacagac actcttatag ccctgtcagt tctccagcac   1020
tggcttccca aggcttttaa aactcctttc ttctttctaa ctctttgtag tcactgtaac   1080
ctatatatgc atatgtaaac agagatatac ttacagagtg atgtatgtgt gatctgagag   1140
ttaatattag taattaagac tgcaataaaa gaacctgtgt ttcccttagc aagggctaca   1200
gagtaaagtg ggcctctctg gtgccagcga agccactgta cttagtgaaa tttattgtca   1260
ttcaatacat tctgatatcg tgtaaactcc taagcacgtc catctgacat agtgtgctaa   1320
tgacaggagt cacctgtatg ccttatgaag cgcatctcag aggtgatggg aaagaaacat   1380
ggggcaaaag atgaagggaa atccaaggca aggaagcaga gacacaggcg tcagtggtgt   1440
ggaaagggag aaaactaggg gcagaataag tgaccttagg gtcacttaga gaaaccaaca   1500
cacacacaca caccccacata tttaaaacgt actttataca gatctgagcg tgcgcactga   1560
cctgtttcct tctatacctt cttgtataga attatctggt ctccactagt tagggcagtg   1620
aaaggacctg ggcccctgga taagttttg ctgttactta actattctag ttttctggag   1680
ggaagagaac ttatggatcc tacatgtata gggaaatact ttcctacaca ttgaaaagaa   1740
gaaatgtagg atattaggaa aacgcacagt agaaacaagt taaagagcaa gaggttatta   1800
aagggcaaaa gttaaggctt tgaaagattt aatacaagga ggtgacagtc ccgtgaaagg   1860
```

```
tgaaccaagg gtacaggaga cggacccagc ctcattctgc aacagccaag aggagggaag    1920
gtgtgcttcc tatgcacgtg ggggcacggg tggccctccg gcacgcgaag acgctgcagt    1980
tgtccataac ctgcggcatc gagctcctcc tgtgctccac gacttagtcg gctcacgcgt    2040
gtcttgcagg aagcatcctc gtgtctccac gcagctctcg cacgccagca caggccaaaa    2100
cccaccacct cacttcttcc cgggctcatc cccagccagc attcgcagtc gagcatgcgt    2160
cgtgacgagg ccaagggacc gagccaatca gaacacgtat tacgcccata agtcggccaa    2220
tcaggaggcg ccttattacc cgggagcctt gcttcacccc gcctcccgc tgacaagcac     2280 gggtcgcgcg gagcaaagcg agcaccccga ggcgagtgcg cccggcaagc cgaggcgtgc    2340
cctttccaag gcggcgagca gaggccgtca ctgtccccgc cgggtccgg gcccccgcgg     2400 cccatgctgg gggcggagcc agggcggagg cggcggcgc ggccggcccc gcgcagtgat     2460
tggcgggcgg ccggcggtgg ctgaggtcct ggtggccgcg cgggcaacgc aggcggagtc    2520
gcggctggcg agccgagagg atgctgctgt ccctggtgct ccacacgtac tctatgcgct    2580
acctgctccc cagcgtcctg ttgctgggct cggcgcccac ctacctgctg gcctggacgc    2640
tgtggcgggt gctctccgcg ctgatgcccg cccgcctgta ccagcgcgtg gacgaccggc    2700
tttactgcgt ctaccagaac atggtgctct tcttcttcga gaactacacc ggggtccagg    2760
tgaggcgcgg ccgcgcaggg ctgcgtgcga gccctcccg cggccggggc ggcgcttgca     2820
acccgggcga acactcgcag cccggcgagc acgtgccgca gctcacggcc tcccgccgcg    2880
gggggaagtt tctggttctc acttcggggt tccttctgga acgtcctgct gaggctgagt    2940
gtgttcccgg gtccgcccca ccccgcccc gggccggctg ttactgccca tctcagtgcc     3000
tgccaaagta gggcactgag tccgaggtgg tgatgctggg actggcttca tttgcacttc    3060
cgaggtcttt tagattagca agacctctag gcgctgacca aagtgacagc tgtgaaggac    3120
gactcctgcc ttgggttcct cccgggtgaa agcgagggcc tagggaggaa atgaatacat    3180
tggttacaat aggagcctca ctgtcgatac agttctcttc agcttggact gggcttcaat    3240
gtgggctgat ctcttgtcag attgcttttct tcctgctact gtttctttct ttctttccac    3300
ccctccctcc cccccccccg ccccgtggag attgaactct gaaaacaata aagagtagaa    3360
agctctccta atgtgaattc gttatatgac atcccataaa aacctacagt tgtacttcct    3420
ttttggtttt cagtttcaaa gaagagctct gtttgggttc tcccagatgt atctatgact    3480
ttccccccca tttctcagtt cttttcattc tgtgttaggg gggtactttg gcgactggat    3540
cccttactga gttttgcgcc agttggagat tatgtctgag gtagggaatt aagacctctc    3600
tgaatcacta tcttttaaa tgttttccta gggaatagga aaatcactgt gcacatcaa      3660 ggtttctgaa aaattgactt ttagaatagg atttcattca gaattttag gaaccccac      3720 actgatggtt tcaaacctcc ctcttacttt actaagtttg tcaagtgaat gtatggtcta    3780
atcgtggata agtatttaat ttcactagca gaagggacaa gacagcgggg agcacaactt    3840
aaagttgctg accttgcaca tgacaagtac ccctcagacg ctcagggacc tctactcaag    3900
tgccacctat attcttgctg cagagacgtt aggatgagtc agaatgaagc aaagttagtg    3960
agtttattga ttgggagaga ggacacgcac ttgaggggga tcaagtgcaa accttattac    4020
cccccaccca ggctacagca gctgttttct aagtgatttt agggctttta agttaacgcc    4080
ttaaaactaa gattaaggag aagagaagga aaaaatgag ttcttctatt ctttccaata    4140
atgagctcta aaaaaaaag aagcaaacca ggatctcaca ctgtagtctt ggtgggcagg    4200
```

```
aactctatgt agacctcaca ggcctcaagt tcacagagat ctgcctgcct ctgtctccag    4260
agtgttagga ctaaaggcat gtaccgccat gtctggatta aactctttta gttatatgaa    4320
atttaaaacg gattcatggc ggtactgaac agtttacata tgagggagaa atgtggttag    4380
gcagtaatat ggatcaaaat aaaatcaaag taattagctg atcactggtc acaagagttt    4440
gagatgtgag cttgtcttct gccttaggtc accagctata gggataatct tttgtttgtt    4500
ttttgtggtt tttgtttgtt tgttttttg tttttttgag acagggtttc tctgtgtagt    4560
cctggctgtc ctggaactca ctctgtaggc caggctggcc tcgaactcag aactccacct    4620
gcctctgcct cccaagtgct gggatgaaag gcgtgcgcca ccacttgcct ataatcttac    4680
ttgtaatggt tttagaatat gtgcacagtg gagagcagtg ttcaagcagc tgtatccaac    4740
caattccact taagagggga gagggtgagg gtgagggcct cctttgctat tcaaaagcag    4800
attgtgtgga cattgcattg gattcttttg ttgttgctgc tgttgttttg ttttgttttt    4860
gagacagaat ttctctatat agccctggct gtcctggaac tcagtttgta gaccaggctg    4920
gcctcgaact cagaaatccg cctgcctctg cctcccaagg gctgggatta aaggcgttgc    4980
attggattct atgcaaatgt aggttctttt ctgttttcgt ttttgctaaa attctgagta    5040
attcatgtat cctttcaagt taaaaaaaat ctttgtgtgt gtgtatgtgt gaatgaatgt    5100
actgcatgca cataaatatt catatccgtg attgtggggc aaatgtacca tggcatggac    5160
atggaggtca taggagaacc ttgggtattg gtatttacct tctactttga gtcaggtctc    5220
ttgcttacca ctgtgtgtgt gccagcttag ctggcttcta aatttctgga ttctgtcctg    5280
tatctgcttc ccatctcact gtaggagcac tccataaaag agagatgagt gtctggcctt    5340
gtatgggttc tgaggctctg aatttgggct cctcaggctt gtgtgacaag tgttttagct    5400
acatctgcta actgcccaca ccaatattag agcctttcgg gtctcctatt agtactgaaa    5460
gtgagcagtg tgttccccta tctgtagggg aagtaatgca gcctttgtaa gttttgctca    5520
ttttgctaac ttgaaatcca ttagaatgtg accagaggga ctagggactg aagagacgtc    5580
agtggttaag aggacagtct gctcttacac tggcctggat ttggtttcca gatcccacaa    5640
tggctgtttc tcaactacct gtaactctgg ctccaggaca gaggtctgac acctctgacc    5700
cccatggata ctagccctca caggcatata tgccttacct ccagtatata tacttcaaac    5760
atattttaa tcttaaaaaa agaaaaaaaa aggaaaagaa aagtctcttt aacattgtga    5820
aaagcccatt tcttaaggct aacacagcag attatttcag gcttagtggt ttagaatcaa    5880
agattctaga tgaatattca cagagactgt agtagttgta ataaaaatga aatatctttt    5940
tttcttgttt gtttatatat atatttttag acagggtctc actcagtagc tcaggttgtc    6000
ttaaattcac ttgaacttac agtaagcctc ctacttcagc atcccaggtc ctagcattac    6060
aaaacttagc caccacactg cctttaacat tttgatattt agagagagag agtgtgtgtg    6120
tgtgtgtgtg tgttgtgtga gtattgcatg tacatgagtg ttcaggtgag catggccctg    6180
tgtgcacaca gggagtccag agcaggatgt gggttgcctt cttctattgt tctatgctta    6240
ttgccttgcc ttggagtctc tcaactcaac caaaagcgca tcattttcag tgaggctagc    6300
cagccagcac actcttggga tttgcccatc tatctctaag ttctgaaatt actggcatgt    6360
gcagacatgc tcaacatctc ttagacatgg gcacctgtgg ttcaaaatca ggtactgatg    6420
aagagcaatt ttttttttcct attgaatcat cactatagcc ttttagaat ttttttttaa    6480
gttattaaaa gttaatgtga atgggccagt ctaatggctc agtggtcaag ggcacctgtc    6540
actaagtctg atgacctgag tttgatcccc gaacccacat agtagaagga gagaactagt    6600
```

```
ctcgagagtt gtcttctaac ctctacaagc acaagctcaa gtcaacccca tacacaaaca    6660
gatatatagg taggtgggta ggtgggtagg tgggtaggta ggtaggtagg tgggtgggtg    6720
atagattgat gtggagttag agagacggct taagcatgaa gacctgagtt cagttcccta    6780
gcaaccacat taaaagccga gcatggctgt gtgtgcctgt ggccccacca ctgtggtgga    6840
tggagacagg gggatcactg tagcttgtgc gctgcctgtc tagctccagt tttagtagag    6900
acccttgtt aggggagtaa ggcaaagagt gatagagcag gccaggagaa gtcctcctcc     6960
tctagcctcc agggagtgtg catggccata cacatgtgtg catacgctac tcacacccac    7020
cccccaaaat taattcatgt tttcaagtat tagagtattt atcttctcat tgcagtgaaa    7080
tccaataaaa gctggttatt ggtgtttgca ggccagctgt gcagtgatac aatatgtgac    7140
tcctcagtac ctggtgaatg ctttcaccac cattatactg cttacatttg ttattaacaa    7200
ttagaatgta ccttaaaata tatttcccat ggctttgact gccaatcccc tctggtccaa    7260
attctagtat tgataagata caagactctt gggttatcat ttatttacaa attaattttg    7320
ggaccatgac ggggtctgca gagtagctag gggtatagag gactgtgcca gcactccttg    7380
gctgagagcc tttatgcaga ataactttaa atgtttcagt gtaccctgct tacgctatag    7440
agtagtgtga aagtcctggg aataagatag tgtgtaggtg taaggtgctg ctgttgctgt    7500
acagtgcgca gactcttcta gggcttgtcc cttgtacaga agctcctctc agcgtctcag    7560
aaacaaagac tttctacgtg ctggccacat aaactggttt gctctttcct tggcgctgtc    7620
ttatcgagca tcctgaactc ttcctgagtc aagtttgcat ctgaatcttg ctgaaggcgc    7680
taaattccag ggacaaaata tgtttactta gaggggactc acaggttatc caatctgacc    7740
cttgtatcgg gactgaattc ttcccacatt ctgcccagat attcattgga acccactatc    7800
ggtgatcttt ttaaaaaaat cttaattgtt tatgtgttca gttttgttcc ttttgctta    7860
tttatcatct ttgcgattct ttcaaacccc aaatgacttg ctttgcttag ctgggagctg    7920
cagaactgtg gacttgggtg tgcctctgct taagccgaat aagcaaaacc tttgattcag    7980
gaaattgttt cccaggtgta gttctagtct aacacagctt aaatctgcta ggaaattggc    8040
tagcgagaga tttacaagac aattttttgaa aaatatggtt aagattttat ttcaatatct    8100
tttgtaaaca taaacaaac ttggcattta gtgtttaatt tttgaagtct cttgtaaaac     8160
aatgttgttt actctttgag aattttctat attttgacca tattcttttt cctcccgcag    8220
ttcttccaca tcttctgcct gtgtagtttt attgttgtta ctgttttact tttttattga    8280
ttctttgtga atttcacatc atgcactcca atcccactca tcttcccagc cttctgtatc    8340
tgccctctgc caatgggaac aaaaaaataa ataacaaaaa aagagaacaa aacaaaaaac    8400
agatctgtgg aagctgcggt ttgtcacggt gtgtctcaca gttcatcctt tagctcagac    8460
atctttactt ggaaatgttc cttgcaatga gtcactggtt tggttctagg cctctgcctt    8520
ctgctacact gtcaatactg ggtcctcact gggagtcttc tccagtatcc tgttgttgcc    8580
ctgtgtcatg gagatcctgt aggttaggat ctgcccgaca ggccccttta cacactccag    8640
cagttcatag atgaggtagg tgttggtgtg tgccaactca gagccctgga tctaggcctg    8700
agtggcagct gagttggtca gcctgccagt tctcttgcat acacatcacc agggccagct    8760
ctactgtgct gcccaggcta ggtgcgggtg ctgtagccaa caagaggcaa tgccagctct    8820
cctgctttca gtgtcctcag ggccagcttt cccacactgc ccagtgccat gctctcccca    8880
gtgccacagc tgatgagggg tctggccagc tctgggcagt cctttgacag caacatggct    8940
```

```
ccaggcagca gcctagacca gggatattca aaaggccttt ggtgataaca tgggtcatag    9000
acaatgacac agaccccaac ccaccccgat gctgcagagt catggaccca gacatggtcc    9060
ttggcagcag tatgggccag gacctcaccg tggcctcagg tggctgtgca ggctgttcct    9120
cggcacctgg gcgtctcttc attgtgtaaa cactattcca cttctctttc ccctctctct    9180
gatacttact tgctcatctt ggtggggtc tcccactcca cccacacagg caaaagtcct     9240
ctgagtgtcc tctgccccac ccatgccgtg tggtattggg tggggcttgt gtagtctttg    9300
aacactttat ttttctattt taaataacag atgcaatcaa acacttttag tgtttgattt    9360
tagtgagaaa gccacatttc cgtactgctt tccgtacaca taccttcctt aggtctataa    9420
gcagtctact gtgaaacttt agatttcttc aaaaagagct tttgtaagta gatctaattt    9480
tgaggagctg tgggaacttg ggaattgaca cttcttaatg gaattagaag ttaattcttt    9540
ctgaattttc atgttacagt tcttagata gtggctgata ttgtaatagc tagagaatgc     9600
aacactaagt aatactttcc caaaggggtt ctgggaactt gggtcttcat ctgtgtgtcc    9660
atagaccagc attcacattt gcactctgtt tcgggtactg tgctggtgtc tagagggtga    9720
agaactatgg agcaaccata ctatacttac tagtggggag acaagcagta acaagaccat    9780
tcacattgac tgctgtgtgg cctcgcttag cctaccgggt agagggtagg tggttagaaa    9840
agtttctctg atcaagtgcc agagcaagtt ctctgaaaaa ggtccggtgt ttggggacat    9900
taggacagtc caggtagagg tgctggtcag tgtagtgaag aagtatatgt gatgagagcg    9960
agaacaatcc ttccacatct attttttaaaa tagccagtgt ctggagaggt ggctcagagc   10020
ataagagcag gtactgcgcc tccagatgac ctgagctgct ccccagtcac aaccacctgt    10080
gactcctgtc ccagagggat caagtgcccc ttctcaggca ctcattcgca catggcgatg    10140
cacctgtaca acatgtacac acaattaagt taaaataag atctttaaaa aaaaaaaaa     10200 acactagcaa atattgcttt tggttagtaa caaagccttt actgaatgct gctgtatacc    10260
agtattgcca ttcatcctta cgtggtaggc accattctta gcttttata gacagaaaac     10320 aggtccaggc agttcatttg tgtagtcttc atggcagtcc agtttggggg ctgcgtttga    10380
agacgtgttt acagttgacg agtgaagtga gttcgctgtt cttggggtat ttgtgctatg    10440
aaagcacaga gaaacaatta cagaaaacac ttgatacctg acattgttgg atggttgttt    10500
accagctttt ccaaatagag gcaaagatgt gcttcactgc ttatgacaag ttcaatcttc    10560
acttcaagac aactcacata cggcagagcg aggcaaagtg gttttcagtt gatactagag    10620
ggaatgtgac accagaattg ctgtgaagac ttcaggctca gtgtttaagg ccatctccgt    10680
tctgtgctgc cctgctgtgt gctgccctgc tgtgtgctgc cctgctgtgc cagtctctgt    10740
ccaccccaac tgctcctttt tgcatcataa aaataatcta tagtgtattt taaactggtc    10800
ctctgtacat ttaaggttca gtccagactt gtgctgctcc ttatctgccg tcaccttacc    10860
ctcccttttt gaatcaataa catcattttg gcatgaaatt actatgtcat aatgtgtaga    10920
ttgtctccta ttcgagattg tagtcagtaa aaggagaatg acccttcctt ttgaacaaaa    10980
agggcaatca atacctcaca gagaatcctg ttcaggaggc tctgtgaccc tgcgttaaat    11040 tttacttta aggaatgggg cttttgaat ggtttgctaa gatggttgtg tttatctaac      11100
gaggttcaca tttactgaga ctattgaatc cccaggacta tggggatata aaatgggtaa    11160
agcaagacag ataaaagaat tctaggactg ccaagaaaca gagcaacctt tgtctgagcg    11220
tttaaaagcc tgtggtcttg gaattgttaa aactgcagca caccaaggtt taccttgttt    11280
ctcccgtggc atttaaggca ggtacagatg gaagtattag gaaggtattt gagtgtctct    11340
```

```
gtgtccacgt aagaggtagt tcacaggctg gcagctttgc tgccatgtct atgggaatcc    11400
aaggacaaga aataaatgag ttcacatcta ggagagttat attaagttcc aggctaggga    11460
ccagtgttgt acattgacaa aatagctgtc attcaggata gaaagaagtt ggtttataac    11520
aaaagacagt aactgtgtaa tgagttaaag accaaaataa atacataaac aaacaacttt    11580
ggagataagg aatagtgcag ctgagtctca gagttttgct tttgttattt ttttaaagat    11640
ttatttattt attttgtgta tagctgtaca gatggttgtg agccttcatg tggttgttgg    11700
gaattgggtt tttaggacct ctgctcactc cagtcaggct tttgttactt ttaagtgagg    11760
ttggagctgt tctttgtatt agtaggtgac tctgtgagtt gtatggatca tggtgaatgt    11820
cacttctctg tgtgcctata taatgttttg tttccttcct gagggatatt tttatttttt    11880
acgttagttt ttttttttctt aaggatttct tgcatattat ccgtatagtt aatattcaga    11940
gtgaaaaaag tttcttgaag acagaacatt ttatttaatt agggtaggct cttctttagc    12000
tcaggctgtc ttcagactca ttatgtaaga tgaccttgaa ctttggacag ccccttctta    12060
gggggtgtgt gccaggattt atgtggtgct tagggtcaaa tccagggctt taggcgtgct    12120
aggccagcac tctaccaatg gggtgtatcc gcaggcttca gatgtggaga gtgtctagta    12180
agacatcggg atcctggagt gagaggcctg ggtataattc cttttctttt gtcacactgt    12240
agcagttctg cttctcagcc tcagttgaga ctggaataca tttgtcatgc tgttctgaag    12300
actttaatgg ttgatcttta ctgtcacctt gactggattt agaatcgcct tggagatgtg    12360
cttatggtat gtctgggagg atgtttccag aaagtgttta ctgaaggtgt cctcatctga    12420
tagggtgggg ccctggactc aataaaaacc ggcatttatc tgtttcctgt ccagggacac    12480
agtgtggcca gctacttcac actcttgctg ccgagccttc ctacatcgaa agactgtatc    12540
ttttcttaaa aggcgaggca aaataaatcc ccaccccccag gattttttttt ggctgtcctg    12600 gaactcaggt ccacctgcat ctgcctcctg agtgctgggt ctacaggagt acccaccagg    12660
cctggctaaa agaaacccctt cttaaattgc tcctgtcaga cactttgaca caacaataag    12720
aaaaataatt catacaaaga ccaagtgaga taatatgtta ttttttttagt tcatagagta    12780 gtaggtaatc catggtgagg gaaaaaaaaa aaaagaaccc ttttgaaata aggacagtat    12840
tgagaaacat gtatgctgat tgtatgagtt ttgtgatatg taagtttcta ctcaattcac    12900
atggtaattg tgcattctga tcattaatca aataattgtg tttactactt taaccttctt    12960
acaaagtata gttttactaa ttagtaattt agtaaattta ttatttattt aatgaaacat    13020
ttcaaattgg actcagaaaa agaccacagt ttttgtacat attatagtag aagtcccttta    13080 gtaggtggaa atcctgtgtt tctttacaag gatatgtcta gaacacgtta aacaaacagg    13140
aggaggtgtg gctgcacccg ttaggctaac cagtcaacat gccttttaaa gccatacgtg    13200
ttgtgtgtga gcattttttt aaatatatag aaaatcccca aaatagctag tataataagc    13260
acacatgcca gtaagcctct tattactgta aaatactgtg taatactttg tgcgttcttt    13320
tatgtgactg cagtaggtct gtttacatca gcatttaccc atacaaggtg gctactgtca    13380
ttcaggcctt ggaaagtttt cagcttcttt gaaacttgtg gggttacttc tccagttgta    13440
tgtgctgtcc atggttggct agacatggca catgactggc gcatggacct aaagacagat    13500
taaagaattc atttcaaatg atttcaagca cagagtttaa attgtacatg cactcttagt    13560
caatgtcctt gtagctgcat tttggtgtaa ttggagggac atggactagt tagctgtttc    13620
ttttacttga tgacagtttt gaatgaaaag catgttagat acaaaataat ttaactgttg    13680
```

```
acccccccccc acacacacac acacactctt tttccctgta tgccttcact cctcgaattg   13740
gtttttatca gatagctgtt ccaggtgtac caggcatata tgaagtagtt tatgtagttt   13800
cgtttatgcc agtgcaatcc tgtgaggagc aattagtaca ttatacttta tagttaatga   13860
gatagatata gagaaagctg atacatcaca tctatttctt gtgtaagatg gagggctggg   13920
attcaaatgt aagtcttagt ccgtgtctta tactttgcag cctgtggtct tagtgatgat   13980
catgttatga agggcaacct cttttttcaga ctgtgtctgc aagacccgtg aattaaatga   14040
ccaaaggcat actaactgta gagaaactgc ccattttatt gatgctaata ttttacatg    14100 gtaggaggaa acttggaaga aatgagaagc cctactcagg gggattttttc aggtgagatt   14160 atgtagtgac tagtgtaaaa gaagctacta aagggatac caagtatggg aaataagtgc    14220
tgcacacctc agggtggtca cacagactca gactgacagc tcaggtcttc ctgctgaaga   14280
aggggacgtc tttgaaagtg agaaattcat gtcttcttta tagaaagttc tactccagct   14340
ctaggccgaa gactggggc agagagcttt tcttgtgcct gcgatttctt aactgttttt    14400
attcaaaatc attcttatgc caaagggca tatttggggt tgagttcttt cagcgatatc    14460
atttatattt gagaccaatg agacgttttt ctcactatgt attgtatttc aactttcatg   14520
ctaaacctac tggactttac tgagataaat caagaacata cctttaaact ttgtagttct   14580
tctttgccac tgtgaccaaa acacatgact gggagaaatg gtttattttg cctcccagtc   14640
ttggtgattt tagtccctca cagcagagaa gcctggtaga gcagctcact gagtggcaac   14700
aggactgtgc tcatgtgatc atggaccagg aagtgtagaa caaagccaga actaggggcc   14760
ctagtaacct acttctgcca gctaggcccc acttcctgaa ggttccacct cctcccctccc  14820 cctcccaaaa aagaaaataa aaatagtacc accaactgga cagcaaacac cccaaacata   14880
agccagtgag gagggaagga gggaggggg aggaaggagg gagagagggg ggaaggagaa    14940
ggagagagag aaggagagag agagggaggg agggagagag agagagagag agagagagaa   15000
cacaccagct ctcaagtaac ttacatgtat gtcatggaac aaattaaaaa ctatgtaacc   15060
agaaaattat tttaagagta tttgatttgt ctgtatttaa ttaattaact gaaaaaaaaa   15120
ggaaaattaa ttccttttctc taaagacttt aaatgaacca ttttttttagt gtatgtgtgt   15180 gtgtgtctag gtcaaaagac aggtctcagg agttgatatt tgaccatgtg aaccctaggg   15240
atcgaacttt tagctcatca gctttggcag caggaatctt tatacactgc atcatctcac   15300
tggccttaga taagttttga aaaaaagtgg aagaatctaa agttacttgg ataattatat   15360
aaaatataag tctgaggttg ggctcaagac ggaaagacat cagtaaggag ccaagagaac   15420
agccccagag agaatctgag aatcaagggt gtgggcaaac atacagtgat ctacactttt   15480
tatctgtaaa tagtttgtaa attcttaacc ctttaaaaaa attccctaac ccctactctg   15540
cagatcagac tgccctggaa ctcattgtag aagcctaagg tggcctcgca ttcacacaat   15600
ccttctgaca cagctcccca agtgctagga ttacaaggat aagctactgt gtctgccttc   15660
ttagcttttt aaattttaaa agcactacaa ccttgtaact agtttatac ttgtcaataa    15720 aataacagta actgggactg gggagatggc tcaggctgct tttccagagg gacccaggtt   15780
cgattcccag gagccacaca atggcttaca atcatctgta gctatagttc ccagggatct   15840
gatgcccttt tctgattcct gcaggcccca ggcaagcatg gggtgtacaa acacacatgc   15900
aggcaaaaca gatgtctttc tgcattgctc ttcacctttt atattgaggc aaggtctctc   15960
acttgaaccc agatctcact gattggctag tgtaactaac tggcttgctc aaggaatccc   16020
tgtctacact tcactaaagc tcttgctgtg tagcccaggc tagcctcaaa ttcctaatcc   16080
```

```
tcctgcttta gccacttaag tgtccgggat ttcaggcatg caccactaca tctggttgaa    16140
aggtatcttt ggatggtttg ggtattatta gcttggaggc tagcgatgtc tccaaagaac    16200
cttacataat ttacatatgc atacatacat acatacataa acatacatac atacacacat    16260
gcatacattt aactggatct gtagttcttg taaagtgtac ccagtggtcc ttaaatagtt    16320
ctactttatt tctaagagtg atcatgatca tgagctggca tcccaatatt aactctgcac    16380
agatcaacta accattggtt acttatttgt ttgatttatg tcgtttgtaa acttgattag    16440
aagtaattag acacgtgtga acacactgtg cagttgtctt agagcagtag cagcagcctt    16500
agtgtgagtc cttgacatct aactttatat tatgtagcta cattgctttt acacagggct    16560
tattaatgcc ctttcaggtt ttgttatcat tatggtattt gtgagtattt caccaccagg    16620
aaggcaaacc tttctggcat agtagactcc aaagcgttca ctaacttatg cataattctt    16680
agtgacaaag tataagaaca actgctaagt aaaagtgatc caaggaagg gaacagatga     16740 gcaacagcag tcatttgctc ccttcaagtc cctttctaat cactggatac ttaacactta    16800
caaaacagaa cagtacagtg aaaacctggc ctcgtccctt ggtttaaaaa cagagtgtag    16860
ccaggagggt acagtggcac atgatgtagt gaccctgact tgatgttcca gctcacaggg    16920
acctctggcc tccctgttgt actcccctgg ctccttagcc tgcatttttg ttcagcacac    16980
aagtggacta acacaagact ccagcacaca gctttcattt ggtcttatgc tcagaaaccc    17040
tttcctctca tttgctaaaa tatatccaac ggacacagta gctctccatt ttacaaatcc    17100
ttaaaatata gagtatgttc ataatatttg cgttatttcc cattatgtta ttatgtatat    17160
gtccatctct tccgctggac tgtagagcct tatatattat tagtgatcaa taacttcttg    17220 tggattttc ttacagggat atcaatcatt ctgtcttact ttatgatcat taacctgtcc     17280
tacatttaag tactttataa gtatgagcta tttatagtgt gtggggctcc caagagaact    17340
ctgatgtttg ttagtcatgg atagagctag ttacattgtg tccttgtctg tttcctttca    17400 cattctttt tttttttaa ttgtcaaagt catgattctt tttgttttct cttttagata     17460
ttgctatatg gagatttgcc aaaaaataaa gaaaatgtaa tatatctagc gaatcatcaa    17520
agcacaggtt tgtatttcat ttgatgaaat ttgggttttt ctagaaatgg taaatgagca    17580
ttaatatgta cacacacata cacacaaaca cacatatgta cacacacata tgttttaaag    17640
acaggatttc atgtgaccca gaatggcctc atactctctg agtagctgag aatgatttta    17700
agcttgtgac acacctgcct tcatctccaa ggtacaggaa ttgcaggtgc tttctttgta    17760
tgcttagctt atgtggtgct gggcatcaaa cccaaggctt catgcaaact aggcaagcac    17820
tgtcccatct gagctacatc cccagcccat caaaatgata ttttaaggtt atttatttaa    17880
tgagttttat cacgtgtgtg tgtatctgtc tgtgggtttg agcttgtgag tacacatgcc    17940
tgtggaggcc agaagaagaa caccagatct tccctggagc ttgagttgca ggtagcgatt    18000
agttatcctg gatggatttg gggaactaaa ctggggtgct ttgaaagaga aatatgtact    18060
cttaactgct gggctttgtc tccagccttt aaaatattaa tcttatatat ttaagtaaac    18120
taagctagct tttgttttta acataaattt gctgtggatt ttgaatctgg cttgcaattt    18180
tattttactt ttttggtggg gagggtaagg ttagtaatgt gaaaggtatg gttttgtcc     18240 aggcttctct tcttccctat ttctcaaaat aacccttag tttatttggt tttctgtctc     18300
tacgttatat tttctagaat atatatatat atatacacac acacacacac acacatatat    18360
atacatatat atatacacac acacatatat agtgggattg gtggacccaa gtgtatacat    18420
```

| | |
|---|---|
| tttaattctt aattctacat ctagccttt atttactctg agacatattc ttgctctgtt | 18480 |
| gcccaggctg gactcaaact caaaattctc ctgcctccgt ctctggagtg atggatcaca | 18540 |
| gttgtatgct gccactgttt gcactctaac tgtgtagttg ttaagctgct tattggtatg | 18600 |
| ctggtgtctg actgctcatt tcctggacac agtgctgtta taattagctg tagttcctgt | 18660 |
| tgctctttaa tcctggtagc ttaattctaa cttgctattt ttccgtcaga gaaggcacaa | 18720 |
| gactagtttc cagtatagaa ctgtatttac ttccaatcag gtcaaatata tatatatttg | 18780 |
| tttgtttgtt tgtttgtttt gttttgtttt gtttgtttgt ttttgagaca gggtttctct | 18840 |
| gtatagccct ggctgtcctg gaactcactc tgtagaccag actgacctcg aactcagaaa | 18900 |
| tccacctgcc tctgcctcct gagtgctggg attaaaggcg tgcgccacca tgcccggcgg | 18960 |
| gtcaaatatt taaaactacc tcttttgaa tgattattga tgaattgtga attatgctgc | 19020 |
| tagtcctgcg gtcccttcat gagggtcctc cccatgaggc acctcacagg tacagggccc | 19080 |
| agccaagagg ccaaatgatt gcctaaagtg tgctttcatt ctccaaataa ttcacctcat | 19140 |
| ccaaaatccc acttcctata ttttctaaac cacggccacg ttgtgtgcat ccgttctatg | 19200 |
| gttcgtttga ttgctttgac aagctcagga cctagcatcc caaagctaac agaacccaac | 19260 |
| cgttaggata ttctgaatgg aaggtcactt gtgctgatgg cttttatttt cctcccaccc | 19320 |
| ccatttggtt gggattgtag ctcttgatac cgcacccca acacacacac agacacccgg | 19380 |
| accatagcta acacagaggt aaaggagctg aaacacgttt ttctctgtgt gacacactgg | 19440 |
| aaaactgatg aagctccaaa gcttgatagg gattttgata tcagatgtat tatcctgggt | 19500 |
| catgttcgtg agactggctc agactctgca tttgactttg agtcgaacca cagagtggcc | 19560 |
| cagagtgact ctctgcttct agccagcctg tctgacacac tggctggccc tcctcaccac | 19620 |
| aatctgacct catgctggtg aggggaattt ttacctggct ggcccccagg acagggcatg | 19680 |
| ggccatggca gcatcctgtc gcagttctgt tgttcagagg tggatcccac tgcaggaaac | 19740 |
| tagagtttcc catcaatgtc tttcttctca gttttatgga ataaaccttt ccttaatgga | 19800 |
| actgtaatcc tacaaggaca ggtgggacca tgtactcttg ctctcctgtg ggtctcacag | 19860 |
| taacagggcg gctgaaggca tggctgtggt tgcctttgcc ttcctttaga gcaggcttcc | 19920 |
| aggaaagcac tgtgagtaag cagcaggtaa cagttcctac ttggtgtttg agatctgaag | 19980 |
| ataacgtggc aagcaagagg ctaagccagt tcctttctta gtttagagag acatttcttg | 20040 |
| actctgcctc caggtgacct cctctaggtc tgataacaac cagcctttgg ggtttgagaa | 20100 |
| cattcttgtt ttttgttttt ggcaacttga aaaaagtacc cagagccttt gcatgttaag | 20160 |
| caagaactct tctgcctaga caagcaactg tgcaacacac acagacacaa gcaagcagct | 20220 |
| caacctaagc atgctgcatt ccaaatgcct ttaagaagcc cacaagttgg gaacatacca | 20280 |
| gaggaatgac tgaactgcgt tagaattgca tgttagtcta cgtgatggaa gaaggcatgg | 20340 |
| agtcttctct aataaaactg ctcatggaag actttgcatg aattccaggc ttccagaggg | 20400 |
| ttcaaaccag caacccaagg tggatttggt tcctggggat gacatattta ggtaaagaga | 20460 |
| gcttaagaat cagtctctga aagtgtaatt tacagaaagt gttctgggac tgctgttggt | 20520 |
| tcagcctgtt cactctcact ctgttcactc tggcctgatg ctcatgaaga gttgaccttt | 20580 |
| accttagtct cagttgctgc ttttacttgg tatcctgctg tgtctacatc cttgctgctt | 20640 |
| ctaacttgtc tgctttcaac actgttcgcc tttaaaattc attccttttc atttcctgtc | 20700 |
| tgatagagta tatggttcag tagatggctg taaagctgag ggctctgcat tctgggagac | 20760 |
| cctgctcatg tgtgctgctt ctgtgtgttc tctgccagtg ggcagagcac ccaggctctc | 20820 |

-continued

```
tgagcctgct ggttgggtct gaatgatatc tattgataga agctttaagg cagtgtacat    20880
atagttccac tcaaaaaccc agtgcagtgc ctggcatatg ggtgacattt agcagtactg    20940
tgaatgatgg tggggatagc ccagtgctgg attcatgggc ataaacccett atgtgtcatc    21000 ccataacact aagaattggt gagacacgac tgtacagacg aggaaagtaa ggtttatttg    21060
cctgttctcc tctcttcaag ttactgaaaa catggcttat ggctagataa gcctcatggc    21120
tagatcactg ctaaagagtc ctgacaacca aattaaatta ttcttgccaa acacaaaat    21180 acagatatcc atgtgaatgt aatacattcc cttacatatt ttaatccagc gttatctcgg    21240
aagcagtgtg cataagtaga gaacagtatt gaatctatat tgtattcttt gactgtactt    21300 atttttttt atttgggata aggtcttacc atataacccc agctggcctt gaacttacca    21360
tatagaccag tctggccttg aactcacaga gatttgcctg cctcagcctc ctccaactct    21420
gagattaaag gccaaacttg ccaccattcc tggcttgtaa gttacttctt aagtgttgtt    21480
actaaaattt ttaaatttaa ggttatggtg taggatagtt tatcttggat gcatgacata    21540
tttaaaaata tttatatatt ctcttaatag ttttttagaag gtataccgga ctccaaaata    21600
taactgctta tttaaatata aaaacagatt tattgttcca taagcttaaa aattaaagtc    21660
tcaggaaaag ataccaaact tggcttttac ctatttatct catttatacc cagaatattc    21720
actggccagc aaactctgta gagcagtgat tctcaacctg tgggtcacaa cctatcctgc    21780
ttatcagata gttacattat gaattgtaac agcagcaaaa tcacagttac gcaatatcaa    21840
caaaataatt ttatggttga gggtcaccat aacgtgagga actgcattaa agggtcacag    21900
atttaggcag gttgagagct atagccacat agagccttta cagggttcat tctcgttgtt    21960
tctatagaaa acgtttatat tagataactt tctcacagac ttggttatat ttccaagaga    22020
tagctgtttt ataatcccta ctctaaaaca attaagattt ttctagaaag ttgattattc    22080
acgtgtaaag agataaaatt ctaggatatt tcatttgtat atgcattatg aaaaaaattt    22140
aaatggtcaa gaattatgcg atagctgtgg aaaagtgccc cattttaaca cactttgaac    22200
tccaggcttt atactgcagt ttgtttgttg ttcctccccc gccccatccc caactttctt    22260
tcatgctagg acagaaccca gggccatgca cgtgattaga atatactcct tcactgagct    22320
gcaccccccc ccccccagtt ctttttatttt attttttatt ttgcgacatt gtctcactaa    22380
gttacctggg taggccttga actcatgatc cttctgcttc agtctccgaa gtagctggga    22440
ttagaggcct gtgctgtcag cctggatgta agagtttgtt gttgatttaa attagatatt    22500
gtctcctcta attaactcca tttgttgtca ttttcatggc cctgagtaca cttcaacagc    22560
atccctgttc atatccttga attcttctct aaatcctagc agacctttcc tgatctttca    22620
ttttctgttc acatggaagg tacctgcagc catttattct caagtcttca atattctgc    22680 ttctcaggac actttcttat ttctttgtat ttcaccatag aagttttgca tgacctcagg    22740
catataagaa caatataatc aaacactgac tgataataaa gagtggagag atttttatat    22800 tttttttgttt tttgtttttt gtttgttttt ttggttgttt ggttggttgg ttggttggtt    22860
tttcgaaaca gggtttctct gtgtagccct ggctatcctg gaactcactc tgtagaccat    22920
gctggtctcg agtgagattt attttttaaat acatagaatt ttagcagtta ttaaagataa    22980
aaggcagtct acatactgtg agatggatag gtttgtatag aagaacttga ctttggctga    23040
atatttgata ctataggatg tagagcattt ccttgttttt cagaattcat caggattttg    23100
attttgtaga tgccagtgct aagaatgttg tttccacaaa cacattgtac aatatggcag    23160
```

```
aattgtgttt agtgtcattt cagaaattgt ttgaaactcc attctaattc taggtcaaaa    23220
ttcatttcat ggaactcaag ccagttttta taaatcaagc attctaatgt aatacaatca    23280
aaagtgcact agttttgtac ttacatgcta aggaatggca ctgatgaaat attcacctac    23340
tttctgtaac agcagaaagc tctatgtata cgaaatgtac ttcacttaat ggcacggtat    23400
tacatatatg ctagcatgtg cagtgagaag cacgcatgtt gcatactcaa aacagaagac    23460
gcaggggcag ctgcacaagg cagcggtggg cagagacact tattcattca tatgtatgtg    23520
gttttgaatt aagttttgct cattgcttat ttaaaaactt ttattcacaa ttttttttgac   23580 cactaaaatc agtttgcaac ccacagtttc aaaagctgca aaataagacc tacatatcta    23640
cctcgcacaa ttgtaaatca cacgagaccc ttgtttgggt attgtaagaa ttgaacactg    23700
tatccaggaa gtcattagta aaaacctaat gtggtgcctt gcttttaaa gatttattta    23760 cttatttaat atatatgccc tatcatatat atacctgcat gctagaagag ggcatcagat    23820
gtcagtagag atggttgtga gccacgatgt ggttgctggg aattgaacgc aggacctctg    23880
gaagagcagc cagtgctctt aaccactgag ccatctctcc agctcttaat gtagtgcctt    23940
ttgtcagaca ttgtgtatat gggatattta gctacagttg tttcacttgc cattttttc    24000 cttataattt tccattcttc atttaaaaag aaatatctct tatttttttt acctgtaatt    24060
aaatattatt caacagttat ttagtatttg ggtgttgggt tacttagtat tttgtagctt    24120
ttaaacattt gttctttctt ttcctgagta tgtttgagtc cctgcatata tgcctgtgca    24180
ctgtgcatgt gcctggtgca cttggggctc atggagggcc tcatatccgt tggaactgga    24240
gttagaggca gagctggctt atgggtacca gacctgggcc ctctgcgaaa gcagcaactg    24300
aatccttaac cactgaacaa aatctcttca gccccatgta ttttgtacct ttgtgtttta    24360
tccttgaaat aaatggcctt ttaagaaatg agaaaagcct ttaatcccag cagaggtaag    24420
tggatcactg agttcaaggc cagcttgtcc acatagttcc aggagagcca gggctacaca    24480
gaggaaaaaa aaaatacaaa aaacaggaaa aacacacacc tccttgattt aagggttttt    24540
tgtttgttgg ttgttttttt tttttgagtt ttggggaggg ggtatatttt taatgtgtc    24600 tgtagttggc tttgttttaa gcattttaat catactttat ttttaaaaaa actaaaagct    24660
tttttaaggc taggtcttgc tatgtggccc tagtgttcct gggacttgct ctgtacaccg    24720
ggttgactct gagcctgtgc gccttctgcc tctgcctcca tagttagatt ctcaggacat    24780
gttacaaaga ctgtgctgtg aagatgagtt tttgttcctg ggagggaagg ttggagctga    24840
cttgtgaggt actgacttgg gtctgcctta cagttgactg gattgttgcg gacatgctgg    24900
ctgccagaca ggatgcccta ggacatgtgc gctacgtact gaaagacaag ttaaaatggc    24960
ttccgctgta tgggttctac tttgctcagg taaactttgt cttttgcccct ttatttcaaa    25020 cttaacacca tttaatgaaa ctatatctga ttttttttgtt tatgtgtttg ttttatggta   25080
cccgtgattg aacatggggt catatgtgtg ctactgagtg acagccttag ttcagacatt    25140
ttttaaagcg actttactta gtattttat ttagaattct atatgtgtgc acatgcatat     25200
gtgtgcttgt gtgcacacgt ggatgcatgt gaggtcgaag acaatttttc agtacaagtg    25260
tgagtgtcac ttttttaggca ccttccactc ttattttgag acagtctcct agacctttgc   25320
tgagttgccc aggctagccg gccagtgagc cctgggcatc taccggtctc tgcctcctta    25380
cctttactta ggttacaagt gtgtgctgct acgcccagct gtttactaga ttctagggat    25440
ccaaatgtgg gtcctcgtaa cttgtgagac aagtactttc caaactgagc cacctcccta    25500
gctcttcttc acggttcctg atggtgtgtg tctagatggc tggttgtccg tatatttaag    25560
```

```
tccagtagca gaaatacaaa tacctaggag tccaatagaa agctacaagt gcagaattga    25620
caatcggtaa tgttcggaaa ttgattcaaa agtagttagt gagtgacaga caggagctaa    25680
aagcagactc tgagctcaga gtgtgaagtg tggagaaatg tgttttctca cagttctgaa    25740
ggctgaaagt ctccccaagg tcaggatgtg ggtggtactg ctgtctccca acacccacct    25800
ctttggatta tagactgcag ccttctccct gtgttctgag ccggcctttc ccacatgtgg    25860
acatccttgg tgggtgttcc accagcaggg cctcagctag tgcccttatt tcacttaact    25920
gtaatgattt tcttaaagac cctgtctcca tacacagtca ctgtggaagc tgaagcttca    25980
atgtaagagt taagggggga gggggaaatt tagtccataa tggtgtcaca ccaatctctg    26040
tagctgagtc catgattcag ttctttaaag gctctgagtg tagacattat cttaattatt    26100
ttgcccattt atgtattatc tttaatttat tttatgtaac tgaatgcctg tgtatatatg    26160
tttctggttc ctagtccata ttttaattcc ttaaaggatg gaggtgtaga cttttgtctt    26220
tttaattttc tatccttccc tcctggcctc ctgtggcctc ttttacgtat ttattatttt    26280
taatttattt tatgtgtttg agtgttttgt atctatgcat tcctggggcc catggaggtc    26340
agaaaaacac attaggtggc ctacaactga gttatgggtg gtttgtgacc atggggtgct    26400
gggacttgat caccagtctc tgagaagact cgtgtctgct gagccttctc tccagtcctg    26460
ggagtgtgga tattttaagg atacttttaa ttgacttggt gaatgacagt agaaaatcaa    26520
tgagttagga tccatcggaa aaagcttttg aactaaatct tttaaagaga aaatatttta    26580
agtgctaaca aaattaaatg tgtattttcc atgatgcagt tttacttggg ctctgtagaa    26640
ataggatttt caggtacata ttgtatatat agttggcaat atttaaatac taactgtcgc    26700
ttgagttctg aaatgtagtt ttatgttttt tactcattag gagtacagtt gccttaataa    26760
ctacggagat tagttattaa agaataattg ctcttctttt ttcttttctg tgtaccagca    26820
tggaggaatt tatgtaaaac gaagtgccaa atttaatgat aaagaaatga gaagcaagct    26880
gcagagctat gtgaacgcag gaacaccggt aagtgcgccc gcttttattc ctcaaggcag    26940
gttaagaagt taagttctta agtcattttg aaaatatatt accccatgtg gagcaatgga    27000
actggttcgg ggttttgttg agataagctg tcctctggcc gtgaggtaag attgctgcag    27060
gtgattgtaa ggtttctcct gagtaacagt cagcatgggc tcgggacggg caagggcagg    27120
ccttagtgtg cagaggatgg agctcactga agccccaaag agttagtctt cacatgagat    27180
tcagttctag aagaagttaa attgcttttct ttctgtgtaa atttggattt ttattgtaga    27240
aattaaagtt tgttttcttt taaaacaaac acaaacccag agcaaagagt ctcctagtga    27300
agagtcattc cgtgtcagta ttttacacaa ctgtttttct gtaaaggggg aaaaagaatt    27360
caaatcttct ctttcaagaa tgctgactgc tgccaactgc ctctcccgt ggcccctctc     27420 tgtatagaca ggcatagcta tggtgaggac ttgggcggct cttgtctttc tcctctctct    27480
gcttctctac ccttctctc gtgccctcca cttaccaggc cctgggaagc tacacaccag     27540
gcaacagtga ccagggcctc ggcctgggct tcgaccaatt actagagcag aaacagcagc    27600
agctgcagtg ttgttttgtg ctgtgcactg tattaggttg tgttttcatc acctttgggt    27660
tttgtgatgt tttgatgaag tcctggtacc attctagttt ttacattctg ggtagataga    27720
gtttattcaa ggtctcaagg catatgaatg gaagagctcc tctttacagc cattcgtgta    27780
gcatgcataa ctgctcttct gtattctctc tagtgtcttt ttttttgtgt gtgaatctga    27840
tgtcttgtta ttcacctaca atgtggagta atggtcataa acatataaag tacttatgcc    27900
```

```
tttatctgcc aaattgtatt taacttttca gcttttaata taacttttta tataataatt   27960
aatttatttt aaaaaaaatt gaataccagc ctgttatagt ggcatatgcc tgtgttccta   28020
gcactcagga gacaaaggca gaagtgtgag aacttcagac tcatactcag ctatatacaa   28080
gaccccaaat ttgtgctaga ttctgcagta cagccatgag tgtccccatc ttagagggag   28140
atcgctcatc cttgtgctgt tctttaagtc ttaccctgca acccactgta agtacactct   28200
tgctcacagt cctttagaat ctcacactct ttctctttac agacaccatg tcattgccca   28260
ctttattatt tatctgatgt ctacaaagat tatgaaagag aaacttgtat gcattctgtg   28320
taaagtactt gacacaaata atagtattca agaatgactt cttaaatgaa cactgaatga   28380
atagtttgtt ctaatttttt tgatcaacaa atcaaaaaat atttagatta aatatctaag   28440
atacaaagca taataccaca tgaatcatta agtgagtaa tcaatcttat aagtgactga    28500
ccctaaaact catagacatt aataattgct ttcattgctt agatataaac tttattgatt   28560
aatacgttct catgaaagtg gttcttggaa ggttctggaa acgaaaatat ttttcttact   28620
gcttttttct tctagtaact gattgaattt ttctgcagtt ccataaagca tctggtcaat   28680
tgctattatc caatatgagg atatataaca aagtattgat ttttaaattt ggcggtgata   28740
agacaagact gggcgtgtga atgagggggt ctctgtttct tgtcccttct cttgggttct   28800
tttccttttg ttggtttgcc ttctccagct gctatgtgat gggttctgat tatcttatta   28860
tatcttattt tgttatttt cattgttatc cttagaagc caacatgtta tatcacctcc     28920
actcccacca ttaggtgtct cacaaatacc ccaagctaaa caaccacatc atgtcatgtt   28980
ctgtatactt ccataagtgt tgttaactct actgactctt gtgagcaggc ccaattggct   29040
ttatccctag ctgggtgacc tgggttcctc cccaacacca taccgtccat caaactgagt   29100 cctttccaa gcacacacca gatactgctc atctgaggac tcttctcatc cacctaagga    29160
ctgcctgctc ctcggcagaa agggcctcta gtcccatacc cttacgccct caccaatgcc   29220
ttaggaacat gtgctcaatg cccctgtggg tcatttccgt ttacagtagg gaaatttgcc   29280
tgataacttg cagcacacct ataaagaggc cttgcttgct ctcatattta gctggagaag   29340
ataatgtact caccaactcc actctatgca acccagtctg ctctgcccat gccagtcaga   29400
cgtgaatctt acacctggat tcagattgat gaatctacaa catcacccac tccatgcttc   29460
cttctaaatc agcagttcta gcctgaatga cagatgctac ccaagtctca tctagttagc   29520
cctgtccgga gtaaccctga ccttgaggat tagaccagga tgcacatcct gcaccagttc   29580
cctttgtcca cctgacttca tcccacccgg gccatagccc atgctcaggc tccaccctcc   29640
atgcacaaag ctggctttc cagcttcctt cacctgtatc agacacaaat agcaaagggg    29700
gtccacgtgc ctaggtccca tcacaagacc atgtgcggta gtttggaaaa cagtctccac   29760
ttgaggctca gatagttgga atcttggctc tcatgtagtt gtactgatta gatcagttta   29820
ggaagtatga ccttctgga aagaacatat aactgggagg ggctttgaga tgtaaaggcc    29880
ccacacaatt cctagttcaa actctactgc ctgctcaaag cttgaggcat gaactctcac   29940
tgttcctgat gtcatggttc ctgtctgctt ccacaattcc ctatcattag gggtcccttt   30000
ccttcctgga atttttaagta taaataaaca cttctttcta aaacaacaag aacaacaaat  30060
ctgacactga taatggattc taaggcgtct tctctggata agaaaaaaaa aagaatatat   30120
ttgcataggt gctgtattac ttttgtcatt ggtataacct gactggaagc aacttaaagg   30180
aagaagaatg tatcttgatt tgtagattaa gagcaccatg actaagaagg catagcagca   30240
caggtgcacc agcaagaaca taggctgcta gctcagatct ctgtagatat gggaacaggg   30300
```

```
caggaagcta gtagtctata aacctcagga cccatcccat ggagttcctt gtcttccagt   30360
gatgtcctgt gtcttaaagt ttcacagttc ccacagcagc acctgccgtc tgggaaccaa   30420
cctgtggtgg atattttaca acgtgatagg catatttcgt ctctagccct gtaggtttat   30480
agccatccta tacttcagtt tatctagtcc acctcagtct gatggtctta tagttccaac   30540
acttcaaaac tacaaagtct taagggccat gggctcgggt ttattagagc agtaacacct   30600
ctactagctt tctgtgttac ccactcctct taaggtctgg ttgaaatcct aataggaagc   30660
agcttgagag gagggtttat tgtggcccat actttgttgg tacattctat catgcaaggg   30720
tggcactgtg atacagccga ggccatccga ggatggtact gttggcttac atctgggtgg   30780
gacaggaaat ggtaattctc aaggcccacc tgcttggtga cttctttcag ttaagcccca   30840
tactctaaat cctctacaac ctcccaacat aatgccacca gctggggatc agctgttgac   30900
agtgctggcc caggggagca gtttaaatcc agaccagggg acctgaaaac agagaactgc   30960
agaggggctg tgggactttta taccagcttt gcagacaaat cacggcattt ctttgtgagc   31020
ttggttcata aacaaatata tattctccta taggctcctt tagtgggtgt ttcatatcca   31080
caaatttgtt cagaaaaaca ctgtgtttta tgctagctgt gtaggagata ataccgctgg   31140
gagtcacttg agcatggata agtgacatag ttcgtcctca tgagtccctg tcctgtttct   31200
gtattatgtt tacttgatga gtttagtttg tcagttggcc accaattaaa aagtatcatt   31260 ttatttttt tacaatactc agttctcaag ttaggagttt tgttattata tggcttcaat   31320
attcacattt taacctttcc aggagttaag tataaaaact tatatcaact gttgacttag   31380
taaatatcta ttacagatac tatattcttc ttagtttata tcatgaatat gaggttgctt   31440
aaagtaagtg atgtaaaata cactagggga tgcttataaa atggaatgtt gtgagttttt   31500
tgaaacacga gtactaaatt cataagtttt taaatagtta cactgttagc ttcagtactg   31560
ctagatacat gtctataatg gctgaagagt ggagcttgga tattataagt gtactctgta   31620
tattcatgca gacatatagc agattccact agtatgtgtg gttaatatgt gctaataaaa   31680
atttaataca aaagtcatgt tttattactg ggaaccagag gggttggttg tgctgatttt   31740
aagtcagtga ctattagcat attctaagaa acagttttag gattttaaag attggcttta   31800
ccataaatgt agagctatgt tttactataa tccatattat ggtcggcctt aattcaatct   31860
ctgcagtttg gttactctgc tcaaagtgaa ggtcatttat aaatgataca cattttctca   31920
ccataggaaa tactacctgg ccaataacag agttagaatt gctaaattga tggtaccaac   31980
aatggactca acacaaacta aagtttattt atgcccacag atgtatcttg tgattttccc   32040
agagggaaca aggtataatg caacatacac aaaactcctt tcagccagtc aggcatttgc   32100
tgctcagcgg ggtaagtaaa gatttaactg tattcagaaa aacactttt taagaagagt   32160 gatctttgtt tccttcagag tcatactaaa gaatatgcgt ttcttgtaag agctaagtga   32220
gagaatatcc gatcttctac agagttaggt atattcttat tagtctgtgt ctgagaggtt   32280
agagacgcag gcttgctatg gcacatttcc catgctgtga attgagttaa aaatgtaggt   32340
aaatgatatc cccaagaaag tatacttttg gagtgactca gtataaagcc tggtgttata   32400
acataaacac gcacgtgcgg atgtatatgt agcacatatg taaacacagg tgtatgcatt   32460
gtaataagaa agtggaggtc ggggcccact gcaggcaagt cttttagtga tgctgagcta   32520
atgctgagag gtagaaagac caagaaggct ggagttgctc attcggcaaa ggtcagagct   32580
cactgtgtgc cataactcga gtgttctgtc tcccttttga tacagttttc ttgttttaa   32640
```

```
ttattagttt tacaattat cccataaaat gtgggctcat tgtggtcatc gttttcataa    32700
agtccttcaa gtatacaccc agcaagtatc taaatacact gggaagaatc agtcagctga    32760
tggcttgaag tttcaggaca tctagtgcca catcatgctt cagaaccgac ccgcacttag    32820
tcagggtcat attcatgcca cgtgaagacg agaggaggcc atgccgtctg acttaggatg    32880
gaaatttcct tcgagcaaac acgaacgggc taggtcttag ttataggcat agtgtctgtg    32940
gttatactag gcagacatta gtggactggg tgttagaagg tacagacagg caagaatttg    33000
ctgtagattt gttccctca tgtgttgaca ccacatctaa cctgctttt gagcttctag    33060 tcctaataat ctcataaaaa tactggttga accagaaatg gtgttgcaaa gctatgatcc    33120
cagctcctgg gatctagggt gggaggatca taaatttgag gccagcttgg gtctgtctta    33180
gagaaaaaag aaaaataaaa agtctggtca aggtaacatg gagcctggaa gtttcacagg    33240
gtgattctgt aaaggtcctg agacaagatg gcctctagtg gcgaatgact tagctgacaa    33300
gaaaactttc ccagcttggt tgacttttca gacttcatac aagtttgtga ataaattaca    33360
ctccttctgc ccttgggact gaactcagat atgtggttgt gggaatggct ttctttccca    33420
caccaccctg catttaaaa attcttctgt agacagtccc accatcctgt agctgttctt    33480
ccttatgtcg ccactttccc tggagagagg cagtgcagac ttcaacccgc ttctccctag    33540
tcgctgttca tagcacatcg aaagacctag tgcttcctgt gaaattgtaa gtacatactg    33600
gagtccagga gaggaggaag ccgaacagag tggagggaat gctgagttct gtcctaagaa    33660
agactgcgtg cttagcaaga tgctgctgct ctcctgtcgt gtctttcttg tcagaactta    33720
tcaaagagaa ggctcgcagt gggtcataat cttcccaagg accagccttc ccagcttctc    33780
gcagcatatc tcattcatgt agatgtttaa tggatatgtg tcaatggggt tgacctaagt    33840
gagatggcaa tgtatgtgag cattctaggt gtgaggttat ggcattaaac tttaatttcc    33900
atctatttgt ggtagttgat aagtaattta gatgttgact ttcatgtatt cctaattatg    33960
accacattga atctacctgc tttctaggcc ttgcagtatt aaaacacgta ctgacaccaa    34020
gaataaaggc cactcacgtt gcttttgatt ctatgaagag tcatttagat gcaatttatg    34080
atgtcacagt ggtttatgaa gggaatgaga aaggttcagg aaaatactca aatccaccat    34140
ccatgactgg taagtccgta tttccataga agctgaatag tacatggtac aggtaagata    34200
aactcttgtt tgttcgcttt gcttagcttg gttcagtttg gttttcagta gagggttcca    34260
ctatgaagct ctggctggcc gggaactcac tatgtagacc aagctggcct tgggctccac    34320
tacacccagc accaatcacc cactcttatc ttttatgctt tttgttttg ctttgagctt    34380 tctttataac atgtttggga aggacattgt cattatttac aagaagaaat atggtctttt    34440
cccaacatgc tagaatttaa agactcagaa ctcttgcctt tgtcagtgac aaagtgagaa    34500
tggctgtgaa gtgacgtggc tttgagtgag aatagttcag gtaactatag ccacagactc    34560
aacatttgaa catgggaaca ggtgagaacg gagtgatgga agattctggc ccctttcaga    34620
gaattcattt tagagagaga tgagagtagt aaggaagaga gaagagagag acgtggtatt    34680
ttgctgcaga ctaaagagat ctcttataat cgcagtacta aggaggaaga agcagaagat    34740
gatgactaca gggccaggct gaacaatcta gtaaaatcct aagtcaggaa gtcagggctg    34800
aggtgcagct cagtaggaga gttgttgtct gccctacaca aggcctggat ttagctccca    34860
gtagcaacga agggaggcga gggtgggcaa aatcgaacac ttactcttgg agactccctg    34920
tatgaatatt accacactcc agtaaatact ctccagagat ttcagatgag attctgcttc    34980
ctggtaaaca ggaggccaag aatattatgt cacactgaac atgggatgga agacatgttc    35040
```

-continued

```
tgaggaatgt ctgcactcca gtgtgatgaa gacttgaagt ttagggacat tttccctccc    35100 tggcccact caccccatct gtattgagta ttccctagt gctcatcttt atttgtatgt     35160
taactttcag gaaggggaag cagattgata ttcaaaccca gccagttttc ttaaatactt    35220
tgtggatggg attggctttg acagtaaatg aggaaatgta aaatgtaaaa gattctaatt    35280
tttaatattt taaaggtgag gttttctgtt agtacgcaga gtgagaggtt tcttactgat    35340
gtctgcgtac ctagaggaag gatggctact tctccaaggc ttgctgttag aagtcagtga    35400
catgggctta acaagagata tgtgctaatg aggttttaat ttcagcttaa tactgcaaat    35460
cataagtgca tagctttatt gttttaaatt cttttagtct taatgtttca tttttaccgt    35520
aagttacttt gtataatcac aaattctaaa ctagtaagac gtgaaatttt cttcttcttt    35580
gttagagttt ctctgcaaac agtgcccaaa actttcatatt cactttgatc gtatagacag    35640
aaatgaagtt ccagaggaac aagaacacat gaaaaagtgg cttcatgagc gctttgagat    35700
aaaagatagg taagtggtaa gagctccagc atttagaaag tgcagttcaa ccaaatttta    35760
ctctcagacc ctgcttgaaa ggagtctttt tatcttcatt atttagtaaa tactaatcat    35820
acctgcatag acaagaccac atatacttaa atgtagcatg tttcatggtg cgttacccctt   35880 gtttaacaat taagtttaac atcctacatc agtttgcctg ttgatttctg taccatgaca    35940
actcaacaca gcgatgcgtt tattccaaag tcgatagcac agcaaaagtg aaactaaagt    36000
ctgtattgtt tcaagaatgc tttttgtgaa ctcgggttaa atcttattct atcctttcgt    36060
gttcacattg tacattttca tgagtcacta taaaaatcat gacatggtgg cctacctgca    36120
gtgtttgctg gacagtaggc tgctgtgtga taagagcctt tcctcttcag ctacacgggg    36180
gacacgaggc tttggggttc aagactgaag cacgggtgag cacaacacct ttgtgttgtg    36240
ggaaggaagg gaattgttct tttcataatg aaattgtccc cttctttgag ttagtagaaa    36300
gtattactag gatagagagt tgaaatgaag ctttatatta gatttatgcc ttgtgttgtc    36360
acgtgtttct acctgacata acttttcaac ccagccgctc aggattattt tgatgatggg    36420
aacaatgtaa gaaggcctat gtatcggtaa ctcactgttg tagctctgtg aagcggctc    36480 acaggcagta gggacgcttc tgtgcttttg tgcctgtcct gctgttagaa tcttacagag    36540
gaggatgaat gaatgaccct ttttattct cttgtctgct tttctaattt tatgggaata    36600
agaacttttg gtaggtctct gtcactggcc tcttgttgtg aagagacacc ttgagcaaag    36660
caactcttct gagagaaagc atttagttgg ggaattcctt acagcttcag aggttgagtt    36720
cgttttcatc atgctgagga cagggaggca ctcaggcagg agaagtagtt gagagccaca    36780
ttctgatcta caggcagaga gagacagact gagcctggca tgggttcttg gaacctcaaa    36840
gcctctcatc cctaccccat ctccccaccc ctatacacac ttcctccaac aaggctacac    36900
cttctaatcc ttcttaaaga gtcaccacat ccagcggcta agcattcaga tatgtgaacc    36960
tgtcggagcc tttcttactc agatcacctc aggaggaaaa ctcctatgct ataagaattt    37020
cttttctttc gcatctttga aagcttgttt ttgtgtgatt agatcctggc ctcacacatg    37080
ctcggcaatc attttactgt tgagctccag cctcagccgt tttcattggc ttatgggatg    37140
cgagctatgg gagagaagct agaaggcctt tcgttttatg agtcgggttg gtggaaccac    37200
ttacagatgg aagatttaca aacaaaaatg aagctggggc catcaaggct cagcactcgc    37260
tgctcttcca gagagttcag gttcattct cagtaaccac atggtggctt tgtaaatgta    37320
acttcatatt caatgaccct gacaccctct tctggcctct gtgggcacca gacacaatca    37380
```

```
tggtatacag acacacacac tagccaacac ccatctacat aaaagtatat aaacatatct   37440
ttatcttaaa aatccccgaa gtcctcatta aatatcttag atccccgccg tgttttgatt   37500
tttgtttccc acgtggtgag gatataatat catgtccata ctgtaaggcg tgaatgccct   37560
cccgtgcctc tcggacacct ctgcactcat ccaagttttc taaggagctg tacttgctca   37620
gcaagtactc aatacctaat aaatggttta tgtttgtttc aacaccaaaa atgtccaaaa   37680
ctgaaagatc aattctgttg ttttccttct ggccataggt tgctcataga gttctatgat   37740
tcaccagatc cagaaagaag aaacaaattt cctgggaaaa gtgttcattc cagactaagt   37800
gtgaagaaga ctttaccttc agtgttgatc ttggggagtt tgactgctgt catgctgatg   37860
acggagtccg gaaggaaact gtacatgggc acctggttgt atggaaccct ccttggctgc   37920
ctgtggtttg ttattaaagc ataagcaagt agcaggctgc agtcacagtc tcttattgat   37980
ggctacacgt tgtatcacat tgtttcctga attaaataag gagttttctt gttgttgttt   38040
ttttgttttg ttttgttctg ttttaagcct tgatgattga acactggata aagtagagtt   38100
tgtgaccaca gccaacatgc atttgatttg gggcaaacac atgtggcttt tcaggtgctg   38160
gggttgctgg agacatggaa gctaagtgga gtttatgctg tttttttttt tttaatgttt   38220
tcatgaatta atctccactt gtaaagatta ttggatactt tctgtaattc agaaggttgt   38280
attttaacac tagtttgcag tatgtttcgc tatattggtt atcttccatt tgactacttg   38340
gcagctcaga ctcttaatac taaagtattt tacattttga agctatgtga tactggtttt   38400
ttgttgttgt tgttgttagt ttctgaaagt caatgaaaga cactgtaatg atgcgttaag   38460
atgttccaag aaaaaggtga gaattattca tggcaaaaaa gatctgtcta gtgtatattt   38520
ttattatatt gctctattta gctaattttc tttatatttg caaaataatg aacatttta    38580 atatttatta aaatgcttga tttgcatacc cccgattcta cagagaataa tgtgtaaagt   38640
gtcagaatag acttgaagct ctgctgtgac tcagtctcct ttgtcagagc ttctagtagc   38700
ccagctactg agctgctttg ttagtacctc cagcacctga gccgttaagt acttataaat   38760
gcaagggacc cgttatcttc atatcggaat agacatgaac agagctctaa ggcgatgaaa   38820
gtctgccagc atcctctctg tcctcgcacg tgccttctgc ctggctccat ttgctttggc   38880
actgcgttcg atctagagtg taggtgctca ctgcttattt cagccctggc tctgtggttt   38940
tgtgtcctcc agtggtgctg ttcactgttg gggtgcaggt ggtgctgccc tgactcagag   39000
gggcagctcc ctggctcctg agggtgagcc ttcttggcta ctacagaagt attgtgcgtt   39060
tgtttatggc aagaaccatc aggattggat aaatgtgtta tttctctttg atttccatgg   39120
agccacactg ttggtacatg tcccctgtga acagagctac ctttcaggag cacatcatac   39180
tgtcgtgagt cacggcacgg tgtgtcctgt gagaagaggc tttctaacgt gtgatttgcc   39240
gtgtttctat gttgtgattt aagcgtgatt gcctactagt cattcaaggt aacatttctg   39300
caaatttcat acagattttt gtcacaaaat tactatacca atgatctagt tgaaatagac   39360
caattgaatc acaataaata attttttta attgagggaa aatttgcttc ttgtttttc    39420 aaagccagaa aacgagccat ttcaaacatc tttgaagagt catgtgctgt cacttgtttt   39480
ctatgtgtta gtgtctatat tcatgtatgg atacacatga acatgtatat tcatacacac   39540
acgccaatag aatataacag cctaaaaaca atccagcttg tgtatcatgt tactgtgctg   39600
aattgtaatg gttttacttt acaaagtgag gctaaaatcg atttcatgtc tttgttaaat   39660
acgttttttc agcaatccta ttagagctta ttttgaccag atcaaaataa gtacaagttc   39720
agagacttta aatatggctg aggtctagag cgatagctca gtagttagga acacatgcca   39780
```

```
ctctttcaag ggcttcagtt cccagcactc atatggaggc tcacagaagg ctggaattcc   39840
agcttcatgg aattggacac atcctctagc ttccatggat ctgtctgtct gtctctccct   39900
tctctctctc tctctctctc tctctctctc tctctctctc tctctcactc actctttaaa   39960
tatcatggat atgctgtgca tttaaatttt aagacacaga accattggaa ttacatggat   40020
tatagctgat tctctttgaa cagggcacag tgttctgcgt aagatctctt gatcattagc   40080
actggactca ctctcctcac aagtagccta tcaaatgtgg tattagaaaa tacattgtgt   40140
caaaatcttt gaaagatgag aagaatctcc taaacatgtt tattttgact tgacatcact   40200
atttcctgaa aattaactgt ctatgattct tttcacatag tgtaagatct tacttgtatc   40260
accatcagct tgcagcttag gggctgcagt tgttctcctt cataagactg ccatccgtgt   40320
gcatgctttt atgtttttca gaaaggatgt tgggatgaaa gtaagaaaac aaataaagtc   40380
tcttcttgtc tctcatgtct gtgatcacta gcatttcaca actcagggat tcatccattt   40440
tccagcagat aaaagggtta gcgattaacc ctgcattctg agtttagaaa gctacaatat   40500 ttttttaaata ttgagcaatg attttaaaaa aatacattgg aatacccccaa attgtgaagc   40560 aatccaaaag ttggactgta taagctaatt tgcctacttt aaaggatgtg accctcaccc   40620
aggaaacctg taggatttac ttaacaaagc tttacatgaa aatgccaccg tggccatttc   40680
ttaaacactg gtggcttctt ccagatttca tttctatgtt tgtttgtttg ttgttgtttt   40740
tttacttaga ttgctgtgag gttttttttt tttataacaa atatacattt ttttctttgt   40800
cacattacat gctttgtcaa tcaaatgacc taactaggtt ggctattaag aaaactacat   40860
attgaaatct gccaaaatgt cggcataaac aaactggctc ctaattgtgt accagatcta   40920
catttgaaag aacagaaatg tctcacaaga caataaggtc atatgtaaaa cactaaataa   40980
actttaacct caacaattgt ttctgaagtg ttgagattaa agactgagtg tttgcggaac   41040
gttgacatgt ccatggccag gctagtttct cgttttcttt ttgtcttaag actaaacatt   41100
ggctggctta aaatattacc agttctatat agtttacatt atagacagaa tatataacat   41160
ttaagtatta gtatgaaaat cagtactttg gtgagactaa tatttggaat atccagatga   41220
tttgatatca tgtaggtaaa gtaagtattt gtgtgactga ctgaacttaa aatctcttat   41280
tcatatatca tggataacag ctgggagttg tgacacatgg ctgccatcca ggcactcgga   41340
aaatccaggt tttgagaaag agagtgtttt ccaagtcagc ctggtctata tagcaagctt   41400
cagact                                                              41406
```

<210> SEQ ID NO 3
<211> LENGTH: 28
<212> TYPE: DNA
<213> ORGANISM: Artificial sequence
<220> FEATURE:
<223> OTHER INFORMATION: Primer

<400> SEQUENCE: 3
gaacaaggta taatgcaaca tacacaaa                                      28

<210> SEQ ID NO 4
<211> LENGTH: 23
<212> TYPE: DNA
<213> ORGANISM: Artificial sequence
<220> FEATURE:
<223> OTHER INFORMATION: Primer

<400> SEQUENCE: 4

```
tggcctttat tcttggtgtc agt                                          23

<210> SEQ ID NO 5
<211> LENGTH: 26
<212> TYPE: DNA
<213> ORGANISM: Artificial sequence
<220> FEATURE:
<223> OTHER INFORMATION: Probe

<400> SEQUENCE: 5
cctttcagcc agtcaggcat ttgctg                                       26

<210> SEQ ID NO 6
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 6
gagtagaggt ccctga                                                  16

<210> SEQ ID NO 7
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 7
ggaatagtgt ttacac                                                  16

<210> SEQ ID NO 8
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 8
gcataagtta gtgaac                                                  16

<210> SEQ ID NO 9
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 9
cttgtctttc agtacg                                                  16

<210> SEQ ID NO 10
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 10
agtgtactta cagtgg                                                  16

<210> SEQ ID NO 11
<211> LENGTH: 16
<212> TYPE: DNA
<213> ORGANISM: Artificial sequence
```

<220> FEATURE:
<223> OTHER INFORMATION: Synthetic oligonucleotide

<400> SEQUENCE: 11
gtattttcct gaacct        16

<210> SEQ ID NO 12
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 12
aagtgttcga ttttgc        16

<210> SEQ ID NO 13
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 13
ccatgtacag tttcct        16

<210> SEQ ID NO 14
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 14
gataaccaat atagcg        16

<210> SEQ ID NO 15
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 15
agctgccaag tagtca        16

<210> SEQ ID NO 16
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 16
agtattaaga gtctga        16

<210> SEQ ID NO 17
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 17
cctttttctt ggaaca        16

<210> SEQ ID NO 18
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 18
gacactttac acatta                                                  16

<210> SEQ ID NO 19
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 19
agcaccactg gaggac                                                  16

<210> SEQ ID NO 20
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 20
cacggcaaat cacacg                                                  16

<210> SEQ ID NO 21
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 21
gattcaattg gtctat                                                  16

<210> SEQ ID NO 22
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 22
ccaattccat gaagct                                                  16

<210> SEQ ID NO 23
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 23
taccacattt gatagg                                                  16

<210> SEQ ID NO 24
<211> LENGTH: 5535
<212> TYPE: DNA
<213> ORGANISM: Homo sapiens

<400> SEQUENCE: 24

```
cggagccccc tgccccggca gggggatgtg gcgatgggtg agggtcatgg ggtgtgagca      60
tccctgagcc atcgatccgg gagggccgcg ggttcccttg ctttgccgcc gggagcggcg     120
cacgcagccc cgcactcgcc tacccggccc cgggcggcgg cgcggcccat gcggctgggg     180
gcggaggctg ggagcgggtg gcgggcgcgg cggcccgggc ccgggcggtg attggccgcc     240
tgctggccgc gactgaggcc cggaggcgg gcggggagcg caggcggagc tcgctgccgc     300
cgagctgaga agatgctgct gtccctggtg ctccacacgt actccatgcg ctacctgctg     360
cccagcgtcg tgctcctggg cacggcgccc acctacgtgt tggcctgggg ggtctggcgg     420
ctgctctccg ccttcctgcc cgcccgcttc taccaagcgc tggacgaccg gctctactgc     480
gtctaccaga gcatggtgct cttcttcttc gagaattaca ccggggtcca gatattgcta     540
tatggagatt tgccaaaaaa taagaaaat ataatatatt tagcaaatca tcaaagcaca     600
gttgactgga ttgttgctga catcttggcc atcaggcaga atgcgctagg acatgtgcgc     660
tacgtgctga agaagggtt aaaatggctg ccattgtatg ggtgttactt tgctcagcat     720
ggaggaatct atgtaaagcg cagtgccaaa tttaacgaga agagatgcg aaacaagttg     780 cagagctacg tggacgcagg aactccaatg tatcttgtga tttttccaga aggtacaagg     840
tataatccag agcaaacaaa agtccttca gctagtcagg catttgctgc ccaacgtggc     900
cttgcagtat taaaacatgt gctaacacca cgaataaagg caactcacgt tgcttttgat     960
tgcatgaaga attatttaga tgcaatttat gatgttacgg tggtttatga agggaaagac    1020
gatggagggc agcgaagaga gtcaccgacc atgacggaat ttctctgcaa agaatgtcca    1080
aaaattcata ttcacattga tcgtatcgac aaaaagatg tcccagaaga acaagaacat    1140
atgagaagat ggctgcatga acgtttcgaa atcaaagata agatgcttat agaatttat    1200 gagtcaccag atccagaaag aagaaaaaga tttcctggga aaagtgttaa ttccaaatta    1260
agtatcaaga agactttacc atcaatgttg atcttaagtg gtttgactgc aggcatgctt    1320
atgaccgatg ctggaaggaa gctgtatgtg aacacctgga tatatggaac cctacttggc    1380
tgcctgtggg ttactattaa agcatagaca agtagctgtc tccagacagt gggatgtgct    1440
acattgtcta ttttggcgg ctgcacatga catcaaattg tttcctgaat ttattaagga    1500
gtgtaaataa agccttgttg attgaagatt ggataataga atttgtgacg aaagctgata    1560
tgcaatggtc ttgggcaaac atacctggtt gtacaacttt agcatcgggg ctgctggaag    1620
ggtaaaagct aaatggagtt ctcctgctc tgtccatttc ctatgaacta atgacaactt    1680
gagaaggctg ggaggattgt gtattttgca agtcagatgc ctgcatttt gagcattaat    1740 ttgcagcgta tttcactttt tctgttattt tcaatttatt acaacttgac agctccaagc    1800
tcttattact aaagtattta gtatcttgca gctagtaat atttcatctt ttgcttattt    1860
ctacaagtca gtgaaataaa ttgtatttag gaagtgtcag gatgttcaaa ggaaagggta    1920
aaaagtgttc atggggaaaa agctctgttt agcacatgat tttattgtat tgcgttatta    1980
gctgatttta ctcattttat atttgcaaaa taaatttcta atatttattg aaattgctta    2040
atttgcacac cctgtacaca cagaaaatgg tataaaatat gagaacgaag tttaaaattg    2100
tgactctgat tcattatagc agaactttaa atttcccagc ttttgaaga tttaagctac    2160 gctattagta cttccctttg tctgtgccat aagtgcttga aaacgttaag gttttctgtt    2220
ttgttttgtt tttttaatat caaaagagtc ggtgtgaacc ttggttggac cccaagttca    2280
caagattttt aaggtgatga gagcctgcag acattctgcc tagatttact agcgtgtgcc    2340
```

-continued

```
ttttgcctgc ttctctttga tttcacagaa tattcattca gaagtcgcgt ttctgtagtg   2400
tggtggattc ccactgggct ctggtccttc ccttggatcc cgtcagtggt gctgctcagc   2460
ggcttgcacg cagacttgct aggaagaaat gcagagccag cctgtgctgc ccactttcag   2520
agttgaactc tttaagccct tgtgagtggg cttcaccagc tactgcagag gcattttgca   2580
tttgtctgtg tcaagaagtt caccttctca agccagtgaa atacagactt aatttgtcat   2640
gactgaacga atttgtttat ttcccattag gtttagtgga gctacacatt aatatgtatc   2700
gccttagagc aagagctgtg ttccaggaac cagatcacga ttttttagcca tggaacaata   2760
tatcccatgg gagaagacct ttcagtgtga actgttctat ttttgtgtta aatttaaac    2820
ttcgatttcc tcatagtcct ttaagttgac atttctgctt actgctactg gattttttgct  2880
gcagaaatat atcagtggcc cacattaaac ataccagttg gatcatgata agcaaaatga   2940
aagaaataat gattaaggga aaattaagtg actgtgttac actgcttctc ccatgccaga   3000
gaataaactc tttcaagcat catctttgaa gagtcgtgtg gtgtgaattg gtttgtgtac   3060
attagaatgt atgcacacat ccatggacac tcaggatata gttggcctaa taatcggggc   3120
atgggtaaaa cttatgaaaa tttcctcatg ctgaattgta attttctctt acctgtaaag   3180
taaaatttag atcaattcca tgtctttgtt aagtacaggg atttaatata ttttgaatat   3240
aatgggtatg ttctaaattt gaactttgag aggcaatact gttggaatta tgtggattct   3300
aactcatttt aacaaggtag cctgacctgc ataagatcac ttgaatgtta ggtttcatag   3360
aactatacta atcttctcac aaaaggtcta taaaatacag tcgttgaaaa aaattttgta   3420
tcaaaatgtt tggaaaatta gaagcttctc cttaacctgt attgatactg acttgaatta   3480
ttttctaaaa ttaagagccg tatacctacc tgtaagtctt ttcacatatc atttaaactt   3540
ttgtttgtat tattactgat ttacagctta gttattaatt tttctttata agaatgccgt   3600
cgatgtgcat gcttttatgt ttttcagaaa agggtgtgtt tggatgaaag taaaaaaaaa   3660
aataaaatct ttcactgtct ctaatggctg tgctgtttaa cattttttga ccctaaaatt   3720
caccaacagt ctcccagtac ataaaatagg cttaatgact ggccctgcat tcttcacaat   3780
atttttcct aagctttgag caaagtttta aaaaaataca ctaaaataat caaaactgtt    3840
aagcagtata ttagtttggt tatataaatt catctgcaat ttataagatg catggccgat   3900
gttaatttgc ttggcaattc tgtaatcatt aagtgatctc agtgaaacat gtcaaatgcc   3960
ttaaattaac taagttggtg aataaaagtg ccgatctggc taactcttac accatacata   4020
ctgatagttt ttcatatgtt tcatttccat gtgattttta aaatttagag tggcaacaat   4080
tttgcttaat atgggttaca taagctttat ttttttccttt gttcataatt atattctttg   4140
aataggtctg tgtcaatcaa gtgatctaac tagactgatc atagatagaa ggaaataagg   4200
ccaagttcaa gaccagcctg ggcaacatat cgagaacctg tctacaaaaa aattaaaaaa   4260
aattagccag gcatggtggc gtacactgag tagtttgtcc cagctactcg ggagggtgag   4320
gtgggaggat cgcttcagcc caggaggttg agattgcagt gagccatgga cataccactg   4380
cactacagcc taggtaacag cacgagaccc caactcttag aaaatgaaaa ggaaatatag   4440
aaatataaaa tttgcttatt atagacacac agtaactccc agatatgtac cacaaaaaat   4500
gtgaaaagag agagaaatgt ctaccaaagc agtatttgt gtgtataatt gcaagcgcat    4560
agtaaaataa ttttaacctt aatttgtttt tagtagtgtt tagattgaag attgagtgaa   4620
atattttctt ggcagatatt ccgtatctgg tggaaagcta caatgcaatg tcgttgtagt   4680
tttgcatggc ttgctttata aacaagattt tttctcccctc cttttgggcc agttttcatt  4740
```

```
acgagtaact cacactttt gattaaagaa cttgaaatta cgttatcact tagtataatt      4800
gacattatat agagactatg taacatgcaa tcattagaat caaaattagt actttggtca      4860
aaatatttac aacattcaca tacttgtcaa atattcatgt aattaactga atttaaaacc      4920
ttcaactatt atgaagtgct cgtctgtaca atcgctaatt tactcagttt agagtagcta      4980
caactcttcg atactatcat caatatttga catcttttcc aatttgtgta tgaaaagtaa      5040
atctattcct gtagcaactg gggagtcata tatgaggtca aagacatata ccttgttatt      5100
ataatatgta tactataata atagctggtt atcctgagca ggggaaaagg ttattttag       5160 gaaaaccact tcaaatagaa agctgaagta cttctaatat actgagggaa gtaaatatg      5220 tggaacaaac tctcaacaaa atgtttattg atgttgatga aacagatcag ttttccatc      5280 cggattatta ttggttcatg attttatatg tgaatatgta agatatgttc tgcaatttta      5340
taaatgttca tgtctttttt taaaaaaggt gctattgaaa ttctgtgtct ccagcaggca      5400
agaatacttg actaactctt tttgtctctt tatggtattt tcagaataaa gtctgacttg      5460
tgtttttgag attattggtg cctcattaat tcagcaataa aggaaaatat gcatctcaaa      5520
aaaaaaaaaa aaaaa                                                       5535

<210> SEQ ID NO 25
<211> LENGTH: 853
<212> TYPE: DNA
<213> ORGANISM: Homo sapiens

<400> SEQUENCE: 25
aacgtactcc atgcgctacc tgctgcccag cgtcgtgctc ctgggcacgg cgcccaccta        60
cgtgttggcc tggggggtct ggcggctgct ctccgccttc ctgcccgccc gcttctacca       120
agcgctggac gaccggctct actgcgtcta ccagagcatg gtgctcttct tcttcgagaa       180
ttacaccggg gtccagaatt tctctgcaaa gaatgtccaa aaattcatat tcacattgat       240
cgtatcgaca aaaaagatgt cccagaagaa caagaacata tgagaagatg gctgcatgaa       300
cgtttcgaaa tcaaagataa gatgcttata gaatttttatg agtcaccaga tccagaaaga       360
agaaaaagat ttcctgggag aagtgttaat tccaaattaa gtatcaagaa gactttacca       420
tcaatgttga tcttaagtgg tttgactgca ggcatgctta tgaccgatgc tggaaggaag       480
ctgtatgtga acacctggat atatggaacc ctacttggct gcctgtgggt tactattaaa       540
gcatagacaa gtagctgtct ccagacagtg ggatgtgcta cattgtctat ttttggcggc       600
tgcacatgac atcaaattgt ttcctgaatt tattaaggag tgtaaataaa gccttgttga       660
ttgaagattg gataatagaa tttgtgacga aagctgatat gcaatggtct tgggcaaaca       720
tacctggttg tacaacttta gcatcggggc tgctggaagg gtaaaagcta aatggagttt       780
ctcctgctct gtccatttcc tatgaactaa tgacaacttg agaaggctgg gaggattgtg       840
tattttgcaa gtc                                                          853

<210> SEQ ID NO 26
<211> LENGTH: 55146
<212> TYPE: DNA
<213> ORGANISM: Homo sapiens

<400> SEQUENCE: 26
atatatatat atggtaaagc attcggcatt cttttaaagt acaactatcc ttgaaaaggg        60
ttacatatta aaccatttt accacagcca aggggagga gaaagatcca aaagtcctgt       120
```

```
ggatctgctt taacatcaat aaaacagtta tccacccttc gtagctttta gtgaaggcta    180
caaaagtatg cttttatgg attacacatg tgcacgcaac tactttaatt actacagaaa    240
aaaacgaggc tccttattaa aaaaaatca gaaacaagtc aacagactc tgaggaaatg     300 aagcaagagt gaattctgaa aaggtctaat aaacagtatg gaaatatcct tgtgggattg   360
ttcttcagct atgcataaac atgtaattat catcattact gtgatgggga aaaacacgga   420
ccctaattct gaaacaccct ggtagcgaga cgggcagg aggggctgct gcgcactcag     480
agcggaggct gaggaggcgg cgtcccttg caaaggactg gcagtgagca gatgggaca    540 ctcgagctgc cccgcgacct gggccgagct gcctacaacc tgggcccagg tgcctgcaag   600
aattagacct ccgataacgt taacacccac tttctcactg ctctaattgt gtgcatcccg   660
gcgcccaggg gcttgtgagc agcaggtgcg cgttccaggc agctccagcg acccttaaac   720
ctgaccgcgc gcacgtccgg cccgagggag cagaacaaga ggcacccgga ccctcctccg   780
gccagcaccc accttcaccc agttccgtca gtcgccacca cctcccttcc cgcgtccgca   840
gccggcccag ctggggagca tgcgcagtgg ccggagccgg gttgcccgcg ccccagcagg   900
tagctgtact gcaactgtcg gcccaaacca accaatcaag agacgtgtta ttgccgccga   960
ggtggaacta tggcaacggg cgaccaatca gaaggcgcgt tgttgccgcg agccccctg   1020 ccccggcagg gggatgtggc gatgggtgag ggtcatgggg tgtgagcatc cctgagccat  1080
cgatccggga gggccgcggg ttcccttgct ttgccgccgg gagcggcgca cgcagccccg  1140
cactcgccta cccggccccg ggcggcggcg cggcccatgc ggctggggc ggaggctggg   1200 agcgggtggc gggcgcggcg gcccgggccc gggcggtgat tggccgcctg ctggccgcga  1260
ctgaggcccg ggaggcgggc ggggagcgca ggcggagctc gctgccgccg agctgagaag  1320
atgctgctgt ccctggtgct ccacacgtac tccatgcgct acctgctgcc cagcgtcgtg  1380
ctcctgggca cggcgcccac ctacgtgttg gcctgggggg tctggcggct gctctccgcc  1440
ttcctgcccg cccgcttcta ccaagcgctg gacgaccggc tctactgcgt ctaccagagc  1500
atggtgctct tcttcttcga gaattacacc ggggtccagg tgagccgcct cccgctcccg  1560
ggtctcggcg tccacccgag ctcccggggg cgcggacctc tccgctcccc cacagctggc  1620
gagggtcacc cggccggccc ggcggaccca gcacggagag cacgtgccgc ctccccgcct  1680
tcctctccgc atgcttcctg ccgttctgcc gagatcgctc tctaggaagc tgtggctgcg  1740
tcgtcctgag gctacgagtg ggacccgccg cccctttccc cgcccctcgc ctgggtctga  1800
tgctgcttag caaagtgggt gcagatgcac gttttaaata atagggcacg cgtttagcag  1860
tttctggcct ttggtccaaa gaggtggtca tgttggaaca gatcggagac gtctacactc  1920
cgaagtgcgc ttttacagtg acctcttgaa acagaagtac aattcggtct tgtgttcttt  1980
cccctggaca agtgaaagct gggcgaagaa atgaatacat tgttaaccg tagaagccta   2040 actagataca tttcttgcca actttaactg ggcttgaatg tgtgggtgat ctgttgtctg   2100
attactttct ttctgttact gtttctctgt agagattgga ttcgtagatt aaacttgaga   2160
aacaaaccat aaaagtggaa ggccctcttt aacagtaggt atttgaagtg ttataaaaaa   2220
aaaaaaaagg tgaattttc ttttatttct cagtttgaaa gaacagcttt attcttggtt   2280
attcctaatg tccacctagt cctcttttac ttttcttggt agggttaggg tggcatgggg   2340
aaatgggacg gtatcatttt gtcttttaa cttttttttt ttccacctac agcagctgtt   2400
tttaccctgt ggtcagtcag gtactatatt tagtttgcag ttgcactgct gatcgaccct   2460
tgatggcccc agttggaagt tgtttggggg gaaggaacta ggagaggcca gggcctccat   2520
```

```
ttaaaccagt gtctgtaagt gtctccttgg aaagaaaaaa agatactgtt ccaggtcatg    2580
gtttcctggt agttgacgtt taaaatgggc ctcatttaaa aatttcaata attcaggcta    2640
attttttccc tttatatggt aactccacca agtttgtcta aatgtatgat ttttatcatg    2700
attaagtttt tacttccaca tcatgtgaca actggcctgg gatgggatat aagctcagaa    2760
cacaaagtca ttcacctctt aaaaaaataa ttctatctgt ggcgggttat gttattttg     2820 ttcaaagagg acacaatatg atgcagaata caccattgaa ggattttttg gtttggcaag    2880
ttcttatttt tttaaatggc tgtaaaacct agcagtgttt ctgaaattgc ataccttacc    2940
tgatgttcag agatccgatt tacttcttga tttcccagca agtgattttg aaaacattta    3000
atctaatcat tcccccacc  gtctgttcaa atcaaggaa  gtggcatcca gcactaattt    3060
tcatgcattt atgaaaggat gcctgaggac ccttaagtat aattcaaaat tttgtttaat    3120
gtgtgttcct tgatgaagtt ctttaggagt cgtagaacga actgattgcc cactgatcat    3180
caaatgcaag ttatgaacat ttaataaaaa tttaaaacca agagtttctt gttcctgcat    3240
ttttattttt attgtatgga ggggacaaat aattattttc tgtttagtaa cagagcaggg    3300
tattttgaat ttattagggt cttttttctgc aatctgggtt tcctgtgtac acaaagctac    3360 cttttcaatat tttttattgt ttctgttaag attaaatcaa tagaggaata aatagctatc    3420
ttcaaacata agacccaaag gaaaaagatt tatagtgatg ttctgtcacc ttatttttta    3480
cctgtgactt tgtaccatta actttgtcac tgagatgttt tgattaaaat ttttagcttg    3540
cttttcttgt tttgttagga cactcttttt tccttgaatt gttttttatca gctttcgttt    3600 gcaaggctag tgatgattct cttgttctgt ataaagtatt gttgactcat ttctgaaggg    3660
agttttagta atttaagagg ttataagttt ttaaataaaa ggtttattaa tttatatata    3720
ttaaagaggc attttaaaat aaaattttt  ttaaatgaca ttttttacacc tttcaactct    3780 aggtttaaaa aataagtggt tcacagtagt tcttgcagaa gaatattttc ttttacatag    3840 aattttttaag ctgaagagaa gtagtagtag gtccatgaga tttatgatct gtgcttggca    3900
ggtaaacctg cttccaacaa atttagttgg attttttcttg gattctgggt aaatacccttt   3960 ttcttcccca atttcactac tttattttca tatgtatctc tgagatagag aaatatttca    4020
gtcagtgctg ctaaaattgt tccttataac tcgtttatcc ttttaggtcc ttccagaatc    4080
tctcattggt actgaaactc aaatgggtac tttcttcacc atttatttct ttagaataag    4140
taataagaat tttataagct ttttttatatt tcacgtaatt tgagactatt gaaaatccag    4200
ttaagtctct ctactgtgtt gagaggcatt gattcaagta cctgtgttac tttcctgtgc    4260
tgccaaaaca gatcacctca aactaagcgg cttaaaataa tagaacttaa gttctcgtga    4320
ttctggaggc cagcactttg aaatcaaggt gtaggctcaa ttttactccc tctggaggcc    4380 ctaggggggaa tccgttcttg tgggtttcaa cttctggtga ctggtggcat tccttggctt    4440
ggggccccat cactttaacc tctgcctttac agtccttgct gccacctctt ctgtctcaca    4500
tctcactctc cctttctctt agaaggatgc ttgtcattgg gtttagagcc cacctggata    4560
ttccgggatg atctcttcat ctcaagatcc ttaattataa ctgcaaagag ccttttttcca   4620 aataagaaaa cattcacagg ttccagggct taggatgtgg acacattttt tgagggggctg   4680 cccttcattc ccccacaaca atgaactcca tagttctgcc tattcagtat tttgtagtta    4740
tttcgtagtt taacttgcct tatttctttta ggtatttacg tattaaagca ttttggtctc    4800
tgctttcttt aacagagaac ctggttttct gtaataagtt tacttacttt cccataatct    4860
```

```
tttagtttct tatttacaga tttaccttca catatccctt aagtagaaca tttgattaac    4920
tgttttattt tcggaacaaa tctgcattct gtataataac caacttattc atatttcggt    4980
attcttttaa ttcttatctg attctgaaat taccatcttg tgattatata tatatatata    5040
tggaaataac tgaaatcctg ataaattaaa ggtgatataa cttctaagac aattaattat    5100
gtatgatgtg gtgaatatac tggtgtttgg tttgtttgcc acttaaaagc cctatctata    5160
ggataggaag taacttgaat gtggaatgct tagagactca gagtaagagg ccgtatatat    5220
atccttgagc tggagtttaa ggaaaactta tgggaaatta aaaggaaagt tggagtactg    5280
acagaggatt gggtaggact catgaaaaag gaatgaagtt accttaaatt ctatcatcgt    5340
gagttaacgt gaaactagat ttatgttagt ttatagccta gaattctatc ctaggaatct    5400
agatatatcc taaatgttga gatagctgca taaacaataa ctgtaatcgt tatgataaat    5460
aatgacaaat cttttagca tgttctgtga agctgataaa tgttaatagg atgtcttcaa    5520
atgtcagaat tctttttct ttgcttcttt tttaaaaaat ttcttttccc ccattcctat    5580
gcaatacact gaaaactgat cattgaaatt tgtaggccaa aaaattaatc aacacgtaat    5640
agattggggt ttgggttttt ttgagtcagg gtcttcttct gtcacccagg ctctggtgcg    5700
gtggcaccat cattgctcat tgcagccttg aatgcctggg ttcaagtgat cctccggagt    5760
agctgccgtg ccattatttc tagctaattt ttaaaagttt ttgtagaaat ggggtctttc    5820
tgtgttgccc aggctggtct tgaattcctg gcctcaggtg atccttctgc cttggcctcc    5880
caaagtgctg ggattacagg tgtgagccac catgcctagc ccctaataaa tattctaatt    5940
accgatttat cttgcttaaa tcagttggta acacttggaa tttacttcag aatatatttt    6000
acattagtgg ctctgactgc taattccccc ttctccaaat gctaatgtaa tataacaata    6060
aaatgcacag ttcttaagtt tatataaaat aaacaggttt tcagttgacc tgctttaagt    6120
gtaaaatagt gtgaaaaaca caagaaagaa gataaagaat ttaagatttt gacatttctc    6180
taatatgccc ttaacttctc caaggattca tactttttt tgtaagacag aatctcacac    6240
tgttgcccaa accagaggtg cagtggtgca gtctccactc actgcaacct ctgccccgg    6300
gctcaagcgg tcctcccacc tcagcctcct gagtagctgg gactacaggt acacagcacc    6360
atgcccagct aatttttttt ttggtatttt ttagtggggg tagagacgag atttgccat    6420
attgcccagt ctggttttga gctcctgggc tcaagtgatc cgtccttgat ccaccatgct    6480
tagctgattc atactcttaa ctgaaacatt gttccaagtt tctcagaaac agtcaaggct    6540
ttttatctag agaacattta taactggatc tttctttgtg tagcactgat tcatcaaact    6600
aatcctaaac tcctaatgag ttaaatttat attctgaatc ttgctgtaaa agcagccatt    6660
cattagaatg aaacatgttt acttagaatt ggagaaggga gcttataagt catctagtct    6720
actccctttt atgacacttc tacattcttt ctgcacttct gccaaaatgt tgcccagcgt    6780
cgtctctgat acctatagtc ctaacaagaa tatgaatcat accttgtatc cttaatttta    6840
ctcttctctg cttatttgcc attcatgtga agaccttaaa tagatcttaa attgcttcct    6900
tcactttagc tgagagtgac aggactgtgt aggtgtgggt gtgttctgc atttgcttat    6960
ttaagcagga taataaaaac ttttactata ggaaattaaa catttcccaa tcaaatacaa    7020
ttccagtcta acacaattaa attctggtta gggaactgct taacttacta gacttatagg    7080
aaaatactaa aaaatgtaa ctagaactct atttttacac tttataaata taaacctctg    7140
tgaacaaacc agttatttca ggttgcattt gtgtatagtt ttttaatgcc tgattttct    7200
attttaaaat cacagatgca attatacatt caaacactgc cacaatactt tgagaaagtt    7260
```

```
aaagtttccc ctactcctac actgcgtaca cctttcctag gtacatccca gtttggtgtg    7320
taactttaga tttcttccaa gagcttttga gtaagtgttt gaattgtggg aaggttcttt    7380
agttaaatga acttcttaca gatcagtttt ttagtacagt agcacgaaat atacctgcat    7440
acctatgggg atacctctgt gccattacga tggaaggcac gggaaaacag cactccgtat    7500
atacctagtt tactttccct cttttgtata tttgtctgat tttgtggagc tgatgcttct    7560
caagtggaat cagaagttaa cttttccttt actattttct cattttatta tggtttctta    7620
actagaggtt gatgttagtg gttggaccat tcaatagtaa gtaatgactt ttcagtaagg    7680
gatctctaga acccagatcc cttaattcct gcaatattcc cgtgtgtaca ttgttccagg    7740
tgctgtcctg ggtaccaagg ggtacaatgt ttgatagaca atgtacctgc cattatggag    7800
gtcacattct agtgtgggaa gacaaacaat aacaagaaaa tgaaaattta ctgtgccatg    7860
ccaggttgtt tagcctggtg ggtgagaggt aggggtttgg aaaatcttac tgagcaagtg    7920
acatttgtgt ggagctctgt aaagggcca gcttggaagg taatgtagtc atccaggtga    7980
gaaatgatgg ttaggggagt ggaaagagtg gatgttaaga ttgaaaagaa ttccaaatct    8040
attttagtgg tagctgatag ggcttttgtga ttgaatgtgg aggaaaaga agagggtggg    8100 ttagtaacac actcagtcgc agttagtgag tgctgctgtg tgcaagtatt gttctattat    8160
gtaaataatt ccatctttac aaagtaggca ccattcttcc tcttttacag acaaggaaaa    8220
gggaacaccc atggttcaca tctgtagtag cctagccagg agtttcaggc acttattttc    8280
tgaagatgct ctgcctggca atgtggttat attggttgaa atgagacccc ctactttcaa    8340
ggtattcatc taggaaagac atgaactgcc aattacaata taggataaca ctgaaattag    8400
agacgtgttt attaactttg ccatacagag gtaaagtaac tctttaaagt aactctttgc    8460
ttgggttagt ggagaaggct ataaaaatta cttggagttt ttactttgaa catgcgtaat    8520
taacatggaa tgtttaggga aaagaggttt tcaattgata acataataaa catgaggagt    8580
ttgaagcatg gcattcaagg ttttctaaat tctgccccgg ttaacttttc cattcgttgg    8640
tttcattcta gtctagcttt tccttctggg ccgcccctcc ccacattaga ccgctcctct    8700
ctggaattcc aactcaagcc cttgcttttc tccatctgtc atgatgttac cccatctcat    8760
tgtcagggta acttttatgt aatattaaca tatataatac tgatataaca ttagcatatt    8820
ttaatgtatg gatcatctcc tctgcaacat tgtaacctct tggagatggc aataatggga    8880
agaatgactt gattttactt tttcttttaa caaaaatggt ggagtagtct gggcacggtg    8940
tggctcatgc ctgtaatccc agcattttgg gaggccaagg agggtggatc acttgaggtc    9000
aggcattcga gaccagtctg gccaacattg tgaaacccca tctctaccaa aaaaatacaa    9060
acacttactg gcatggtgg tgtgtgcctg tagtcctagc tactcaggag gctgaggtgg    9120
gagaatcact tgaacatggg aggtagaggc tccagcttgg gcgacagagt gagaccctgt    9180
ctcaaaagaa aaaaaggta aagggccag gtgcggaggc tcacgctggt aatccaagca    9240
ctttgggagg ctgaggcaat ggatcacctg aggtcgggag ttcgagatca gcctgaccaa    9300
catggagaaa ccccttctct actaaaaata caaaattagc cgggcgtggt ggtgcctgcc    9360
tgtaatctca gctacatggg aggctgaggc aggagaatca cttgagccca ggagacagag    9420
gttgtggtaa gccaagatgg caccattgca ctccagactg ggcaacaaga gcgaaattcc    9480
gtctcaaaac aaacaaacaa acaaaacaaa acagagagaa aaggcagagt actctaggga    9540
attctagtct gtgtttctgt ggaaatgtat atgaatctca cttttaaggg atggagattt    9600
```

```
ttgaatggca taactagttg ataagttttg ctctaacagg gtacccaagt ctagtgagtc   9660
cgattcattc tttccttaaa tagatgaagg aggaagaaac atgactccac cctcaagagt   9720
aaggcagaat gagcaaagtc agagaagtta aaaagaatt ctcacgcagc cagcagtgca    9780
gagaaacctt ggtttagttg tgaatcaaaa ccagtacttt ttgtaatttt tgagcctatg   9840
caattctcca aggttttatg ttgtttcttc tgtttctctg taggcaccag aaatcaaaac   9900
cccaaataag aaagtgttac ttgaagattt tagagtactt atttgtgtat aagtgtaagt   9960
aatatttgga agacgacttt actgcgctcc tccagcttgg catgagaatt ccagggcgg   10020 aaagaaagga gggtgatggt acctggaaag gagagtcatg ttaagtccca gccacatatt  10080
aagtgctaac cacctactgt taaaaggtgt aatgttctag actgacaaaa tacatagtct  10140
ctaccgtaaa gtaacacata atttagcagt gcagaaagat gtcacttaaa agaaaacttg  10200
aatatatgct gagatagttc acaaattaaa gaaatgaaca aagaactgag gaaataaagg  10260
aggaatacaa ctgtgtccaa atgaatactt aactgggtgg gagctgttgc atatgtaagc  10320
aggtggttca cctaaaagtt ggatgtaacg tagttaacgc cagctcttgg tgcacttaca  10380
tattgcattg cttccgggct taatttgtgt tcatatagga ataaattttt tgttggtttt  10440
taattttact ccttgtaatt ccgtagttga tattcaaagt gaaaaaatt acataagctt   10500 ctaatatatg agaagtcttc tcacttgaca tttttatt ggaattttg cagagagtag    10560 ttttgtcaca gtcaaaagat tttgggatct tgcagtgaga aacctaggtg taattcctat   10620
ttctctgcca ttccgtatgt catctggatt aagtgtcaac ttctcagtct caagattctc   10680
gtccttaaat ggaatacttt ttgtcatgct attttgaaga caaatgaga taatacgtga    10740 aactgcctag ctcagtgaat ggtacatcat agatactcag aaaaaacaca ccctctaaaa   10800
taagaacagt accaaaagac aggatgtaaa ataagggcag taccaaaaga cacatgcatg   10860
ctgagtgtat gagaaagaac tttgtggcct tcttgggtgg cacaggccat ggcagttcca   10920
cagcatgacg tggttgctgt gggtggtaga gcagacatgc cgctcccccgt cactgcctgg  10980 ctttgatgct tgctttcttc agctgagagg acgcagctgt gatatgaagg tcttgtgtgt   11040
acagtcgtga cctcacattt ccaatttcct gctggcagaa cccacagtct acaacgtacg   11100
agcaccagag ttgacgtgag acagacagca tacagaggct tgtaacatcc ttctggaaaa   11160
cactgtgtaa gctttcagtg cgaataaaca tgatcagtgg caagttctgt tagatgtagt   11220
ctgcaagcat cctgatttta ctgggcaaga ctatgttgat ttacaggcgg ctgatgattc   11280
catggatagc ccactactag tattttaca aatttcacaa gacattctta ctggaagatt    11340
gccctgttct tatgatactg ctgccctttt agcttcattt gctgttcaga ctaaacttgg   11400
agagtacagt cagtcagaga acttgctagg ccacctctca ggttattctt tcattcctga   11460
tcatcctcaa aattttgaaa agaaattgt aaaaattaca tcagcaacat ataggcttat    11520
gtccttgaga agcagcagtt aattacctaa acacagcaag taccttagaa ctctgtggag   11580
ttgaattgca ctatgcaagg gatcaagtaa caataaaatt atgattggaa tgatgtcaag   11640
aggaattctg atttataaca ggctatgaat gagtaccttt ccatggtcga agattgtaaa   11700
aatttgtttt aagtgcaaac agttttttat tcagctttga aaatgacttg cataaatctg   11760
gagaaagatt atcaggattt aatatggtga attatatggc atgtaaacat ttgtggaaag   11820
caagtttaga acatcacata ttcttctgtt tggacagacc acttccaact agaaagaatt   11880
tttttgcaca ttatttaca ttaggttcaa aattcctaat gcatggtggg agaactgaag    11940
ttcagttagt tcagtatggc aaagaaaagg caaataaaga cagactactt gcaggatcct  12000
```

```
caagtaagcc attgacgtgg aaattaatag tttgggaagt agtaggcagg aattcaatat   12060
ctgatgaaaa gattagaaac ataaagcctt ccatcacaat tcccacccgg aacaggaatt   12120
cctactcatc aaaattctgc attcatacaa gagggaacct gattatgacc atcttctgtt   12180
ggtcatttgg tagattatgt ggttcacact tcttccaaat atttgcaaat cagacatcac   12240
cattatcagc acaagctaat agcatcattc gggaatcatc actattacag gacacccctg   12300
gagatgggta gcctccagct ttaccaccca aacaagctaa gaaaaactgt tggaaccaaa   12360
ttcattattt acattttcaa caagatctgg aagatcatat taatgaaacg ttgatgttct   12420
atcttctctt aaaaaatctg ctcctaatgg tggtattcta catgataatc atgttctaat   12480
ccgagtgaac ctgacgaaaa tggaaggttt ggagtcaatg caaggggga tatgatcaga   12540 agatgtctgt gatcgtgtcc tgagaagcac caggaacacc tttgacctca gtgactctcg   12600
attgaagaga agaccaagtt gtattgatca gtggttggga ctttacagaa cacacccatg   12660
attggattgt cctgcttttt aaagccaact gtgagagaca ttctggggaa ctcatgcttc   12720
tagttctacc tatgctgcat atgatgtagt ggaagaagtg ctagaaaatg agacagactt   12780
ccagtacatt ctggagaaag ccccactaga tagtgtccac caggatgacc atgtgctgtg   12840
ggagtcagtg atccagctaa ccgagggctt atcgctggaa cattctggac acaatttgat   12900
caacttatca aaaaaaaaac ttggaatgac aatttctggt gccagattac cttagaacct   12960
ttgcaaaaat agatagagat agttttcctt atgatgttac atgggttatt tttaaaggta   13020
atgaaaacta catcagtgta attccagcat cataagtcag aacagtgctt gtcaaggggc   13080
gttaccacac acttgaacag atttttggca gatgacttgg gaacaaggct cctccatgtt   13140
tgtaatgttg accacacaag ttgaatgtgg cagagttaaa tgaccccaat attggccaga   13200
acccacagga agttcatcct atggatgcta ccaagccttc tgccactgag aagaaggaag   13260
cactgtcttt atcttcagga agatcacact gctgtttaac caagagaaaa attagagagt   13320
catcaatcac gcagatccag tacagagggt ggcctgacca tggagaccct gatgattcag   13380 tgacttctg gattttgttt ttcatatgca aaataagagg gctagcaagg aaaaacccct   13440
tgttgtttct tgcagtgctg gagttggaag aaccagcgtt cttaatacta tggaaacagc   13500
catgtgtctc attgatctca ttgaatgcag tcagccagtt tattcactag acatggtaag   13560
aacaatgaga gagcagtgag ccgtgatggt ccaaacacct agtcattaca gttttgcgtg   13620
tgaagtacta ttttgaaagc ttatgaagaa ggctttgctg aagaaagcaa aaggaaaaaa   13680
agaactttgt catctgttag gttccattta ttgcatgata attgtgtttg tattgattat   13740
tgggcaagta gctgtttgct atttttgatct tatttcagaa gggcataata atttttactat   13800 tcaatgaaac gttttaaacg gggtagaaaa agactagttt ttgtatgctt tacagcagaa   13860
atcttataat gattaactgg taatatattt cgttggcata aaaatacatt taaaagttca   13920
agtaattata acattgtaa attgtatatg taatcatatt gaaattgaaa ttctttatag   13980
ctgtacttct gtgtaatcaa agactgggga gagatagact agctagctct ttctcttatc   14040
cattaatcac ttaacagagt tttgaataaa aagttccatt tcatgggata agaataatga   14100
caggttaacc tattttagtt ggttactatg ttctaggtgt tgtatgaagt agtttacata   14160
gtttcactga tttcactaca atcccaggag gagtagttac tattattaca ctcattttac   14220
aggcaaagaa ataggtttgg aggggttggg tgttttgccc aagttctcat cgtaaaatga   14280
cagatgagga ttcaaattca agtcttaatt gaagtccatt actttagaac ctacctctta   14340
```

```
gtggctctta tgttacagta taagggagag cagactgttc ctttacccctt gtagggtagc   14400 tagggcttgt gaattaagag actgattaac aggagaagag gcatacacat tttttttgacg   14460 ttagtatttt tacatgcaca gggaaggagg gttttatttt tattttttatt tttatcttta   14520 ttttaaagag acaggggtct tgctgtgttg ccagggctgg actcaaactc ctgaagccaa   14580
gcgattcttc tgcttgagat tcctgagtag cagggactat aggtgtgctc ctctgtgctt   14640
ggctaaagaa ggggtttgta tgtgattttt aacaaaggct gataaattgt gaaaaagtga   14700
ctagtcaaag gagaagagga tttcagctcc caggggtggt aaattgtggg aagatgacta   14760
ggaaatgtat agtaataagg tttgctatgc aggtttatttt tgccagtttc tggtctccta   14820
ataagggaca gggaaacacc tttacagatg gaaattcata tcacctttcc acagggaaat   14880
ttatgtcctg ccttaggcag ttaggggaag ggcagagaat tcttcctgta tctgctgtgt   14940
ctcaggtgcc ttcagctcaa aataatcctt atgccaaagt agcatatttg ggtgtggcat   15000
attctctgat ctcttttcaac agcatcatct atacttaaca acagcaaaag ttttttttaa   15060
aaaatcatgt ttcaagattt gcatgtggaa acaaatgga catgattgag ataaatgaag   15120
aatatatatt ttttaacaaa gaatgctgta tatttatgtc tctgtgacat tgtgttatgg   15180
aggctaaggt gttaagcatg tgattacttt agatgccgta tgactacctg tttttaagat   15240 taaaaagaa tcaataggca gtttatatgt catgggagca agttaaaaac aacacagatg   15300
tgatgaaggc gaggtgaaac tggtccgcat ctaattcagg ccttctcctg aaagccagtg   15360
tgtgcaagat aaataagttt ttttgacgaa agcagaataa ctagtttgtc ctttgtgatg   15420
aagatagtta ttcagaaatc attttttattg gctacctctg aattaataaa tgaaaagaga   15480 aattttttttt tctgtagggg atgtctgatg agttcttaaa aagtggatga acctgaaatt   15540
atcatgaaca agcaatcata atgaacttaa aattacttaa agagttatga aaaacaaaaa   15600
gaaaagccgt atgttttctt gtgccttatt ttgaagtgac aaattatttg cagggtacat   15660
ttgtagacgg aactaatgtg atttaaaaaa tgagtactag atttacagaa tgaagccttt   15720
aaaaagtcac tggtgcactt taattatttt atttatgttt attctgaaac tacctttatt   15780
ttgaaaatga ggtatagctt tgcctactgg tgacaaaagt gtaaataatt cagtaaacat   15840
ctgttaaaaa ccagcttggt gctaggctct tggggtagaa aactgatcag gccattgagg   15900
agctcatagt ccctaagggg ctggggactt gtcattaggg gtgcagtgtg ttctggatgc   15960
tcctgaagga gtgtgggcag gtgcgcacca ccatgcctgg ctaatctttt tataattatg   16020
tagagacagg gtctggctgt gctgcccatg ctgggtttga acttctgggc ttaagagatc   16080
ttccctccct gccccctaccg accccgcccg cccactccac ctcagcctcc ccaaagcact   16140
gggattgcag gcatgggcca ctatgcctgg gctgtgcaaa actttttaaat cagtgcatac   16200 tcaatggtct tgatgcaatt ctggcttgtt ggtaagagaa tggggattta ctcacaagcc   16260
acgatgtcac ttttaactct gaacagatca agctattggt attactcatt tatgtcatcg   16320
ataaacttta tgaataaaaa ctcattgtgc aaatgtttaa acatactaca tacatagcac   16380
tgtgcagttt ctaaggaaag taatggaaac ctttgtcaca tccctggctt ccagaacttt   16440
atgttatcta agtgcatttg tctgcaaagt tgtgggtta attgcccctt tctttcttct   16500 cttttttaaga tattaataaa tagtgtcatg accaaaagat aatccttatg gacaagatag   16560
atctaaaaag ccttagctaa tttataatct tgcataatcc atgatgacaa gatgcagaaa   16620
caaaaatgcc cagaataaaa acttagcacc attagcagcc atttccttttt aagtctttac   16680 aagtatactc ccagtttctt gaaaaattta ttctaaaata tgtaagacac acaaaacagc   16740
```

```
agaaggacta atacaggtac atcgaacacc tgtgtgccta ccgcccagtt taaaaataaa    16800
ctggaatgat gtttctctca tacttacaga ataaagtttt aatctttagc atggaattca    16860
aaagacttct gccattccag ttcagagcca cccttctggt ctccttgctc ctcagccgcg    16920
acactgccca tgttcccaac aggcctccag ggttactgct tccattcgtt cttattctca    16980
tgaacatttt ccttcatctc atctgccaga atcctaccta ataatactcc tgctctgcag    17040
tttacagttc tttaaaatta aaaaaggttg tgtacccttt agtgtcctga aaaagaaaa     17100 aacaaattta aaaccttaaa aaggtaccat attttcatag tatttgcgtt atgtctcatt    17160
acagttcctg tggacatgtc tgtctctttt actagattga ttgtgggctc tttgaaggaa    17220
gatatatctt atgaacagtg ttttatatat tgttagcaat caatgaatgc ttgctatatt    17280
tttctcatga ggatattgat tattctattt taatttatta ccgttaacct gtactataca    17340
taactgcttt ctgtacctgc gctatttatg atctctgagg ctcctgtgag aaatctaatt    17400
tttgttaatc atggatggaa atattcacaa catcattcgt cagtttcttc acattgtctt    17460
cctttgtata ttacagatgt tttaaaatat caaagtaatg ttttttttgtt ttatctttta    17520 gatattgcta tatggagatt tgccaaaaaa taaagaaaat ataatatatt tagcaaatca    17580
tcaaagcaca ggtttgtatt tcatttgcat gaaacatagg ttttctaca gatggcacat     17640 gggcattcaa ataccgttc ttatatttaa atgaagtggg ttttttaaaa cagcaatttt     17700
ctgtgcagat attcacctg ttcttgtatt tttgtgattt tactttttgg aaagtcagaa      17760
acttgaaagc tatgaatttt cctaaactta ccttctccct ctgttggatg taagtaagct    17820
atcttcttac ttgcttgctt tgttttttcct ttgtgtagct ctttaaagag tgtattcatt     17880 cttttttgtaa gtgatgttc tagaagtagc attggtgggt cgaagtgtgt atacatttta      17940 cattttgat tgctaagctg cagaaaagct gtattggtat gtaagtactc gtttccttac       18000
tatgctcgtc atttctagtg tctgctcttc cttccttct tcaaatgggt ttggtttaat        18060
tctagttgct actgttccat cagaggaatt gcagagaact ggtcttcaaa acagtgcagt    18120
atatacttta ggtgaagata cttctaaaaa cctttgtatt ttgaggtaat tctagagtcc     18180
caagaatttg caaaaagagt acattgtcag caatattttt cccaatggtg acatcttaat    18240
ataactgtag cacagtagca gaatcaggaa attgtcattg ggtaaggtac ttttttaattc    18300 tccaaataat tcagccctcc aaaaaaatcc cacttcttat gttttcaaac ctgtagctac    18360
ttttgatgcg tacttcctaa attgcatttt tattacttta aaaatataa tacctagaag     18420 ctcaaagctg gaaacagcct gatcaatata gtactcttaa gctaaaaaca acctgatcaa    18480
tatagtactc ttagggaaat cacttatgcc tgtggctttt tttaaatttt cttcctgtca     18540
gctgtctctt catgattttg tggttttat tactgcttat accatagatg aggtatagaa       18600
agtaaaagaa gttaaaatgc attttctca atttagtgaa ttaatgatta cattcagatt      18660
tataggacaa gggttgaagc tacaaggggt tgataggaat cttgatgtat ctgagtattt     18720
tccccaactt tattacatga ctggttcaga ctattttatc taattacatt tcactcttgg    18780
caaaaatagc aaaacagtca accaatggtc aatgctgctg agaactctgg cctgtgcaga    18840
catattggct gttttacttc taataccatt ctgcttttcc tgtcctgctg ctgatggatg     18900
tttcttccag gttttaaata tcaaacaaaa gggatctgtg ggcccagtac agggaatggc    18960
tcttgataga tttgattttc ctgcatttcc tttattttga tccagtgtta atttcatgta     19020
gagttgtctg tttaacagga ttctcttaaa attccttctt cagtttacct gccagctttt    19080
```

```
ctttgtccag gtttcagtat gaactccact cgattaatag agctctctag tagtgacttg    19140
tggagtgggt tctctgaaca tttctggaag tgttgctgat agtgataata ttgatcacta    19200
gtactgttaa tttgtgtgct tactacatgt tggcttttat atgtattcct tcagattaag    19260
gacttctaga aaacatccat gaaaaaacag attaaaaaaa acaattctgc atgtatttgg    19320
gactagaagg tactatggga aggataatct tcatactcag accatactga cctgaatttc    19380
atttatcagt ttagagaacc acttccccct cccttcaccc tacctccgag tgcctgtgac    19440
tttgtatcac cgctctggca ccacatcctc atcccagcag gatttgggaa ggctgctttt    19500
tgaaagcctt ttaaaattct gtaagttgag aaaatactag gggaatgatt ttaaatttct    19560
ttagaattac aggctttagt cagtatatga cagagccttt tcctagaaaa atgtgcatat    19620
aaaaatttgc atgtagtttt agggtttcag agacccctaa agcctatcca tagacgtggt    19680
tcattgtctg attgtgttta ggtacccttc taaaacccett ttgagatgtt aggaatcaca    19740
acagagtatc tctgaaaatg taattagcgg aaagaatatt tcaaagactg ttgttctgct    19800
tagactttct agtttgtctt ctgccaggct tgccggaata aatgagtttc ctggcctgat    19860
actcaaaaga attgacattt aaattagtct ctctcttccc ttgttttcgc ttgacacatc    19920
cttgtctcta cattctgtct ctgtctctgt tagcttattt ctctctcgag tcagcaggat    19980
atagtggctg ttatttcttc cccttatcct tcaactatct acttttgaca acactttgcc    20040
tttttttttt tgagatggag tttcactctt gttgcccagg ctgggtgtaa tggtgcaatc    20100
tcagctcact gcaacctttg cctcccgggt tcaagccatt ttcctgcctc agcctcccga    20160
gtagctggga ttacagacat gcaccaccac gcctggctaa ttttgtattt tcagtagaga    20220
tggggtttca ccatgttggt caggctggtc ttgaactcct gacctcaggt gatctgcctg    20280
cctcggcctc ccaaagtgca gggattacag gcgtgagcca ctgtgccctg cctgctattt    20340 gccttttaa tctcatgaaa tgttctcttt tcttggctga agtgtcactt ttcttgttga    20400
acagcatgcg tggtgagtag aatgttataa aaagggatgg actttggagt tagagagacc    20460
caggttcctg ttcggcattg cagaaatgct gttctgcaat aggctgtgtg tcagtgggca    20520
aattacttat ctctcagagc cttattggta aggtgtgagt gatagctcct ttcaggcacc    20580
ttacagaggc tgtctcctaa tcctggtagc gtacctggct catagatggc atttaaaagt    20640
ggttgtgatg acagtcatag ctcaccatta gcatagcgct ggatccatgg cagggaagcg    20700
ctgcacatgc agtatctctt ggactacaca gggccctcat gaattaggaa ctgctgtttc    20760
atgaggatag ggatgaggaa attagacttg ctgcccctca ctgccttcca ctcctctcct    20820
ccaagttaat gggaactatg actctgcttt ggcttgattg ccatggaaga ttctcacaca    20880
gccaaattta ttgctatctt agttaaatta tgccagaaca caaaatatga agttattgtc    20940
aaagtaatat aatctcagct gtaactgaga tagtcagaaa ctgtctgtaa tctgatgtcc    21000
tatctgaaag gtagctgaga ataaacaaga aataaagaga attcagtagc aaatattggt    21060
gacacaaagc ttttatattt tgactagtta agctagttct taaatgtttc cactaaaata    21120
ttcaagttta agggcatagc ccagggcagc ttattatgaa catgatgtat tttggaaatc    21180
ttacactttc tcttaaaagt tcttgggagg ggcatgtgag gccataatat aaccataaaa    21240
ccatttgttt taaaataaaa cccatttta aaattcttcc aaataaaaaa attattgcag    21300
gaaaaaatgc taaacctggt ttttaacttt gtacgccaac tatatttcca agatgtgctg    21360
tagcctggta accatacaga accatacaga attagttctc agaatttatt gtctgcttac    21420
ttttgcattt ggtacaggta taacagggtc gattatatgg tttctaagac atgactagaa    21480
```

```
agaaatatgt ttatcagtta ttatttcttc catctaaatt agaagggct agggagaggg    21540
cttcaacagg aatttatata ctttagagaa aagtgatcat tgatagccca atagtataga    21600
tatctcaacc caataacaca ggttgtgtct gtctctggga tcatacactg taggggagaa    21660
tctttgcaag caacattcta cttatagga gccataacaa aagtttcata tgtataataa    21720
ttataagtct taagtcatca agaaaaagtt aacttgtgaa tgataatccc tgattaaaaa    21780
gagagatgta taataatgga taagagattt ttccttggtta attttagta ttaaaatggc    21840
taaatctttt ttgggatatt ctgactagta tggtgcattg tctaatagat ttcccatagc    21900
tgagagctaa tcatcttgta atctgtggaa aactgtcctc tttggctaaa actttattgt    21960
aattcctcta aatcctcagc ttttattttc tacagacttt tttttttttt taacatttcc    22020
ttcctctgac tcactccttt tgttctcatt ttcatggcct gagaacatgg gtgatgatag    22080
aattattctt ttcacagatt aacagttttc ttttcgagta tcgttgagct catgtgtgta    22140
ttaactagag aagtctccct tacatttcat ttttatgttt tctttctcat caggagatag    22200
tttgtagcca tttactttca aatccaagtt tctgcggttc ttaagacctg tatcatttgt    22260
ctcctgaatt tcacttcatt tcctctttaa accatgtcct ctgtttccca tcttctgcac    22320
ccactttgcc acttcctgtt tgtttaattg gcaagggcca ctctctgtgt tggaaatttt    22380
ttcttttga aagctcaact aacaacttct aggaagtttt ttattgctac tgttatcaat    22440
tcataccatc ttaccttgt ttttgcaacc ctttgttaat aacatattta tttaactata    22500
gttattagca gtctgagatc atttacttg gttacataag gagcacatat atctacccag    22560
catcattgta aggcatgtga gacctttgtt tgattgctgt cctaacctag taccgagtcc    22620
taaaaactca ttagtagaag atgaagtgtc cttgccttt gctgaacata tatatacaca    22680
ctgaatattt agtggcaatt catagttgca tttggccatt ttttgtttat aattccccct    22740
ttctcattaa aaaactttg ttttctagac tttaggattt agagaagctc attttgttcc    22800
atacacatgc tgctgttgga ttatttaggt attttgtgac tgtattttat ctttgaaata    22860
aaaagccttt caagaaatgc aaaaaaaaaa agctcaaaaa acagaaaatg tatatttttt    22920
aaatatctca gatagattta aagaaatttt aaacatccta atcataggac ttttttttt    22980
tttttttttt tttttttttt ggagacggag tctcgctgtc gcccaggctg gagtgcagtg    23040
gcgcaatctc ggttcactgc aggctccgcc ccctggggtt cacgccattc tcctgcctca    23100
gcctcccgag tagctgggac tacaggcgcc cgccacctcg cccggctaat ttttttgtatt    23160
tttagtagag acggggtttc accgtgttag ccaggatggt ctcgatctcc tgacctcgtg    23220
atccgcccgc ctcggcctcc caaagtgctg ggattacagg cgtgagccac cgcgcccggc    23280
catcatagta cttttgaagc ccattcatag tacaacctgt gaagagcctc atgtacgcgc    23340
taactgggtc ctgtctctgc agttgactgg attgttgctg acatcttggc catcaggcag    23400
aatgcgctag gacatgtgcg ctacgtgctg aaagaagggt taaaatggct gccattgtat    23460
gggtgttact ttgctcaggt aacttgtttc catgcttttc tctctatata tgtagtttat    23520
aaattttttt tttttttttt ggagacagtc tcactttatt gctcaggctg agtgcagtgg    23580
tgtgaacaca gctcactgca gccttgacct ctggggctca agtgaacctc ctgcctctgc    23640
ctcccaagta gttgggaccg taggtgccca ccatcatgcc cggctaaatt ttctattttt    23700
tgtagagatg ggggtctcgc tgtgttgccc aggctggtct tggactcaag caatctgcct    23760
gtctcagcct accaaaatgc tggattatag gtgtgaactg ccatacccaa ccctataaaa    23820
```

```
atgttatatt ttaaaattta acaatatact tcatgtgaat gtatggtttt taaaatgggt      23880
ttaatagttt attctcagtt gaagtaattt tgtttggcat ttttagtggt gtgtatttat      23940
atacgtctga ttatccatat gcggttttcc ttcagcatct gtggggattg gttttagaac      24000
caccacagat accaaaatct gaggtgttca agaccctcat atagaatggg atagtatttg      24060
catataacct gtgcactact ttaaatcatc tctagattac ttataatatc taatacatta      24120
taaatgccat gtaaatggtt gttatacttt attttttatt tgtattattt taattgttat      24180
attattttta attttttattt gttcacatat ttttgatctg tgatttgttg aatctgcaga      24240
tgtggaactc atggatgtga agggccagct gcagtaaaat gaaagagcaa aaatgcaaat      24300
gtacaaagtt caaacaaata ggaaatttaa aggcatagaa tttgataggc aattacatta      24360
aactgttgat aacagtaatt agtgatctgt atgatattaa aaaaaaaaag caaactgtat      24420
atataaaact tactttctcc agttctggag ctagacatc caagatcaag gtgttgacag       24480
ggttagtttc tcccaaggcc tctctcccag gcttgcagac agcatccttc ttcctgtgtc      24540
ctcaggtggt ttttttccct gtgcccaagc accgctggac ctgcttcctc ttcttagaag      24600
gactagttac actggatgac taatccttct acagagactg ctaaggtccc actctgaggc      24660 cctttttaa ccttaattac cacctctaag tccctctctc tgaatacagt cacagtggga       24720
actattaggg ctttagtaga ctgatttggg ggaacacact tctgtccgta acagtgccac      24780
ataaatatct ttagcaggat tgattttta aaatccctaa agatcgtgag acatgttaag       24840
gacgcttttt agtgactctg taataagtgg gtggaagaat tgggagttaa atccatctga      24900
tggatcaggt ttttatttt taaaaatgtg tatttaagaa agaaagcatt ttcattttaa       24960
ctgccaacaa aactaaactt catgtgtttt ccaatacagt gtcacatgca gttttttga      25020 attatgttga gacaaggcaa ttttcagcta aatgttcttt agaagctaat gtttgaagat      25080
attaaatata gattaaattc tgaaatgtag ttttcattct gtacttttg caagagaagt       25140 tgccttttg atgactctgg ccaattgtta ttttaaaagt aaatgctctt tctcccgatt       25200
tgattgtggc agcatggagg aatctatgta aagcgcagtg ccaaatttaa cgagaaagag      25260
atgcgaaaca agttgcagag ctacgtggac gcaggaactc cagtaagagc ctacccgttt      25320 ttattttct taccagctct cagtttctaa atttaagaat taaattaaaa tctaagaatt       25380
gttttgacaa tgtatttcc catgtgtaat tactaattca gggttatgct gaggtaacag       25440
aaaccctcta tgtacaggta ggcaggtttt tcagccatca gaaagattgc tgtaaacaac      25500
taggtccttt gctggtcagt ggaccttaaa gaggaataaa aagagcattt ggtgtcgttc      25560
agagtctata aatagaacta actgcatttt aacctgacat ttaagctagt ttacaagctc      25620
atcttacttc ttgtcttctt tagtatcaga tttggtttta gaagcagcaa ctgttttctg      25680
ttagtgcaaa ttttgaatgt cttacatgta cagaaaaacc aaaaaggat gaatctctac       25740 aaatgttaaa tcattcagtg taaataatat tttataaaac tttattccac aaaagtgggg      25800
agagttcaat ctgctttgta tagaatgctg attgctgcca aaggcttttc ccctggttcc      25860
ctccggagac aaagcaccat gatcaccggg gcgacttggg cttttctcttt cagtacatga      25920 catgtgctca gaagcttagc tcgtgtgcac aggctttccc tttcctttct ggctccctcc      25980
ctctgtcttc cctcctctcc tcctgccctc ccctcaccag gggtcctggg cagcagctgg      26040
agctcatggt gaaggaagaa ttcttcacgg tcagctggcg aagtgcctgg tgtgagcatt      26100
gtttattcac atgcctcttc taggtgtttt tacattagaa cattgcatct gttttgggca      26160
tgtgttgggt gacagaagca gaatggaatg agatgaacag tgacccttta tcctgttata      26220
```

```
gctaaccctt gagaaccaag cttggtgtct tcaaagggtc tgtttagtct gaaacagtgt   26280
ggtgaatttg ggcagaattg tggtcattgc atgtaggtct ccaaaagaca gaataagttg   26340
gtaatatggt ttatcgactt tttacaaaaa aaatttaaaa atcatgaatt tataccttaa   26400
aatgtccatc ccacttctct cccagctgtc cagtcacccc agcaatggat gactgctgtg   26460
gagttccttc tgtgtcctgc tgtgggcatt gtatatatga agcaaatgaa gatagctgcc   26520
ttttgggtga tgttggcatc ctatgcacag tggccccttg cttttttgcc cccatgaata   26580
tagctgccag tggcgctagg gctgaaaaaa tcagctcttt acacttgtca tgtgtcttgt   26640
ttatgtggct gccttcgtga gtttcttctt gtttttggtt tgcagcagtt taagtatcat   26700
atatctgagt gtcatttaaa aatttttacc tggattggtc ctctgagctt ggatctatga   26760
tttggtgtct gttattaatt ttggaaattt ctttgctctt atttccttaa atattattcc   26820
taccccagtc tttcttctcc agttatgttt gtgttggttc atttctcgct gttctttagt   26880
tcttagatgc attattcgtt ttttgttggt tttttttta atttttttt ttacgccccc   26940 tccctttttt cttttgtgt tacattttgg ataatttctg ttgacccacc tttgagttca   27000
tggattcttc ctttggctgt gttgagtcta ctggtgagcc agtttaaggc actcttcatc   27060
tctgctactg cgtgtttcat tcctcacatt tcccttgac cctgtttcat agtttccatc   27120
tctgtgctag tgtatctatc tgatcataaa gcttagtcac gttttccagt tgaaccttta   27180
tcattttatt atacttgcag ttctcttaaa ttccctgctt gataattcca acatctgggc   27240
catatctgag tctgcaaatt ttgattactt tatctcttca gattgtgctt tatcttgcct   27300
ttgtcatact tcctaagatt ttgcctaacg ctgggccttt tttgtaagac aggagaaatg   27360
gaggcaagtt gtcttgatac ctggaaatgg atagacttgt cttctgctt ggcctttagt   27420 gttgaggagt ggagtcagtc cactgaggag gtgcactgca tttgggtttt gctcatgtgc   27480
tttttctcac agcttcaggt ttctgtagaa ctcattactt tgtttgtagg ttggggatgt   27540
cctcccgcta gagcttttcc tcagtgtcta tttcacactc agcgttttca catagcacct   27600
tggagtggct ctcttcttta tgcctttccc cactatactt cttggatact tgttactgaa   27660
ctctcgctag tttggtggta aaggagagg gaagggaagt gtcttttcat tcttagggag   27720
aatctcaggg gtggagcctt ctctgatcct gccttgcttc tggctgtaag tctgtgccca   27780
gtatgtattc ctgcctttac taagagtttt tccctgttct cttcacccag cctcatcgag   27840
tattcatccg tgccccatgg gtagcagggt tttgttgccc ctgttcatca gtttcaggct   27900
gctgttccat aggaaaggta gaaagaagga tgtgggctgg gccctgagcc cttcccacag   27960
ggctgctttt ccctcccaca agcctacatc cagtcttccc tgaccgcagt gtgttttcct   28020
ttttctttgt cttgtgagta cacaggaggt ctgtgggtcg agcctgtgaa atgtgctgca   28080
ttctccttgt gtctgtagcc caggggttcg tctgttccac tggctcatac ttggctttct   28140
gcaaaattgt taaaattttt agctaaattc ttttactgg tatctgttac attggccccc   28200
aactaaacaa ccacttgcat cttgtttctc ctttgagttt tccatgtttc cttagacttt   28260
tgggttagtt ggttgccttg caaccttgca gctctctgaa gggtctaaga aaagtcatga   28320
atctacagct tgtcagtgtt gttgttgttg tagggttggc agtagtattc cttcagcatt   28380
ctacatactt aatggaagcc gcctcccatt tttggttaat aaatttcaaa acttggaaca   28440
atgttagatt tacaaaaacg tcagaaagaa cagagtgttc ctgtttattc tttatatagc   28500
cttttttttt tttttttttt ttttgagttg gagtctcggt ctgtcaccca ggctggagtg   28560
```

```
cagtggcacg atcttggctc actgcaacct ctgcctcacg ggttcaagca atctcctgcc   28620
tcagcctcct gagtagctgg gattacaggc gtgcaccgcc atgcccggct aattttttgta  28680 tttttagtag agacagggtt tcaccatgtt ggccaggctg gtctcgaact cctgacctct   28740
tgatccgccc gcctcggccc cccacagtgc tgggattata ggtgtgagcc accacgccca   28800
gccttcttca tctagcttta acatctaatg ttgacatctt acataacatg gtatatattt   28860
gtcaaaacta agaaataaac attggtacca cactattaat tgtactacag attttttattc  28920 agactttacc aggttttcca ctaatgtcct ttttctgttc taaaatacaa tccagaatag   28980
atacaaatcc attcaacttc agtgttttaa attattgttt ttcattatat gaagtgctgt   29040 gtggttttttg tcaaatctgt tattttggtt ttaatcttca agcttgtctt tgtttcttta  29100
agtgataaag gcataattta aaaggtgtgt tgggttattt cagtgcctaa agtcttgtct   29160
gagtcacttg ttttctgctg ttcttgctta tggtactttc tttccttgtt tgctttgtta   29220
tcttcctttg ctgctggctg tgtttggtta agttatttgt ggaaatcagt tgaagcctca   29280
ggtgggagtg tctttctccg gagaacattt ctacctgttt tagctgggcc ccttaaggct   29340
cctctagcgt gggccccacc caaacgagat tctgagttga aggtgaactg agccattcag   29400
gcagtgcagc cagggttgca gatgcacgtg agacctgctc acctctcatt tactttcacc   29460
ctgagagtag agcctttggt gtttcgttca cttgtctgat tctctcttca cagttctatt   29520
agaaggtcca tgggttttgg tttctgtgcc cttcatctta tgagtcttgt aaatcaaagt   29580
tctgttttat gcttacttct gctttactgt gtttgcttaa tttcagtctt aacatcttgc   29640
caactcttgg gtacttttaa aataatgtta tatccagctt tttaagttgt tttcagtagg   29700
aaggttgatt caaataacct agtctggtta tgggctacga gaatagcctc cctgttttt    29760 gtgggcaaaa ttccagcctt ttatgttcct agcgcagtgt ggataacaga ctggcaggtt   29820
caagaggccg tgctgagcag cttttcactgt aaggtcactg tcccaggtcg ggtttctaag  29880
aatctggatg gttgtttcat ttcttaatat gtacgccctg tgagagcgga tacatcttgc   29940
tcaggttctt atgattcttt tgtttctgaa ggtgaattaa gtaagtgaca tggtagaata   30000
tgttaagtca actttcgtgt ggcttactag ttctcatgaa tctattccat gattgtatca   30060
gttcttattc ggtattagta tttaagaaat gcagaatttt gtttcaaaaa atatatttgt   30120
attataagtt gtgaagaaat acatctccat aattattgct gggacaatac agtattttct   30180
taaggaactt attggttgtg gatgcaaatg aagcatattt gtgataaaaa taactaatag   30240
aagtcatttt gttagactat gagctagtaa aacttatggc acaaacatgg agacttaaca   30300 cttttttcttc cagctttcac ttaagttcct tttcagatag gaggcagcct ggtggataag   30360
agtattggtt ttgaaattag attcaggttt aaatcccaga tcttctgttt aatctttatt   30420
ttatttcagg tagattttct ggataacttg ctatagctta tacatcagta cttgccactt   30480
caattttatg ttatggagag acggcttctt tccttaaacc tcacgaacca acctctgcta   30540
gcttctaagt ttttcctgc cacttcttta cctctctcag ccttcagaga attaaaggga   30600
gttagggcct tgctctggat taggatttgc tttaagggag tgttgtggct ggtttgatgt   30660
tttatctaga gcactcaaac tttctccata tcagcaataa ggctgttttg ctttctaatc   30720
attcatgtgt tcagtgaagt agcactttta attctcttta agaacttttc ctttgcatcc   30780
gcaacttggc tgtttagtgg aaaggaccta gcttttgacc taccttggct ttcaacatac   30840
cttcctcact aagccatttc tagctattga tgtaaagtga gagacatgca actcttcctt   30900
tcactggaac gcttagcagc cattgtaggg ttattaattg gcctaatttc aatattgttg   30960
```

```
tgtctcaggg aatagggaaa cccaaggggc ggtagagaga aagagagaca ggagaacagg   31020
ccatcattgg agcagtcaga acacacacga catttatcaa ttaaatttgt catcttatat   31080
gggtgcaatt catggcaccc ccaaacaatt acaatagtaa catcagagat cacagatcac   31140
aataacagat ataataatat gaaatattgt gagattaccg aaatatgaca cagagacgtg   31200
aggtgagcac atactgttgg aaaaatggca ccaatagact tgctcgatgc agggttgtca   31260
taaaccttca atgggaaaaa aatgcaattt ccgtgaagct cagtaaagcg aagcatgata   31320
aaatgagatg agcctgtcac tcctaagaat gttcctgtac aagttttttg catctgttac   31380 ttacctttc ctatttgtga atagtatctt ttttgagtac gtgtgttttt ttattttat    31440 acatttatat gtatcttttg aagaacatac ttttaagctt aatttattga ttttttttct   31500
ctcataattt ccacttttg tatcctattt aagaagtcct tgccaaactt aaggttgcta    31560
agattttctc ctttgttttc ttctggaaat tttagagttt tgcttttaca tttagttcta   31620
ggatttattt ataattaatg ttttcatatg gtgtaagatc gaagttcata ttttttaat    31680 ataggtaacc atcactatag aaaagattat ttccccccaa tgtttgaaat aagtagactg   31740
aatatagatg ggtctgttat ccctagatca atggagcatt tgttctgtta tattgatcta   31800
tatatatata tccttatgcc aataccatac tgtcttaata atgcttgctt tgcagtaagt   31860
ttttaaatag tgtagttgtc ttctaaattt gttctttctt ttcaaagttg ttttggctat   31920
tttaggtttt ttgcatttct gtgtgaatta tagaattagc tcgacaattt ctacccaaag   31980
tttgtgggct tttcattttg attgtattga agatatagat gaatttggga agaattgata   32040
taacaggatt gaatctttgg attcatgaac gtagcctgca tttgtttact taggtcttct   32100
ttatttatct cagtgtgttt tgtagtttaa tgtacagatt tgcacatctt ttgccagata   32160
tatccctaag aatttcagtt tttgatacta ttgtagatga catttaaaaa aatttcaagt   32220
ttttgtttgt tgacctaggc atatatttga ctttttaata tactaaccct gctaaactta   32280
tttatcatct agtaacttac aaaatatatt ccttaggatt tcctacataa acaatcatgt   32340
cattgttata gaaataacag ttttactttg tccttttttaa tcttgatggc ttttatttct   32400
ttttcttgct aaattttctg gctagacctc ctagtacagc cttgactaga actggtgtga   32460
gggaaatcct ttccatattc ctcatcttta gggaaaagca ctcattcttt tatccattct   32520
ttagttccta gccccattgc ccttcctaaa ttttttctca tcattttcct tcatcacacc   32580
ttgttctttt tctttgcaat catatcatga tatgtaacga catgttttta tttatctgtt   32640
taatgtattt cttttcctca cttgtccatg aagggaagga ccatatgtgt tgttatcctt   32700
tgtgcagttc ctggaacata ataagtatat aagaaatagt ttctgaatta gctgtgaatg   32760
aattcatgcc ttcctgctgt ctgtcaatgt tcttttaaat taaacatcta agacagcaaa   32820
taataccaca tgagttatta acctgagaaa taatcgtttt atttataaat gactgagttg   32880
aaagctgata gcccacagta attgctttca tggctttgaa tataaacctt actgttacaa   32940
aacacatttt catgaaaatg aatgtgtggt gtttggaact agctttaatg tttgtcttcc   33000 tgttttcct tctagttgct ataatataat aaggaatttt gtatgttttt cctaattgta    33060 cccactttc tacattttct taacagatct ggtgaatctt cattattaaa tataattata    33120
catataaatt attgtttaat aataatatta attattaaaa ataatataaa ttattaaata   33180
taaagataca tataatatta tctgttaatt tctaagttag gtgtgggttc tgaagactat   33240
tatatgaatg aacaaaaagc ttgcatattt gcgtggaagc tgaaagtacg aaattttag    33300
```

```
ataccattat accagtatct aaagaaaaaa ttcagtacca cataggtttt taagtaggag    33360
ctgtatgatc ataggtcatc cagatgaagg aaggcttctg taccagacgt acagaggtag    33420
acagtgttgt ctgagtactg tctgagatct ggcaagaatg aatccaataa acgtagtttt    33480
ctcccatgag ctcctgtctt gtttcctgta ttctgtttgt atttgaaaag atttggtgtg    33540
cataacttat ttttgtcttt tggctgtcaa tcaaagttat tagtgtagtt tttgtaactc    33600
agttctcaag ctaggagttt ttgctgtata attttaatgt ttctgttttt actttcctaa    33660
gcagataagc gtaaaaactt agactaattg attacttatt aaacgtccag cttgatattc    33720
ttctttatat tattttagtt tcagtttata aacaaatga ggtttcttat aaataaaatt     33780
taaaatgcac taaaggagct gtgtgaaata ggaattctgt gtgaagcttt tgaatgtgaa    33840
catttagaac gtttcacatg gtgggaattt actatatgat tttcatcaaa tgaggtactt    33900
tttagtgttg gtacttaacg atactgattt ctaaaatttg tatttctaaa aatgacgtat    33960
tacaggatct gaaagggcaa aaactcattg aggctttgta tgagtcagcg tttcatggcc    34020 tattttaat tagtgaatta ttagcatata attagaaatg ttttagatt cttcatggct      34080 gacctaccaa tgaatgtagc actgcattta aaatatagtt cacgttatgt tcatatttaa    34140
ttgttgcatt ttgtttgccc ctcttgaaac gaaggtcaca tgtaaataaa tatacatttt    34200
ctcctactgt aggaaatact ctgttagcat tagtaggttt agcttttta ggttaacaat     34260 aacaaaaaca aagctcacac aaaataaacc aaatttgctc tatgtcccac agatgtatct    34320
tgtgattttt ccagaaggta caaggtataa tccagagcaa acaaaagtcc tttcagctag    34380
tcaggcattt gctgcccaac gtggtaagta aaaatttgag tgtttgaaca aataattttc    34440
aaagataata acattttag ttttcttcc tggaaaagat acttttgttt tacagttgaa      34500
ggaatgaatg tattcattcc ttgaattagt gtacatatta tctcttagga aatgaagttt    34560
cttctcctta attcactttc atgctattat tacatatatc tgagaaatta agttgaagtg    34620
cttgttacga tacatattct tgtgccatgg atttatttaa aatctatcta agtacatgat    34680
tatgtagatg gaagcttttt ctacagtgta tgggttatat gtaatggagc ttctgttttg    34740
taagatgaca gacctaagtt ggagtccaaa ctcgtacttt tattagctgt atggttgcaa    34800
cttggaagtt gtgtaatgtt gctgagcttg cttcttcatc tcttaaaaga acatatgcct    34860
tataagtaga tctaaatctg tgtgaggatt agattagaaa atatgtcaag tttctattgg    34920
agaagttaca caaagttggt ccacagtgct tggaagctgt taatgtcttc aacaatggta    34980
atgttcttaa tatccatatt ttagaaaatt gaataattgg tacaccaata agctatgcaa    35040
tttaaccaaa ttgggaagta tacagaaaac agtggctatg ctatgttctt agaggtgtct    35100
ttgaagcttg actgtgattt agtgtgtgat ctccatatgt tgatagtcac tcactgagca    35160
aataccttgt tggtgacatt acagcagggc ctatgacagt gctgtctaat ggaactttct    35220
gcaataatgg taaagttctt catctgttct gtccagtgtg ctggctccta ccaatgtggt    35280
ttttgagcat tcaacatgtg actagtgcat gaaactaatt tttaatttta tttaatttta    35340
gtttaattaa aaataagggg gagttttac aaggtgctta caagagcaga tatgtcatag      35400
gtatatgaca tcatttgtaa cagtactttt aaaaaatgcc agtttgtttt taaacacatg    35460
tcctattaag taaggagtgt ttcagaatag gagggttcag ttggtctccc catctgccag    35520
ctctcttttg actttcattg cttcctctgt ctaatagaca tgacgttctg tcatttcagt    35580
tgctcttttg caatgccatt gtctcttttg cccttttcac atttattaaa cagaacaaaa    35640
caaaaaccac tctcgaatct gtagtctacc tttgttgtaa gcacttttc cagtactcac     35700
```

```
tctgccctca atttgttttg gtctgatttg aaattctctc cctagacttc tgtggggctg    35760
ttctccatta tcctcccaac tctctggcga ttacttccta gcctcctttc cagcctcttt    35820
ctgcttcatt tctccctgct acatgtgtta tttccagtgt caggttttgg tgtttgatta    35880
atttcacttt ttgtttctca tggtggcctt cctctaaatc catggcttta gccatcgttt    35940
ccttgactgc tgatgactcg caaaagcttc ctcccctcca tgtctctctg cctaactctg    36000
gacccatttg tacaattgtc cattagagag cttcgcttga ctggcccaaa aggatgtctc    36060
aaactcagca tattgaagat agaatttatc cttccatgca tacactcata tttcttgtct    36120
tggtaactcc atcattcagt ttttttgcct aagttttatt cacaaaaaga acaaattgat    36180
agcagttgca tacctcttat aggaaactta gacatggagg aagaagctgt tcagatgggg    36240
tcctgcagaa gtgcaggcac tgtggtaata tttaaacttt tctcagctgt tcgaggggtt    36300
ttgttttaac taattttcct tagacttgtt ttaggtattt ggctttctaa tggttataag    36360
ggatgtggaa ttaaatgtat cttaatctgc cacctggacc cattaaagta agcccctatg    36420
gtggtttttt ttttttaatt gccatggtta aaccatagt tgctagcgaa ggtgacatac     36480
ttaagctttt tgaactctct taaaagaaaa cagaaattta atgatgtgtc tataatggca    36540
aaccagatac ctagaatttc catgttattc atagggtgaa taacactggc gattgtagag    36600
atttgagagt tctttcaaaa caggagaaca aagggaataa gctacaaagc aattttttc     36660
tttgtagact taactgaata aaaattattt ttatgtctca aacatcatat gaacaaattt    36720
agttggcaaa tggcaagcta ataatatttt ataatatagg atattaatat acttaatatt    36780
acaaaagtgc ttcataatta gaaaagacat aaactagaaa aatgggaaaa gggcatgaat    36840
aagaaattca agagatacaa atgacccaca cacttgaaca aatgtttatt ctttctcata    36900
atcaaagaag tagaaattaa atgaatactt tgaagccaac ttctgagaaa gcatagcaaa    36960
caagaaagct agtgctcagc tttgtgtggt aacggcactc tcgctcttaa gaaggtgtgt    37020
ttgctccctg tggctgctct caggcagggc cacaaacttg gtggcttaaa acaccacaga    37080
tttcttctct tacatttgag aagtctgaaa tgggtcttac tcagctgaaa tcaaggtgtt    37140
ggcagggctg cagtcctttg tggaggcttg gggggatctt gttctcctgt acggggtcct    37200
gtgcttggtt cggggtcctg tgcttggtct gggatcctgt gcttggttcg aggtcctgtg    37260
ctgggtccag tgctctgctt ttaccacctt gaagttcatc tggaaatggc actggctcgc    37320
ccacaccata tagctgactc tggttctccc tcctcctcac tcgctctaaa cctgtgttt     37380
tggctgattt ctaatctctc tttccttggc ccttctgcag cttgcagggc cttctgcagc    37440
tcttgtctgc cccagccccg gggtctgccc atcccagtgc tgggctgttc tgttcctgcc    37500
ctgccttcc tcagccttg gcaaccctgt ttgttttctc ccttccttag cagtggaaa      37560
catcgtaaga tcaatgctga ctgccttctg cagccaagcc aggccatttc atttcagccg    37620
agccaagtct gtgtggagca gttcttttat ttttctcctt ttgactacct catggttttc    37680
acggattttt gttctcttca cattcaagga ttttttgctt tcagaaagtt atatttctct    37740
ggaaagagtg cacccaatat ccctttgat ttcaaaatct taatgtggag tctcttgact     37800
tggatttctt tggaagaaac tgctgaagct gccatgtcta agaagaaaac tttggagaaa    37860
aattttcttc ttagacatgg caacgtcaac agtttctaag ctcttgattc cgtctaccct    37920
gtctccatcg ttgcctcagt catctgcctt acttctctgc aggggtttct cccagcttgc    37980
aaatgtactc caattctgaa ataactaagt ctatagctgt gcaaagagaa gtctgggccc    38040
```

```
cttgctttct tgtgtttgac tccatccact ctccagaaat gaatcccact tctcacttaa    38100
ccactgacct ccaaagcatc gtatcatttg tgtcagttgt catatttgtt aactttcaca    38160
taacttttga cattatttat acctttataa ccaggaaata attttaactt tattgtagaa    38220
ataaacaatg gagtataatt tttcttgttg aagataaata tcacctcctc ttcctttaaa    38280
catctcttcc ctttgttttt gtattacatt ggtttccccc cttttttat ttcctgggtt     38340 gtcgtattcc ctgttattat ttttaccttt ttttttttaa tgtggatgtt tccggagtct    38400
gtatttcttg ccttttcatc ttctgccctt tattattctc agccactgcc attacttcag    38460
ttatccattc ccatggtttc cacatgctta gcttcggttg attcttgcca ttttacagac    38520
catatttcca actacttcta gaatgttttg ttccttcagc ctcagtatgc ccaatttgaa    38580
ctcatgttct ctctccccct tctttcttcc ttctttcttt cgctctctct cccttccttc    38640
ttttctttcc ctccctccct ttcttccttc cctcactcgt tctctcttgc ttgcttgctt    38700
tctctcctct ctctcttttc tttctgcatt cttctccctc cctctcttcc ttctctcccc    38760
cactccccaa cttccaggct aaagcagtcc tcctgagtag ttaggactac agacatacac    38820
gtgccaccgc gcccggctcc gtgttctctt tgtttccctg cctcctgctc ttccacttat    38880
ctttgcatgg caggtgggtg cacgcaggca tgctctgcat gtcttcctct tggccattcc    38940
ccttctagtt atggtgtggc tttatctacg cgttctggag cagaagccta gtcacaaagc    39000 tatttttta aaacattcat gataattcat ttccttttat gttttaaaaa tactagcttt     39060
ctgtctttat ttccttacta acttacttgg atgccagtaa ttagttgttt tagtgaacac    39120
cacagagtga tattttgaaa ctttggactt cataaagttg gatgagctcc agtagcaaag    39180
aaggaagtgt taactagttt aactgacaaa taaatgcttc ccagcttggt gtgcgattga    39240 gattttttgtt gcaagtttgt gaatcaattt aactgcccct gccctgggga ctaaagtcag   39300
atacgtgctt gtgggaatct ttgtctttcc cacaccaccc tgcattttaa aacctcttgt    39360
gtgggacagt cccaccatgt aatagctgtt cttccttact cagctacttt ccctccagag    39420
aggccagtag aaaatctaga ctagtttttt atagtctatt ttcatgtcac ttattgagag    39480
ctactgtttt ctgttaaatt gtcagtaaat attttaatca aggaaaaggg aggtaatagg    39540
aaggagagaa gaacaaatcc ttaaccctag taggaaccta atgaatggga tttgttctgg    39600
ataattgcag tagtccccca gctaaagaac cttttaaaaa tatgtcagat atacccaaga    39660
ggattgaaat cgtatgttca tacaaaagct tgttcacctg cagccttcat atgcaattcc    39720
tatgaatgtt catagcagca ttattcataa tagccaaagt atggatgcaa cccaaatgtc    39780
catgaagcaa ttataggta aacaaaatgt gatctgttca cacagtggaa tactaactat     39840
tcagccataa aaaggaatga agcactgagt cctgcagcca cacagatgaa cctcagatcc    39900
atgctgagcg aaagaagcca gaaacaggag gccatgtgct gtgtgactgt atttctagga    39960
aatcttgagt caccatgggc aagatgctat cacctttgtt cagtggccag aagcgagggc    40020
actaatattt acccttgccg gggtctacta gattgaagcg tttccgctag gccataaact    40080
tccaacacgg tgacttgtac atgtagatat ttgatcaata tatagcaaat gaatattgat    40140
ttaaacagaa aaaggcaagt gagagtgctt tctaaactta gagccctaaa tatatgaggt    40200
tgtggaatta atagattctg ttgtgtgtgt ttgagggaat ttaaaaataa tttagatgtt    40260
aaacagtata ttgtggaggt gttttgtaac taattaatga cggcactgaa ttgacttcta    40320
ggccttgcag tattaaaaca tgtgctaaca ccacgaataa aggcaactca cgttgctttt    40380
gattgcatga agaattattt agatgcaatt tatgatgtta cggtggttta tgaagggaaa    40440
```

```
gacgatggag ggcagcgaag agagtcaccg accatgacgg gtaagtgtgt tcacgcacct   40500
gaaatgcctg tacacggtat atacagtgca catgtttatg tagaattcag ttttacaaag   40560
taggttaagt gtactttttt ccttcattac atttacccgg tatattttc  aagatgttat   40620 taagatgtaa cagtggagat ttcattagtc ctgcaaagtg tggtatttct tggctgtcgt   40680
gtgagtcctg tggactcacc aattatcatt aatccagcct ctttctactc aaagttcaca   40740
cttaaaagga aagctctgta aaagggagga agacgtgaag aaggagcacg cccggcagta   40800
ctgagtgcac gttattagtc agtgctgccc ttttgctgta ttttcgtaa  aatatttatt   40860 aaatttgggt gtcattgtga caagaagaaa tgcagttaag tgtgaccttt ttttttcccc   40920
aaacatgtta ggttttaaga acctttgagc tattgtcaga tataaccaga aaaaaataga   40980
attttaagtg agcaggataa cttagttaaa ctaaccaaac atagtgttag ctgttagaga   41040
aatgtaaaca tggaaatagg caaacaggga agtgtgtgga gtttctgttt cctttttcaaa  41100 atatctgttt gagctggggt tgagagagaa cactaggctt catggggttt ttttgttttt   41160
cgttttttgt tttgagacaa gagtttcgct ctgtcgccca ggctggagtg cagtggcgca   41220
atcttggctc actgcaacct ccgcctccca cgttcacacg attctcctgc ctcagcctcc   41280
tgagtagctg gaactacatg cgtgtgccac catgcatgac taatatttgt attttagta   41340 gatatgcgat ttcaccttgt tggccaggct ggtctcaaac tccttacctc aggtgatcca   41400
cgcacctcgg cctcccaaat gagctttgtg ttttacctc  atcagctgtt tggggttgag   41460
ccactatgta tgtcagtgtg cttgtatcag taggatctac tgagggcaga tgttcaaaat   41520
atgagcctcc agcacgtttt acatggaaac cctcacctga agcattcgtc tgaagttgat   41580
gtgccttgga aatttatag  agtaatattt ttaactacaa caaaacatttt ataaaagtag   41640 acattattaa agcattcaga agtgagcaag gatagaaatt attctgccca accttacacg   41700
taggccttct agacgtagta ctgtgcaccg ttacattatc taacactgtc tgtgtgtcat   41760
ctttggatgt tagggatttt tccaaagttc agtgagatta tagttgtcaa atgattagtc   41820
tgttaaataa tgataagatg agggtcactc aggttttaaa agaaaagctc tttgactgaa   41880
agagagagca gctgtctact gcagaaagtt agggagggag gctggaggag tgaggcccag   41940
gggctagcta gtataaaaat tggttatggt cgaaggaaaa aaaaatgtaa catatttata   42000
tctgaaagat gattgttctc ataattgtat ataacacaga gtaattgtaa agtagaaaac   42060
taaggtgttt ttcattttag atgtaaatgt ttagaatatg taatgcatca gtttaaaaat   42120
taaaactgta cgaaatgcac agtgaaacgt cttccttgct ttccaccctg ctacctggcc   42180
ttcccttctc cttcctagcg ataaccagtt ttcttaattt gttgtgcgtt gtatgtgcaa   42240
atttaagtat atcttcttat tctaccatcc ctcccttctt acagaaaagt ggcatattaa   42300
tatttttctc ttttaaacta tcgaaggagt tacttaccta tttttgcatt tgaaaacaga   42360
cagttcatca agattgtcgt tggtttatta aacatagttt aagattaaac aagtgtttat   42420
aaccaatgaa aaacagatag actccccata ataaccttgt ttaaatgctg ctacttttat   42480
catgtcccct cctgtctaag aacccccttgg ttcagcagag ctcatgggta aggccagcct   42540
ctgttgcctg ccatcggagg aatgcgttcc agccgtgatc tctgccttgc cttcgcttcc   42600
tcctgtgctg tgccgtgaag cctcggccgt ggtgaagctg gctgactgag tcctcctgca   42660
ccccatgcat attcagtagt tgaaggcttt tgtgtggccaa tcctgctttc cacaggaaac   42720
caccctctct tttgttgccc tcatccaagg ctactgttct cccacagtga caggcggcac   42780
```

| | |
|---|---|
| ctttcccagc atagcactgt gccttctcct gcccctgctc ttgcagtact gctgtggcac | 42840 |
| tgatggcgtg tgttacagtg ctggcactta gcacagggct ctgcctttct ctcttcccag | 42900 |
| ccgcatcata agtgccttga ggaagccaaa accttctgtg agttgcattg cctgggttcc | 42960 |
| aacctcccac tgccctgctt atcctctgct acatgtgagc tgactgtggc tttggggtgg | 43020 |
| tcactgccta tgtgtattca ttacaaattg tctccttttg aaagattgac ctttctgact | 43080 |
| tacccagata ccataaagaa aataaaatct tatcacttca gtcaaggata aagtatttct | 43140 |
| gaattaaagg aaaaatacac cagagtaaaa tcaagactga aagacaaact gggaaattat | 43200 |
| ttacaaccta gatcatagaa aagggtcat ttccttcttg cgtaaagtgc acttacaaat | 43260 |
| tgataagaag atgactgata actagaaaga aaaatgggta agaacaaca atagacattt | 43320 |
| cacatttaac ctcattcatg ataaggtaag tgcaaatgaa aactacaggg gataccttt | 43380 |
| ttttttttaa tccattagat tggcaaacat cccaaggttt gatcataggc tcagtgggtg | 43440 |
| agattcaagt attatcaggc attttttatac tttgctgtta ggaatgcaat gtagtacaaa | 43500 |
| cctttgtaga agttgctttg gaaatgtctc tcagatgtac aaatgcattc acattttaga | 43560 |
| tttagcattc ccgcttttctg agacattatt caacatgtat acgtgtgcac ataagatata | 43620 |
| ataataacac gttttttcctt ctagtgtgtt gcttttaacc tgtagcttga aaaaactctg | 43680 |
| ctttcattgt tttttttttgt tttctgtcac tggctcagcc ctgctttcaa ttgtttatat | 43740 |
| gaattgatgg gtgttctggt ctggttataa tctactttag tttaagagtc actttaaatt | 43800 |
| atatgacatc tgatataagt tgtgttaggt agaaaattct gtaacttgga atactgtaag | 43860 |
| tactttgtgg ccacatttca ttagtattaa atattatctc tatatatagt aggctattta | 43920 |
| atattcatat tttatgatgc aattaagaaa taattttttt ctgaagttgg tagattgttg | 43980 |
| atatgccatg gcccagtgtt tctcaaagca ttctggggga tcactgtttg tcagaattag | 44040 |
| ctgcagtgat tgttgaacat gcagggcctc tgctccactc cacgttgcta ccaggacgct | 44100 |
| ctgcaggtga gagctgggaa gctgtagaag ctgcagtgct aacaaatgct acaggaattc | 44160 |
| ttgtagtcac cttcatgagg tcttatgttg aggagaggca gccagtagtg tcccttgtcc | 44220 |
| ttcccgttttt atggtgtaag tttcatttta agggaggtat aaatcaaagc ccacctgggc | 44280 |
| attctctcat ggttcactgc ttcttgtaat catggaagat gtcattgcgg cagagacgaa | 44340 |
| acagtgtagt ttgattacta ttgatttttt tttaattatt tttctgaagt ggctgttgta | 44400 |
| atgtaataaa ttgtgtgctt aaggacaacc tttggtattc tatttgagta ttgtgtatga | 44460 |
| tcctagttaa gttttttcta ccagtatttt catattacaa catatttact ttccatttct | 44520 |
| attaatattt ttatatttaa agtatggagg ccgggcacag tggctcacgc gtgtaatccc | 44580 |
| agcattttgg gatgctgagg cgggtggatc acaaggtcag gagttctaga ccagcgtgac | 44640 |
| caacacggtg aaatcccatc tctactaaaa atacaaaaat tagccgggca cagtggtagg | 44700 |
| cacctgtaat tccagctact caggaggctg aggtagggga atcacttgaa tccgggaggc | 44760 |
| agcagttgca gtgagctaag atcgtgccac tggactctag cctggctgac agagcaagaa | 44820 |
| tccgcctaaa aaaaaggga tcagggaaga ggggattaca gataacccaa agaagaagga | 44880 |
| aaaatctcca caagttcacc tgtccagcgg taaccccaat ttggatattt tccttttaaca | 44940 |
| atttggatat tttcctttaa atcctctttt ttataatgtc tatatgttgg agagagtatg | 45000 |
| tgcctttacg tattttttaa agatgagatt tctgtgtgtg tctatatctc ctgttcttca | 45060 |
| tatttcttg tgtgttataa acagctgtac atgtcagtat atatacttcc gtaactttt | 45120 |
| tttaaaggct atatagtgtt cattgatgtg atttaacagc agttatctcc ccggcttcat | 45180 |

```
cttgttggaa tgtgggtcct gtgtgttgcc ttcagagcaa atggggcttg gttttgcagc   45240
aagtagacct gtgacctgta cgaatagttg gaagactttc tctattaccc aagtgtatca   45300
gtatacttta gtgcctacta gaaatttatg ggtagaaaaa caataatatc ttagagtatt   45360
ttttcctaga ttccctaagg tgctataggg tgattttac tcatgtaaca tgaactatcc    45420
ttcaactaag atagtttttg caaatgtgga tatataagta ctttattaaa cctataggaa   45480
gtatttatac cacttatttc ctcccttcag tgttagaacc tcctaaatgg catttgacat   45540
tgaactgctt tccactttgt cgcatgctcc tctcattgtc cctacctggg tcctgaacct   45600
tagggacttg gctgttatag ccccaccatg gctacgctgg gccttggtcg tctctgagac   45660
ttagtttctt catcttacaa ggagataata acagcccctg cctgcgtaga attgcagaga   45720
tcaaatgaaa taattaacat actcaaaagc atgccgtaaa cacattctga gcacatgtac   45780
gttttaggaa aaacaaaagg acccatgcac atttcggagt gcttttgtct cagcagcact   45840
gcctcttctt ccaaagctga cgtcttagta gaggccctgc cacgtcctga gcactgtact   45900
ccacgaagca ttctatttct gacattcgaa atgcagtctg ttccatcttc cttacaatct   45960
gtatgccagc acttgaaata ccgggtatct gcagtgttga ccaggtgatt acttaattat   46020
ggaaatgttg aggtggagat ctagataatt cagtgaaggc aggaaaattg gtgtcggaat   46080
ctgtcttttt atgtgtcaga aatagaaata agatagggtg agaagtaatt tgtggctaaa   46140
acactataat agctaacaca tagtgcatac tgtgtgccaa gcactcctgt aggtgcttga   46200
aatcttctat tattattatc cctactttat agacttgcac ccttaggcac agagaggcgg   46260
acagttgtcc aaggttaccc cagaggtgga gatccaggct acctgactcc accatgtgtg   46320
ctcttcccta gggcacagtt gtgctgctaa aaatacttt taagcagttc tttgattatt    46380
cagatgatag tactgtagga aaattaagac aaaaataatg aaaaattaaa atctttattt   46440
tagtgttttg cacatgtatt attaaagcca gtttactcct ggaagtgtgt aagaatacag   46500 ggtattttg atcacctaaa tgctgcatgt tactaagagc tcgacactga agtcaagaag    46560
agcagttgca gagagtactt agcaaaaacg ggaagtgtgt ggggttgaag gagcaaagac   46620
aagtcttcct cggacggtgg agtgtagaat tcatcatttc tcagaacacg tctttgaacg   46680
cattttcaat ttgaggccaa aggtctcagc ctcccactcg gcatacctcc tacccttagt   46740
cagctcttaa atcttaggaa tatttctttg ttcttcaagg aacttaaata tgttaacatt   46800
cttacctgtc cacagggagc cccctacaaa gaagggagtt tctagtctcc gttctttctt   46860
ggaataaata atagcctcat accttgtgca atcgaggctg aaaagactg tctccttttt    46920 tcaaataagc aagtcttaga aactacagtt gtttacaggg ctcatggcta ttccacagta   46980
ataattttgg ttcttttacc aattatataa tatgttaaaa tatggcaagt atcaggaaag   47040
caaggagtgg caatgattag aaaccaatgg ccaagttaga gaggagggc aattgctccc    47100 ccaagtttgt tgtggctgtg tagcagtcag tgacagaag ctgtgtgtca ggcgacaagc    47160
aaagttgagg attatcaggc gcctgtgagt gcccagctgt gtgccaggtc aggaggtgcc   47220
atcgtgagcc agaccagctt cctctcggcc cctgtggagc tcgcagtctg tgggggaggc   47280
agcagtcacc atggtgacag gtgacacact aggatgggg tggtggtggt aggcatttgc    47340
gggtcccttc agagaggtga gtatggactt agaggaggct ccagcttcct attcctgggc   47400
tgtctatagc actaaaagtt gtcacatgaa aaataacatt tggtactatt gatttaactt   47460
aatgacttat gtaattgtag ttgacttaga aattataaca tgctcttcta cttcagcttg   47520
```

```
aaacccccaa ccaccagttt ataatccttt tttttaact tttgtttatt tttcctaagg    47580
aatctgtact ttttcttcat tttacaactt tttttgtcct gttaccttat tttcatttt     47640
actttatatg accatgagtt ctaaaatagt aaaaaaaaag aattatttt gttctttgtt    47700
agaatttctc tgcaaagaat gtccaaaaat tcatattcac attgatcgta tcgacaaaaa    47760
agatgtccca gaagaacaag aacatatgag aagatggctg catgaacgtt tcgaaatcaa    47820
agataagtga gtaacaacag ttccagcact tccggaactt cggttcaact agatttcagt    47880
atagtcaaca atttgaaacc aatgtaaatg gttatattgt ctcaagaata catttataa    47940
attcaaatca aattttatgc atgtctgatc gtgttttaaa ctttacttgt acaaatcagt    48000
ctaaaagaac ttgttacagt gggcccatct acttgcattg atagtatttc ttggacaata    48060
ctacgtgata acatagcaaa ttaaattaaa aacaacaaca aacacacaaa aaaactttcc    48120
agtgtcagat gcccggacct acctgtcagg tcacataaag tggtgttact gtgtgaggtc    48180
tggctgttgg gccagtgtgc gcagaaaagc aagggagggg tagaggacta tgcggacgtg    48240
caggtggaca tgatgctgtt atatttgttg gaaatagaag ggggcagttg acagcgttat    48300
atccaaagtg tcttctgtgg ttaattatat tcagaaattt tagccaattg ttttattctc    48360
taaatatgta ctttctgctc aagaaactat cattgttctt cttttccttg ttttacagta    48420
cagtgttttt aattaaccct cctgggttaa ctttaccagg tgaaaatgat taaaagtgta    48480
ataggttaac aatgaaactt taagcttcta ttttcattg actcttaact gtacatgatg    48540
taatgtattc agcgagccat tcaggaccac tttggcccat ggaagaaatt taaaagtaag    48600
atctacatgt attgacatga aaatatgttc tcagaaaaaa gactaatgta tttaatgtcc    48660
tacttatttt ataagtattt agaatacctc tggacatttt aaaacaatga ttattgctag    48720
ggtgtgtgat ttataaagca atagaagcgc tttcccttc tgtttgtgtt ttagattatt    48780
atatcgggta tgttctgcta tcataacttt acaaatctta tgtaatatgg gaaaatgagt    48840
taactatgct gttttccttc ttttacctgc ctttctaatt ctgtgggaat aaaggcgttt    48900
ttgagacagc ccaggtgcag tgagcagtcc atatccatgg attccacatt catggattcc    48960
accaagcaca gaccaaaaat actcagaaaa aaaggggggct ggctgtggtg gctcatgcat    49020
gtaatcccag cactttggga ggctaaggca ggcaaattgc ttgagcccag aagttcaaga    49080
cagcctgggc aacatggcaa aaccctgtct ctacagaaaa tacaaaaatt agccaggcgt    49140
gcacctgtag tcccagctac tcaggaggcc gaggtgcgag gatcacctga gcctggaagg    49200
ttgagactgc agtgagctat cattgtgcca actccagcct ggtaacagag tgccttttt     49260
caaaaaaaaa aaaaaaaag gatttgggag gatatgcata tgttatattc aaatacatgc    49320
cattttattc atatatcagg gacttgagca tcctttgatc ttggtctctg ccgggtatcc    49380
tgggaccagc cccctgtcga tacagaggga ccgctgtcta agaaccgctg gtcctatctt    49440
tgacttctgg cggaatagga gctccatgta aaaggaggag aagctgcag cgggttatta    49500
gccatttgtg agtcaggtca ctgtaaaact ttatcaaaag tttaaagac aaaaagcatc     49560
ctcataaaat gccttaaaac cacctgttga atattacat atacaattca tgtatactaa    49620
tcatagagca tattaaagat attttagaag actagaaact tctattaaac caagtttctg    49680
gatgtttccg tattcatcct tattttccag ggacctgcat aacttttcca gcgtgtaata    49740
gctacctgat tgatattttt tgaattgaaa tactgaagtg actaaaatct aaactttttc    49800
cattctggcc ataggatgct tatagaattt tatgagtcac cagatccaga aagaagaaaa    49860
agatttcctg ggaaaagtgt taattccaaa ttaagtatca agaagacttt accatcaatg    49920
```

```
ttgatcttaa gtggtttgac tgcaggcatg cttatgaccg atgctggaag gaagctgtat    49980
gtgaacacct ggatatatgg aaccctactt ggctgcctgt gggttactat taaagcatag    50040
acaagtagct gtctccagac agtgggatgt gctacattgt ctattttttgg cggctgcaca    50100 tgacatcaaa ttgttttcctg aatttattaa ggagtgtaaa taaagccttg ttgattgaag    50160
attggataat agaatttgtg acgaaagctg atatgcaatg gtcttgggca aacatacctg    50220
gttgtacaac tttagcatcg gggctgctgg aagggtaaaa gctaaatgga gtttctcctg    50280
ctctgtccat ttcctatgaa ctaatgacaa cttgagaagg ctgggaggat tgtgtatttt    50340
gcaagtcaga tggctgcatt tttgagcatt aatttgcagc gtatttcact ttttctgtta    50400
ttttcaattt attacaactt gacagctcca agctcttatt actaaagtat ttagtatctt    50460
gcagctagtt aatatttcat cttttgctta tttctacaag tcagtgaaat aaattgtatt    50520
taggaagtgt caggatgttc aaaggaaagg gtaaaaagtg ttcatgggga aaaagctctg    50580
tttagcacat gattttattg tattgcgtta ttagctgatt ttactcattt tatatttgca    50640
aaataaattt ctaatatttta ttgaaattgc ttaatttgca caccctgtac acacagaaaa    50700
tggtataaaa tatgagaacg aagtttaaaa ttgtgactct gattcattat agcagaactt    50760
taaatttccc agcttttttga agatttaagc tacactatta gtacttccct ttgtctgtgc    50820
cataagtgct tgaaaacgtt aaggttttct gttttgtttt gttttttttaa tatcaaaaga    50880 gtcggtgtga accttggttg gaccccaagt tcacaagatt tttaaggtga tgagagcctg    50940
cagacattct gcctagattt actagcgtgt gccttttgcc tgcttctctt tgatttcaca    51000
gaatattcat tcagaagtcg cgtttctgta gtgtggtgga ttcccactgg gctctggtcc    51060
ttcccttgga tcccgtcagt ggtgctgctc agcggcttgc acgcagactt gctaggaaga    51120
aatgcagagc cagcctgtgc tgcccacttt cagagttgaa ctctttaagc ccttgtgagt    51180
gggcttcacc agctactgca gaggcatttt gcatttgtct gtgtcaagaa gttcaccttc    51240
tcaagccagt gaaatacaga cttaatttgt catgactgaa cgaatttgtt tatttcccat    51300
taggtttagt ggagctacac attaatatgt atcgccttag agcaagagct gtgttccagg    51360
aaccagatca cgatttttag ccatggaaca atatatccca tgggagaaga cctttcagtg    51420
tgaactgttc tatttttgtg ttataattta aacttcgatt tcctcatagt cctttaagtt    51480
gacatttctg cttactgcta ctggattttt gctgcagaaa tatatcagtg cccacatta    51540 aacataccag ttggatcatg ataagcaaaa tgaaagaaat aatgattaag ggaaaattaa    51600
gtgactgtgt tacactgctt ctcccatgcc agagaataaa ctctttcaag catcatcttt    51660
gaagagtcgt gtggtgtgaa ttggtttgtg tacattagaa tgtatgcaca catccatgga    51720
cactcaggat atagttggcc taataatcgg ggcatggta aaacttatga aaatttcctc    51780
atgctgaatt gtaattttct cttacctgta aagtaaaatt tagatcaatt ccatgtcttt    51840
gttaagtaca gggatttaat atattttgaa tataatgggt atgttctaaa tttgaacttt    51900
gagaggcaat actgttggaa ttatgtggat tctaactcat tttaacaagg tagcctgacc    51960
tgcataagat cacttgaatg ttaggtttca tagaactata ctaatcttct cacaaaaggt    52020
ctataaaata cagtcgttga aaaaatttt gtatcaaaat gtttggaaaa ttagaagctt    52080
ctccttaacc tgtattgata ctgacttgaa ttatttttcta aaattaagag ccgtatacct    52140
acctgtaagt cttttcacat atcatttaaa cttttgtttg tattattact gatttacagc    52200
ttagttatta attttttcttt ataagaatgc cgtcgatgtg catgctttta tgttttttcag    52260
```

```
aaaagggtgt gtttggatga aagtaaaaaa aaaaataaaa tctttcactg tctctaatgg    52320
ctgtgctgtt taacattttt tgaccctaaa attcaccaac agtctcccag tacataaaat    52380
aggcttaatg actggccctg cattcttcac aatattttc cctaagcttt gagcaaagtt     52440
ttaaaaaaat acactaaaat aatcaaaact gttaagcagt atattagttt ggttatataa    52500
attcatctgc aatttataag atgcatggcc gatgttaatt tgcttggcaa ttctgtaatc    52560
attaagtgat ctcagtgaaa catgtcaaat gccttaaatt aactaagttg gtgaataaaa    52620
gtgccgatct ggctaactct tacaccatac atactgatag ttttcatat gtttcatttc     52680 catgtgattt ttaaaattta gagtggcaac aattttgctt aatatgggtt acataagctt    52740
tattttttcc tttgttcata attatattct ttgaataggt ctgtgtcaat caagtgatct    52800
aactagactg atcatagata gaaggaaata aggccaagtt caagaccagc ctgggcaaca    52860
tatcgagaac ctgtctacaa aaaaattaaa aaaaattagc caggcatggt ggcgtacact    52920
gagtagtttg tcccagctac tcgggagggt gaggtgggag gatcgcttca gcccaggagg    52980
ttgagattgc agtgagccat ggacatacca ctgcactaca gcctaggtaa cagcacgaga    53040
ccccaactct tagaaaatga aaggaaata tagaaatata aaatttgctt attatagaca     53100
cacagtaact cccagatatg taccacaaaa aatgtgaaaa gagagagaaa tgtctaccaa    53160
agcagtattt tgtgtgtata attgcaagcg catagtaaaa taatttaac cttaatttgt     53220 ttttagtagt gtttagattg aagattgagt gaaatattt cttggcagat attccgtatc     53280
tggtggaaag ctacaatgca atgtcgttgt agttttgcat ggcttgcttt ataaacaaga    53340
ttttttctcc ctccttttgg gccagttttc attacgagta actcacactt tttgattaaa    53400
gaacttgaaa ttacgttatc acttagtata attgacatta tatagagact atgtaacatg    53460
caatcattag aatcaaaatt agtactttgg tcaaaatatt tacaacattc acatacttgt    53520
caaatattca tgtaattaac tgaatttaaa accttcaact attatgaagt gctcgtctgt    53580
acaatcgcta atttactcag tttagagtag ctacaactct tcgatactat catcaatatt    53640
tgacatcttt tccaatttgt gtatgaaaag taaatctatt cctgtagcaa ctggggagtc    53700
atatatgagg tcaaagacat ataccttgtt attataatat gtatactata ataatagctg    53760
gttatcctga gcaggggaaa aggttatttt taggaaaacc acttcaaata gaaagctgaa    53820
gtacttctaa tatactgagg gaagtataat atgtggaaca aactctcaac aaaatgttta    53880
ttgatgttga tgaaacagat cagttttcc atccggatta ttattggttc atgattttat     53940
atgtgaatat gtaagatatg ttctgcaatt ttataaatgt tcatgtcttt ttttaaaaaa    54000
ggtgctattg aaattctgtg tctccagcag gcaagaatac ttgactaact cttttgtct     54060 ctttatggta ttttcagaat aaagtctgac ttgtgttttt gagattattg gtgcctcatt    54120
aattcagcaa taaggaaaaa tatgcatctc aaaaattggt gataaaaagt tatttcttgt    54180
atatgtgata aagtttacat gttgtgtata tatgttgtat tgccaaatac ggctattaaa    54240
tactacgtca tattttaaag gttcagtttg tagtgatagt aaacaagcag tgcactaagc    54300
ctcttgcggg catcatctca tctcactgtc atcacaaacc ccatgccaca gcgtagcttg    54360
accactaaaa gtaatgcatc tgcaagcata ctgccaggtt ttggatagtt tgtaccaaca    54420
gttaccttat caaggtaaat cccagactct aaaagagttg gtgctgtgtc actacatgca    54480
taactttaaa taaatttcct gccgggcgcg gtggctcacg cctgtaatcc cagcagtttg    54540
ggaggccgag gcaagtggat cacttgaggt caggagtttg agaccagcct ggccaacgtg    54600
gtgaaaccct gtctctacta aaaatacaaa aattagccag gcgtgtggtg gcaggcacct    54660
```

```
gtaatcccag ctacttggga ggatgaggca ggagaatcat ttgaatcctg caggcggagg    54720
ttgcagtgag ccaagatggc gtcattgcac tccagcctgg gcgacaagag cgagactccg    54780
tattaaaaaa aaaaaaaaaa aaaaaattcc tctcctgttt gagctttccc ttacctgtaa    54840
agaggggaga atatgtattt acttcaaaga gttcagggaa atgactctca ctagtttgag    54900
attctaggta taaaaataca ttcttatata attttaacac caatgtgaga gattattatt    54960
cttgctaaac caattcagtt ttatttgctg tctaaaatgt gtgaataagt aattgtccat    55020
tattttctga agtgttttgg aactcaacac atgattgtga ggaggatttg ttgctaaaca    55080
tctttctggt tattcaagct cgtgtatact gtgctctgtt gagacatgca gagttacttt    55140
ctgtct                                                                55146

<210> SEQ ID NO 27
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 27
ggccaatacg ccgtca                                                         16
```

MODULATION OF AGPAT5 EXPRESSION

STATEMENT OF GOVERNMENT SUPPORT

This invention was made with government support under HL028481 awarded by National Institute of Health. The government has certain rights in the invention.

SEQUENCE LISTING

The present application is being filed along with a Sequence Listing in electronic format. The Sequence Listing is provided as a file entitled BIOL0241USASEQ_ST25.txt, created on May 8, 2017 which is 144 MB in size. The information in the electronic format of the sequence listing is incorporated herein by reference in its entirety.

FIELD OF THE INVENTION

Provided herein are methods, compounds, and compositions for reducing expression of 1-acylglycerol-3-phosphate O-acyltransferase 5 (also known as AGPAT5, LPAATE or 1AGPAT5) mRNA and protein in an animal. Also, provided herein are methods, compounds, and compositions comprising an AGPAT5 inhibitor for reducing AGPAT5 related diseases or conditions in an animal. Such methods, compounds, and compositions are useful, for example, to treat, prevent, delay or ameliorate a cardiometabolic disease, disorder or condition, or a physiological marker thereof, in an animal.

BACKGROUND

Diabetes and obesity (sometimes collectively referred to as "diabesity") are interrelated in that obesity is known to exacerbate the pathology of diabetes and greater than 60% of diabetics are obese. Most human obesity is associated with insulin resistance and leptin resistance. In fact, it has been suggested that obesity may have an even greater impact on insulin action than diabetes itself (Sindelka et al., *Physiol Res.*, 2002, 51, 85-91). Additionally, several compounds on the market for the treatment of diabetes are known to induce weight gain, a very undesirable side effect to the treatment of this disease.

Cardiovascular disease is also interrelated to obesity and diabetes. Cardiovascular disease encompasses a wide variety of etiologies and has an equally wide variety of causative agents and interrelated players. Many causative agents contribute to symptoms such as elevated plasma levels of cholesterol, including non-high density lipoprotein cholesterol (non-HDL-C), as well as other lipid-related disorders. Such lipid-related disorders, generally referred to as dyslipidemia, include hyperlipidemia, hypercholesterolemia and hypertriglyceridemia among other indications. Elevated non-HDL cholesterol is associated with atherogenesis and its sequelae, including cardiovascular diseases such as arteriosclerosis, coronary artery disease, myocardial infarction, ischemic stroke, and other forms of heart disease. These rank as the most prevalent types of illnesses in industrialized countries. Indeed, an estimated 12 million people in the United States suffer with coronary artery disease and about 36 million require treatment for elevated cholesterol levels.

Epidemiological and experimental evidence has shown that high levels of circulating triglyceride (TG) can contribute to cardiovascular disease and a myriad of metabolic disorders (Valdivielso et al., 2009, *Atherosclerosis* Zhang et al., 2008, *Circ Res.* 1; 102(2):250-6). TG derived from either exogenous or endogenous sources is incorporated and secreted in chylomicrons from the intestine or in very low density lipoproteins (VLDL) from the liver. Once in circulation, TG is hydrolyzed by lipoprotein lipase (LpL) and the resulting free fatty acids can then be taken up by local tissues and used as an energy source. Due to the profound effect LpL has on plasma TG and metabolism in general, discovering and developing compounds that affect LpL activity are of great interest.

Metabolic syndrome is a combination of medical disorders that increase one's risk for cardiovascular disease and diabetes. The symptoms or physiological markers of metabolic syndrome, include high blood pressure, high triglycerides, decreased HDL and obesity, tend to appear together in some individuals. It affects a large number of people in a clustered fashion. In some studies, the prevalence in the USA is calculated as being up to 25% of the population. Metabolic syndrome is known under various other names, such as (metabolic) syndrome X, insulin resistance syndrome, Reaven's syndrome or CHAOS.

Despite several drugs for treating cardiometabolic diseases commercially available, the high prevalence of cardiovascular disorders and metabolic disorders shows that there remains a need for improved approaches to treat these conditions. It is therefore an object herein to provide compounds and methods for the treatment of such diseases and disorder.

AGPAT5 is a lipid acyltransferase gene that is important in the conversion of lysophosphatidic acid to phosphatidic acid and biochemical studies indicate that Agpat5 is localized to the mitochondria where its function is unknown (Prasad et al., 2011, J Lipid Res 52, 451-462). A genome-wide association scan (GWAS) surveying the murine genome for common variants associated with insulin resistance (IR) found an association between AGPAT5 and IR (Parks et al., unpublished).

The potential role of AGPAT5 in IR makes it an attractive target for investigation. Antisense technology is emerging as an effective means for reducing the expression of certain gene products and may therefore prove to be uniquely useful in a number of therapeutic, diagnostic, and research applications for the modulation of AGPAT5.

SUMMARY OF THE INVENTION

Provided herein are compositions, compounds and methods for modulating expression of AGPAT5 mRNA and protein. In certain embodiments, AGPAT5 modulators include nucleic acids, proteins and small molecules. In certain embodiments, the AGPAT5 modulator is an AGPAT5 specific inhibitor. In certain embodiments, the AGPAT5 specific inhibitor decreases expression of AGPAT5 mRNA and protein. In certain embodiments, AGPAT5 specific inhibitors include nucleic acids, proteins and small molecules. In certain embodiments, the AGPAT5 specific inhibitor is a nucleic acid. In certain embodiments, the nucleic acid is an antisense compound. In certain embodiments, the antisense compound is a modified oligonucleotide. In certain embodiments, the modified oligonucleotide can be single stranded or double stranded.

Certain embodiments disclosed herein provide a method of reducing AGPAT5 expression in an animal comprising administering to the animal a compound or composition comprising an AGPAT5 specific inhibitor.

Certain embodiments disclosed herein provide a method of reducing insulin resistance in an animal comprising administering to the animal a compound or composition comprising an AGPAT5 specific inhibitor.

Certain embodiments disclosed herein provide a method of increasing insulin sensitivity in an animal comprising administering to the animal a compound or composition comprising an AGPAT5 specific inhibitor.

Certain embodiments disclosed herein provide a method of reducing liver triglyceride levels in an animal comprising administering to the animal a compound or composition comprising an AGPAT5 specific inhibitor.

Certain embodiments disclosed herein provide a method of reducing insulin levels in an animal comprising administering to the animal a compound or composition comprising an AGPAT5 specific inhibitor.

Certain embodiments disclosed herein provide a method of increasing glucose tolerance in an animal comprising administering to the animal a compound or composition comprising an AGPAT5 specific inhibitor.

Certain embodiments disclosed herein provide a method of increasing glucose clearance in an animal comprising administering to the animal a compound or composition comprising an AGPAT5 specific inhibitor.

Certain embodiments disclosed herein provide a method of reducing the ratio of fat to body weight in an animal comprising administering to the animal a compound or composition comprising an AGPAT5 specific inhibitor.

Certain embodiments disclosed herein provide a method of ameliorating a metabolic and/or cardiovascular disease, disorder or condition, or a symptom or physiological marker thereof, in an animal comprising administering to the animal a therapeutically effective amount of a compound or composition comprising an AGPAT5 specific inhibitor. In certain embodiments, the therapeutically effective amount of the compound or composition administered to the animal reduces insulin resistance in a diabetic or non-diabetic animal.

Certain embodiments disclosed herein provide a method for treating an animal at risk for a metabolic and/or cardiovascular disease, disorder or condition, or a symptom or physiological marker thereof, comprising administering to said animal a therapeutically effective amount of a compound or composition comprising an AGPAT5 specific inhibitor. In certain embodiments, the therapeutically effective amount of the compound or composition administered to the animal reduces insulin resistance in a pre-diabetic or non-diabetic animal.

Certain embodiments disclosed herein provide compounds or compositions comprising an AGPAT5 modulator. In certain embodiments, the AGPAT5 modulator is an AGPAT5 specific inhibitor. In certain embodiments, AGPAT5 specific inhibitor is a nucleic acid, polypeptide, antibody, small molecules, or other agent capable of inhibiting the expression of AGPAT5. In certain embodiments, the nucleic acid is an antisense compound or composition targeting AGPAT5. In certain embodiments, the antisense compound or composition is single stranded. In certain embodiments, the antisense compound or composition is double stranded. In certain embodiments, the antisense compound or composition targeting AGPAT5 is an oligonucleotide. In certain embodiments, the oligonucleotide is single stranded. In certain embodiments, the oligonucleotide is double stranded. In certain embodiments, the oligonucleotide is a modified oligonucleotide. In certain embodiments, the modified oligonucleotide is single stranded. In certain embodiments, the modified oligonucleotide is double stranded.

Certain embodiments disclosed herein provide an antisense compound or composition comprising a modified oligonucleotide that is 10 to 30 linked nucleosides in length targeted to AGPAT5. The AGPAT5 target can have a nucleobase sequence selected from any one of SEQ ID NOs: 1-2, 24-26. In certain embodiments, the nucleobase sequence of the modified oligonucleotide is at least 70%, 75%, 80%, 85%, 90%, 95% or 100% complementary to the nucleobase sequences recited in any one of SEQ ID NOs: 1-2, 24-26 as measured over the entirety of the modified oligonucleotide. In certain embodiments, the modified oligonucleotide comprises a nucleobase sequence comprising a portion of at least 8, at least 9, at least 10, at least 11, at least 12, at least 13, at least 14, at least 15, or 16 contiguous nucleobases complementary to an equal length portion of SEQ ID NO: 1, 2, 24, 25 or 26.

Certain embodiments disclosed herein provide an antisense compound or composition comprising a modified oligonucleotide that is 10 to 30 linked nucleosides in length wherein the nucleobase sequence of the modified oligonucleotide comprises at least 8, at least 9, at least 10, at least 11, at least 12, at least 13, at least 14, at least 15, or 16 contiguous nucleobases of a sequence recited in any one of SEQ ID NOs: 6-23.

Certain embodiments provide compositions and methods for use in therapy. Certain embodiments provide compositions and uses for preventing, treating, delaying, slowing the progression and/or ameliorating AGPAT5 related diseases, disorders, and conditions, or symptoms or physiological markers thereof. In certain embodiments, such diseases, disorders, and conditions are cardiovascular and/or metabolic diseases, disorders, and conditions, or symptoms or physiological markers thereof. In certain embodiments, the compositions and uses for therapy include administering therapeutically effective amount of an AGPAT5 specific inhibitor to an individual in need thereof. In certain embodiments, the AGPAT5 specific inhibitor is a nucleic acid, protein or small molecule. In certain embodiments, the nucleic acid is an antisense compound. In certain embodiments, the antisense compound is a modified oligonucleotide.

DETAILED DESCRIPTION OF THE INVENTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated-by-reference for the portions of the document discussed herein, as well as in their entirety.

Definitions

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques can be used for chemical synthesis, and chemical analysis. Where permitted, all patents, applications, published applications and other publications, GEN-BANK Accession Numbers and associated sequence information obtainable through databases such as National Center for Biotechnology Information (NCBI) and other data referred to throughout in the disclosure herein are incorporated by reference for the portions of the document discussed herein, as well as in their entirety.

Unless otherwise indicated, the following terms have the following meanings:

"2'-O-methoxyethyl" (also 2'-MOE and 2'-O(CH$_2$)$_2$—OCH$_3$) refers to an O-methoxy-ethyl modification of the 2' position of a furosyl ring. A 2'-O-methoxyethyl modified sugar is a modified sugar.

"2'-O-methoxyethyl nucleotide" means a nucleotide comprising a 2'-O-methoxyethyl modified sugar moiety.

"3' target site" or "3' stop site" refers to the nucleotide of a target nucleic acid which is complementary to the 3'-most nucleotide of a particular antisense compound.

"5' target site" or "5' start site" refers to the nucleotide of a target nucleic acid which is complementary to the 5'-most nucleotide of a particular antisense compound.

"5-methylcytosine" means a cytosine modified with a methyl group attached to the 5' position. A 5-methylcytosine is a modified nucleobase.

"About" means within ±10% of a value. For example, if it is stated, "a marker may be increased by about 50%", it is implied that the marker may be increased between 45%-55%.

"Active pharmaceutical agent" means the substance or substances in a pharmaceutical composition that provide a therapeutic benefit when administered to an individual. For example, in certain embodiments an antisense oligonucleotide targeted to AGPAT5 is an active pharmaceutical agent.

"Active target region" or "target region" means a region to which one or more active antisense compounds is targeted.

"Active antisense compounds" means antisense compounds that reduce target nucleic acid levels or protein levels.

"Adipogenesis" means the development of fat cells from preadipocytes. "Lipogenesis" means the production or formation of fat, either fatty degeneration or fatty infiltration.

"Adiposity" or "Obesity" refers to the state of being obese or an excessively high amount of body fat or adipose tissue in relation to lean body mass. The amount of body fat includes concern for both the distribution of fat throughout the body and the size and mass of the adipose tissue deposits. Body fat distribution can be estimated by skin-fold measures, waist-to-hip circumference ratios, or techniques such as ultrasound, computed tomography, or magnetic resonance imaging. According to the Center for Disease Control and Prevention, individuals with a body mass index (BMI) of 30 or more are considered obese. The term "Obesity" as used herein includes conditions where there is an increase in body fat beyond the physical requirement as a result of excess accumulation of adipose tissue in the body. The term "obesity" includes, but is not limited to, the following conditions: adult-onset obesity; alimentary obesity; endogenous or metabolic obesity; endocrine obesity; familial obesity; hyperinsulinar obesity; hyperplastic-hypertrophic obesity; hypogonadal obesity; hypothyroid obesity; lifelong obesity; morbid obesity and exogenous obesity.

"Administered concomitantly" refers to the co-administration of two agents in any manner in which the pharmacological effects of both manifest in the patient at the same time. Concomitant administration does not require that both agents be administered in a single pharmaceutical composition, in the same dosage form, or by the same route of administration. The effects of both agents need not manifest themselves at the same time. The effects need only be overlapping for a period of time and need not be coextensive.

"Administering" means providing an agent to an animal, and includes, but is not limited to, administering by a medical professional and self-administering.

"Agent" means an active substance that can provide a therapeutic benefit when administered to an animal. "First Agent" means a therapeutic compound of the invention. For example, a first agent can be an antisense oligonucleotide targeting AGPAT5. "Second agent" means a second therapeutic compound of the invention (e.g. a second antisense oligonucleotide targeting AGPAT5) and/or a non-AGPAT5 therapeutic compound.

"Amelioration" refers to a lessening of at least one indicator, sign, physiological marker or symptom of an associated disease, disorder, or condition. The severity of indicators can be determined by subjective or objective measures, which are known to those skilled in the art.

"Antibody" refers to a molecule that reacts specifically with an antigen in some way, where the antibody and the antigen are each defined in terms of the other. Antibody may refer to a complete antibody molecule or any fragment or region thereof, such as the heavy chain, the light chain, Fab region, and Fc region.

"AGPAT5" means any nucleic acid or protein of AGPAT5.

"AGPAT5 expression" means the level of mRNA transcribed from the gene encoding AGPAT5 or the level of protein translated from the mRNA. AGPAT5 expression can be determined by art known methods such as a Northern or Western blot.

"AGPAT5 nucleic acid" means any nucleic acid encoding AGPAT5. For example, in certain embodiments, an AGPAT5 nucleic acid includes a DNA sequence encoding AGPAT5, a RNA sequence transcribed from DNA encoding AGPAT5 (including genomic DNA comprising introns and exons), and a mRNA sequence encoding AGPAT5. "AGPAT5 mRNA" means a mRNA encoding an AGPAT5 protein.

"Animal" refers to a human or non-human animal, including, but not limited to, mice, rats, rabbits, dogs, cats, pigs, and non-human primates, including, but not limited to, monkeys and chimpanzees.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is capable of undergoing hybridization to a target nucleic acid through hydrogen bonding.

"Antisense inhibition" means reduction of target nucleic acid levels or target protein levels in the presence of an antisense compound complementary to a target nucleic acid compared to target nucleic acid levels or target protein levels in the absence of the antisense compound.

"Antisense oligonucleotide" means a single-stranded oligonucleotide having a nucleobase sequence that permits hybridization to a corresponding region or segment of a target nucleic acid.

"Atherosclerosis" means a hardening of the arteries affecting large and medium-sized arteries and is characterized by the presence of fatty deposits. The fatty deposits are called "atheromas" or "plaques," which consist mainly of cholesterol and other fats, calcium and scar tissue, and damage the lining of arteries.

"Bicyclic sugar" means a furosyl ring modified by the bridging of two non-geminal ring atoms. A bicyclic sugar is a modified sugar.

"Bicyclic nucleic acid" or "BNA" refers to a nucleoside or nucleotide wherein the furanose portion of the nucleoside or nucleotide includes a bridge connecting two carbon atoms on the furanose ring, thereby forming a bicyclic ring system.

"Cap structure" or "terminal cap moiety" means chemical modifications, which have been incorporated at either terminus of an antisense compound.

"Cardiovascular disease" or "cardiovascular disorder" refers to a group of conditions related to the heart, blood vessels, or the circulation. Examples of cardiovascular diseases or disorders include, but are not limited to, aneurysm, angina, arrhythmia, atherosclerosis, cerebrovascular disease (stroke), coronary heart disease, hypertension, dyslipidemia, hyperlipidemia, and hypercholesterolemia.

"Cardiometabolic disease, disorder or condition" are diseases, disorders and conditions concerning both the cardiovascular system and the metabolic system. Examples of cardiometabolic diseases or disorders include, but are not limited to, diabetes, obesity, insulin resistance and dyslipidemias.

"Chemically distinct region" refers to a region of an antisense compound that is in some way chemically different than another region of the same antisense compound. For example, a region having 2'-O-methoxyethyl nucleotides is chemically distinct from a region having nucleotides without 2'-O-methoxyethyl modifications.

"Chimeric antisense compound" means an antisense compound that has at least two chemically distinct regions.

"Co-administration" means administration of two or more agents to an individual. The two or more agents can be in a single pharmaceutical composition, or can be in separate pharmaceutical compositions. Each of the two or more agents can be administered through the same or different routes of administration. Co-administration encompasses parallel or sequential administration.

"Cholesterol" is a sterol molecule found in the cell membranes of all animal tissues. Cholesterol must be transported in an animal's blood plasma by lipoproteins including very low density lipoprotein (VLDL), intermediate density lipoprotein (IDL), low density lipoprotein (LDL), and high density lipoprotein (HDL). "Plasma cholesterol" refers to the sum of all lipoproteins (VDL, IDL, LDL, HDL) esterified and/or non-esterified cholesterol present in the plasma or serum.

"Cholesterol absorption inhibitor" means an agent that inhibits the absorption of exogenous cholesterol obtained from diet.

"Complementarity" means the capacity for pairing between nucleobases of a first nucleic acid and a second nucleic acid. In certain embodiments, complementarity between the first and second nucleic acid may be between two DNA strands, between two RNA strands, or between a DNA and an RNA strand. In certain embodiments, some of the nucleobases on one strand are matched to a complementary hydrogen bonding base on the other strand. In certain embodiments, all of the nucleobases on one strand are matched to a complementary hydrogen bonding base on the other strand. In certain embodiments, a first nucleic acid is an antisense compound and a second nucleic acid is a target nucleic acid. In certain such embodiments, an antisense oligonucleotide is a first nucleic acid and a target nucleic acid is a second nucleic acid.

"Contiguous nucleobases" means nucleobases immediately adjacent to each other.

"Coronary heart disease (CHD)" means a narrowing of the small blood vessels that supply blood and oxygen to the heart, which is often a result of atherosclerosis.

"Deoxyribonucleotide" means a nucleotide having a hydrogen at the 2' position of the sugar portion of the nucleotide. Deoxyribonucleotides may be modified with any of a variety of substituents.

"Diabetes mellitus" or "diabetes" is a syndrome characterized by disordered metabolism and abnormally high blood sugar (hyperglycemia) resulting from insufficient levels of insulin or reduced insulin sensitivity. The characteristic symptoms are excessive urine production (polyuria) due to high blood glucose levels, excessive thirst and increased fluid intake (polydipsia) attempting to compensate for increased urination, blurred vision due to high blood glucose effects on the eye's optics, unexplained weight loss, and lethargy.

"Diabetic dyslipidemia" or "type 2 diabetes with dyslipidemia" means a condition characterized by Type 2 diabetes, reduced HDL-C, elevated triglycerides, and elevated small, dense LDL particles.

"Diluent" means an ingredient in a composition that lacks pharmacological activity, but is pharmaceutically necessary or desirable. For example, the diluent in an injected composition can be a liquid, e.g. saline solution.

"Dyslipidemia" refers to a disorder of lipid and/or lipoprotein metabolism, including lipid and/or lipoprotein overproduction or deficiency. Dyslipidemias may be manifested by elevation of lipids such as cholesterol and triglycerides as well as lipoproteins such as low-density lipoprotein (LDL) cholesterol.

"Dosage unit" means a form in which a pharmaceutical agent is provided, e.g. pill, tablet, or other dosage unit known in the art. In certain embodiments, a dosage unit is a vial containing lyophilized antisense oligonucleotide. In certain embodiments, a dosage unit is a vial containing reconstituted antisense oligonucleotide.

"Dose" means a specified quantity of a pharmaceutical agent provided in a single administration, or in a specified time period. In certain embodiments, a dose can be administered in one, two, or more boluses, tablets, or injections. For example, in certain embodiments where subcutaneous administration is desired, the desired dose requires a volume not easily accommodated by a single injection, therefore, two or more injections can be used to achieve the desired dose. In certain embodiments, the pharmaceutical agent is administered by infusion over an extended period of time or continuously. Doses can be stated as the amount of pharmaceutical agent per hour, day, week, or month. Doses can be expressed as mg/kg or g/kg.

"Effective amount" or "therapeutically effective amount" means the amount of active pharmaceutical agent sufficient to effectuate a desired physiological outcome in an individual in need of the agent. The effective amount can vary among individuals depending on the health and physical condition of the individual to be treated, the taxonomic group of the individuals to be treated, the formulation of the composition, assessment of the individual's medical condition, and other relevant factors.

"Fully complementary" or "100% complementary" means each nucleobase of a nucleobase sequence of a first nucleic acid has a complementary nucleobase in a second nucleobase sequence of a second nucleic acid. In certain embodiments, a first nucleic acid is an antisense compound and a target nucleic acid is a second nucleic acid.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region can be referred to as a "gap segment" and the external regions can be referred to as "wing segments."

"Glucose" is a monosaccharide used by cells as a source of energy and metabolic intermediate. "Plasma glucose" refers to glucose present in the plasma.

"High density lipoprotein-C (HDL-C)" means cholesterol associated with high density lipoprotein particles. Concentration of HDL-C in serum (or plasma) is typically quantified in mg/dL or nmol/L. "serum HDL-C" and "plasma HDL-C" mean HDL-C in serum and plasma, respectively.

"HMG-CoA reductase inhibitor" means an agent that acts through the inhibition of the enzyme HMG-CoA reductase, such as atorvastatin, rosuvastatin, fluvastatin, lovastatin, pravastatin, and simvastatin.

"Hybridization" means the annealing of complementary nucleic acid molecules. In certain embodiments, complementary nucleic acid molecules include an antisense compound and a target nucleic acid.

"Hypercholesterolemia" means a condition characterized by elevated cholesterol or circulating (plasma) cholesterol, LDL-cholesterol and VLDL-cholesterol, as per the guidelines of the Expert Panel Report of the National Cholesterol Educational Program (NCEP) of Detection, Evaluation of Treatment of high cholesterol in adults (see, Arch. Int. Med. (1988) 148, 36-39).

"Hyperlipidemia" or "hyperlipemia" is a condition characterized by elevated serum lipids or circulating (plasma) lipids. This condition manifests an abnormally high concentration of fats. The lipid fractions in the circulating blood are cholesterol, low density lipoproteins, very low density lipoproteins and triglycerides.

"Hypertriglyceridemia" means a condition characterized by elevated triglyceride levels.

"Identifying" or "selecting a subject having a metabolic or cardiovascular disease" means identifying or selecting a subject having been diagnosed with a metabolic disease, a cardiovascular disease, or a metabolic syndrome; or, identifying or selecting a subject having any symptom of a metabolic disease, cardiovascular disease, or metabolic syndrome including, but not limited to, hypercholesterolemia, hyperglycemia, hyperlipidemia, hypertriglyceridemia, hypertension, increased insulin resistance, decreased insulin sensitivity, above normal body weight, and/or above normal body fat content or any combination thereof. Such identification may be accomplished by any method, including but not limited to, standard clinical tests or assessments, such as measuring serum or circulating (plasma) cholesterol, measuring serum or circulating (plasma) blood-glucose, measuring serum or circulating (plasma) triglycerides, measuring blood-pressure, measuring body fat content, measuring body weight, and the like.

"Identifying" or "selecting a diabetic subject" means identifying or selecting a subject having been identified as diabetic or identifying or selecting a subject having any symptom or physiological marker of diabetes (type 1 or type 2) such as, but not limited to, having a fasting glucose of at least 110 mg/dL, glycosuria, polyuria, polydipsia, increased insulin resistance, and/or decreased insulin sensitivity.

"Identifying" or "selecting an obese subject" means identifying or selecting a subject having been diagnosed as obese or identifying or selecting a subject with a BMI over 30 and/or a waist circumference of greater than 102 cm in men or greater than 88 cm in women.

"Identifying" or "selecting a subject having dyslipidemia" means identifying or selecting a subject diagnosed with a disorder of lipid and/or lipoprotein metabolism, including lipid and/or lipoprotein overproduction or deficiency. Dyslipidemias may be manifested by elevation of lipids such as cholesterol and triglycerides as well as lipoproteins such as low-density lipoprotein (LDL) cholesterol.

"Identifying" or "selecting" a subject having increased adiposity" means identifying or selecting a subject having an increased amount of body fat (or adiposity) that includes concern for one or both the distribution of fat throughout the body and the size and mass of the adipose tissue deposits. Body fat distribution can be estimated by skin-fold measures, waist-to-hip circumference ratios, or techniques such as ultrasound, computer tomography, or magnetic resonance imaging. According to the Center for Disease Control and Prevention, individuals with a body mass index (BMI) of 30 or more are considered obese.

"Immediately adjacent" means there are no intervening elements between the immediately adjacent elements.

"Individual" or "subject" or "animal" means a human or non-human animal selected for treatment or therapy.

"Inhibiting the expression or activity" refers to a reduction or blockade of the expression or activity and does not necessarily indicate a total elimination of expression or activity.

"Insulin resistance" or "IR" is defined as the condition in which normal amounts of insulin are inadequate to produce a normal insulin response from cells, e.g., fat, muscle and/or liver cells. Insulin resistance in fat cells results in hydrolysis of stored triglycerides, which elevates free fatty acids in the blood plasma. Insulin resistance in muscle reduces glucose uptake whereas insulin resistance in liver reduces glucose storage, with both effects serving to elevate blood glucose. High plasma levels of insulin and glucose due to insulin resistance often leads to metabolic syndrome and type 2 diabetes.

"Insulin sensitivity" is a measure of how effectively an individual processes glucose. An individual having high insulin sensitivity effectively processes glucose whereas an individual with low insulin sensitivity does not effectively process glucose.

"Internucleoside linkage" refers to the chemical bond between nucleosides.

"Intravenous administration" means administration into a vein.

"Linked nucleosides" means adjacent nucleosides which are bonded together.

"Lipid-lowering" means a reduction in one or more lipids in a subject. Lipid-lowering can occur with one or more doses over time.

"Lipid-lowering agent" means an agent, for example, an AGPAT5-specific modulator, provided to a subject to achieve a lowering of lipids in the subject. For example, in certain embodiments, a lipid-lowering agent is provided to a subject to reduce one or more of apoB, apoC-III, total cholesterol, LDL-C, VLDL-C, IDL-C, non-HDL-C, triglycerides, small dense LDL particles, and Lp(a) in a subject.

"Lipid-lowering therapy" means a therapeutic regimen provided to a subject to reduce one or more lipids in a subject. In certain embodiments, a lipid-lowering therapy is provided to reduce one or more of apoB, apoC-III, total cholesterol, LDL-C, VLDL-C, IDL-C, non-HDL-C, triglycerides, small dense LDL particles, and Lp(a) in a subject.

"Lipoprotein", such as VLDL, LDL and HDL, refers to a group of proteins found in the serum, plasma and lymph and are important for lipid transport. The chemical composition of each lipoprotein differs in that the HDL has a higher proportion of protein versus lipid, whereas the VLDL has a lower proportion of protein versus lipid.

"Low density lipoprotein-cholesterol (LDL-C)" means cholesterol carried in low density lipoprotein particles. Concentration of LDL-C in serum (or plasma) is typically quantified in mg/dL or nmol/L. "Serum LDL-C" and "plasma LDL-C" mean LDL-C in the serum and plasma, respectively.

"Major risk factors" refers to factors that contribute to a high risk for a particular disease or condition. In certain embodiments, major risk factors for coronary heart disease include, without limitation, cigarette smoking, hypertension, low HDL, family history of coronary heart disease, age, and other factors disclosed herein. In certain embodiments, major risk factors for Type 2 diabetes include, without limitation, obesity, sedentary lifestyle, hypertension, family history of diabetes, age, low HDL, high TG and other factors.

"Metabolic disorder" or "metabolic disease" refers to a condition characterized by an alteration or disturbance in metabolic function. "Metabolic" and "metabolism" are terms well known in the art and generally include the whole range of biochemical processes that occur within a living organism. Metabolic disorders include, but are not limited to, hyperglycemia, prediabetes, diabetes (type 1 and type 2), obesity, insulin resistance, metabolic syndrome, non-alcoholic fatty liver disease (NAFLD), nonalcoholic steatohepatitis (NASH), and dyslipidemia due to type 2 diabetes.

"Metabolic syndrome" means a condition characterized by a clustering of lipid and non-lipid cardiovascular risk factors of metabolic origin. In certain embodiments, metabolic syndrome is identified by the presence of any 3 of the following factors: waist circumference of greater than 102 cm in men or greater than 88 cm in women; serum triglyceride of at least 150 mg/dL; HDL-C less than 40 mg/dL in men or less than 50 mg/dL in women; blood pressure of at least 130/85 mmHg; and fasting glucose of at least 110 mg/dL. These determinants can be readily measured in clinical practice (JAMA, 2001, 285: 2486-2497).

"Mismatch" or "non-complementary nucleobase" refers to the case when a nucleobase of a first nucleic acid is not capable of pairing with the corresponding nucleobase of a second or target nucleic acid.

"Mixed dyslipidemia" means a condition characterized by elevated cholesterol and elevated triglycerides.

"Modified internucleoside linkage" refers to a substitution or any change from a naturally occurring internucleoside bond (i.e. a phosphodiester internucleoside bond).

"Modified nucleobase" refers to any nucleobase other than adenine, cytosine, guanine, thymidine, or uracil. An "unmodified nucleobase" means the purine bases adenine (A) and guanine (G), and the pyrimidine bases thymine (T), cytosine (C), and uracil (U).

"Modified nucleoside" means a nucleoside having, independently, one or more modified sugar moiety or modified nucleobase.

"Modified nucleotide" means a nucleotide having, independently, one or more modified sugar moiety, modified internucleoside linkage, or modified nucleobase. A "modified nucleoside" means a nucleoside having, independently, one or more modified sugar moieties or modified nucleobases.

"Modified oligonucleotide" means an oligonucleotide comprising at least one modified nucleotide.

"Modified sugar" refers to a substitution or change from a natural sugar. Representative modified sugars include 2'-O-alkyl sugars (such as 2'-O-methoxyethyl sugars and 2'-O-methyl sugars), 2'-amino sugars, 2'-fluoro sugars, 4'-thio sugars, cyclopentyl or cyclohexyl sugar analogs, and bicyclic sugars, such as a locked nucleic acid ("LNA"), as well as sugars modified with a constrained ethyl, a 3'-fluoro-HNA, a 4'-CH(CH$_3$)—O-2' bridge, or a 4'-(CH$_2$)$_n$—O-2' bridge, wherein n is 1 or 2, but the term "modified sugar" should be understood to include any suitable replacement for a natural sugar in a nucleic acid sequence.

"Modulating" refers to changing or adjusting a feature in a cell, tissue, organ or organism. For example, modulating AGPAT5 mRNA can mean to increase or decrease the level of AGPAT5 mRNA and/or AGPAT5 protein in a cell, tissue, organ or organism. Modulating AGPAT5 mRNA and/or protein can lead to an increase or decrease in insulin resistance or insulin sensitivity in a cell, tissue, organ or organism. A "modulator" effects the change in the cell, tissue, organ or organism. For example, an AGPAT5 antisense oligonucleotide can be a modulator that increases or decreases the amount of AGPAT5 mRNA and/or AGPAT5 protein in a cell, tissue, organ or organism.

"Motif" means the pattern of chemically distinct regions in an antisense compound.

"MTP inhibitor" means an agent that inhibits the enzyme microsomal triglyceride transfer protein.

"Naturally occurring internucleoside linkage" means a 3' to 5' phosphodiester linkage.

"Natural sugar moiety" means a sugar found in DNA (2'-H) or RNA (2'-OH).

"Non-alcoholic fatty liver disease" or "NAFLD" means a condition characterized by fatty inflammation of the liver that is not due to excessive alcohol use (for example, alcohol consumption of over 20 g/day). In certain embodiments, NAFLD is related to insulin resistance and metabolic syndrome. NAFLD encompasses a disease spectrum ranging from simple triglyceride accumulation in hepatocytes (hepatic steatosis) to hepatic steatosis with inflammation (steatohepatitis), fibrosis, and cirrhosis.

"Nonalcoholic steatohepatitis" or "NASH" occurs from progression of NAFLD beyond deposition of triglycerides. A "second hit" capable of inducing necrosis, inflammation, and fibrosis is required for development of NASH. Candidates for the second-hit can be grouped into broad categories: factors causing an increase in oxidative stress and factors promoting expression of proinflammatory cytokines. It has been suggested that increased liver triglycerides lead to increased oxidative stress in hepatocytes of animals and humans, indicating a potential cause-and-effect relationship between hepatic triglyceride accumulation, oxidative stress, and the progression of hepatic steatosis to NASH (Browning and Horton, *J Clin Invest*, 2004, 114, 147-152). Hypertriglyceridemia and hyperfattyacidemia can cause triglyceride accumulation in peripheral tissues (Shimamura et al., *Biochem Biophys Res Commun*, 2004, 322, 1080-1085).

"Nucleic acid" refers to molecules composed of monomeric nucleotides. A nucleic acid includes ribonucleic acids (RNA), deoxyribonucleic acids (DNA), single-stranded nucleic acids, double-stranded nucleic acids, small interfering ribonucleic acids (siRNA), and microRNAs (miRNA). A nucleic acid can also comprise a combination of these elements in a single molecule.

"Nucleobase" means a heterocyclic moiety capable of pairing with a base of another nucleic acid.

"Nucleobase sequence" means the order of contiguous nucleobases independent of any sugar, linkage, or nucleobase modification.

"Nucleoside" means a nucleobase linked to a sugar.

"Nucleoside mimetic" includes those structures used to replace the sugar or the sugar and the base and not necessarily the linkage at one or more positions of an oligomeric compound such as for example nucleoside mimetics having morpholino, cyclohexenyl, cyclohexyl, tetrahydropyranyl, bicyclo or tricyclo sugar mimetics e.g. non furanose sugar units.

"Nucleotide" means a nucleoside having a phosphate group covalently linked to the sugar portion of the nucleoside.

"Nucleotide mimetic" includes those structures used to replace the nucleoside and the linkage at one or more positions of an oligomeric compound such as for example peptide nucleic acids or morpholinos (morpholinos linked by —N(H)—C(=O)—O— or other non-phosphodiester linkage).

"Oligomeric compound" or "oligomer" refers to a polymeric structure comprising two or more sub-structures and capable of hybridizing to a region of a nucleic acid molecule. In certain embodiments, oligomeric compounds are oligonucleosides. In certain embodiments, oligomeric compounds are oligonucleotides. In certain embodiments, oligomeric compounds are antisense compounds. In certain embodiments, oligomeric compounds are antisense oligonucleotides. In certain embodiments, oligomeric compounds are chimeric oligonucleotides.

"Oligonucleotide" means a polymer of linked nucleosides each of which can be modified or unmodified, independent one from another.

"Parenteral administration" means administration by a manner other than through the digestive tract. Parenteral administration includes topical administration, subcutaneous administration, intravenous administration, intramuscular administration, intraarterial administration, intraperitoneal administration, or intracranial administration, e.g. intrathecal or intracerebroventricular administration. Administration can be continuous, or chronic, or short or intermittent.

"Peptide" means a molecule formed by linking at least two amino acids by amide bonds. Peptide refers to polypeptides and proteins.

"Pharmaceutical agent" means a substance that provides a therapeutic benefit when administered to an individual. For example, in certain embodiments, an antisense oligonucleotide targeted to AGPAT5 is pharmaceutical agent.

"Pharmaceutical composition" means a mixture of substances suitable for administering to an individual. For example, a pharmaceutical composition can comprise one or more active agents and a sterile aqueous solution.

"Pharmaceutically acceptable carrier" means a medium or diluent that does not interfere with the structure or function of the oligonucleotide. Certain, of such carries enable pharmaceutical compositions to be formulated as, for example, tablets, pills, dragees, capsules, liquids, gels, syrups, slurries, suspension and lozenges for the oral ingestion by a subject. Certain of such carriers enable pharmaceutical compositions to be formulated for injection or infusion. For example, a pharmaceutically acceptable carrier can be a sterile aqueous solution.

"Pharmaceutically acceptable salts" means physiologically and pharmaceutically acceptable salts of antisense compounds, i.e., salts that retain the desired biological activity of the parent oligonucleotide and do not impart undesired toxicological effects thereto.

"Phosphorothioate linkage" means a linkage between nucleosides where the phosphodiester bond is modified by replacing one of the non-bridging oxygen atoms with a sulfur atom. A phosphorothioate linkage is a modified internucleoside linkage.

"Portion" means a defined number of contiguous (i.e. linked) nucleobases of a nucleic acid. In certain embodiments, a portion is a defined number of contiguous nucleobases of a target nucleic acid. In certain embodiments, a portion is a defined number of contiguous nucleobases of an antisense compound.

"Prevent" refers to delaying or forestalling the onset or development of a disease, disorder, or condition for a period of time from minutes to indefinitely. Prevent also means reducing risk of developing a disease, disorder, or condition.

"Prodrug" means a therapeutic agent that is prepared in an inactive form that is converted to an active form within the body or cells thereof by the action of endogenous enzymes or other chemicals or conditions.

"Side effects" means physiological responses attributable to a treatment other than the desired effects. In certain embodiments, side effects include injection site reactions, liver function test abnormalities, renal function abnormalities, liver toxicity, renal toxicity, central nervous system abnormalities, myopathies, and malaise. For example, increased aminotransferase levels in serum can indicate liver toxicity or liver function abnormality. For example, increased bilirubin can indicate liver toxicity or liver function abnormality.

"Single-stranded oligonucleotide" means an oligonucleotide which is not hybridized to a complementary strand.

"Specifically hybridizable" refers to an antisense compound having a sufficient degree of complementarity with a target nucleic acid to induce a desired effect, while exhibiting minimal or no effects on non-target nucleic acids under conditions in which specific binding is desired, i.e. under physiological conditions in the case of in vivo assays and therapeutic treatments.

"Statin" means an agent that inhibits the activity of HMG-CoA reductase.

"Subcutaneous administration" means administration just below the skin.

"Targeting" or "targeted" means the process of design and selection of an antisense compound that will specifically hybridize to a target nucleic acid and induce a desired effect.

"Target nucleic acid," "target RNA," and "target RNA transcript" all refer to a nucleic acid capable of being targeted by antisense compounds.

"Target region" is defined as a portion of the target nucleic acid having at least one identifiable structure, function, or characteristic.

"Target segment" means the sequence of nucleotides of a target nucleic acid to which one or more antisense compound is targeted. "5' target site" or "5' start site" refers to the 5'-most nucleotide of a target segment. "3' target site" or "3' stop site" refers to the 3'-most nucleotide of a target segment.

"Therapeutically effective amount" means an amount of an agent that provides a therapeutic benefit to an individual.

"Therapeutic lifestyle change" means dietary and lifestyle changes intended to lower fat/adipose tissue mass and/or cholesterol. Such change can reduce the risk of developing cardiometabolic disease, and may include recommendations for dietary intake of total daily calories, total fat, saturated fat, polyunsaturated fat, monounsaturated fat, carbohydrate, protein, cholesterol, insoluble fiber, as well as recommendations for physical activity.

"Triglyceride" or "TG" means a lipid or neutral fat consisting of glycerol combined with three fatty acid molecules.

"Type 2 diabetes" (also known as "type 2 diabetes mellitus" or "diabetes mellitus, type 2", and formerly called "diabetes mellitus type 2", "non-insulin-dependent diabetes (NIDDM)", "obesity related diabetes", or "adult-onset diabetes") is a metabolic disorder that is primarily characterized by insulin resistance, relative insulin deficiency, and hyperglycemia.

"Treat" refers to administering a pharmaceutical composition to effect an alteration or improvement of a disease, disorder, or condition.

"Unmodified nucleotide" means a nucleotide composed of naturally occurring nucleobases, sugar moieties, and internucleoside linkages. In certain embodiments, an unmodified nucleotide is a RNA nucleotide (i.e. β-D-ribonucleosides) or a DNA nucleotide (i.e. β-D-deoxyribonucleoside).

Certain Embodiments

Certain embodiments provide methods, compounds, and compositions for modulating a cardiometabolic disease, disorder or condition, or a symptom thereof, in an animal by administering a therapeutically effective amount of the compound or composition to the animal, wherein the compound or composition comprises an AGPAT5 modulator. Modulation of AGPAT5 can lead to a decrease of AGPAT5 mRNA and protein expression in order to treat, prevent, ameliorate or delay the cardiometabolic disease, disorder or condition, or a symptom thereof. In certain embodiments, the AGPAT5 modulator is an AGPAT5 specific inhibitor. In certain embodiments, AGPAT5 specific inhibitors are nucleic acids (including antisense compounds), peptides, antibodies, small molecules, and other agents capable of inhibiting the expression of AGPAT5 mRNA and/or AGPAT5 protein.

In certain embodiments disclosed herein, AGPAT5 has the murine sequence as set forth in GENBANK Accession No. NM_026792.3 (incorporated herein as SEQ ID NO: 1) and/or GENBANK Accession No. NT_039455.7 truncated from nucleotides 15844020 to 15885425 (incorporated herein as SEQ ID NO: 2). In certain embodiments disclosed herein, AGPAT5 has the human sequence as set forth in GENBANK Accession No. NM_018361.3 (incorporated herein as SEQ ID NO: 24), GENBANK Accession No. AK310545.1 (incorporated herein as SEQ ID NO: 25) and/or GENBANK Accession No. NT_023736.17 truncated from nucleotides 6554870 to 6610015 (incorporated herein as SEQ ID NO: 26).

Certain embodiments disclosed herein provide compounds or compositions comprising an AGPAT5 modulator. In certain embodiments, the AGPAT5 modulator is an AGPAT5 specific inhibitor. In certain embodiments, AGPAT5 specific inhibitor is a nucleic acid, polypeptide, antibody, small molecules, or other agent capable of inhibiting the expression of AGPAT5. In certain embodiments, the nucleic acid is an antisense compound or composition targeting AGPAT5. In certain embodiments, the antisense compound or composition is single stranded. In certain embodiments, the antisense compound or composition is double stranded. In certain embodiments, the antisense compound or composition targeting AGPAT5 is an oligonucleotide. In certain embodiments, the oligonucleotide is single stranded. In certain embodiments, the oligonucleotide is double stranded. In certain embodiments, the oligonucleotide is a modified oligonucleotide. In certain embodiments, the modified oligonucleotide is single stranded. In certain embodiments, the modified oligonucleotide is double stranded.

Certain embodiments disclosed herein provide an antisense compound or composition comprising a modified oligonucleotide that is 10 to 30 linked nucleosides in length targeted to AGPAT5. The AGPAT5 target can have a nucleobase sequence selected from any one of SEQ ID NOs: 1-2, 24-26. In certain embodiments, the nucleobase sequence of the modified oligonucleotide is at least 70%, 75%, 80%, 85%, 90%, 95% or 100% complementary to the nucleobase sequences recited in any one of SEQ ID NOs: 1-2, 24-26 as measured over the entirety of the modified oligonucleotide. In certain embodiments, the modified oligonucleotide comprises a nucleobase sequence comprising a portion of at least 8, at least 9, at least 10, at least 11, at least 12, at least 13, at least 14, at least 15, or 16 contiguous nucleobases complementary to an equal length portion of SEQ ID NO: 1, 2, 24, 25 or 26.

Certain embodiments disclosed herein provide an antisense compound or composition comprising a modified oligonucleotide that is 10 to 30 linked nucleosides in length wherein the nucleobase sequence of the modified oligonucleotide comprises at least 8, at least 9, at least 10, at least 11, at least 12, at least 13, at least 14, at least 15, or 16 contiguous nucleobases of a sequence recited in any one of SEQ ID NOs: 6-23.

Certain embodiments disclosed herein provide an antisense compound or composition comprising a modified oligonucleotide that is 10 to 30 linked nucleosides in length wherein the nucleobase sequence of the modified oligonucleotide consists of a sequence recited in any one of SEQ ID NOs: 6-23.

In certain embodiments, the modified oligonucleotide consists of 10 to 50, 10 to 30, 12 to 30, 13 to 24, 14 to 24, 15 to 30, 15 to 24, 15 to 20, 15 to 18, 16 to 30, 16 to 24, 16 to 20, 16 to 18, 18 to 24 or 19 to 22 linked nucleosides. In certain embodiments, the modified oligonucleotide consists of 8, 9, 10, 11, 12, 13, 14, 15, 16, 17, 18, 19, 20, 21, 22, 23, 24, 25, 26, 27, 28, 29 or 30 linked nucleosides or a range defined by any two of these values. In certain embodiments, the modified oligonucleotide is 16 linked nucleosides in length. In certain embodiments, the modified oligonucleotide is 20 linked nucleosides in length.

In certain embodiments, at least one internucleoside linkage of said modified oligonucleotide is a modified internucleoside linkage. In certain embodiments, each internucleoside linkage is a phosphorothioate internucleoside linkage.

In certain embodiments, at least one nucleoside of the modified oligonucleotide comprises a modified sugar. In certain embodiments, at least one modified sugar is a bicyclic sugar. In certain embodiments, at least one modified sugar comprises a 2'-O-methoxyethyl, a constrained ethyl, a 3'-fluoro-HNA, a 4'-CH(CH$_3$)—O-2' bridge or a 4'-(CH$_2$)$_n$—O-2' bridge, wherein n is 1 or 2.

In certain embodiments, at least one nucleoside of said modified oligonucleotide comprises a modified nucleobase. In certain embodiments, the modified nucleobase is a 5-methylcytosine.

Certain embodiments disclosed herein provide an antisense compound or composition comprising a modified oligonucleotide with: a) a gap segment consisting of linked deoxynucleosides; b) a 5' wing segment consisting of linked nucleosides; and c) a 3' wing segment consisting of linked nucleosides. The gap segment is positioned between the 5' wing segment and the 3' wing segment and each nucleoside of each wing segment comprises a modified sugar. In certain embodiments, at least one internucleoside linkage is a phosphorothioate linkage. In certain embodiments, and at least one cytosine is a 5-methylcytosine. In certain embodiments, the modified oligonucleotide is 16 linked nucleosides in length. In certain embodiments, the modified oligonucleotide is 20 linked nucleosides in length.

In certain embodiments, the antisense compound or composition comprises a modified oligonucleotide consisting of 10 to 30 linked nucleosides and comprises: a) a gap segment consisting of ten linked deoxynucleosides; b) a 5' wing segment consisting of five linked nucleosides; and c) a 3' wing segment consisting of five linked nucleosides. The gap segment is positioned between the 5' wing segment and the 3' wing segment and each nucleoside of each wing segment comprises a modified sugar. In certain embodiments, at least one internucleoside linkage is a phosphorothioate linkage. In certain embodiments, and at least one cytosine is a 5-methylcytosine. In certain embodiments, the modified oligonucleotide is 16 linked nucleosides in length. In certain embodiments, the modified oligonucleotide is 20 linked nucleosides in length.

Certain embodiments disclosed herein provide antisense compounds or compositions comprising a modified oligonucleotide consisting of 16 linked nucleosides, the modified oligonucleotide having a nucleobase sequence comprising at least 8 contiguous nucleobases of a nucleobase sequence selected from any of SEQ ID NOs: 6-23 and comprising: a) a gap segment consisting of ten linked deoxynucleosides; b) a 5' wing segment consisting of three linked nucleosides; and c) a 3' wing segment consisting of three linked nucleosides. The gap segment is positioned between the 5' wing segment and the 3' wing segment with each nucleoside of each wing segment comprising a 4'-CH(CH$_3$)—O-2' sugar. In certain embodiments, at least one internucleoside linkage is a phosphorothioate linkage. In certain embodiments, at least one cytosine is a 5-methylcytosine.

Certain embodiments disclosed herein provide antisense compounds or compositions comprising a modified oligonucleotide consisting of 16 linked nucleosides, the modified oligonucleotide having a nucleobase sequence selected from any of SEQ ID NOs: 6-23 and comprising: a) a gap segment consisting of ten linked deoxynucleosides; b) a 5' wing segment consisting of three linked nucleosides; and c) a 3' wing segment consisting of three linked nucleosides. The gap segment is positioned between the 5' wing segment and the 3' wing segment with each nucleoside of each wing segment comprising a 4'-CH(CH$_3$)—O-2' sugar. In certain embodiments, at least one internucleoside linkage is a phosphorothioate linkage. In certain embodiments, at least one cytosine is a 5-methylcytosine.

In certain embodiments, the antisense compounds or compositions disclosed herein comprise a modified oligonucleotide consisting of 16 linked nucleosides having a nucleobase sequence comprising at least 8 contiguous nucleobases complementary to an equal length portion of a sequence selected from any of SEQ ID NOs: 1-2, 24-26 wherein the modified oligonucleotide comprises: a) a gap segment consisting of ten linked deoxynucleosides; b) a 5' wing segment consisting of three linked nucleosides; and c) a 3' wing segment consisting of three linked nucleosides. The gap segment is positioned between the 5' wing segment and the 3' wing segment and each nucleoside of each wing segment comprises a modified sugar. In certain embodiments, at least one internucleoside linkage is a phosphorothioate linkage. In certain embodiments, at least one cytosine is a 5-methylcytosine.

In certain embodiments, the antisense compounds or compositions disclosed herein comprise a modified oligonucleotide consisting of 20 linked nucleosides having a nucleobase sequence comprising at least 8 contiguous nucleobases complementary to an equal length portion of a sequence selected from any of SEQ ID NOs: 1-2, 24-26 wherein the modified oligonucleotide comprises: a) a gap segment consisting of ten linked deoxynucleosides; b) a 5' wing segment consisting of five linked nucleosides; and c) a 3' wing segment consisting of five linked nucleosides. The gap segment is positioned between the 5' wing segment and the 3' wing segment and each nucleoside of each wing segment comprises a modified sugar. In certain embodiments, at least one internucleoside linkage is a phosphorothioate linkage. In certain embodiments, at least one cytosine is a 5-methylcytosine.

In certain embodiments, the modified oligonucleotide consists of 20 linked nucleosides and comprises: a) a gap segment consisting of ten linked deoxynucleosides; b) a 5' wing segment consisting of five linked nucleosides; and c) a 3' wing segment consisting of five linked nucleosides. The gap segment is positioned between the 5' wing segment and the 3' wing segment and each nucleoside of each wing segment comprises a 2'-O-methoxyethyl sugar, each internucleoside linkage is a phosphorothioate linkage and each cytosine residue is a 5-methylcytosine.

Certain embodiments disclosed herein provide a method of reducing AGPAT5 expression in an animal comprising administering to the animal a compound or composition comprising an AGPAT5 specific inhibitor. In certain embodiments, the AGPAT5 specific inhibitor is a nucleic acid, peptide, antibody, small molecule or other agent capable of inhibiting the expression of AGPAT5. In certain embodiments, the AGPAT5 specific inhibitor comprises an antisense compound. In certain embodiments, the AGPAT5 specific inhibitor comprises a modified oligonucleotide.

Certain embodiments disclosed herein provide a method of reducing insulin resistance in an animal comprising administering to the animal a compound or composition comprising an AGPAT5 specific inhibitor. In certain embodiments, the AGPAT5 specific inhibitor is a nucleic acid, peptide, antibody, small molecule or other agent capable of inhibiting the expression of AGPAT5. In certain embodiments, the AGPAT5 specific inhibitor comprises an antisense compound. In certain embodiments, the AGPAT5 specific inhibitor comprises a modified oligonucleotide.

Certain embodiments disclosed herein provide a method of increasing insulin sensitivity in an animal comprising administering to the animal a compound or composition comprising an AGPAT5 specific inhibitor. In certain embodiments, the AGPAT5 specific inhibitor is a nucleic acid, peptide, antibody, small molecule or other agent capable of inhibiting the expression of AGPAT5. In certain embodiments, the AGPAT5 specific inhibitor comprises an antisense compound. In certain embodiments, the AGPAT5 specific inhibitor comprises a modified oligonucleotide.

Certain embodiments disclosed herein provide a method of reducing liver triglyceride levels in an animal comprising administering to the animal a compound or composition comprising an AGPAT5 specific inhibitor. In certain embodiments, the AGPAT5 specific inhibitor is a nucleic acid, peptide, antibody, small molecule or other agent capable of inhibiting the expression of AGPAT5. In certain embodiments, the AGPAT5 specific inhibitor comprises an antisense compound. In certain embodiments, the AGPAT5 specific inhibitor comprises a modified oligonucleotide.

Certain embodiments disclosed herein provide a method of reducing insulin levels in an animal comprising administering to the animal a compound or composition comprising an AGPAT5 specific inhibitor. In certain embodiments, the AGPAT5 specific inhibitor is a nucleic acid, peptide, antibody, small molecule or other agent capable of inhibiting the expression of AGPAT5. In certain embodiments, the AGPAT5 specific inhibitor comprises an antisense compound. In certain embodiments, the AGPAT5 specific inhibitor comprises a modified oligonucleotide.

Certain embodiments disclosed herein provide a method of increasing glucose tolerance in an animal comprising administering to the animal a compound or composition comprising an AGPAT5 specific inhibitor. In certain embodiments, the AGPAT5 specific inhibitor is a nucleic acid, peptide, antibody, small molecule or other agent capable of inhibiting the expression of AGPAT5. In certain embodiments, the AGPAT5 specific inhibitor comprises an antisense compound. In certain embodiments, the AGPAT5 specific inhibitor comprises a modified oligonucleotide.

Certain embodiments disclosed herein provide a method of increasing glucose clearance in an animal comprising administering to the animal a compound or composition comprising an AGPAT5 specific inhibitor. In certain embodiments, the AGPAT5 specific inhibitor is a nucleic acid, peptide, antibody, small molecule or other agent capable of inhibiting the expression of AGPAT5. In certain embodiments, the AGPAT5 specific inhibitor comprises an antisense compound. In certain embodiments, the AGPAT5 specific inhibitor comprises a modified oligonucleotide.

Certain embodiments disclosed herein provide a method of reducing the ratio of fat to body weight in an animal comprising administering to the animal a compound or composition comprising an AGPAT5 specific inhibitor. In certain embodiments, the AGPAT5 specific inhibitor is a nucleic acid, peptide, antibody, small molecule or other agent capable of inhibiting the expression of AGPAT5. In certain embodiments, the AGPAT5 specific inhibitor comprises an antisense compound. In certain embodiments, the AGPAT5 specific inhibitor comprises a modified oligonucleotide.

Certain embodiments disclosed herein provide a method of ameliorating metabolic and/or cardiovascular disease in an animal comprising administering to the animal a therapeutically effective amount of a compound or composition comprising an AGPAT5 specific inhibitor. In certain embodiments, the AGPAT5 specific inhibitor is a nucleic acid, peptide, antibody, small molecule or other agent capable of inhibiting the expression of AGPAT5. In certain embodiments, the AGPAT5 specific inhibitor comprises an antisense compound. In certain embodiments, the AGPAT5 specific inhibitor comprises a modified oligonucleotide. In certain embodiments, the therapeutically effective amount of the compound or composition administered to the animal reduces insulin resistance in a diabetic or non-diabetic animal.

Certain embodiments disclosed herein provide a method for treating an animal at risk for a metabolic and/or cardiovascular disease comprising administering to said animal a therapeutically effective amount of a compound or composition comprising an AGPAT5 specific inhibitor. In certain embodiments, the AGPAT5 specific inhibitor is a nucleic acid, peptide, antibody, small molecule or other agent capable of inhibiting the expression of AGPAT5. In certain embodiments, the AGPAT5 specific inhibitor comprises an antisense compound. In certain embodiments, the AGPAT5 specific inhibitor comprises a modified oligonucleotide. In certain embodiments, the therapeutically effective amount of the compound or composition administered to the animal reduces insulin resistance in a pre-diabetic or non-diabetic animal.

In certain embodiments, the metabolic and/or cardiovascular disease is obesity, diabetes, insulin resistance, dyslipidemia, non-alcoholic fatty liver disease (NAFLD), hypertension, hyperglycemia, or metabolic syndrome, or a combination thereof. In certain embodiments, the NAFLD is hepatic steatosis or steatohepatitis. In certain embodiments, the diabetes is type 2 diabetes or type 2 diabetes with dyslipidemia.

In certain embodiments, administering the compound or composition disclosed herein reduces triglyceride levels, insulin levels, insulin resistance levels, glucose levels or a combination thereof. In certain embodiments, the levels are independently reduced by at least 5%, at least 10%, at least 20%, at least 30%, at least 35%, or at least 40%.

In certain embodiments, administering the compound or composition disclosed herein increases glucose tolerance, glucose clearance and/or insulin sensitivity. In certain embodiments, glucose tolerance, glucose clearance and/or insulin sensitivity is increased by at least 5%, at least 10%, at least 20%, at least 30%, at least 35%, or at least 40%.

Certain embodiments provide uses of the compounds and compositions described herein for inhibiting AGPAT5 expression. In certain embodiments, the compounds or compositions inhibit AGPAT5 by at least 5%, at least 10%, at least 20%, at least 30%, at least 35%, at least 40%, at least 45%, at least 50%, at least 55%, at least 60%, at least 65%, at least 70%, at least 75%, at least 80%, at least 85%, at least 90% or at least 95%. In a preferred embodiment, an antisense compound comprising a modified oligonucleotide decreases AGPAT5 by at least 50%. In a preferred embodiment, an antisense compound comprising a modified oligonucleotide decreases AGPAT5 by at least 55%. In a preferred embodiment an antisense compound comprising a modified oligonucleotide decreases AGPAT5 by at least 60%. In a preferred embodiment, an antisense compound comprising a modified oligonucleotide decreases AGPAT5 by at least 65%. In a preferred embodiment, an antisense compound comprising a modified oligonucleotide decreases AGPAT5 by at least 70%. In a preferred embodiment, an antisense compound comprising a modified oligonucleotide decreases AGPAT5 by at least 75%. In a preferred embodiment, an antisense compound comprising a modified oligonucleotide decreases AGPAT5 by at least 80%. In a preferred embodiment, an antisense compound comprising a modified oligonucleotide decreases AGPAT5 by at least 85%. In a preferred embodiment, an antisense compound comprising a modified oligonucleotide decreases AGPAT5 by at least 90%. In a preferred embodiment, an antisense compound comprising a modified oligonucleotide decreases AGPAT5 by at least 95%.

Certain embodiments provide uses of the compounds and compositions described herein for use in therapy. In certain embodiments, the therapy is used in treating, preventing, delaying the onset or slowing progression of a disease related to elevated AGPAT5. In certain embodiments, the disease is a cardiovascular and/or metabolic disease, disorder or condition, or symptom or marker thereof. In certain embodiments, the metabolic and/or cardiovascular disease includes, but is not limited to, obesity, diabetes, insulin resistance, dyslipidemia, hyperglycemia, non-alcoholic fatty liver disease (NAFLD), nonalcoholic steatohepatitis (NASH), metabolic syndrome, high blood pressure, or a combination thereof. The dyslipidemia can be hypertriglyceridemia. The diabetes can be type 2 diabetes or type 2 diabetes with dyslipidemia.

In certain embodiments, the compounds or compositions disclosed herein further comprise a conjugate group. In certain embodiments, the conjugate group is a carbohydrate group. In certain embodiments, the conjugate group is a GalNAc group.

In certain embodiments, the compounds or compositions disclosed herein comprise a salt of the antisense compound. In certain embodiments, the compounds or compositions disclosed herein comprise a salt of the modified oligonucleotide.

In certain embodiments, the compounds or compositions disclosed herein further comprise a pharmaceutically acceptable carrier or diluent.

In certain embodiments, the animal is a human.

In certain embodiments, administration comprises parenteral administration. In certain embodiments, parenteral administration comprises subcutaneous administration.

In certain embodiments, the compounds or compositions disclosed herein are designated as a first agent and the methods or uses disclosed herein further comprise administering a second agent. In certain embodiments, the first agent and the second agent are co-administered. In certain embodiments the first agent and the second agent are co-administered sequentially or concomitantly.

In certain embodiments, the second agent is a glucose-lowering agent. The glucose lowering agent can include, but is not limited to, a therapeutic lifestyle change, PPAR agonist, a dipeptidyl peptidase (IV) inhibitor, a GLP-1 analog, insulin or an insulin analog, an insulin secretagogue, a SGLT2 inhibitor, a human amylin analog, a biguanide, an alpha-glucosidase inhibitor, or a combination thereof. The glucose-lowering agent can include, but is not limited to metformin, sulfonylurea, rosiglitazone, meglitinide, thiazolidinedione, alpha-glucosidase inhibitor or a combination thereof. The sulfonylurea can be acetohexamide, chlorpropamide, tolbutamide, tolazamide, glimepiride, a glipizide, a glyburide, or a gliclazide. The meglitinide can be nateglinide or repaglinide. The thiazolidinedione can be pioglitazone or rosiglitazone. The alpha-glucosidase can be acarbose or miglitol.

In certain embodiments, the second agent is a lipid-lowering therapy. In certain embodiments the lipid lowering therapy can include, but is not limited to, a therapeutic lifestyle change, HMG-CoA reductase inhibitor, cholesterol absorption inhibitor, MTP inhibitor (e.g., a small molecule, polypeptide, antibody or antisense compound targeted to MTP), ApoB inhibitor (e.g., a small molecule, polypeptide, antibody or antisense compound targeted to ApoB), ApoC3 inhibitor (e.g., a small molecule, polypeptide, antibody or antisense compound targeted to ApoC3), PCSK9 inhibitor (e.g., a small molecule, polypeptide, antibody or antisense compound targeted to PCSK9), CETP inhibitor (e.g., a small molecule, polypeptide, antibody or antisense compound targeted to CETP), fibrate, beneficial oil (e.g., krill or fish oils (e.g., Vascepa$^R$), flaxseed oil, or other oils rich in omega-3 fatty acids such as α-linolenic acid (ALA), docosahexaenoic acid (DHA) or eicosapentaenoic acid (EPA)), or any combination thereof. The HMG-CoA reductase inhibitor can be atorvastatin, rosuvastatin, fluvastatin, lovastatin, pravastatin, or simvastatin. The cholesterol absorption inhibitor can be ezetimibe. The fibrate can be fenofibrate, bezafibrate, ciprofibrate, clofibrate, gemfibrozil and the like.

In certain embodiments, use of a compound or composition disclosed herein results in a reduction of lipid levels (e.g., triglyceride levels), insulin resistance levels, glucose levels or a combination thereof. One or more of the levels can be independently reduced by at least 5%, at least 10%, at least 20%, at least 30%, at least 35%, at least 40%, at least 45%, at least 50%, at least 55%, at least 60%, at least 65%, at least 70%, at least 75%, at least 80%, at least 85%, at least 90% or at least 95%. Administering the compound can result in improved insulin sensitivity (e.g., hepatic insulin sensitivity), glucose clearance and/or glucose tolerance by at least 5%, at least 10%, at least 20%, at least 30%, at least 35%, at least 40%, at least 45%, at least 50%, at least 55%, at least 60%, at least 65%, at least 70%, at least 75%, at least 80%, at least 85%, at least 90% or at least 95%. Administering the compound disclosed herein can result in a reduction in insulin, insulin resistance, obesity, glucose, lipids, glucose resistance, cholesterol, or improvement in insulin sensitivity or any combination thereof.

Certain embodiments provide the use of a compound or composition as described herein in the manufacture of a medicament for treating, ameliorating, delaying or preventing one or more diseases, disorders, conditions, symptoms or physiological markers associated with AGPAT5. In certain embodiments, the compound or composition as described herein is used in the manufacture of a medicament for treating, ameliorating, delaying or preventing one or more of a metabolic disease or a cardiovascular disease, or a symptom or physiological marker thereof.

Certain embodiments provide a kit for treating, preventing, delaying, or ameliorating one or more of a metabolic disease or a cardiovascular disease as described herein wherein the kit comprises: a) a compound or composition as described herein; and optionally b) an additional agent or therapy as described herein. The kit can further include instructions or a label for using the kit to treat, prevent, or ameliorate one or more of a metabolic disease or a cardiovascular disease.

Antisense Compounds

Oligomeric compounds include, but are not limited to, oligonucleotides, oligonucleosides, oligonucleotide analogs, oligonucleotide mimetics, antisense compounds, antisense oligonucleotides, and siRNAs. An oligomeric compound can be "antisense" to a target nucleic acid, meaning that is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound targeted to AGPAT5 nucleic acid is 10 to 30 nucleotides in length. In other words, antisense compounds are from 10 to 30 linked nucleobases. In other embodiments, the antisense compound comprises a modified oligonucleotide consisting of 8 to 80, 10 to 80, 12 to 50, 12 to 30, 15 to 30, 18 to 24, 19 to 22, or 20 linked nucleobases. In certain such embodiments, the antisense compound comprises a modified oligonucleotide consisting of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked nucleobases in length, or a range defined by any two of the above values.

In certain embodiments, the antisense compound comprises a shortened or truncated modified oligonucleotide. The shortened or truncated modified oligonucleotide can have a single nucleoside deleted from the 5' end (5' truncation), or alternatively from the 3' end (3' truncation). A shortened or truncated oligonucleotide can have two or more nucleosides deleted from the 5' end, or alternatively can have two or more nucleosides deleted from the 3' end. Alternatively, the deleted nucleosides can be dispersed throughout the modified oligonucleotide, for example, in an antisense compound having one or more nucleosides deleted from the 5' end and one or more nucleoside deleted from the 3' end.

When a single additional nucleoside is present in a lengthened oligonucleotide, the additional nucleoside can be located at the 5', 3' end or central portion of the oligonucleotide. When two or more additional nucleosides are present, the added nucleosides can be adjacent to each other, for example, in an oligonucleotide having two nucleosides added to the 5' end (5' addition), or alternatively to the 3' end (3' addition) or the central portion, of the oligonucleotide. Alternatively, the added nucleosides can be dispersed throughout the antisense compound, for example, in an oligonucleotide having one or more nucleosides added to the 5' end, one or more nucleosides added to the 3' end, and/or one or more nucleosides added to the central portion.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Certain Antisense Compound Motifs and Mechanisms

In certain embodiments, antisense compounds have chemically modified subunits arranged in patterns, or motifs, to confer to the antisense compounds properties such as enhanced inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may confer another desired property e.g., serve as a substrate for the cellular endonuclease RNase H, which cleaves the RNA strand of an RNA:DNA duplex.

Antisense activity may result from any mechanism involving the hybridization of the antisense compound (e.g., oligonucleotide) with a target nucleic acid, wherein the hybridization ultimately results in a biological effect. In certain embodiments, the amount and/or activity of the target nucleic acid is modulated. In certain embodiments, the amount and/or activity of the target nucleic acid is reduced. In certain embodiments, hybridization of the antisense compound to the target nucleic acid ultimately results in target nucleic acid degradation. In certain embodiments, hybridization of the antisense compound to the target nucleic acid does not result in target nucleic acid degradation. In certain such embodiments, the presence of the antisense compound hybridized with the target nucleic acid (occupancy) results in a modulation of antisense activity. In certain embodiments, antisense compounds having a particular chemical motif or pattern of chemical modifications are particularly suited to exploit one or more mechanisms. In certain embodiments, antisense compounds function through more than one mechanism and/or through mechanisms that have not been elucidated. Accordingly, the antisense compounds described herein are not limited by particular mechanism.

Antisense mechanisms include, without limitation, RNase H mediated antisense; RNAi mechanisms, which utilize the RISC pathway and include, without limitation, siRNA, ssRNA and microRNA mechanisms; and occupancy based mechanisms. Certain antisense compounds may act through more than one such mechanism and/or through additional mechanisms.

RNase H-Mediated Antisense

In certain embodiments, antisense activity results at least in part from degradation of target RNA by RNase H. RNase H is a cellular endonuclease that cleaves the RNA strand of an RNA:DNA duplex. It is known in the art that single-stranded antisense compounds which are "DNA-like" elicit RNase H activity in mammalian cells. Accordingly, antisense compounds comprising at least a portion of DNA or DNA-like nucleosides may activate RNase H, resulting in cleavage of the target nucleic acid. In certain embodiments, antisense compounds that utilize RNase H comprise one or more modified nucleosides. In certain embodiments, such antisense compounds comprise at least one block of 1-8 modified nucleosides. In certain such embodiments, the modified nucleosides do not support RNase H activity. In certain embodiments, such antisense compounds are gapmers, as described herein. In certain such embodiments, the gap of the gapmer comprises DNA nucleosides. In certain such embodiments, the gap of the gapmer comprises DNA-like nucleosides. In certain such embodiments, the gap of the gapmer comprises DNA nucleosides and DNA-like nucleosides.

Certain antisense compounds having a gapmer motif are considered chimeric antisense compounds. In a gapmer an internal region having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE and 2'-O—CH$_3$, among others), and bicyclic sugar modified nucleosides (such bicyclic sugar modified nucleosides may include those having a constrained ethyl). In certain embodiments, nucleosides in the wings may include several modified sugar moieties, including, for example 2'-MOE and bicyclic sugar moieties such as constrained ethyl or LNA. In certain embodiments, wings may include several modified and unmodified sugar moieties. In certain embodiments, wings may include various combinations of 2'-MOE nucleosides, bicyclic sugar moieties such as constrained ethyl nucleosides or LNA nucleosides, and 2'-deoxynucleosides.

Each distinct region may comprise uniform sugar moieties, variant, or alternating sugar moieties. The wing-gap-wing motif is frequently described as "X-Y-Z", where "X" represents the length of the 5'-wing, "Y" represents the length of the gap, and "Z" represents the length of the 3'-wing. "X" and "Z" may comprise uniform, variant, or alternating sugar moieties. In certain embodiments, "X" and "Y" may include one or more 2'-deoxynucleosides. "Y" may comprise 2'-deoxynucleosides. As used herein, a gapmer described as "X-Y-Z" has a configuration such that the gap is positioned immediately adjacent to each of the 5'-wing and the 3' wing. Thus, no intervening nucleotides exist between the 5'-wing and gap, or the gap and the 3'-wing. Any of the antisense compounds described herein can have a gapmer motif. In certain embodiments, "X" and "Z" are the same; in other embodiments they are different. In certain embodiments, "Y" is between 8 and 15 nucleosides. X, Y, or Z can be any of 1, 2, 3, 4, 5, 6, 7, 8, 9, 10, 11, 12, 13, 14, 15, 16, 17, 18, 19, 20, 25, 30 or more nucleosides.

In certain embodiments, the antisense compound targeted to an AGPAT5 nucleic acid has a gapmer motif in which the gap consists of 6, 7, 8, 9, 10, 11, 12, 13, 14, 15, or 16 linked nucleosides.

In certain embodiments, the antisense oligonucleotide has a sugar motif described by Formula A as follows: (J)$_m$-(B)$_n$-(J)$_p$-(B)$_r$-(A)$_t$-(D)$_g$-(A)$_v$-(B)$_w$-(J)$_x$-(B)$_y$-(J)$_z$ wherein:
each A is independently a 2'-substituted nucleoside;
each B is independently a bicyclic nucleoside;
each J is independently either a 2'-substituted nucleoside or a 2'-deoxynucleoside;
each D is a 2'-deoxynucleoside;
m is 0-4; n is 0-2; p is 0-2; r is 0-2; t is 0-2; v is 0-2; w is 0-4; x is 0-2; y is 0-2; z is 0-4; g is 6-14; provided that:
at least one of m, n, and r is other than 0;
at least one of w and y is other than 0;
the sum of m, n, p, r, and t is from 2 to 5; and
the sum of v, w, x, y, and z is from 2 to 5.

RNAi Compounds

In certain embodiments, antisense compounds are interfering RNA compounds (RNAi), which include double-stranded RNA compounds (also referred to as short-interfering RNA or siRNA) and single-stranded RNAi compounds (or ssRNA). Such compounds work at least in part through the RISC pathway to degrade and/or sequester a target nucleic acid (thus, include microRNA/microRNA-mimic compounds). In certain embodiments, antisense compounds comprise modifications that make them particularly suited for such mechanisms.

i. ssRNA Compounds

In certain embodiments, antisense compounds including those particularly suited for use as single-stranded RNAi compounds (ssRNA) comprise a modified 5'-terminal end. In certain such embodiments, the 5'-terminal end comprises a modified phosphate moiety. In certain embodiments, such modified phosphate is stabilized (e.g., resistant to degradation/cleavage compared to unmodified 5'-phosphate). In certain embodiments, such 5'-terminal nucleosides stabilize the 5'-phosphorous moiety. Certain modified 5'-terminal nucleosides may be found in the art, for example in WO/2011/139702.

In certain embodiments, the 5'-nucleoside of an ssRNA compound has Formula IIc:

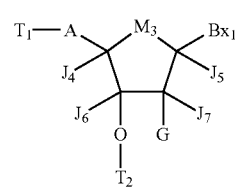

wherein:
T$_1$ is an optionally protected phosphorus moiety;
T$_2$ is an internucleoside linking group linking the compound of Formula IIc to the oligomeric compound;
A has one of the formulas:

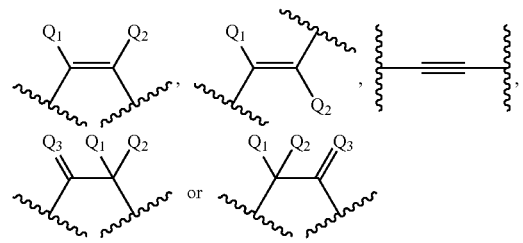

Q$_1$ and Q$_2$ are each, independently, H, halogen, C$_1$-C$_6$ alkyl, substituted C$_1$-C$_6$ alkyl, C$_1$-C$_6$ alkoxy, substituted C$_1$-C$_6$ alkoxy, C$_2$-C$_6$ alkenyl, substituted C$_2$-C$_6$ alkenyl, C$_2$-C$_6$ alkynyl, substituted C$_2$-C$_6$ alkynyl or N(R$_3$)(R$_4$);
Q$_3$ is O, S, N(R$_5$) or C(R$_6$)(R$_7$);
each R$_3$, R$_4$ R$_5$, R$_6$ and R$_7$ is, independently, H, C$_1$-C$_6$ alkyl, substituted C$_1$-C$_6$ alkyl or C$_1$-C$_6$ alkoxy;
M$_3$ is O, S, NR$_{14}$, C(R$_{15}$)(R$_{16}$), C(R$_{15}$)(R$_{16}$)C(R$_{17}$)(R$_{18}$), C(R$_{15}$)=C(R$_{17}$), OC(R$_{15}$)(R$_{16}$) or OC(R$_{15}$)(Bx$_2$);
R$_{14}$ is H, C$_1$-C$_6$ alkyl, substituted C$_1$-C$_6$ alkyl, C$_1$-C$_6$ alkoxy, substituted C$_1$-C$_6$ alkoxy, C$_2$-C$_6$ alkenyl, substituted C$_2$-C$_6$ alkenyl, C$_2$-C$_6$ alkynyl or substituted C$_2$-C$_6$ alkynyl;
R$_{15}$, R$_{16}$, R$_{17}$ and R$_{18}$ are each, independently, H, halogen, C$_1$-C$_6$ alkyl, substituted C$_1$-C$_6$ alkyl, C$_1$-C$_6$ alkoxy, substituted C$_1$-C$_6$ alkoxy, C$_2$-C$_6$ alkenyl, substituted C$_2$-C$_6$ alkenyl, C$_2$-C$_6$ alkynyl or substituted C$_2$-C$_6$ alkynyl;
Bx$_1$ is a heterocyclic base moiety;
or if Bx$_2$ is present then Bx$_2$ is a heterocyclic base moiety and Bx$_1$ is H, halogen, C$_1$-C$_6$ alkyl, substituted C$_1$-C$_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

$J_4$, $J_5$, $J_6$ and $J_7$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

or $J_4$ forms a bridge with one of $J_5$ or $J_7$ wherein said bridge comprises from 1 to 3 linked biradical groups selected from O, S, $NR_{19}$, $C(R_{20})(R_{21})$, $C(R_{20})=C(R_{21})$, $C[=C(R_{20})(R_{21})]$ and $C(=O)$ and the other two of $J_5$, $J_6$ and $J_7$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

each $R_{19}$, $R_{20}$ and $R_{21}$ is, independently, H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

G is H, OH, halogen or $O-[C(R_8)(R_9)]_n-[(C=O)_m-X_1]_j-Z$;

each $R_8$ and $R_9$ is, independently, H, halogen, $C_1$-$C_6$ alkyl or substituted $C_1$-$C_6$ alkyl;

$X_1$ is O, S or $N(E_1)$;

Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to about 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=X_2)N(J_1)(J_2)$;

$X_2$ is O, S or $NJ_3$;

each $J_1$, $J_2$ and $J_3$ is, independently, H or $C_1$-$C_6$ alkyl;

when j is 1 then Z is other than halogen or $N(E_2)(E_3)$; and wherein said oligomeric compound comprises from 8 to 40 monomeric subunits and is hybridizable to at least a portion of a target nucleic acid.

In certain embodiments, $M_3$ is O, CH=CH, $OCH_2$ or $OC(H)(Bx_2)$. In certain embodiments, $M_3$ is O.

In certain embodiments, $J_4$, $J_5$, $J_6$ and $J_7$ are each H. In certain embodiments, $J_4$ forms a bridge with one of $J_5$ or $J_7$.

In certain embodiments, A has one of the formulas:

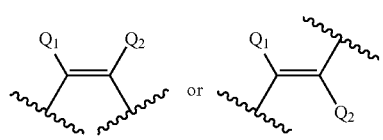

wherein:

$Q_1$ and $Q_2$ are each, independently, H, halogen, $C_1$-$C_6$ alkyl, substituted $C_1$-$C_6$ alkyl, $C_1$-$C_6$ alkoxy or substituted $C_1$-$C_6$ alkoxy. In certain embodiments, $Q_1$ and $Q_2$ are each H. In certain embodiments, $Q_1$ and $Q_2$ are each, independently, H or halogen. In certain embodiments, $Q_1$ and $Q_2$ is H and the other of $Q_1$ and $Q_2$ is F, $CH_3$ or $OCH_3$.

In certain embodiments, $T_1$ has the formula:

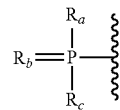

wherein:

$R_a$ and $R_c$ are each, independently, protected hydroxyl, protected thiol, $C_1$-$C_6$ alkyl, substituted $C_1$-$C_6$ alkyl, $C_1$-$C_6$ alkoxy, substituted $C_1$-$C_6$ alkoxy, protected amino or substituted amino; and $R_b$ is O or S. In certain embodiments, $R_b$ is O and $R_a$ and $R_c$ are each, independently, $OCH_3$, $OCH_2CH_3$ or $CH(CH_3)_2$.

In certain embodiments, G is halogen, $OCH_3$, $OCH_2F$, $OCHF_2$, $OCF_3$, $OCH_2CH_3$, $O(CH_2)_2F$, $OCH_2CHF_2$, $OCH_2CF_3$, $OCH_2-CH=CH_2$, $O(CH_2)_2-OCH_3$, $O(CH_2)_2-SCH_3$, $O(CH_2)_2-OCF_3$, $O(CH_2)_3-N(R_{10})(R_{11})$, $O(CH_2)_2-ON(R_{10})(R_{11})$, $O(CH_2)_2-O(CH_2)_2-N(R_{10})(R_{11})$, $OCH_2C(=O)-N(R_{10})(R_{11})$, $OCH_2C(=O)-N(R_{12})-(CH_2)_2-N(R_{10})(R_{11})$ or $O(CH_2)_2-N(R_{12})-C(=NR_{13})[N(R_{10})(R_{11})]$ wherein $R_{10}$, $R_{11}$, $R_{12}$ and $R_{13}$ are each, independently, H or $C_1$-$C_6$ alkyl. In certain embodiments, G is halogen, $OCH_3$, $OCF_3$, $OCH_2CH_3$, $OCH_2CF_3$, $OCH_2-CH=CH_2$, $O(CH_2)_2-OCH_3$, $O(CH_2)_2-O(CH_2)_2-N(CH_3)_2$, $OCH_2C(=O)-N(H)CH_3$, $OCH_2C(=O)-N(H)-(CH_2)_2-N(CH_3)_2$ or $OCH_2-N(H)-C(=NH)NH_2$. In certain embodiments, G is F, $OCH_3$ or $O(CH_2)_2-OCH_3$. In certain embodiments, G is $O(CH_2)_2-OCH_3$.

In certain embodiments, the 5'-terminal nucleoside has Formula IIe:

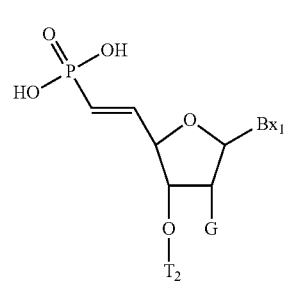

In certain embodiments, antisense compounds, including those particularly suitable for ssRNA comprise one or more type of modified sugar moieties and/or naturally occurring sugar moieties arranged along an oligonucleotide or region thereof in a defined pattern or sugar modification motif. Such motifs may include any of the sugar modifications discussed herein and/or other known sugar modifications.

In certain embodiments, the oligonucleotides comprise or consist of a region having uniform sugar modifications. In certain such embodiments, each nucleoside of the region comprises the same RNA-like sugar modification. In certain embodiments, each nucleoside of the region is a 2'-F nucleoside. In certain embodiments, each nucleoside of the region is a 2'-OMe nucleoside. In certain embodiments, each nucleoside of the region is a 2'-MOE nucleoside. In certain embodiments, each nucleoside of the region is a cEt nucleoside. In certain embodiments, each nucleoside of the region is an LNA nucleoside. In certain embodiments, the uniform region constitutes all or essentially all of the oligonucleotide. In certain embodiments, the region constitutes the entire oligonucleotide except for 1-4 terminal nucleosides.

In certain embodiments, oligonucleotides comprise one or more regions of alternating sugar modifications, wherein the nucleosides alternate between nucleotides having a sugar modification of a first type and nucleotides having a sugar modification of a second type. In certain embodiments, nucleosides of both types are RNA-like nucleosides. In certain embodiments the alternating nucleosides are selected from: 2'-OMe, 2'-F, 2'-MOE, LNA, and cEt. In certain embodiments, the alternating modifications are 2'-F and 2'-OMe. Such regions may be contiguous or may be interrupted by differently modified nucleosides or conjugated nucleosides.

In certain embodiments, the alternating region of alternating modifications each consist of a single nucleoside (i.e., the pattern is $(AB)_xA_y$, wherein A is a nucleoside having a sugar modification of a first type and B is a nucleoside having a sugar modification of a second type; x is 1-20 and y is 0 or 1). In certain embodiments, one or more alternating regions in an alternating motif includes more than a single nucleoside of a type. For example, oligonucleotides may include one or more regions of any of the following nucleoside motifs:

AABBAA;
ABBABB;
AABAAB;
ABBABAABB;
ABABAA;
AABABAB;
ABABAA;
ABBAABBABABAA;
BABBAABBABABAA; or
ABABBAABBABABAA;

wherein A is a nucleoside of a first type and B is a nucleoside of a second type. In certain embodiments, A and B are each selected from 2'-F, 2'-OMe, BNA, and MOE.

In certain embodiments, oligonucleotides having such an alternating motif also comprise a modified 5' terminal nucleoside, such as those of formula IIc or IIe.

In certain embodiments, oligonucleotides comprise a region having a 2-2-3 motif. Such regions comprises the following motif:

$$-(A)_2-(B)_x-(A)_2-(C)_y-(A)_3-$$

wherein: A is a first type of modified nucleoside;
B and C, are nucleosides that are differently modified than A, however, B and C may have the same or different modifications as one another;
x and y are from 1 to 15.

In certain embodiments, A is a 2'-OMe modified nucleoside. In certain embodiments, B and C are both 2'-F modified nucleosides. In certain embodiments, A is a 2'-OMe modified nucleoside and B and C are both 2'-F modified nucleosides.

In certain embodiments, oligonucleosides have the following sugar motif:

$$5'-(Q)-(AB)_xA_y-(D)_z$$

wherein:
Q is a nucleoside comprising a stabilized phosphate moiety. In certain embodiments, Q is a nucleoside having Formula IIc or IIe;
A is a first type of modified nucleoside;
B is a second type of modified nucleoside;
D is a modified nucleoside comprising a modification different from the nucleoside adjacent to it. Thus, if y is 0, then D must be differently modified than B and if y is 1, then D must be differently modified than A. In certain embodiments, D differs from both A and B.

X is 5-15;
Y is 0 or 1;
Z is 0-4.

In certain embodiments, oligonucleosides have the following sugar motif:

$$5'-(Q)-(A)_x-(D)_z$$

wherein:
Q is a nucleoside comprising a stabilized phosphate moiety. In certain embodiments, Q is a nucleoside having Formula IIc or IIe;
A is a first type of modified nucleoside;
D is a modified nucleoside comprising a modification different from A.
X is 11-30;
Z is 0-4.

In certain embodiments A, B, C, and D in the above motifs are selected from: 2'-OMe, 2'-F, 2'-MOE, LNA, and cEt. In certain embodiments, D represents terminal nucleosides. In certain embodiments, such terminal nucleosides are not designed to hybridize to the target nucleic acid (though one or more might hybridize by chance). In certain embodiments, the nucleobase of each D nucleoside is adenine, regardless of the identity of the nucleobase at the corresponding position of the target nucleic acid. In certain embodiments the nucleobase of each D nucleoside is thymine.

In certain embodiments, antisense compounds, including those particularly suited for use as ssRNA comprise modified internucleoside linkages arranged along the oligonucleotide or region thereof in a defined pattern or modified internucleoside linkage motif. In certain embodiments, oligonucleotides comprise a region having an alternating internucleoside linkage motif. In certain embodiments, oligonucleotides comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate internucleoside linkages. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least one block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

Oligonucleotides having any of the various sugar motifs described herein, may have any linkage motif. For example, the oligonucleotides, including but not limited to those described above, may have a linkage motif selected from non-limiting the table below:

| 5' most linkage | Central region | 3'-region |
| --- | --- | --- |
| PS | Alternating PO/PS | 6 PS |
| PS | Alternating PO/PS | 7 PS |
| PS | Alternating PO/PS | 8 PS | ii. siRNA Compounds

In certain embodiments, antisense compounds are double-stranded RNAi compounds (siRNA). In such embodiments, one or both strands may comprise any modification motif described above for ssRNA. In certain embodiments, ssRNA compounds may be unmodified RNA. In certain embodiments, siRNA compounds may comprise unmodified RNA nucleosides, but modified internucleoside linkages.

Several embodiments relate to double-stranded compositions wherein each strand comprises a motif defined by the location of one or more modified or unmodified nucleosides. In certain embodiments, compositions are provided comprising a first and a second oligomeric compound that are fully or at least partially hybridized to form a duplex region and further comprising a region that is complementary to and hybridizes to a nucleic acid target. It is suitable that such a composition comprise a first oligomeric compound that is an antisense strand having full or partial complementarity to a nucleic acid target and a second oligomeric compound that is a sense strand having one or more regions of complementarity to and forming at least one duplex region with the first oligomeric compound.

The compositions of several embodiments modulate gene expression by hybridizing to a nucleic acid target resulting in loss of its normal function. In some embodiments, the target nucleic acid is AGPAT5. In certain embodiment, the degradation of the targeted AGPAT5 is facilitated by an activated RISC complex that is formed with compositions disclosed herein.

Several embodiments are directed to double-stranded compositions wherein one of the strands is useful in, for example, influencing the preferential loading of the opposite strand into the RISC (or cleavage) complex. The compositions are useful for targeting selected nucleic acid molecules and modulating the expression of one or more genes. In some embodiments, the compositions of the present invention hybridize to a portion of a target RNA resulting in loss of normal function of the target RNA.

Certain embodiments are drawn to double-stranded compositions wherein both the strands comprises a hemimer motif, a fully modified motif, a positionally modified motif or an alternating motif. Each strand of the compositions of the present invention can be modified to fulfil a particular role in for example the siRNA pathway. Using a different motif in each strand or the same motif with different chemical modifications in each strand permits targeting the antisense strand for the RISC complex while inhibiting the incorporation of the sense strand. Within this model, each strand can be independently modified such that it is enhanced for its particular role. The antisense strand can be modified at the 5'-end to enhance its role in one region of the RISC while the 3'-end can be modified differentially to enhance its role in a different region of the RISC.

The double-stranded oligonucleotide molecules can be a double-stranded polynucleotide molecule comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof. The double-stranded oligonucleotide molecules can be assembled from two separate oligonucleotides, where one strand is the sense strand and the other is the antisense strand, wherein the antisense and sense strands are self-complementary (i.e. each strand comprises nucleotide sequence that is complementary to nucleotide sequence in the other strand; such as where the antisense strand and sense strand form a duplex or double-stranded structure, for example wherein the double-stranded region is about 15 to about 30, e.g., about 15, 16, 17, 18, 19, 20, 21, 22, 23, 24, 25, 26, 27, 28, 29 or 30 base pairs; the antisense strand comprises nucleotide sequence that is complementary to nucleotide sequence in a target nucleic acid molecule or a portion thereof and the sense strand comprises nucleotide sequence corresponding to the target nucleic acid sequence or a portion thereof (e.g., about 15 to about 25 or more nucleotides of the double-stranded oligonucleotide molecule are complementary to the target nucleic acid or a portion thereof). Alternatively, the double-stranded oligonucleotide is assembled from a single oligonucleotide, where the self-complementary sense and antisense regions of the siRNA are linked by means of a nucleic acid based or non-nucleic acid-based linker(s).

The double-stranded oligonucleotide can be a polynucleotide with a duplex, asymmetric duplex, hairpin or asymmetric hairpin secondary structure, having self-complementary sense and antisense regions, wherein the antisense region comprises nucleotide sequence that is complementary to nucleotide sequence in a separate target nucleic acid molecule or a portion thereof and the sense region having nucleotide sequence corresponding to the target nucleic acid sequence or a portion thereof. The double-stranded oligonucleotide can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siRNA molecule capable of mediating RNAi.

In certain embodiments, the double-stranded oligonucleotide comprises separate sense and antisense sequences or regions, wherein the sense and antisense regions are covalently linked by nucleotide or non-nucleotide linkers molecules as is known in the art, or are alternately non-covalently linked by ionic interactions, hydrogen bonding, van der waals interactions, hydrophobic interactions, and/or stacking interactions. In certain embodiments, the double-stranded oligonucleotide comprises nucleotide sequence that is complementary to nucleotide sequence of a target gene. In another embodiment, the double-stranded oligonucleotide interacts with nucleotide sequence of a target gene in a manner that causes inhibition of expression of the target gene.

As used herein, double-stranded oligonucleotides need not be limited to those molecules containing only RNA, but further encompasses chemically modified nucleotides and non-nucleotides. In certain embodiments, the short interfering nucleic acid molecules lack 2'-hydroxy (2'-OH) containing nucleotides. In certain embodiments short interfering nucleic acids optionally do not include any ribonucleotides (e.g., nucleotides having a 2'-OH group). Such double-stranded oligonucleotides that do not require the presence of ribonucleotides within the molecule to support RNAi can however have an attached linker or linkers or other attached or associated groups, moieties, or chains containing one or more nucleotides with 2'-OH groups. Optionally, double-stranded oligonucleotides can comprise ribonucleotides at about 5, 10, 20, 30, 40, or 50% of the nucleotide positions. As used herein, the term siRNA is meant to be equivalent to other terms used to describe nucleic acid molecules that are capable of mediating sequence specific RNAi, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically modified siRNA, post-transcriptional gene silencing RNA (ptgsRNA), and others. In addition, as used herein, the term RNAi is meant to be equivalent to other terms used to describe sequence specific RNA interference, such as post transcriptional gene silencing, translational inhibition, or epigenetics. For example, double-stranded oligonucleotides can be used to epigenetically silence genes at both the post-transcriptional level and the pre-transcriptional level. In a non-limiting example, epigenetic regulation of gene expression by siRNA molecules of the invention can result from siRNA mediated modification of chromatin structure or methylation pattern to alter gene expression (see, for example, Verdel et al., 2004, Science, 303, 672-676; Pal-Bhadra et al., 2004, Science, 303, 669-672; Allshire, 2002, Science, 297, 1818-1819; Volpe et al., 2002, Science, 297, 1833-1837; Jenuwein, 2002, Science, 297, 2215-2218; and Hall et al., 2002, Science, 297, 2232-2237).

It is contemplated that compounds and compositions of several embodiments provided herein can target AGPAT5 by a dsRNA-mediated gene silencing or RNAi mechanism, including, e.g., "hairpin" or stem-loop double-stranded RNA effector molecules in which a single RNA strand with self-complementary sequences is capable of assuming a double-stranded conformation, or duplex dsRNA effector molecules comprising two separate strands of RNA. In various embodiments, the dsRNA consists entirely of ribonucleotides or consists of a mixture of ribonucleotides and deoxynucleotides, such as the RNA/DNA hybrids disclosed, for example, by WO 00/63364, filed Apr. 19, 2000, or U.S. Ser. No. 60/130,377, filed Apr. 21, 1999. The dsRNA or dsRNA effector molecule may be a single molecule with a region of self-complementarity such that nucleotides in one segment of the molecule base pair with nucleotides in another segment of the molecule. In various embodiments, a dsRNA that consists of a single molecule consists entirely of ribonucleotides or includes a region of ribonucleotides that is complementary to a region of deoxyribonucleotides. Alternatively, the dsRNA may include two different strands that have a region of complementarity to each other.

In various embodiments, both strands consist entirely of ribonucleotides, one strand consists entirely of ribonucleotides and one strand consists entirely of deoxyribonucleotides, or one or both strands contain a mixture of ribonucleotides and deoxyribonucleotides. In certain embodiments, the regions of complementarity are at least 70%, 80%, 90%, 95%, 98%, or 100% complementary to each other and to a target nucleic acid sequence. In certain embodiments, the region of the dsRNA that is present in a double-stranded conformation includes at least 19, 20, 21, 22, 23, 24, 25, 26, 27, 28, 29, 30, 50, 75, 100, 200, 500, 1000, 2000 or 5000 nucleotides or includes all of the nucleotides in a cDNA or other target nucleic acid sequence being represented in the dsRNA. In some embodiments, the dsRNA does not contain any single stranded regions, such as single stranded ends, or the dsRNA is a hairpin. In other embodiments, the dsRNA has one or more single stranded regions or overhangs. In certain embodiments, RNA/DNA hybrids include a DNA strand or region that is an antisense strand or region (e.g, has at least 70%, 80%, 90%, 95%, 98%, or 100% complementarity to a target nucleic acid) and an RNA strand or region that is a sense strand or region (e.g, has at least 70%, 80%, 90%, 95%, 98%, or 100% identity to a target nucleic acid), and vice versa.

In various embodiments, the RNA/DNA hybrid is made in vitro using enzymatic or chemical synthetic methods such as those described herein or those described in WO 00/63364, filed Apr. 19, 2000, or U.S. Ser. No. 60/130,377, filed Apr. 21, 1999. In other embodiments, a DNA strand synthesized in vitro is complexed with an RNA strand made in vivo or in vitro before, after, or concurrent with the transformation of the DNA strand into the cell. In yet other embodiments, the dsRNA is a single circular nucleic acid containing a sense and an antisense region, or the dsRNA includes a circular nucleic acid and either a second circular nucleic acid or a linear nucleic acid (see, for example, WO 00/63364, filed Apr. 19, 2000, or U.S. Ser. No. 60/130,377, filed Apr. 21, 1999.) Exemplary circular nucleic acids include lariat structures in which the free 5' phosphoryl group of a nucleotide becomes linked to the 2' hydroxyl group of another nucleotide in a loop back fashion.

In other embodiments, the dsRNA includes one or more modified nucleotides in which the 2' position in the sugar contains a halogen (such as fluorine group) or contains an alkoxy group (such as a methoxy group) which increases the half-life of the dsRNA in vitro or in vivo compared to the corresponding dsRNA in which the corresponding 2' position contains a hydrogen or an hydroxyl group. In yet other embodiments, the dsRNA includes one or more linkages between adjacent nucleotides other than a naturally-occurring phosphodiester linkage. Examples of such linkages include phosphoramide, phosphorothioate, and phosphorodithioate linkages. The dsRNAs may also be chemically modified nucleic acid molecules as taught in U.S. Pat. No. 6,673,661. In other embodiments, the dsRNA contains one or two capped strands, as disclosed, for example, by WO 00/63364, filed Apr. 19, 2000, or U.S. Ser. No. 60/130,377, filed Apr. 21, 1999.

In other embodiments, the dsRNA can be any of the at least partially dsRNA molecules disclosed in WO 00/63364, as well as any of the dsRNA molecules described in U.S. Provisional Application 60/399,998; and U.S. Provisional Application 60/419,532, and PCT/US2003/033466, the teaching of which is hereby incorporated by reference. Any of the dsRNAs may be expressed in vitro or in vivo using the methods described herein or standard methods, such as those described in WO 00/63364.

Occupancy

In certain embodiments, antisense compounds are not expected to result in cleavage or the target nucleic acid via RNase H or to result in cleavage or sequestration through the RISC pathway. In certain such embodiments, antisense activity may result from occupancy, wherein the presence of the hybridized antisense compound disrupts the activity of the target nucleic acid. In certain such embodiments, the antisense compound may be uniformly modified or may comprise a mix of modifications and/or modified and unmodified nucleosides.

Target Nucleic Acids, Target Regions and Nucleotide Sequences

Nucleotide sequences that encode AGPAT5 include, without limitation, the following: the murine sequence as set forth in GENBANK Accession No. NM_026792.3 (incorporated herein as SEQ ID NO: 1) or GENBANK Accession No. NT_039455.7 truncated from nucleotides 15844020 to 15885425 (incorporated herein as SEQ ID NO: 2); the human sequence as set forth in GENBANK Accession No. NM_018361.3 (incorporated herein as SEQ ID NO: 24), GENBANK Accession No. AK310545.1 (incorporated herein as SEQ ID NO: 25) or GENBANK Accession No. NT_023736.17 truncated from nucleotides 6554870 to 6610015 (incorporated herein as SEQ ID NO: 26).

It is understood that the sequence set forth in each SEQ ID NO in the Examples contained herein is independent of any modification to a sugar moiety, an internucleoside linkage, or a nucleobase. As such, antisense compounds defined by a SEQ ID NO can comprise, independently, one or more modifications to a sugar moiety, an internucleoside linkage, or a nucleobase. Antisense compounds described by Isis Number (Isis No) indicate a combination of nucleobase sequence and motif.

In certain embodiments, a target region is a structurally defined region of the target nucleic acid. For example, a target region can encompass a 3' UTR, a 5' UTR, an exon, an intron, an exon/intron junction, a coding region, a translation initiation region, translation termination region, or other defined nucleic acid region. The structurally defined regions for AGPAT5 can be obtained by accession number from sequence databases such as NCBI and such information is incorporated herein by reference. In certain embodiments, a target region can encompass the sequence from a 5' target site of one target segment within the target region to a 3' target site of another target segment within the target region.

In certain embodiments, a "target segment" is a smaller, sub-portion of a target region within a nucleic acid. For example, a target segment can be the sequence of nucleotides of a target nucleic acid to which one or more antisense compound is targeted. "5' target site" or "5' start site" refers to the 5'-most nucleotide of a target segment. "3' target site" or "3' stop site" refers to the 3'-most nucleotide of a target segment.

Targeting includes determination of at least one target segment to which an antisense compound hybridizes, such that a desired effect occurs. In certain embodiments, the desired effect is a reduction in mRNA target nucleic acid levels. In certain embodiments, the desired effect is reduction of levels of protein encoded by the target nucleic acid or a phenotypic change associated with the target nucleic acid.

A target region can contain one or more target segments. Multiple target segments within a target region can be overlapping. Alternatively, they can be non-overlapping. In certain embodiments, target segments within a target region are separated by no more than about 300 nucleotides. In certain embodiments, target segments within a target region are separated by a number of nucleotides that is, is about, is no more than, is no more than about, 250, 200, 150, 100, 90, 80, 70, 60, 50, 40, 30, 20, or 10 nucleotides on the target nucleic acid, or is a range defined by any two of the preceding values. In certain embodiments, target segments within a target region are separated by no more than, or no more than about, 5 nucleotides on the target nucleic acid. In certain embodiments, target segments are contiguous. Contemplated are target regions defined by a range having a starting nucleic acid that is any of the 5' target sites or 3' target sites listed herein.

Suitable target segments can be found within a 5' UTR, a coding region, a 3' UTR, an intron, an exon, or an exon/intron junction. Target segments containing a start codon or a stop codon are also suitable target segments. A suitable target segment can specifically exclude a certain structurally defined region such as the start codon or stop codon.

The determination of suitable target segments can include a comparison of the sequence of a target nucleic acid to other sequences throughout the genome. For example, the BLAST algorithm can be used to identify regions of similarity amongst different nucleic acids. This comparison can prevent the selection of antisense compound sequences that can hybridize in a non-specific manner to sequences other than a selected target nucleic acid (i.e., non-target or off-target sequences).

There can be variation in activity (e.g., as defined by percent reduction of target nucleic acid levels) of the antisense compounds within an active target region. In certain embodiments, reductions in AGPAT5 mRNA levels are indicative of inhibition of AGPAT5 protein expression. Reductions in levels of an AGPAT5 protein are also indicative of inhibition of target mRNA expression. Further, phenotypic changes, such as a reduction of the level of triglyceride, insulin resistance or glucose levels, can be indicative of inhibition of AGPAT5 mRNA and/or protein expression.

Hybridization

In some embodiments, hybridization occurs between an antisense compound disclosed herein and an AGPAT5 nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art (Sambrook and Russell, Molecular Cloning: A Laboratory Manual, $3^{rd}$ Ed., 2001). In certain embodiments, the antisense compounds provided herein are specifically hybridizable with an AGPAT5 nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as an AGPAT5 nucleic acid).

An antisense compound can hybridize over one or more segments of an AGPAT5 nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 75%, 80%, 85%, 86%, 87%, 88%, 89%, 90%, 91%, 92%, 93%, 94%, 95%, 96%, 97%, 98%, 99%, or 100% complementary to an AGPAT5 nucleic acid, a target region, target segment, or specified portion thereof. In certain embodiments, the antisense compounds provided herein, or a specified portion thereof, are, or are at least, 70%, 75%, 80%, 85%, 86%, 87%, 88%, 89%, 90%, 91%, 92%, 93%, 94%, 95%, 96%, 97%, 98%, 99%, or 100% complementary to the sequence of one or more of SEQ ID NOs: 1-2, 24-26. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining noncomplementary nucleobases can be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e. 100% complementary) to a target nucleic acid, or specified portion thereof. For example, an antisense compound can be fully complementary to an AGPAT5 nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound can be fully complementary to the target sequence, depending on whether the remaining 10 nucleobases of the antisense compound are also complementary to the target sequence.

The location of a non-complementary nucleobase can be at the 5' end or 3' end of the antisense compound. Alternatively, the non-complementary nucleobase or nucleobases can be at an internal position of the antisense compound. When two or more non-complementary nucleobases are present, they can be either contiguous (i.e. linked) or non-contiguous. In one embodiment, a non-complementary nucleobase is located in the wing segment of a gapmer antisense oligonucleotide.

In certain embodiments, antisense compounds that are, or are up to 10, 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as an AGPAT5 nucleic acid, or specified portion thereof.

In certain embodiments, antisense compounds that are, or are up to 10, 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as an AGPAT5 nucleic acid, or specified portion thereof.

The antisense compounds provided herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 10 nucleobase portion of a target segment. In certain embodiments, the antisense compounds are complementary to at least a 15 nucleobase portion of a target segment. Also contemplated are antisense compounds that are complementary to at least an 8, 9, 10, 11, 12, 13, 14, 15, 16, 17, 18, 19, 20, or more nucleobase portion of a target segment, or a range defined by any two of these values.

Identity

The antisense compounds provided herein can also have a defined percent identity to a particular nucleotide sequence, SEQ ID NO, or the sequence of a compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases can be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, 75%, 80%, 85%, 90%, 95%, 96%, 97%, 98%, 99% or 100% identical to one or more of the antisense compounds or SEQ ID NOs, or a portion thereof, disclosed herein.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides can also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to an AGPAT5 nucleic acid comprise one or more modified internucleoside linkages. In certain embodiments, the modified internucleoside linkages are phosphorothioate linkages. In certain embodiments, each internucleoside linkage of an antisense compound is a phosphorothioate internucleoside linkage.

In certain embodiments, oligonucleotides comprise modified internucleoside linkages arranged along the oligonucleotide or region thereof in a defined pattern or modified internucleoside linkage motif. In certain embodiments, internucleoside linkages are arranged in a gapped motif. In such embodiments, the internucleoside linkages in each of two wing regions are different from the internucleoside linkages in the gap region. In certain embodiments the internucleoside linkages in the wings are phosphodiester and the internucleoside linkages in the gap are phosphorothioate. The nucleoside motif is independently selected, so such oligonucleotides having a gapped internucleoside linkage motif may or may not have a gapped nucleoside motif and if it does have a gapped nucleoside motif, the wing and gap lengths may or may not be the same.

In certain embodiments, oligonucleotides comprise a region having an alternating internucleoside linkage motif. In certain embodiments, oligonucleotides of the present invention comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

In certain embodiments, oligonucleotides comprise one or more methylphosphonate linkages. In certain embodiments, oligonucleotides having a gapmer nucleoside motif comprise a linkage motif comprising all phosphorothioate linkages except for one or two methylphosphonate linkages. In certain embodiments, one methylphosphonate linkage is in the central gap of an oligonucleotide having a gapmer nucleoside motif.

In certain embodiments, it is desirable to arrange the number of phosphorothioate internucleoside linkages and phosphodiester internucleoside linkages to maintain nuclease resistance. In certain embodiments, it is desirable to arrange the number and position of phosphorothioate internucleoside linkages and the number and position of phosphodiester internucleoside linkages to maintain nuclease resistance. In certain embodiments, the number of phosphorothioate internucleoside linkages may be decreased and the number of phosphodiester internucleoside linkages may be increased. In certain embodiments, the number of phosphorothioate internucleoside linkages may be decreased and the number of phosphodiester internucleoside linkages may be increased while still maintaining nuclease resistance. In certain embodiments it is desirable to decrease the number of phosphorothioate internucleoside linkages while retaining nuclease resistance. In certain embodiments it is desirable to increase the number of phosphodiester internucleoside linkages while retaining nuclease resistance.

Modified Sugar Moieties

Antisense compounds of the invention can optionally contain one or more nucleosides wherein the sugar group has been modified. Such sugar modified nucleosides may impart enhanced nuclease stability, increased binding affinity, or some other beneficial biological property to the antisense compounds. In certain embodiments, nucleosides comprise chemically modified ribofuranose ring moieties. Examples of chemically modified ribofuranose rings include without limitation, addition of substituent groups (including 5' and 2' substituent groups, bridging of non-geminal ring atoms to form bicyclic nucleic acids (BNA), replacement of the ribosyl ring oxygen atom with S, N(R), or $C(R_1)(R_2)$ (R, $R_1$ and $R_2$ are each independently H, $C_1$-$C_{12}$ alkyl or a protecting group) and combinations thereof. Examples of chemically modified sugars include 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein LNA is substituted with for example a 5'-methyl or a 5'-vinyl group).

Examples of nucleosides having modified sugar moieties include without limitation nucleosides comprising 5'-vinyl, 5'-methyl (R or S), 4'-S, 2'-F, 2'-OCH$_3$, 2'-OCH$_2$CH$_3$, 2'-OCH$_2$CH$_2$F and 2'-O(CH$_2$)$_2$OCH$_3$ substituent groups. The substituent at the 2' position can also be selected from allyl, amino, azido, thio, O-allyl, O—C$_1$-C$_{10}$ alkyl, OCF$_3$, OCH$_2$F, O(CH$_2$)$_2$SCH$_3$, O(CH$_2$)$_2$—O—N(R$_m$)(R$_n$), —O—CH$_2$—C(=O)—N(R$_m$)(R$_n$), and —O—CH$_2$—C(=O)—N(R$_l$)—(CH$_2$)$_2$—N(R$_m$)(R$_n$), where each R$_l$, R$_m$ and R$_n$ is, independently, H or substituted or unsubstituted C$_1$-C$_{10}$ alkyl.

As used herein, "bicyclic nucleosides" refer to modified nucleosides comprising a bicyclic sugar moiety. Examples of bicyclic nucleic acids (BNAs) include without limitation nucleosides comprising a bridge between the 4' and the 2' ribosyl ring atoms. In certain embodiments, antisense compounds provided herein include one or more BNA nucleosides wherein the bridge comprises one of the formulas: 4'-(CH$_2$)—O—2' (LNA); 4'-(CH$_2$)—S—2; 4'-(CH$_2$)$_2$—O-2' (ENA); 4'-CH(CH$_3$)—O-2' and 4'-CH(CH$_2$OCH$_3$)—O-2' (and analogs thereof see U.S. Pat. No. 7,399,845, issued on Jul. 15, 2008); 4'-C(CH$_3$)(CH$_3$)—O-2' (and analogs thereof see PCT/US2008/068922 published as WO/2009/006478, published Jan. 8, 2009); 4'-CH$_2$—N(OCH$_3$)-2' (and analogs thereof see PCT/US2008/064591 published as WO/2008/150729, published Dec. 11, 2008); 4'-CH$_2$—O—N(CH$_3$)-2' (see published U.S. Patent Application US2004-0171570, published Sep. 2, 2004); 4'-CH$_2$—N(R)—O-2', wherein R is H, C$_1$-C$_{12}$ alkyl, or a protecting group (see U.S. Pat. No. 7,427,672, issued on Sep. 23, 2008); 4'-CH$_2$—C(H)(CH$_3$)-2' (see Chattopadhyaya et al., *J. Org. Chem.*, 2009, 74, 118-134); and 4'-CH$_2$—C(=CH$_2$)-2' (and analogs thereof see PCT/US2008/066154 published as WO 2008/154401, published on Dec. 8, 2008).

Further bicyclic nucleosides have been reported in published literature (see for example: Srivastava et al., *J. Am. Chem. Soc.*, 2007, 129(26) 8362-8379; Frieden et al., *Nucleic Acids Research*, 2003, 21, 6365-6372; Elayadi et al., *Curr. Opinion Invens. Drugs*, 2001, 2, 558-561; Braasch et al., *Chem. Biol.*, 2001, 8, 1-7; Orum et al., *Curr. Opinion Mol. Ther.*, 2001, 3, 239-243; Wahlestedt et al., *Proc. Natl. Acad. Sci. U.S.A.*, 2000, 97, 5633-5638; Singh et al., *Chem. Commun.*, 1998, 4, 455-456; Koshkin et al., *Tetrahedron*, 1998, 54, 3607-3630; Kumar et al., *Bioorg. Med. Chem. Lett.*, 1998, 8, 2219-2222; Singh et al., *J. Org. Chem.*, 1998, 63, 10035-10039; U.S. Pat. Nos. 7,399,845; 7,053,207; 7,034,133; 6,794,499; 6,770,748; 6,670,461; 6,525,191; 6,268,490; U.S. Patent Publication Nos.: US2008-0039618; US2007-0287831; US2004-0171570; U.S. patent applications, Ser. Nos. 12/129,154; 61/099,844; 61/097,787; 61/086,231; 61/056,564; 61/026,998; 61/026,995; 60/989,574; International applications WO 2007/134181; WO 2005/021570; WO 2004/106356; WO 94/14226; and PCT International Applications Nos.: PCT/US2008/068922; PCT/US-2008/066154; and PCT/US2008/064591). Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

As used herein, "monocyclic nucleosides" refer to nucleosides comprising modified sugar moieties that are not bicyclic sugar moieties. In certain embodiments, the sugar moiety, or sugar moiety analogue, of a nucleoside may be modified or substituted at any position.

As used herein, "4'-2' bicyclic nucleoside" or "4' to 2' bicyclic nucleoside" refers to a bicyclic nucleoside comprising a furanose ring comprising a bridge connecting two carbon atoms of the furanose ring connects the 2' carbon atom and the 4' carbon atom of the sugar ring.

In certain embodiments, bicyclic sugar moieties of BNA nucleosides include, but are not limited to, compounds having at least one bridge between the 4' and the 2' carbon atoms of the pentofuranosyl sugar moiety including without limitation, bridges comprising 1 or from 1 to 4 linked groups independently selected from —[C(R$_a$)(R$_b$)]$_n$—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—; wherein: x is 0, 1, or 2; n is 1, 2, 3, or 4; each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl or a protecting group.

In certain embodiments, the bridge of a bicyclic sugar moiety is, —[C(R$_a$)(R$_b$)]$_n$—, —[C(R$_a$)(R$_b$)]$_n$—O—, —C(R$_a$R$_b$)—N(R)—O— or —C(R$_a$R$_b$)—O—N(R)—. In certain embodiments, the bridge is 4'-CH$_2$-2', 4'-(CH$_2$)$_2$-2', 4'-(CH$_2$)$_3$-2', 4'-CH$_2$—O-2', 4'-(CH$_2$)$_2$—O-2', 4'-CH$_2$—O—N(R)-2' and 4'-CH$_2$—)—O-2'- wherein each R is, independently, H, a protecting group or C$_1$-C$_{12}$ alkyl.

In certain embodiments, bicyclic nucleosides are further defined by isomeric configuration. For example, a nucleoside comprising a 4'-(CH$_2$)—O-2' bridge, may be in the α-L configuration or in the β-D configuration. Previously, α-L-methyleneoxy (4'-CH$_2$—O-2') BNA's have been incorporated into antisense oligonucleotides that showed antisense activity (Frieden et al., *Nucleic Acids Research*, 2003, 21, 6365-6372).

In certain embodiments, bicyclic nucleosides include those having a 4' to 2' bridge wherein such bridges include without limitation, α-L-4'-(CH$_2$)—O-2', β-D-4'-CH$_2$—O-2', 4'-(CH$_2$)$_2$—O-2', 4'-CH$_2$—O—N(R)-2', 4'-CH$_2$—N(R)—O-2', 4'-CH(CH$_3$)—O-2', 4'-CH$_2$—S-2', 4'-CH$_2$—N(R)-2', 4'-CH$_2$—CH(CH$_3$)-2', and 4'-(CH$_2$)$_3$-2', wherein R is H, a protecting group or C$_1$-C$_{12}$ alkyl.

In certain embodiment, bicyclic nucleosides have the formula:

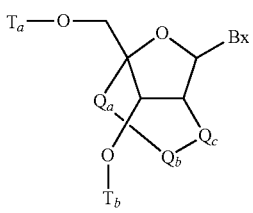

wherein:

Bx is a heterocyclic base moiety;

$-Q_a-Q_b-Q_c-$ is $-CH_2-N(R_c)-CH_2-$, $-C(=O)-N(R_c)-CH_2-$, $-CH_2-O-N(R_c)-$, $-CH_2-N(R_c)-O-$ or $-N(R_c)-O-CH_2$;

$R_c$ is $C_1$-$C_{12}$ alkyl or an amino protecting group; and $T_a$ and $T_b$ are each, independently H, a hydroxyl protecting group, a conjugate group, a reactive phosphorus group, a phosphorus moiety or a covalent attachment to a support medium.

In certain embodiments, bicyclic nucleosides have the formula:

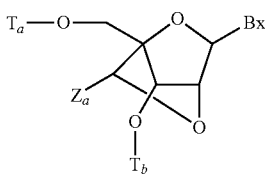

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_a$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, substituted amide, thiol or substituted thiol.

In one embodiment, each of the substituted groups, is, independently, mono or poly substituted with substituent groups independently selected from halogen, oxo, hydroxyl, $OJ_c$, $NJ_cJ_d$, $SJ_c$, $N_3$, $OC(=X)J_c$, and $NJ_eC(=X)NJ_cJ_d$, wherein each $J_c$, $J_d$ and $J_e$ is, independently, H, $C_1$-$C_6$ alkyl, or substituted $C_1$-$C_6$ alkyl and X is O or $NJ_c$.

In certain embodiments, bicyclic nucleosides have the formula:

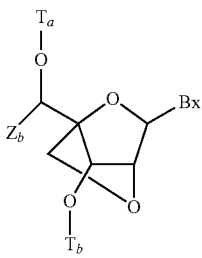

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_b$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl or substituted acyl ($C(=O)-$).

In certain embodiments, bicyclic nucleosides have the formula:

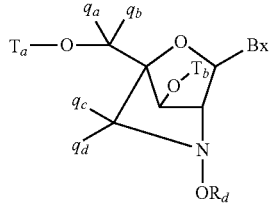

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$R_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

each $q_a$, $q_b$, $q_c$ and $q_d$ is, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

In certain embodiments, bicyclic nucleosides have the formula:

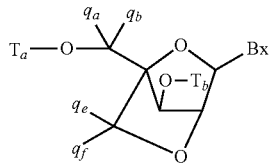

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$q_a$, $q_b$, $q_c$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SOJ_j$, $SO_2J_j$, $NJ_jJ_k$, $N_3$, CN, $C(=O)OJ_j$, $C(=O)NJ_jJ_k$, $C(=O)J_j$, $-O-C(=O)NJ_jJ_k$, $N(H)C(=NH)NJ_jJ_k$, $N(H)C(=O)NJ_jJ_k$ or $N(H)C(=S)NJ_jJ_k$;

or $q_e$ and $q_f$ together are $=C(q_g)(q_h)$;

$q_g$ and $q_h$ are each, independently, H, halogen, $C_1$-$C_{12}$ alkyl or substituted $C_1$-$C_{12}$ alkyl.

The synthesis and preparation of adenine, cytosine, guanine, 5-methyl-cytosine, thymine and uracil bicyclic nucleosides having a 4'-CH$_2$—O-2' bridge, along with their oligomerization, and nucleic acid recognition properties have been described (Koshkin et al., *Tetrahedron*, 1998, 54, 3607-3630). The synthesis of bicyclic nucleosides has also been described in WO 98/39352 and WO 99/14226.

Analogs of various bicyclic nucleosides that have 4' to 2' bridging groups such as 4'-CH$_2$—O-2' and 4'-CH$_2$—S-2', have also been prepared (Kumar et al., *Bioorg. Med. Chem. Lett.*, 1998, 8, 2219-2222). Preparation of oligodeoxyribonucleotide duplexes comprising bicyclic nucleosides for use as substrates for nucleic acid polymerases has also been described (Wengel et al., WO 99/14226). Furthermore, synthesis of 2'-amino-BNA, a novel conformationally restricted high-affinity oligonucleotide analog has been described in the art (Singh et al., *J. Org. Chem.*, 1998, 63, 10035-10039). In addition, 2'-amino- and 2'-methylamino-BNA's have been prepared and the thermal stability of their duplexes with complementary RNA and DNA strands has been previously reported.

In certain embodiments, bicyclic nucleosides have the formula:

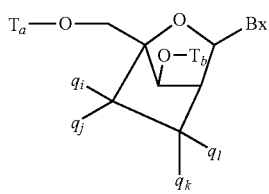

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

each $q_i$, $q_j$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$; and $q_i$ and $q_j$ or $q_i$ and $q_k$ together are =C($q_g$)($q_h$), wherein $q_g$ and $q_h$ are each, independently, H, halogen, $C_1$-$C_{12}$ alkyl or substituted $C_1$-$C_{12}$ alkyl.

One carbocyclic bicyclic nucleoside having a 4'-(CH$_2$)$_3$-2' bridge and the alkenyl analog bridge 4'-CH=CH—CH$_2$-2' have been described (Frier et al., *Nucleic Acids Research*, 1997, 25(22), 4429-4443 and Albaek et al., *J. Org. Chem.*, 2006, 71, 7731-7740). The synthesis and preparation of carbocyclic bicyclic nucleosides along with their oligomerization and biochemical studies have also been described (Srivastava et al., *J. Am. Chem. Soc.* 2007, 129(26), 8362-8379).

In certain embodiments, bicyclic nucleosides include, but are not limited to, (A) α-L-methyleneoxy (4'-CH$_2$—O-2') BNA, (B) β-D-methyleneoxy (4'-CH$_2$—O-2') BNA, (C) ethyleneoxy (4'-(CH$_2$)$_2$—O-2') BNA, (D) aminooxy (4'-CH$_2$—O—N(R)-2') BNA, (E) oxyamino (4'-CH$_2$—N(R)—O-2') BNA, (F) methyl(methyleneoxy) (4'-CH(CH$_3$)—O-2') BNA (also referred to as constrained ethyl or cEt), (G) methylene-thio (4'-CH$_2$—S-2') BNA, (H) methylene-amino (4'-CH$_2$—N(R)-2') BNA, (I) methyl carbocyclic (4'-CH$_2$—CH(CH$_3$)-2') BNA, (J) propylene carbocyclic (4'-(CH$_2$)$_3$-2') BNA, and (K) vinyl BNA as depicted below.

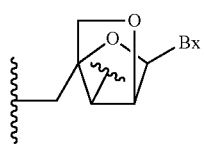
(A)

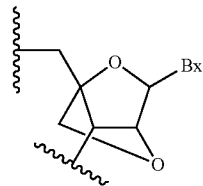
(B)

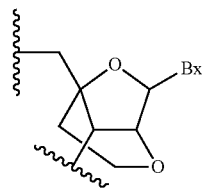
(C)

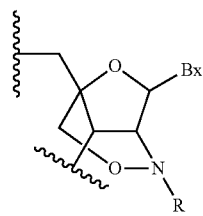
(D)

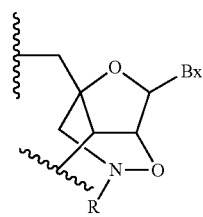
(E)

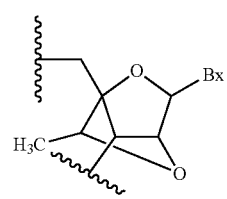
(F)

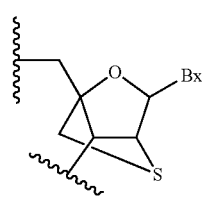
(G)

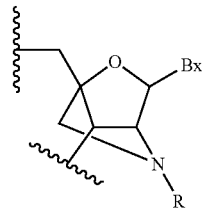
(H)

-continued

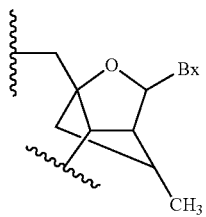

(I)

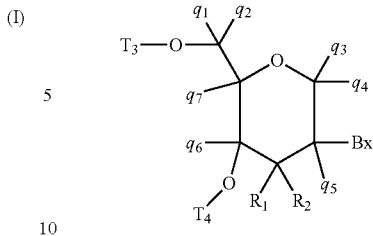

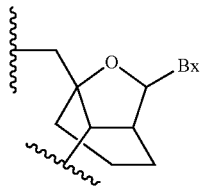

(J)

wherein:
Bx is a heterocyclic base moiety;
$T_3$ and $T_4$ are each, independently, an internucleoside linking group linking the tetrahydropyran nucleoside analog to the oligomeric compound or one of $T_3$ and $T_4$ is an internucleoside linking group linking the tetrahydropyran nucleoside analog to an oligomeric compound or oligonucleotide and the other of $T_3$ and $T_4$ is H, a hydroxyl protecting group, a linked conjugate group or a 5' or 3'-terminal group;

$q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl; and one of $R_1$ and $R_2$ is hydrogen and the other is selected from halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$ and CN, wherein X is O, S or $NJ_1$ and each $J_1$, $J_2$ and $J_3$ is, independently, H or $C_1$-$C_6$ alkyl.

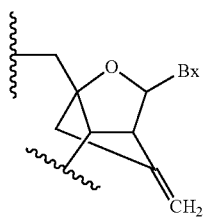

(K)

In certain embodiments, $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides are provided wherein one of $R_1$ and $R_2$ is F. In certain embodiments, $R_1$ is fluoro and $R_2$ is H; $R_1$ is methoxy and $R_2$ is H, and $R_1$ is methoxyethoxy and $R_2$ is H.

In certain embodiments, sugar surrogates comprise rings having more than 5 atoms and more than one heteroatom. For example nucleosides comprising morpholino sugar moieties and their use in oligomeric compounds has been reported (see for example: Braasch et al., *Biochemistry*, 2002, 41, 4503-4510; and U.S. Pat. Nos. 5,698,685; 5,166,315; 5,185,444; and 5,034,506). As used here, the term "morpholino" means a sugar surrogate having the following formula:

wherein Bx is the base moiety and R is, independently, H, a protecting group, $C_1$-$C_6$ alkyl or $C_1$-$C_6$ alkoxy.

As used herein, the term "modified tetrahydropyran nucleoside" or "modified THP nucleoside" means a nucleoside having a six-membered tetrahydropyran "sugar" substituted for the pentofuranosyl residue in normal nucleosides and can be referred to as a sugar surrogate. Modified THP nucleosides include, but are not limited to, what is referred to in the art as hexitol nucleic acid (HNA), anitol nucleic acid (ANA), manitol nucleic acid (MNA) (see Leumann, *Bioorg. Med. Chem.*, 2002, 10, 841-854) or fluoro HNA (F-HNA) having a tetrahydropyranyl ring system as illustrated below.

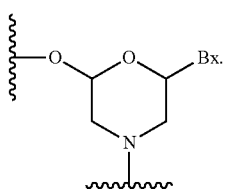

In certain embodiments, morpholinos may be modified, for example by adding or altering various substituent groups from the above morpholino structure. Such sugar surrogates are referred to herein as "modified morpholinos."

Combinations of modifications are also provided without limitation, such as 2'-F-5'-methyl substituted nucleosides (see PCT International Application WO 2008/101157 published on Aug. 21, 2008 for other disclosed 5', 2'-bis substituted nucleosides) and replacement of the ribosyl ring oxygen atom with S and further substitution at the 2'-posi-

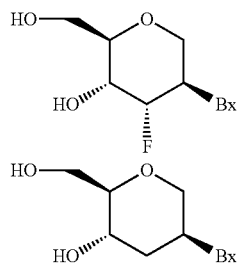

In certain embodiment, sugar surrogates are selected having the formula:

tion (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'-CH$_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379).

In certain embodiments, antisense compounds comprise one or more modified cyclohexenyl nucleosides, which is a nucleoside having a six-membered cyclohexenyl in place of the pentofuranosyl residue in naturally occurring nucleosides. Modified cyclohexenyl nucleosides include, but are not limited to those described in the art (see for example commonly owned, published PCT Application WO 2010/036696, published on Apr. 10, 2010, Robeyns et al., *J. Am. Chem. Soc.*, 2008, 130(6), 1979-1984; Horváth et al., *Tetrahedron Letters*, 2007, 48, 3621-3623; Nauwelaerts et al., *J. Am. Chem. Soc.*, 2007, 129(30), 9340-9348; Gu et al., *Nucleosides, Nucleotides & Nucleic Acids*, 2005, 24(5-7), 993-998; Nauwelaerts et al., *Nucleic Acids Research*, 2005, 33(8), 2452-2463; Robeyns et al., *Acta Crystallographica, Section F: Structural Biology and Crystallization Communications*, 2005, F61(6), 585-586; Gu et al., *Tetrahedron*, 2004, 60(9), 2111-2123; Gu et al., *Oligonucleotides*, 2003, 13(6), 479-489; Wang et al., *J. Org. Chem.*, 2003, 68, 4499-4505; Verbeure et al., *Nucleic Acids Research*, 2001, 29(24), 4941-4947; Wang et al., *J. Org. Chem.*, 2001, 66, 8478-82; Wang et al., *Nucleosides, Nucleotides & Nucleic Acids*, 2001, 20(4-7), 785-788; Wang et al., *J. Am. Chem.*, 2000, 122, 8595-8602; Published PCT application, WO 06/047842; and Published PCT Application WO 01/049687; the text of each is incorporated by reference herein, in their entirety). Certain modified cyclohexenyl nucleosides have Formula X.

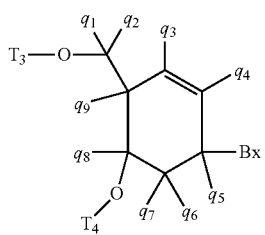

X wherein independently for each of said at least one cyclohexenyl nucleoside analog of Formula X:

Bx is a heterocyclic base moiety;

$T_3$ and $T_4$ are each, independently, an internucleoside linking group linking the cyclohexenyl nucleoside analog to an antisense compound or one of $T_3$ and $T_4$ is an internucleoside linking group linking the tetrahydropyran nucleoside analog to an antisense compound and the other of $T_3$ and $T_4$ is H, a hydroxyl protecting group, a linked conjugate group, or a 5'- or 3'-terminal group; and $q_1$, $q_2$, $q_3$, $q_4$, $q_5$, $q_6$, $q_7$, $q_8$ and $q_9$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or other sugar substituent group.

Many other monocyclic, bicyclic and tricyclic ring systems are known in the art and are suitable as sugar surrogates that can be used to modify nucleosides for incorporation into oligomeric compounds as provided herein (see for example review article: Leumann, Christian *J. Bioorg. & Med. Chem.*, 2002, 10, 841-854). Such ring systems can undergo various additional substitutions to further enhance their activity.

As used herein, "2'-modified sugar" means a furanosyl sugar modified at the 2' position. In certain embodiments, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In certain embodiments, 2' modifications are selected from substituents including, but not limited to: $O[(CH_2)_nO]_mCH_3$, $O(CH_2)_nNH_2$, $O(CH_2)_nCH_3$, $O(CH_2)_nF$, $O(CH_2)_nONH_2$, $OCH_2C(=O)N(H)CH_3$, and $O(CH_2)_nON[(CH_2)_nCH_3]_2$, where n and m are from 1 to about 10. Other 2'-substituent groups can also be selected from: $C_1$-$C_{12}$ alkyl, substituted alkyl, alkenyl, alkynyl, alkaryl, aralkyl, O-alkaryl or O-aralkyl, SH, SCH$_3$, OCN, Cl, Br, CN, F, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving pharmacokinetic properties, or a group for improving the pharmacodynamic properties of an antisense compound, and other substituents having similar properties. In certain embodiments, modified nucleosides comprise a 2'-MOE side chain (Baker et al., *J. Biol. Chem.*, 1997, 272, 11944-12000). Such 2'-MOE substitution have been described as having improved binding affinity compared to unmodified nucleosides and to other modified nucleosides, such as 2'-O-methyl, O-propyl, and O-aminopropyl. Oligonucleotides having the 2'-MOE substituent also have been shown to be antisense inhibitors of gene expression with promising features for in vivo use (Martin, *Helv. Chim. Acta*, 1995, 78, 486-504; Altmann et al., *Chimia*, 1996, 50, 168-176; Altmann et al., *Biochem. Soc. Trans.*, 1996, 24, 630-637; and Altmann et al., *Nucleosides Nucleotides*, 1997, 16, 917-926).

As used herein, "2'-modified" or "2'-substituted" refers to a nucleoside comprising a sugar comprising a substituent at the 2' position other than H or OH. 2'-modified nucleosides, include, but are not limited to, bicyclic nucleosides wherein the bridge connecting two carbon atoms of the sugar ring connects the 2' carbon and another carbon of the sugar ring; and nucleosides with non-bridging 2' substituents, such as allyl, amino, azido, thio, O-allyl, O—$C_1$-$C_{10}$ alkyl, —OCF$_3$, O—(CH$_2$)$_2$—O—CH$_3$, 2'-O(CH$_2$)$_2$SCH$_3$, O—(CH$_2$)$_2$—O—N(R$_m$)(R$_n$), or —O—CH$_2$—C(=O)—N(R$_m$)(R$_n$), where each R$_m$ and R$_n$ is, independently, H or substituted or unsubstituted $C_1$-$C_{10}$ alkyl. 2'-modified nucleosides may further comprise other modifications, for example at other positions of the sugar and/or at the nucleobase.

As used herein, "2'-F" refers to a nucleoside comprising a sugar comprising a fluoro group at the 2' position of the sugar ring.

As used herein, "2'-OMe" or "2'-OCH$_3$", "2'-O-methyl" or "2'-methoxy" each refers to a nucleoside comprising a sugar comprising an —OCH$_3$ group at the 2' position of the sugar ring.

As used herein, "MOE" or "2'-MOE" or "2'-OCH$_2$CH$_2$OCH$_3$" or "2'-O-methoxyethyl" each refers to a nucleoside comprising a sugar comprising a —OCH$_2$CH$_2$OCH$_3$ group at the 2' position of the sugar ring.

Methods for the preparations of modified sugars are well known to those skilled in the art. Some representative U.S.

patents that teach the preparation of such modified sugars include without limitation, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,670,633; 5,700,920; 5,792,847 and 6,600,032 and International Application PCT/US2005/019219, filed Jun. 2, 2005 and published as WO 2005/121371 on Dec. 22, 2005, and each of which is herein incorporated by reference in its entirety.

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

In nucleotides having modified sugar moieties, the nucleobase moieties (natural, modified or a combination thereof) are maintained for hybridization with an appropriate nucleic acid target.

In certain embodiments, antisense compounds comprise one or more nucleosides having modified sugar moieties. In certain embodiments, the modified sugar moiety is 2'-MOE. In certain embodiments, the 2'-MOE modified nucleosides are arranged in a gapmer motif. In certain embodiments, the modified sugar moiety is a bicyclic nucleoside having a (4'-CH(CH$_3$)—O-2') bridging group. In certain embodiments, the (4'-CH(CH$_3$)—O-2') modified nucleosides are arranged throughout the wings of a gapmer motif.

Modified Nucleobases

Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications can impart nuclease stability, binding affinity or some other beneficial biological property to antisense compounds. Modified nucleobases include synthetic and natural nucleobases such as, for example, 5-methylcytosine (5-me-C). Certain nucleobase substitutions, including 5-methylcytosine substitutions, are particularly useful for increasing the binding affinity of an antisense compound for a target nucleic acid. For example, 5-methylcytosine substitutions have been shown to increase nucleic acid duplex stability by 0.6-1.2° C. (Sanghvi, Y. S., Crooke, S. T. and Lebleu, B., eds., Antisense Research and Applications, CRC Press, Boca Raton, 1993, pp. 276-278).

Additional modified nucleobases include 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH3) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties can also include those in which the purine or pyrimidine base is replaced with other heterocycles, for example 7-deaza-adenine, 7-deazaguanosine, 2-aminopyridine and 2-pyridone. Nucleobases that are particularly useful for increasing the binding affinity of antisense compounds include 5-substituted pyrimidines, 6-azapyrimidines and N-2, N-6 and O-6 substituted purines, including 2 aminopropyladenine, 5-propynyluracil and 5-propynylcytosine.

In certain embodiments, antisense compounds targeted to an AGPAT5 nucleic acid comprise one or more modified nucleobases. In certain embodiments, shortened or gap-widened antisense oligonucleotides targeted to an AGPAT5 nucleic acid comprise one or more modified nucleobases. In certain embodiments, the modified nucleobase is 5-methylcytosine. In certain embodiments, each cytosine is a 5-methylcytosine.

Compositions and Methods for Formulating Pharmaceutical Compositions

Antisense oligonucleotides can be admixed with pharmaceutically acceptable active or inert substance for the preparation of pharmaceutical compositions or formulations. Compositions and methods for the formulation of pharmaceutical compositions are dependent upon a number of criteria, including, but not limited to, route of administration, extent of disease, or dose to be administered.

Antisense compound targeted to an AGPAT5 nucleic acid can be utilized in pharmaceutical compositions by combining the antisense compound with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound targeted to an AGPAT5 nucleic acid and a pharmaceutically acceptable diluent. In certain embodiments, the pharmaceutically acceptable diluent is PBS. In certain embodiments, the antisense compound is an antisense oligonucleotide.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound.

Conjugated Antisense Compounds

In certain embodiments, the oligomeric compounds as provided herein are modified by covalent attachment of one or more conjugate groups. As used herein, "conjugate group" means a radical group comprising a group of atoms that are attached to an oligomeric compound. In general, conjugate groups modify one or more properties of the compound to which they are attached, including, but not limited to pharmacodynamic, pharmacokinetic, binding, absorption, cellular distribution, cellular uptake, charge and/or clearance properties. Conjugate groups are routinely used in the chemical arts and can include a conjugate linker that covalently links the conjugate group to an oligomeric compound. In certain embodiments, conjugate groups include a cleavable moiety that covalently links the conjugate group to an oligomeric compound. In certain embodiments, conjugate groups include a conjugate linker and a cleavable moiety to covalently link the conjugate group to an oligomeric compound. In certain embodiments, a conjugate group has the general formula:

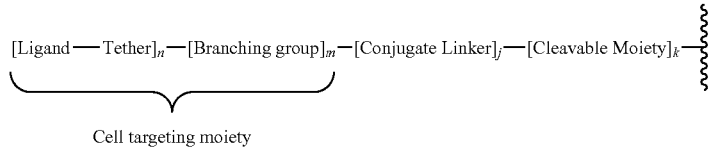

Cell targeting moiety wherein n is from 1 to about 3, m is 0 when n is 1 or m is 1 when n is 2 or 3, j is 1 or 0, k is 1 or 0 and the sum of j and k is at least one.

In certain embodiments, n is 1, j is 1 and k is 0. In certain embodiments, n is 1, j is 0 and k is 1. In certain embodiments, n is 1, j is 1 and k is 1. In certain embodiments, n is 2, j is 1 and k is 0. In certain embodiments, n is 2, j is 0 and k is 1. In certain embodiments, n is 2, j is 1 and k is 1. In certain embodiments, n is 3, j is 1 and k is 0. In certain embodiments, n is 3, j is 0 and k is 1. In certain embodiments, n is 3, j is 1 and k is 1.

Conjugate groups are shown herein as radicals, providing a bond for forming covalent attachment to an oligomeric compound such as an antisense oligonucleotide. In certain embodiments, the point of attachment on the oligomeric compound is at the 3'-terminal nucleoside or modified nucleoside. In certain embodiments, the point of attachment on the oligomeric compound is the 3'-oxygen atom of the 3'-hydroxyl group of the 3' terminal nucleoside or modified nucleoside. In certain embodiments, the point of attachment on the oligomeric compound is at the 5'-terminal nucleoside or modified nucleoside. In certain embodiments the point of attachment on the oligomeric compound is the 5'-oxygen atom of the 5'-hydroxyl group of the 5'-terminal nucleoside or modified nucleoside. In certain embodiments, the point of attachment on the oligomeric compound is at any reactive site on a nucleoside, a modified nucleoside or an internucleoside linkage.

As used herein, "cleavable moiety" and "cleavable bond" mean a cleavable bond or group of atoms that is capable of being split or cleaved under certain physiological conditions. In certain embodiments, a cleavable moiety is a cleavable bond. In certain embodiments, a cleavable moiety comprises a cleavable bond. In certain embodiments, a cleavable moiety is a group of atoms. In certain embodiments, a cleavable moiety is selectively cleaved inside a cell or sub-cellular compartment, such as a lysosome. In certain embodiments, a cleavable moiety is selectively cleaved by endogenous enzymes, such as nucleases. In certain embodiments, a cleavable moiety comprises a group of atoms having one, two, three, four, or more than four cleavable bonds.

In certain embodiments, conjugate groups comprise a cleavable moiety. In certain such embodiments, the cleavable moiety covalently attaches the oligomeric compound to the conjugate linker. In certain such embodiments, the cleavable moiety covalently attaches the oligomeric compound to the cell-targeting moiety.

In certain embodiments, a cleavable bond is selected from among: an amide, a polyamide, an ester, an ether, one or both esters of a phosphodiester, a phosphate ester, a carbamate, a di-sulfide, or a peptide. In certain embodiments, a cleavable bond is one of the esters of a phosphodiester. In certain embodiments, a cleavable bond is one or both esters of a phosphodiester. In certain embodiments, the cleavable moiety is a phosphodiester linkage between an oligomeric compound and the remainder of the conjugate group. In certain embodiments, the cleavable moiety comprises a phosphodiester linkage that is located between an oligomeric compound and the remainder of the conjugate group. In certain embodiments, the cleavable moiety comprises a phosphate or phosphodiester. In certain embodiments, the cleavable moiety is attached to the conjugate linker by either a phosphodiester or a phosphorothioate linkage. In certain embodiments, the cleavable moiety is attached to the conjugate linker by a phosphodiester linkage. In certain embodiments, the conjugate group does not include a cleavable moiety.

In certain embodiments, the cleavable moiety is a cleavable nucleoside or a modified nucleoside. In certain embodiments, the nucleoside or modified nucleoside comprises an optionally protected heterocyclic base selected from a purine, substituted purine, pyrimidine or substituted pyrimidine. In certain embodiments, the cleavable moiety is a nucleoside selected from uracil, thymine, cytosine, 4-N-benzoylcytosine, 5-methylcytosine, 4-N-benzoyl-5-methylcytosine, adenine, 6-N-benzoyladenine, guanine and 2-N-isobutyrylguanine.

In certain embodiments, the cleavable moiety is 2'-deoxy nucleoside that is attached to either the 3' or 5'-terminal nucleoside of an oligomeric compound by a phosphodiester linkage and covalently attached to the remainder of the conjugate group by a phosphodiester or phosphorothioate linkage. In certain embodiments, the cleavable moiety is 2'-deoxy adenosine that is attached to either the 3' or 5'-terminal nucleoside of an oligomeric compound by a phosphodiester linkage and covalently attached to the remainder of the conjugate group by a phosphodiester or phosphorothioate linkage. In certain embodiments, the cleavable moiety is 2'-deoxy adenosine that is attached to the 3'-oxygen atom of the 3'-hydroxyl group of the 3'-terminal nucleoside or modified nucleoside by a phosphodiester linkage. In certain embodiments, the cleavable moiety is 2'-deoxy adenosine that is attached to the 5'-oxygen atom of the 5'-hydroxyl group of the 5'-terminal nucleoside or modified nucleoside by a phosphodiester linkage. In certain embodiments, the cleavable moiety is attached to a 2'-position of a nucleoside or modified nucleoside of an oligomeric compound.

As used herein, "conjugate linker" in the context of a conjugate group means a portion of a conjugate group comprising any atom or group of atoms that covalently link the cell-targeting moiety to the oligomeric compound either directly or through the cleavable moiety. In certain embodiments, the conjugate linker comprises groups selected from alkyl, amino, oxo, amide, disulfide, polyethylene glycol, ether, thioether (—S—) and hydroxylamino (—O—N(H)—). In certain embodiments, the conjugate linker comprises groups selected from alkyl, amino, oxo, amide and ether groups. In certain embodiments, the conjugate linker comprises groups selected from alkyl and amide groups. In certain embodiments, the conjugate linker comprises groups selected from alkyl and ether groups. In certain embodiments, the conjugate linker comprises at least one phosphorus linking group. In certain embodiments, the conjugate linker comprises at least one phosphodiester group. In certain embodiments, the conjugate linker includes at least one neutral linking group.

In certain embodiments, the conjugate linker is covalently attached to the oligomeric compound. In certain embodiments, the conjugate linker is covalently attached to the oligomeric compound and the branching group. In certain embodiments, the conjugate linker is covalently attached to the oligomeric compound and a tethered ligand. In certain embodiments, the conjugate linker is covalently attached to the cleavable moiety. In certain embodiments, the conjugate linker is covalently attached to the cleavable moiety and the branching group. In certain embodiments, the conjugate linker is covalently attached to the cleavable moiety and a tethered ligand. In certain embodiments, the conjugate linker includes one or more cleavable bonds. In certain embodiments, the conjugate group does not include a conjugate linker.

As used herein, "branching group" means a group of atoms having at least 3 positions that are capable of forming covalent linkages to two or more tether-ligands and the remainder of the conjugate group. In general a branching group provides a plurality of reactive sites for connecting tethered ligands to the oligomeric compound through the conjugate linker and/or the cleavable moiety. In certain embodiments, the branching group comprises groups selected from alkyl, amino, oxo, amide, disulfide, polyethylene glycol, ether, thioether and hydroxylamino groups. In certain embodiments, the branching group comprises a branched aliphatic group comprising groups selected from alkyl, amino, oxo, amide, disulfide, polyethylene glycol, ether, thioether and hydroxylamino groups. In certain such embodiments, the branched aliphatic group comprises groups selected from alkyl, amino, oxo, amide and ether groups. In certain such embodiments, the branched aliphatic group comprises groups selected from alkyl, amino and ether groups. In certain such embodiments, the branched aliphatic group comprises groups selected from alkyl and ether groups. In certain embodiments, the branching group comprises a mono or polycyclic ring system.

In certain embodiments, the branching group is covalently attached to the conjugate linker. In certain embodiments, the branching group is covalently attached to the cleavable moiety. In certain embodiments, the branching group is covalently attached to the conjugate linker and each of the tethered ligands. In certain embodiments, the branching group comprises one or more cleavable bond. In certain embodiments, the conjugate group does not include a branching group.

In certain embodiments, conjugate groups as provided herein include a cell-targeting moiety that has at least one tethered ligand. In certain embodiments, the cell-targeting moiety comprises two tethered ligands covalently attached to a branching group. In certain embodiments, the cell-targeting moiety comprises three tethered ligands covalently attached to a branching group.

As used herein, "tether" means a group of atoms that connect a ligand to the remainder of the conjugate group. In certain embodiments, each tether is a linear aliphatic group comprising one or more groups selected from alkyl, substituted alkyl, ether, thioether, disulfide, amino, oxo, amide, phosphodiester and polyethylene glycol groups in any combination. In certain embodiments, each tether is a linear aliphatic group comprising one or more groups selected from alkyl, ether, thioether, disulfide, amino, oxo, amide and polyethylene glycol groups in any combination. In certain embodiments, each tether is a linear aliphatic group comprising one or more groups selected from alkyl, substituted alkyl, phosphodiester, ether and amino, oxo, amide groups in any combination. In certain embodiments, each tether is a linear aliphatic group comprising one or more groups selected from alkyl, ether and amino, oxo, amide groups in any combination. In certain embodiments, each tether is a linear aliphatic group comprising one or more groups selected from alkyl, amino and oxo groups in any combination. In certain embodiments, each tether is a linear aliphatic group comprising one or more groups selected from alkyl and oxo groups in any combination. In certain embodiments, each tether is a linear aliphatic group comprising one or more groups selected from alkyl and phosphodiester in any combination. In certain embodiments, each tether comprises at least one phosphorus linking group or neutral linking group.

In certain embodiments, tethers include one or more cleavable bond. In certain embodiments, each tethered ligand is attached to a branching group. In certain embodiments, each tethered ligand is attached to a branching group through an amide group. In certain embodiments, each tethered ligand is attached to a branching group through an ether group. In certain embodiments, each tethered ligand is attached to a branching group through a phosphorus linking group or neutral linking group. In certain embodiments, each tethered ligand is attached to a branching group through a phosphodiester group. In certain embodiments, each tether is attached to a ligand through either an amide or an ether group. In certain embodiments, each tether is attached to a ligand through an ether group.

In certain embodiments, each tether comprises from about 8 to about 20 atoms in chain length between the ligand and the branching group. In certain embodiments, each tether comprises from about 10 to about 18 atoms in chain length between the ligand and the branching group. In certain embodiments, each tether comprises about 13 atoms in chain length.

In certain embodiments, the present disclosure provides ligands wherein each ligand is covalently attached to the remainder of the conjugate group through a tether. In certain embodiments, each ligand is selected to have an affinity for at least one type of receptor on a target cell. In certain embodiments, ligands are selected that have an affinity for at least one type of receptor on the surface of a mammalian liver cell. In certain embodiments, ligands are selected that have an affinity for the hepatic asialoglycoprotein receptor (ASGP-R). In certain embodiments, each ligand is a carbohydrate. In certain embodiments, each ligand is, independently selected from galactose, N-acetyl galactoseamine, mannose, glucose, glucosamine and fucose. In certain embodiments, each ligand is N-acetyl galactoseamine (GalNAc). In certain embodiments, the targeting moiety comprises 1 to 3 ligands. In certain embodiments, the targeting moiety comprises 3 ligands. In certain embodiments, the targeting moiety comprises 2 ligands. In certain embodiments, the targeting moiety comprises 1 ligand. In certain embodiments, the targeting moiety comprises 3 N-acetyl galactoseamine ligands. In certain embodiments, the targeting moiety comprises 2 N-acetyl galactoseamine ligands. In certain embodiments, the targeting moiety comprises 1 N-acetyl galactoseamine ligand.

In certain embodiments, each ligand is a carbohydrate, carbohydrate derivative, modified carbohydrate, multivalent carbohydrate cluster, polysaccharide, modified polysaccharide, or polysaccharide derivative. In certain embodiments, each ligand is an amino sugar or a thio sugar. For example, amino sugars may be selected from any number of compounds known in the art, for example glucosamine, sialic acid, α-D-galactosamine, N-Acetylgalactosamine, 2-acetamido-2-deoxy-D-galactopyranose (GalNAc), 2-Amino-3-O—[(R)-1-carboxyethyl]-2-deoxy-β-D-glucopyranose (β-muramic acid), 2-Deoxy-2-methylamino-L-glucopyranose, 4,6-Dideoxy-4-formamido-2,3-di-O-methyl-D-mannopyranose, 2-Deoxy-2-sulfoamino-D-glucopyranose and N-sulfo-D-glucosamine, and N-Glycoloyl-α-neuraminic acid. For example, thio sugars may be selected from the group consisting of 5-Thio-β-D-glucopyranose, Methyl 2,3,4-tri-O-acetyl-1-thio-6-O-trityl-α-D-glucopyranoside, 4-Thio-β-D-galactopyranose, and ethyl 3,4,6,7-tetra-O-acetyl-2-deoxy-1,5-dithio-α-D-gluco-heptopyranoside.

In certain embodiments, conjugate groups as provided herein comprise a carbohydrate cluster. As used herein, "carbohydrate cluster" means a portion of a conjugate group wherein two or more carbohydrate residues are attached to a branching group through tether groups. (see, e.g., Maier et al., "Synthesis of Antisense Oligonucleotides Conjugated to a Multivalent Carbohydrate Cluster for Cellular Targeting," *Bioconjugate Chemistry*, 2003, (14): 18-29, which is incorporated herein by reference in its entirety, or Rensen et al., "Design and Synthesis of Novel N-Acetylgalactosamine-Terminated Glycolipids for Targeting of Lipoproteins to the Hepatic Asiaglycoprotein Receptor," *J. Med. Chem.* 2004, (47): 5798-5808, for examples of carbohydrate conjugate clusters).

As used herein, "modified carbohydrate" means any carbohydrate having one or more chemical modifications relative to naturally occurring carbohydrates.

As used herein, "carbohydrate derivative" means any compound which may be synthesized using a carbohydrate as a starting material or intermediate.

As used herein, "carbohydrate" means a naturally occurring carbohydrate, a modified carbohydrate, or a carbohydrate derivative.

In certain embodiments, conjugate groups are provided wherein the cell-targeting moiety has the formula:

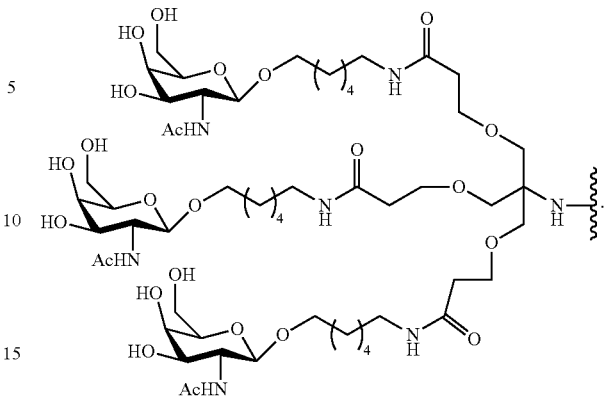

In certain embodiments, conjugate groups are provided wherein the cell-targeting moiety has the formula:

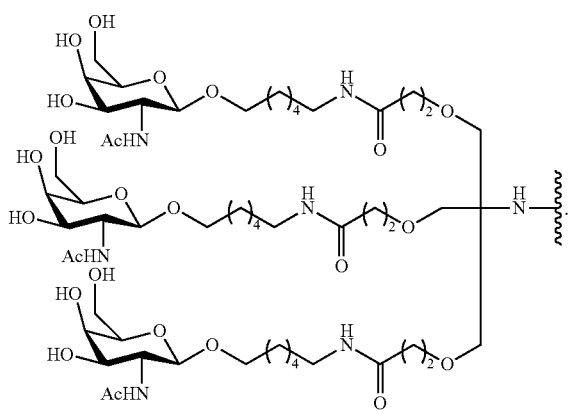

In certain embodiments, conjugate groups are provided wherein the cell-targeting moiety has the formula:

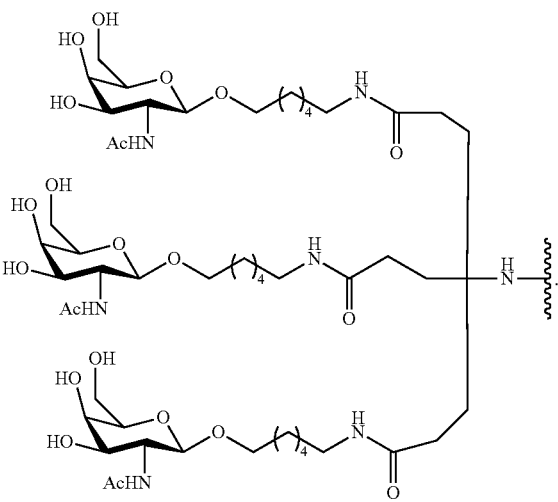

In certain embodiments, conjugate groups are provided wherein the cell-targeting moiety has the formula:

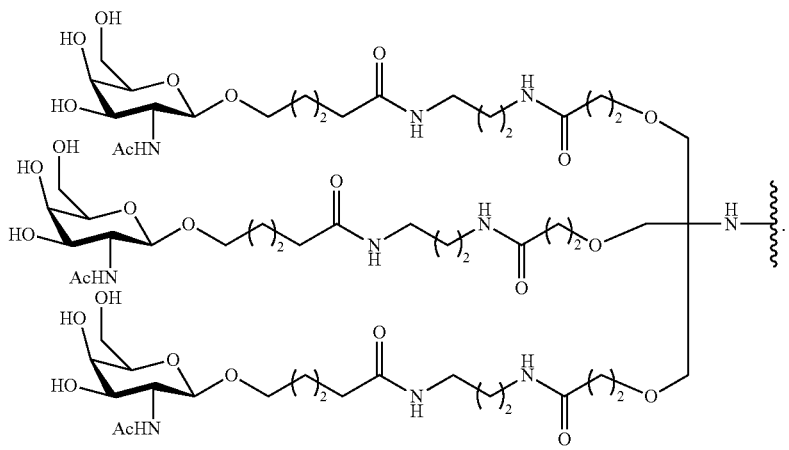

In certain embodiments, conjugate groups have the formula:

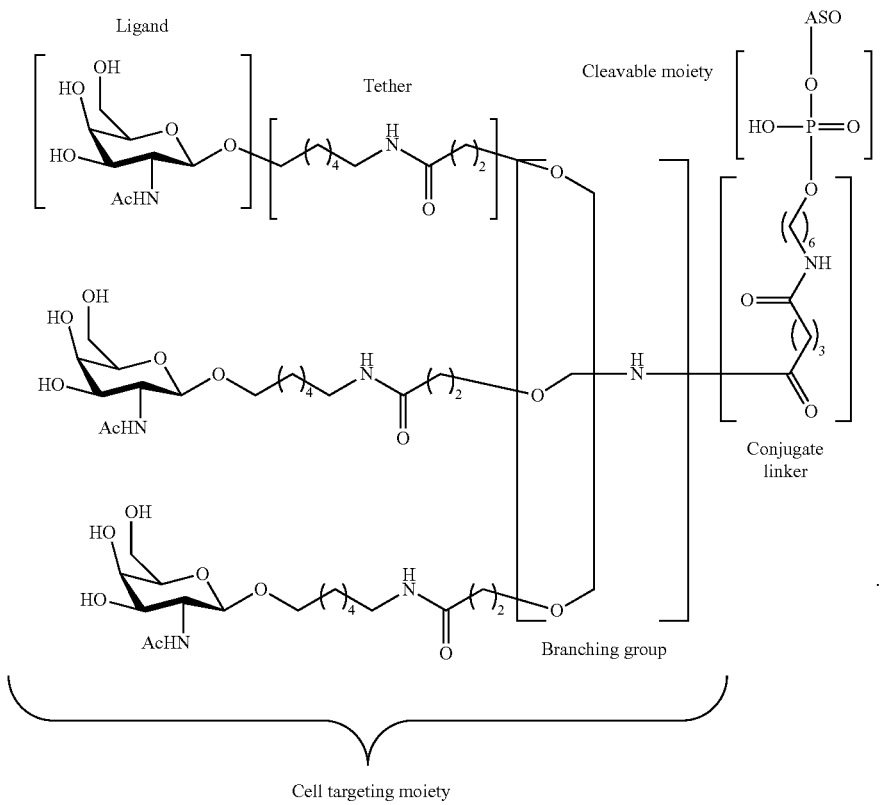

037254, each of which is incorporated by reference herein in its entirety.

Representative United States patents, United States patent application publications, and international patent application publications that teach the preparation of certain of the above noted conjugates, conjugated oligomeric compounds such as antisense compounds, tethers, conjugate linkers, branching groups, ligands, cleavable moieties as well as other modifications include without limitation, U.S. Pat. Nos. 5,994,517, 6,300,319, 6,660,720, 6,906,182, 7,262,177, 7,491,805, 8,106,022, 7,723,509, U.S. 2006/0148740, US 2011/0123520, WO 2013/033230 and WO 2012/

Representative publications that teach the preparation of certain of the above noted conjugates, conjugated oligomeric compounds such as antisense compounds, tethers, conjugate linkers, branching groups, ligands, cleavable moieties as well as other modifications include without limitation, BIESSEN et al., "The Cholesterol Derivative of a Triantennary Galactoside with High Affinity for the Hepatic Asialoglycoprotein Receptor: a Potent Cholesterol Lowering Agent" J. Med. Chem. (1995) 38:1846-1852, BIESSEN et al., "Synthesis of Cluster Galactosides with High Affinity for the Hepatic Asialoglycoprotein Receptor" J. Med. Chem.

(1995) 38:1538-1546, LEE et al., "New and more efficient multivalent glyco-ligands for asialoglycoprotein receptor of mammalian hepatocytes" Bioorganic & Medicinal Chemistry (2011) 19:2494-2500, RENSEN et al., "Determination of the Upper Size Limit for Uptake and Processing of Ligands by the Asialoglycoprotein Receptor on Hepatocytes in Vitro and in Vivo" J. Biol. Chem. (2001) 276(40):37577-37584, RENSEN et al., "Design and Synthesis of Novel N-Acetylgalactosamine-Terminated Glycolipids for Targeting of Lipoproteins to the Hepatic Asialoglycoprotein Receptor" J. Med. Chem. (2004) 47:5798-5808, SLIEDREGT et al., "Design and Synthesis of Novel Amphiphilic Dendritic Galactosides for Selective Targeting of Liposomes to the Hepatic Asialoglycoprotein Receptor" J. Med. Chem. (1999) 42:609-618, and Valentijn et al., "Solid-phase synthesis of lysine-based cluster galactosides with high affinity for the Asialoglycoprotein Receptor" Tetrahedron, 1997, 53(2), 759-770, each of which is incorporated by reference herein in its entirety.

Representative United States patents, United States patent application publications, and international patent application publications that teach the preparation of certain of the above noted conjugates, conjugated antisense compounds, tethers, linkers, branching groups, ligands, cleavable moieties as well as other modifications include without limitation, U.S. Pat. Nos. 5,994,517, 6,300,319, 6,660,720, 6,906,182, 7,262,177, 7,491,805, 8,106,022, 7,723,509, US 2006/0148740, US 2011/0123520, PCT/US2014/036452, WO 2013/033230 and WO 2012/037254, each of which is incorporated by reference herein in its entirety.

Representative publications that teach the preparation of certain of the above noted conjugates, conjugated antisense compounds, tethers, linkers, branching groups, ligands, cleavable moieties as well as other modifications include without limitation, BIESSEN et al., "The Cholesterol Derivative of a Triantennary Galactoside with High Affinity for the Hepatic Asialoglycoprotein Receptor: a Potent Cholesterol Lowering Agent" J. Med. Chem. (1995) 38:1846-1852, BIESSEN et al., "Synthesis of Cluster Galactosides with High Affinity for the Hepatic Asialoglycoprotein Receptor" J. Med. Chem. (1995) 38:1538-1546, LEE et al., "New and more efficient multivalent glyco-ligands for asialoglycoprotein receptor of mammalian hepatocytes" Bioorganic & Medicinal Chemistry (2011) 19:2494-2500, RENSEN et al., "Determination of the Upper Size Limit for Uptake and Processing of Ligands by the Asialoglycoprotein Receptor on Hepatocytes in Vitro and in Vivo" J. Biol. Chem. (2001) 276(40):37577-37584, RENSEN et al., "Design and Synthesis of Novel N-Acetylgalactosamine-Terminated Glycolipids for Targeting of Lipoproteins to the Hepatic Asialoglycoprotein Receptor" J. Med. Chem. (2004) 47:5798-5808, SLIEDREGT et al., "Design and Synthesis of Novel Amphiphilic Dendritic Galactosides for Selective Targeting of Liposomes to the Hepatic Asialoglycoprotein Receptor" J. Med. Chem. (1999) 42:609-618, and Valentijn et al., "Solid-phase synthesis of lysine-based cluster galactosides with high affinity for the Asialoglycoprotein Receptor" Tetrahedron, 1997, 53(2), 759-770, each of which is incorporated by reference herein in its entirety.

In certain embodiments, conjugated antisense compounds comprise an RNase H based oligonucleotide (such as a gapmer) or a splice modulating oligonucleotide (such as a fully modified oligonucleotide) and any conjugate group comprising at least one, two, or three GalNAc groups. In certain embodiments a conjugated antisense compound comprises any conjugate group found in any of the following references: Lee, Carbohydr Res, 1978, 67, 509-514; Connolly et al., J Biol Chem, 1982, 257, 939-945; Pavia et al., Int J Pep Protein Res, 1983, 22, 539-548; Lee et al., Biochem, 1984, 23, 4255-4261; Lee et al., Glycoconjugate J, 1987, 4, 317-328; Toyokuni et al., Tetrahedron Lett, 1990, 31, 2673-2676; Biessen et al., J Med Chem, 1995, 38, 1538-1546; Valentijn et al., Tetrahedron, 1997, 53, 759-770; Kim et al., Tetrahedron Lett, 1997, 38, 3487-3490; Lee et al., Bioconjug Chem, 1997, 8, 762-765; Kato et al., Glycobiol, 2001, 11, 821-829; Rensen et al., J Biol Chem, 2001, 276, 37577-37584; Lee et al., Methods Enzymol, 2003, 362, 38-43; Westerlind et al., Glycoconj J, 2004, 21, 227-241; Lee et al., Bioorg Med Chem Lett, 2006, 16(19), 5132-5135; Maierhofer et al., Bioorg Med Chem, 2007, 15, 7661-7676; Khorev et al., Bioorg Med Chem, 2008, 16, 5216-5231; Lee et al., Bioorg Med Chem, 2011, 19, 2494-2500; Kornilova et al., Analyt Biochem, 2012, 425, 43-46; Pujol et al., Angew Chemie Int Ed Engl, 2012, 51, 7445-7448; Biessen et al., J Med Chem, 1995, 38, 1846-1852; Sliedregt et al., J Med Chem, 1999, 42, 609-618; Rensen et al., J Med Chem, 2004, 47, 5798-5808; Rensen et al., Arterioscler Thromb Vasc Biol, 2006, 26, 169-175; van Rossenberg et al., Gene Ther, 2004, 11, 457-464; Sato et al., J Am Chem Soc, 2004, 126, 14013-14022; Lee et al., J Org Chem, 2012, 77, 7564-7571; Biessen et al., FASEB J, 2000, 14, 1784-1792; Rajur et al., Bioconjug Chem, 1997, 8, 935-940; Duff et al., Methods Enzymol, 2000, 313, 297-321; Maier et al., Bioconjug Chem, 2003, 14, 18-29; Jayaprakash et al., Org Lett, 2010, 12, 5410-5413; Manoharan, Antisense Nucleic Acid Drug Dev, 2002, 12, 103-128; Merwin et al., Bioconjug Chem, 1994, 5, 612-620; Tomiya et al., Bioorg Med Chem, 2013, 21, 5275-5281; International applications WO1998/013381; WO2011/038356; WO1997/046098; WO2008/098788; WO2004/101619; WO2012/037254; WO2011/120053; WO2011/100131; WO2011/163121; WO2012/177947; WO2013/033230; WO2013/075035; WO2012/083185; WO2012/083046; WO2009/082607; WO2009/134487; WO2010/144740; WO2010/148013; WO1997/020563; WO2010/088537; WO2002/043771; WO2010/129709; WO2012/068187; WO2009/126933; WO2004/024757; WO2010/054406; WO2012/089352; WO2012/089602; WO02013/166121; WO2013/165816; U.S. Pat. Nos. 4,751,219; 8,552,163; 6,908,903; 7,262,177; 5,994,517; 6,300,319; 8,106,022; 7,491,805; 7,491,805; 7,582,744; 8,137,695; 6,383,812; 6,525,031; 6,660,720; 7,723,509; 8,541,548; 8,344,125; 8,313,772; 8,349,308; 8,450,467; 8,501,930; 8,158,601; 7,262,177; 6,906,182; 6,620,916; 8,435,491; 8,404,862; 7,851,615; Published U.S. Patent Application Publications US2011/0097264; US2011/0097265; US2013/0004427; US2005/0164235; US2006/0148740; US2008/0281044; US2010/0240730; US2003/0119724; US2006/0183886; US2008/0206869; US2011/0269814; US2009/0286973; US2011/0207799; US2012/0136042; US2012/0165393; US2008/0281041; US2009/0203135; US2012/0035115; US2012/0095075; US2012/0101148; US2012/0128760; US2012/0157509; US2012/0230938; US2013/0109817; US2013/0121954; US2013/0178512; US2013/0236968; US2011/0123520; US2003/0077829; US2008/0108801; and US2009/0203132; each of which is incorporated by reference in its entirety.

Cell Culture and Antisense Compounds Treatment

The effects of antisense compounds on the level, activity or expression of AGPAT5 nucleic acids can be tested in vitro in a variety of cell types. Cell types used for such analyses are available from commercial vendors (e.g. American Type Culture Collection, Manassus, Va.; Zen-Bio, Inc., Research Triangle Park, N.C.; Clonetics Corporation, Walkersville, Md.) and cells are cultured according to the vendor's instructions using commercially available reagents (e.g. Invitrogen Life Technologies, Carlsbad, Calif.). Illustrative cell types include, but are not limited to, HepG2 cells, Hep3B cells, Huh7 (hepatocellular carcinoma) cells, primary hepatocytes, A549 cells, GM04281 fibroblasts and LLC-MK2 cells.

In Vitro Testing of Antisense Oligonucleotides

Described herein are methods for treatment of cells with antisense oligonucleotides, which can be modified appropriately for treatment with other antisense compounds.

In general, cells are treated with antisense oligonucleotides when the cells reach approximately 60-80% confluence in culture.

One reagent commonly used to introduce antisense oligonucleotides into cultured cells includes the cationic lipid transfection reagent LIPOFECTIN® (Invitrogen, Carlsbad, Calif.). Antisense oligonucleotides are mixed with LIPOFECTIN® in OPTI-MEM® 1 (Invitrogen, Carlsbad, Calif.) to achieve the desired final concentration of antisense oligonucleotide and a LIPOFECTIN® concentration that typically ranges 2 to 12 ug/mL per 100 nM antisense oligonucleotide.

Another reagent used to introduce antisense oligonucleotides into cultured cells includes LIPOFECTAMINE 2000® (Invitrogen, Carlsbad, Calif.). Antisense oligonucleotide is mixed with LIPOFECTAMINE 2000® in OPTI-MEM® 1 reduced serum medium (Invitrogen, Carlsbad, Calif.) to achieve the desired concentration of antisense oligonucleotide and a LIPOFECTAMINE® concentration that typically ranges 2 to 12 ug/mL per 100 nM antisense oligonucleotide.

Another reagent used to introduce antisense oligonucleotides into cultured cells includes Cytofectin® (Invitrogen, Carlsbad, Calif.). Antisense oligonucleotide is mixed with Cytofectin® in OPTI-MEM® 1 reduced serum medium (Invitrogen, Carlsbad, Calif.) to achieve the desired concentration of antisense oligonucleotide and a Cytofectin® concentration that typically ranges 2 to 12 ug/mL per 100 nM antisense oligonucleotide.

Another reagent used to introduce antisense oligonucleotides into cultured cells includes Oligofectamine™ (Invitrogen Life Technologies, Carlsbad, Calif.). Antisense oligonucleotide is mixed with Oligofectamine™ in Opti-MEM™-1 reduced serum medium (Invitrogen Life Technologies, Carlsbad, Calif.) to achieve the desired concentration of oligonucleotide with an Oligofectamine™ to oligonucleotide ratio of approximately 0.2 to 0.8 µL per 100 nM.

Another reagent used to introduce antisense oligonucleotides into cultured cells includes FuGENE 6 (Roche Diagnostics Corp., Indianapolis, Ind.). Antisense oligomeric compound was mixed with FuGENE 6 in 1 mL of serum-free RPMI to achieve the desired concentration of oligonucleotide with a FuGENE 6 to oligomeric compound ratio of 1 to 4 µL of FuGENE 6 per 100 nM.

Another technique used to introduce antisense oligonucleotides into cultured cells includes electroporation (Sambrook and Russell, Molecular Cloning: A Laboratory Manual, $3^{rd}$ Ed., 2001).

Cells are treated with antisense oligonucleotides by routine methods. Cells are typically harvested 16-24 hours after antisense oligonucleotide treatment, at which time RNA or protein levels of target nucleic acids are measured by methods known in the art and described herein. In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art. Antisense oligonucleotides are typically used at concentrations ranging from 1 nM to 300 nM when transfected with LIPOFECTAMINE2000®, Lipofectin or Cytofectin. Antisense oligonucleotides are used at higher concentrations ranging from 625 to 20,000 nM when transfected using electroporation.

RNA Isolation

RNA analysis can be performed on total cellular RNA or poly(A)+ mRNA. Methods of RNA isolation are well known in the art (Sambrook and Russell, Molecular Cloning: A Laboratory Manual, $3^{rd}$ Ed., 2001). RNA is prepared using methods well known in the art, for example, using the TRIZOL® Reagent (Invitrogen, Carlsbad, Calif.) according to the manufacturer's recommended protocols.

Analysis of Inhibition of Target Levels or Expression

Inhibition of levels or expression of an AGPAT5 nucleic acid can be assayed in a variety of ways known in the art (Sambrook and Russell, Molecular Cloning: A Laboratory Manual, $3^{rd}$ Ed., 2001). For example, target nucleic acid levels can be quantitated by, e.g., Northern blot analysis, competitive polymerase chain reaction (PCR), or quantitative real-time PCR. RNA analysis can be performed on total cellular RNA or poly(A)+ mRNA. Methods of RNA isolation are well known in the art. Northern blot analysis is also routine in the art. Quantitative real-time PCR can be conveniently accomplished using the commercially available ABI PRISM® 7600, 7700, or 7900 Sequence Detection System, available from PE-Applied Biosystems, Foster City, Calif. and used according to manufacturer's instructions.

Quantitative Real-Time PCR Analysis of Target RNA Levels

Quantitation of target RNA levels can be accomplished by quantitative real-time PCR using the ABI PRISM® 7600, 7700, or 7900 Sequence Detection System (PE-Applied Biosystems, Foster City, Calif.) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents are obtained from Invitrogen (Carlsbad, Calif.). RT and real-time-PCR reactions are carried out by methods well known to those skilled in the art.

Gene (or RNA) target quantities obtained by real time PCR can be normalized using either the expression level of a gene whose expression is constant, such as cyclophilin A or GADPH or by quantifying total RNA using RIBOGREEN® (Life Technologies™, Inc. Carlsbad, Calif.). Cyclophilin A or GADPH expression can be quantified by real time PCR, by being run simultaneously with the target, multiplexing, or separately. Total RNA can be quantified using RIBOGREEN® RNA quantification reagent. Methods of RNA quantification by RIBOGREEN® are taught in Jones, L. J., et al, (Analytical Biochemistry, 1998, 265, 368-374). A CYTOFLUOR® 4000 instrument (PE Applied Biosystems) can be used to measure RIBOGREEN® fluorescence.

Methods for designing real-time PCR probes and primers are well known in the art, and can include the use of software such as PRIMER EXPRESS® Software (Applied Biosystems, Foster City, Calif.). Probes and primers used in real-time PCR were designed to hybridize to AGPAT5 specific sequences and are disclosed in the Examples below. The target specific PCR probes can have FAM covalently linked to the 5' end and TAMRA or MGB covalently linked to the 3' end, where FAM is the fluorescent dye and TAMRA or MGB is the quencher dye.

Analysis of Protein Levels

Antisense inhibition of AGPAT5 nucleic acids can be assessed by measuring AGPAT5 protein levels. Protein levels of AGPAT5 can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS) (Sambrook and Russell, Molecular Cloning: A Laboratory Manual, $3^{rd}$ Ed., 2001). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art.

In Vivo Testing of Antisense Compounds

Antisense compounds, for example, antisense oligonucleotides, are tested in animals to assess their ability to inhibit expression of AGPAT5 and produce phenotypic changes. Testing can be performed in normal animals, or in experimental disease models. For administration to animals, antisense oligonucleotides are formulated in a pharmaceutically acceptable diluent, such as phosphate-buffered saline. Administration includes parenteral routes of administration. Following a period of treatment with antisense oligonucleotides, RNA is isolated from tissue and changes in AGPAT5 nucleic acid expression are measured. Changes in AGPAT5 protein levels are also measured.

Certain Indications

In certain embodiments, provided herein are methods of treating an individual comprising administering one or more pharmaceutical compositions as described herein. In certain embodiments, the individual has a cardiometabolic disease, disorder or condition, or physiological marker thereof. In certain embodiments, the individual has one or more of diabetes (Type I or Type II), metabolic syndrome, insulin resistance, dyslipidemia, hypertriglyceridemia, hyperglycemia, non-alcoholic fatty liver disease (NAFLD), nonalcoholic steatohepatitis (NASH), diabetes (e.g., Type 2 diabetes) and high blood pressure.

In certain embodiments, the compounds targeted to AGPAT5 described herein modulate lipid and/or energy metabolism in an animal. In certain embodiments, the compounds targeted to AGPAT5 described herein modulate physiological markers or phenotypes of dyslipidemia, hypertriglyceridemia, metabolic syndrome, insulin resistance, NAFLD, NASH and/or diabetes. For example, administration of the compounds to animals can modulate one or more of triglyceride levels, glucose levels, insulin levels, insulin sensitivity, insulin resistance or AGPAT5 levels. In certain embodiments, the modulation of the physiological markers or phenotypes can be associated with inhibition of AGPAT5 by the compounds.

In certain embodiments, the compounds targeted to AGPAT5 described herein reduce and/or prevent one or more of hepatic TG accumulation (i.e. hepatic steatosis), dyslipidemia, metabolic syndrome, non-alcoholic fatty liver disease (NAFLD), nonalcoholic steatohepatitis (NASH), diabetes (e.g., Type 1 or Type 2 diabetes), insulin resistance and high blood pressure. In certain embodiments, the compounds targeted to AGPAT5 described herein improve insulin sensitivity.

In certain embodiments, administration of an antisense compound targeted to an AGPAT5 nucleic acid results in reduction of AGPAT5 expression by about at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 99%, or a range defined by any two of these values.

In certain embodiments, pharmaceutical compositions comprising an antisense compound targeted to AGPAT5 are used for the preparation of a medicament for treating a patient suffering from, or susceptible to, a cardiometabolic disease, disorder or condition, or a symptom or physiological marker thereof. In certain embodiments, pharmaceutical compositions comprising an antisense compound targeted to AGPAT5 are used in the preparation of a medicament for treating a patient suffering from, or susceptible to, one or more of diabetes (Type I or Type II), metabolic syndrome, insulin resistance, dyslipidemia, hypertriglyceridemia, non-alcoholic fatty liver disease (NAFLD), nonalcoholic steatohepatitis (NASH), diabetes (e.g., Type 2 diabetes) and high blood pressure.

Administration

In certain embodiments, the compounds and compositions as described herein are administered parenterally.

In certain embodiments, parenteral administration is by infusion. Infusion can be chronic or continuous or short or intermittent. In certain embodiments, infused pharmaceutical agents are delivered with a pump.

In certain embodiments, parenteral administration is by injection. The injection can be delivered with a syringe or a pump. In certain embodiments, the injection is a bolus injection. In certain embodiments, the injection is administered directly to a tissue or organ. In certain embodiments, the injection is subcutaneous.

Certain Combination Therapies

In certain embodiments, a first agent comprising the modified oligonucleotide disclosed herein is co-administered with one or more secondary agents. In certain embodiments, such second agents are designed to treat the same disease, disorder or condition as the first agent described herein. In certain embodiments, such second agents are designed to treat a different disease, disorder, or condition as the first agent described herein. In certain embodiments, such second agents are designed to treat an undesired side effect of one or more pharmaceutical compositions as described herein. In certain embodiments, second agents are co-administered with the first agent to treat an undesired effect of the first agent. In certain embodiments, second agents are co-administered with the first agent to produce a combinational effect. In certain embodiments, second agents are co-administered with the first agent to produce a synergistic effect.

In certain embodiments, a first agent and one or more second agents are administered at the same time. In certain embodiments, the first agent and one or more second agents are administered at different times. In certain embodiments, the first agent and one or more second agents are prepared together in a single pharmaceutical formulation. In certain embodiments, the first agent and one or more second agents are prepared separately.

In certain embodiments, second agents include, but are not limited to a glucose-lowering agent or a lipid-lowering agent. The glucose lowering agent can include, but is not limited to, a therapeutic lifestyle change, PPAR agonist, a dipeptidyl peptidase (IV) inhibitor, a GLP-1 analog, insulin or an insulin analog, an insulin secretagogue, a SGLT2 inhibitor, a human amylin analog, a biguanide, an alpha-glucosidase inhibitor, or a combination thereof. The glucose-lowering agent can include, but is not limited to metformin, sulfonylurea, rosiglitazone, meglitinide, thiazolidinedione, alpha-glucosidase inhibitor or a combination thereof. The sulfonylurea can be acetohexamide, chlorpropamide, tolbutamide, tolazamide, glimepiride, a glipizide, a glyburide, or a gliclazide. The meglitinide can be nateglinide or repaglinide. The thiazolidinedione can be pioglitazone or rosiglitazone. The alpha-glucosidase can be acarbose or miglitol. In certain embodiments the lipid lowering therapy can include, but is not limited to, a therapeutic lifestyle change, niacin, HMG-CoA reductase inhibitor, cholesterol absorption inhibitor, MTP inhibitor (e.g., a small molecule, polypeptide, antibody or antisense compound targeted to MTP), fibrate, PCSK9 inhibitor (e.g., PCSK9 antibodies, polypeptides, small molecules nucleic acid compounds targeting PCSK9), CETP inhibitor (e.g., small molecules such as torcetrapib and anacetrapib, polypeptides, antibodies or nucleic acid compounds targeted to CETP), apoC-III inhibitor (e.g., a small molecule, polypeptide, antibody or nucleic acid compounds targeted to apoC-III), apoB inhibitor (e.g., a small molecule, polypeptide, antibody or nucleic acid compounds targeted to apoB), beneficial oils rich in omega-3 fatty acids, omega-3 fatty acids or any combination thereof. The HMG-CoA reductase inhibitor can be atorvastatin, rosuvastatin, fluvastatin, lovastatin, pravastatin, simvastatin and the like. The cholesterol absorption inhibitor can be ezetimibe. The fibrate can be fenofibrate, bezafibrate, ciprofibrate, clofibrate, gemfibrozil and the like. The beneficial oil rich in omega-3 fatty acids can be krill, fish (e.g., Vascepa$^R$), flaxseed oil and the like. The omega-3 fatty acid can be ALA, DHA, EPA and the like.

Advantages of the Invention

Provided herein, for the first time, are methods and compositions for the modulation of AGPAT5 that can treat, delay, prevent and/or ameliorate a cardiometabolic disease, disorder or condition, or a physiological marker thereof. In a particular embodiment, for the first time AGPAT5 inhibitors (e.g., antisense oligonucleotides targeting a nucleic acid encoding AGPAT5) are provided for reducing of insulin, insulin resistance, glucose and triglyceride levels in an animal. In a particular embodiment, for the first time AGPAT5 inhibitors (e.g., antisense oligonucleotides targeting a nucleic acid encoding AGPAT5) are provided for increasing insulin sensitivity, glucose clearance and glucose tolerance in an animal

EXAMPLES

Non-Limiting Disclosure and Incorporation by Reference

While certain compounds, compositions and methods described herein have been described with specificity in accordance with certain embodiments, the following examples serve only to illustrate the compounds described herein and are not intended to limit the same. Each of the references recited in the present application is incorporated herein by reference in its entirety.

Example 1: Antisense Inhibition of Mouse AGPAT5 by Oligomeric Compounds

A series of oligomeric compounds was designed to target different regions of mouse 1-acylglycerol-3-phosphate-O-acyltransferase 5 (AGPAT5). The oligomeric compounds are targeted to the mouse mRNA SEQ ID NO: 1 (GENBANK Accession No. NM_026792.3) and/or the mouse genomic SEQ ID NO: 2 (GENBANK Accession No. NT_039455.7 truncated from nucleotides 15844020 to 15885425).

The compounds were analyzed for their effects on gene target mRNA levels. Mouse bEND cells were plated at a density of 20,000 cells per well in 96 well plates and were transfected using electroporation with 3,000 nM compound or with no compound for untreated controls. After approximately 24 hours, RNA was isolated from the cells and AGPAT5 transcript levels were measured by quantitative real-time PCR using primer probe set RTS3749 (forward: 5'-GAACAAGGTATAATGCAACATACACAAA-3', SEQ ID NO: 3; reverse: 5'-TGGCCTTTATTCTTGGTGTCAGT-3', SEQ ID NO: 4; probe: 5'-CCTTTCAGCCAGTCAG-GCATTTGCTG-3', SEQ ID NO: 5). AGPAT5 RNA transcript levels were adjusted according to total RNA content, as measured by RIBOGREEN®. Results for the compounds that exhibited greatest inhibition of AGPAT5 transcript expression are presented as average percent inhibition of AGPAT5, relative to untreated control cells, in Table 1.

All compounds in Table 1 are chimeric oligonucleotides ("gapmers") 16 nucleotides in length, composed of a central "gap" region consisting of ten 2'-deoxynucleotides, which is flanked on both sides (5' and 3') by three-nucleotide "wings". The "gap" region elicits RNase H activity, and the "wing" regions increase binding affinity to the target. The wings are composed of 4'-CH(CH$_3$)—O-2' nucleotides, also known as constrained ethyl or cEt nucleotides. The internucleoside (backbone) linkages are phosphorothioate throughout the oligonucleotides. All cytosine residues are 5-methylcytosines. The start and stop sites for the compounds are listed in Table 1.

TABLE 1

Oligomeric compounds targeting mouse AGPAT5

| ISIS No. | Sequence 5' to 3' | Start site on SEQ ID NO: 1 | Stop site on SEQ ID NO: 1 | Start site on SEQ ID NO: 2 | Stop site on SEQ ID NO: 2 | % Inhibition | SEQ ID NO. |
|---|---|---|---|---|---|---|---|
| 574936 | GAGTAGAGGTCCCTGA | n/a | n/a | 3882 | 3897 | 63.3 | 6 |
| 574938 | GGAATAGTGTTTACAC | n/a | n/a | 9144 | 9159 | 61.5 | 7 |
| 574979 | GCATAAGTTAGTGAAC | n/a | n/a | 16656 | 16671 | 60.8 | 8 |

TABLE 1-continued

Oligomeric compounds targeting mouse AGPAT5

| ISIS No. | Sequence 5' to 3' | Start site on SEQ ID NO: 1 | Stop site on SEQ ID NO: 1 | Start site on SEQ ID NO: 2 | Stop site on SEQ ID NO: 2 | % Inhibition | SEQ ID NO. |
|---|---|---|---|---|---|---|---|
| 574842 | CTTGTCTTTCAGTACG | 632 | 647 | 24935 | 24950 | 66.5 | 9 |
| 574981 | AGTGTACTTACAGTGG | n/a | n/a | 28183 | 28198 | 59.8 | 10 |
| 574905 | GTATTTTCCTGAACCT | 992 | 1007 | 34112 | 34127 | 54.3 | 11 |
| 574948 | AAGTGTTCGATTTTGC | n/a | n/a | 34887 | 34902 | 63.9 | 12 |
| 574919 | CCATGTACAGTTTCCT | 1308 | 1323 | 37873 | 37888 | 48.8 | 13 |
| 574933 | GATAACCAATATAGCG | 1743 | 1758 | 38308 | 38323 | 68.6 | 14 |
| 574868 | AGCTGCCAAGTAGTCA | 1766 | 1781 | 38331 | 38346 | 58.6 | 15 |
| 574935 | AGTATTAAGAGTCTGA | 1781 | 1796 | 38346 | 38361 | 61.8 | 16 |
| 574874 | CCTTTTTCTTGGAACA | 1897 | 1912 | 38462 | 38477 | 68.1 | 17 |
| 574880 | GACACTTTACACATTA | 2063 | 2078 | 38628 | 38643 | 64.2 | 18 |
| 574890 | AGCACCACTGGAGGAC | 2379 | 2394 | 38944 | 38959 | 60.7 | 19 |
| 574959 | CACGGCAAATCACACG | 2663 | 2678 | 39228 | 39243 | 52.2 | 20 |
| 574962 | GATTCAATTGGTCTAT | 2790 | 2805 | 39355 | 39370 | 53.1 | 21 |
| 574968 | CCAATTCCATGAAGCT | 3276 | 3291 | 39841 | 39856 | 50 | 22 |
| 574972 | TACCACATTTGATAGG | 3542 | 3557 | 40107 | 40122 | 48.7 | 23 |

Example 2: Antisense Inhibition of Mouse AGPAT5 in Vivo

Select compounds listed in Table 1 were further evaluated for antisense inhibition of mouse AGPAT5 in vivo. Male C57BL/6 mice were injected intraperitoneally (i.p.) once per week for 6 weeks (a total of 6 doses) with 10 mg/kg or 25 mg/kg of a compound listed in Table 2 or with PBS. Each treatment group consisted of 4 animals. Two days following the final dose, the mice were sacrificed, and hepatic AGPAT5 mRNA expression was quantitated using qRT-PCR, as described in Example 1. The results presented in Table 2 are the average values for each treatment group relative to the average values for the PBS control group.

TABLE 2

Antisense inhibition of mouse AGPAT5 in vivo

| ISIS No. | Dose (mg/kg) | % Inhibition |
|---|---|---|
| 574979 | 10 | 19.4 |
|  | 25 | 61.5 |
| 574948 | 10 | 81.5 |
|  | 25 | 76.0 |
| 574933 | 10 | 43.0 |
|  | 25 | 88.1 |
| 574935 | 10 | 27.7 |
|  | 25 | 72.5 |
| 574880 | 10 | 68.7 |
|  | 25 | 86.3 |

Example 3: Effect of an Oligomeric Compound Targeting Mouse AGPAT5 in a Diet-Induced Obesity Mouse Model ISIS 574933 (see Tables 1-2) was selected for evaluation in a diet-induced obesity (DIO) mouse model. Male C57BL/6 mice were fed a high fat diet comprising 60% of total calories as fat beginning at 3 weeks of age and continuing until they were sacrificed. After consuming the high fat diet for 3 months, baseline levels of plasma transaminases, cholesterol, glucose, HDL, LDL, triglycerides (TG), nonesterified fatty acids (NEFA), and 3-hydroxy-butyrate (3HB) were measured, and body weights of the mice were assessed. Following the baseline assessments, the mice were i.p. injected once per week for 9 weeks (a total of 10 doses) with one of the three doses for ISIS 574933 listed in Table 3, with 25 mg/kg of control cEt gapmer ISIS 549144 (control ASO) that is not targeted to any mouse gene, or with PBS. Each treatment group consisted of 8 animals.

Five days before the final oligonucleotide or PBS dose was administered, an i.p. glucose tolerance test was performed. Following an overnight fast, baseline blood glucose (time=0 minutes) was measured using a glucometer (Abbott Laboratories, Bedford, Mass.). Animals were subsequently i.p. injected with 1.5 mg/kg glucose, and additional blood glucose measurements were performed at the time points listed in Table 3. The average results for each treatment group are presented in Table 3, and show that after about 8 weeks of treatment with ISIS 574933, treated mice were able to clear glucose at a higher rate than control treated mice, indicating an improvement in glucose tolerance with ISIS 574933 treatment.

Two days following the final oligonucleotide or PBS dose, the mice were sacrificed. Liver and adipose mRNA levels of AGPAT5 were evaluated using qRT-PCR, as described in Example 1, except that the AGPAT5 mRNA levels were normalized to Cyclophilin A instead of RIBOGREEN®. Results are presented in Table 4 as average % inhibition of AGPAT5 mRNA expression relative to the PBS control group. ISIS 574933 was able to knockdown AGPAT5 expression by more than 70% in both the liver and adipose tissue. Insulin levels were also measured at this time using an ELISA kit from ALPCO according to the manufacturer's instructions. The average results for each treatment group are presented in Table 4 and show that the mice had significantly reduced plasma insulin levels. Taken together, the data in Tables 3-4 show that ISIS 574933 treatment decreased insulin resistance and increased insulin sensitivity, indicated by the decreased levels of insulin needed to affect glucose levels.

Body weights, organ weights, and epididymal white adipose tissue weights (epiWAT) were assessed (Table 5), and plasma transaminases, cholesterol, glucose, HDL, LDL, TG, NEFA, and 3HB levels were measured (Table 6). Body weights and plasma marker results are presented in Tables 5 and 6, respectively, as average percent change relative to baseline levels for each treatment group. The data show that ISIS 574933 ameliorated the body weight gain in the treated mice compared to the control ASO treated mice.

TABLE 3

Effect of ISIS 574933 on glucose tolerance in a DIO mouse model

| ISIS No. | Dose (mg/kg) | Glucose (mg/dL) | | | | | |
|---|---|---|---|---|---|---|---|
| | | 0 minutes | 15 minutes | 30 minutes | 60 minutes | 90 minutes | 120 minutes |
| PBS | n/a | 147 | 347 | 459 | 460 | 418 | 351 |
| 549144 | 25 | 141 | 439 | 476 | 448 | 397 | 310 |
| 574933 | 5 | 139 | 384 | 464 | 434 | 375 | 326 |
| | 10 | 152 | 356 | 390 | 425 | 382 | 321 |
| | 25 | 128 | 336 | 370 | 358 | 313 | 243 |

TABLE 4

Effect of ISIS 574933 on AGPAT5 mRNA levels and insulin levels in a DIO mouse model

| ISIS No. | Dose (mg/kg) | % mRNA Inhibition in liver | % mRNA inhibition in adipose | Insulin (ng/mL) |
|---|---|---|---|---|
| PBS | n/a | 0.0 | 0.0 | 46.2 |
| 549144 | 25 | 4.3 | 1.8 | 22.1 |
| 574933 | 5 | 78.4 | 52.4 | 25.4 |
| | 10 | 88.8 | 72.2 | 11.9 |
| | 25 | 92.8 | 79.8 | 3.9 |

TABLE 5

Effect of ISIS 574933 on body and organ weights in a DIO mouse model

| ISIS No. | Dose (mg/kg) | % Body weight change | Kidney weight (g) | Liver weight (g) | Spleen weight (g) | epiWAT mass (g) |
|---|---|---|---|---|---|---|
| PBS | n/a | 22.8 | 0.38 | 2.6 | 0.12 | 1.5 |
| 549144 | 25 | 24.6 | 0.38 | 2.5 | 0.13 | 1.9 |
| 574933 | 5 | 20.8 | 0.37 | 2.1 | 0.14 | 1.8 |
| | 10 | 23.7 | 0.35 | 2.6 | 0.15 | 1.6 |
| | 25 | 13.4 | 0.33 | 2.6 | 0.48 | 1.6 |

TABLE 6

% change of plasma markers relative to baseline values in a DIO mouse model

| ISIS No. | Dose | ALT | AST | Cholesterol | Glucose | HDL | LDL | TG | NEFA | 3HB |
|---|---|---|---|---|---|---|---|---|---|---|
| PBS | n/a | 425 | 132 | 14.9 | −2.8 | 26.2 | 40.0 | 25.6 | −61.9 | 51.2 |
| 549144 | 25 | 291 | 109 | 26.7 | −2.5 | 36.4 | 52.5 | 43.4 | −57.3 | 45.1 |
| 574933 | 5 | 234 | 123 | 10.2 | 1.4 | 30.0 | 35.6 | 39.1 | −29.7 | 3.4 |
| | 10 | 485 | 207 | 36.8 | 0.6 | 57.6 | 61.2 | 12.2 | −31.4 | 52.1 |
| | 25 | 1400 | 727 | 17.3 | −4.2 | 37.3 | 37.7 | 27.7 | −45.3 | 23.9 |

Example 4: Effect of an Oligomeric Compound Targeting Mouse AGPAT5 in a Diet-Induced Obesity Mouse Model ISIS 574933 (see Table 1) was further evaluated in the diet-induced obesity (DIO) mouse model described in Example 3 fed the high fat diet for a longer time period. After feeding the male C57BL/6 mice the high fat diet for nearly 5 months, baseline levels of plasma transaminases, cholesterol, glucose, HDL, triglycerides (TG), nonesterified fatty acids (NEFA), and 3-hydroxybutyrate (3HB) were measured, and body weights of the mice were assessed. MRI scans were also performed to analyze body fat, lean, and water masses of the mice using an EchoMRI whole body composition analyzer (Echo Medical Systems, Houston, Tex.). Following the baseline assessments, the mice were i.p. injected once per week for 8 weeks (a total of 9 doses) with 25 mg/kg of ISIS 574933 or with PBS. Each treatment group consisted of 6 animals.

Two days before the final oligonucleotide or PBS dose was administered, an i.p. glucose tolerance test (IPGTT) was performed as described in Example 3. The results are presented in Table 7, and show that after 8 weeks of treatment with ISIS 574933, treated mice were able to clear plasma glucose at a higher rate than PBS treated mice indicating ISIS 574933 improves glucose tolerance.

Insulin levels were measured using the ALPCO ELISA kit 4 weeks following the first dose (midpoint of the oligonucleotide treatment) and 8 weeks following the first dose (end of the oligonucleotide treatment). The average results for each treatment group are presented in Table 8 and show that the ISIS 574933 treated mice had significantly reduced plasma insulin levels at both the 4 and 8 week timepoints. Taken together, the data in Tables 7-8 indicate that ISIS 574933 treatment decreased insulin resistance and and increased insulin sensitivity as measured by the decreased levels of insulin needed to affect glucose levels.

MRI scans were performed to analyze body fat, lean mass, and water mass 7 weeks following the first oligonucleotide dose. The results are presented in Table 9 as average percent change for each treatment group relative to baseline levels and show that ISIS 574933 ameliorated the fat gain in the treated mice compared to the PBS treated mice.

Five days following the final oligonucleotide or PBS dose, the mice were sacrificed. Liver mRNA levels of AGPAT5 were evaluated using qRT-PCR as described in Example 1, except that the AGPAT5 mRNA levels were normalized to Cyclophilin A instead of RIBOGREEN®. Results are presented in Table 8 as average percent inhibition of AGPAT5 mRNA expression relative to the PBS control group and show that ISIS 574933 was able to significantly knockdown AGPAT5 expression in the liver.

Body weights, organ weights, and epididymal white adipose tissue weights (epiWAT) were assessed, and plasma transaminases, cholesterol, creatinine, glucose, HDL, TG, BUN, NEFA, and 3HB levels were measured. Body weights and plasma marker results are presented in Tables 10 and 11, respectively, as average percent change relative to baseline levels, with the exceptions of creatinine and BUN, which are presented as average absolute levels at time of sacrifice for each treatment group. Organ weights and epiWAT ratios are presented in Table 10 as average absolute levels at time of sacrifice for each treatment group. The data show that ISIS 574933 administration ameliorated the body weight gain in the treated mice compared to the PBS treated mice.

Liver triglycerides were also measured, and the average results for each treatment group are presented in Table 12.

The data show that ISIS 574933 significantly reduced the level of liver triglycerides (hepatic steatosis) in the treated mice.

TABLE 7

Effect of ISIS 574933 on glucose tolerance in a DIO mouse model

| | Glucose (mg/dL) | | | | |
|---|---|---|---|---|---|
| ISIS No. | 0 minutes | 15 minutes | 30 minutes | 60 minutes | 90 minutes | 120 minutes |
| PBS | 100 | 315 | 306 | 214 | 159 | 137 |
| 574933 | 105 | 257 | 250 | 202 | 163 | 138 |

TABLE 8

Effect of ISIS 574933 on AGPAT5 mRNA levels and insulin levels in a DIO mouse model

| ISIS No. | % mRNA Inhibition in liver | Insulin at 4 weeks (ng/mL) | Insulin at 8 weeks (ng/mL) |
|---|---|---|---|
| PBS | 0.0 | 55.3 | 33.3 |
| 574933 | 86.6 | 6.0 | 4.0 |

TABLE 9

% change of body fat, lean mass, and water mass in a DIO mouse model

| ISIS No. | Body fat | Lean mass | Total fluids | Free water | Fat/Body weight |
|---|---|---|---|---|---|
| PBS | 21.4 | 10.3 | 49.5 | 11.3 | 8.4 |
| 574933 | −9.4 | 5.3 | 11.1 | 5.4 | −8. |

TABLE 10

Effect of ISIS 574933 on body and organ weights in a DIO mouse model

| ISIS No. | % Body weight change | Liver weight (g) | Kidney weight (g) | Spleen weight (g) | epiWAT mass (g) |
|---|---|---|---|---|---|
| PBS | 9.2 | 2.5 | 0.42 | 0.17 | 1.1 |
| 574933 | −0.8 | 1.7 | 0.43 | 0.26 | 1.2 |

TABLE 11

% change of plasma markers relative to baseline values in a DIO mouse model

| ISIS No. | ALT | AST | Cholesterol | Glucose | HDL | TG | NEFA | 3HB | Creatinine (mg/dL) | BUN (mg/dL) |
|---|---|---|---|---|---|---|---|---|---|---|
| PBS | 12.5 | −3.1 | −21.8 | −6.7 | −22.4 | 9.7 | 7.1 | 156 | 0.13 | 25.1 |
| 574933 | 169 | −16.1 | 12.3 | 23.4 | 8.7 | 18.0 | −34.2 | 57.8 | 0.10 | 22.0 |

TABLE 12

Liver triglycerides in a DIO mouse model

| ISIS No. | Liver triglycerides (mg TG/g liver wet weight) |
|---|---|
| PBS | 226 |
| 574933 | 51 |

Example 5: In Vivo Antisense Inhibition of Murine 1-Acylglycerol-3-phosphate O-Acyltransferase 5 (AGPAT5)

Several antisense oligonucleotides were designed that were targeted to murine AGPAT5 (GENBANK Accession No. NM_026792.3, incorporated herein as SEQ ID NO: 1) mRNA.

ISIS 574933 (GATAACCAATATAGCG; SEQ ID NO: 14), which was one of the designed antisense oligonucleotides to target both rat and mouse AGPAT5, is a 3-10-3 cEt gapmer, and is 16 nucleosides in length, wherein the central gap segment is comprised of ten 2'-deoxynucleosides and is flanked on both sides (in the 5' and 3' directions) by wings comprising 3 nucleosides each. Each nucleoside in the 5' wing segment and each nucleoside in the 3' wing segment has a cEt modification. The internucleoside linkages throughout the gapmer are phosphorothioate (P=S) linkages. All cytosine residues throughout the gapmer are 5-methylcytosines. ISIS 574933 is targeted to nucleobases 1743 to 1758 of SEQ ID NO: 1.

ISIS 549144 (GGCCAATACGCCGTCA; SEQ ID NO: 27) is a control oligonucleotide with no known gene target. It was designed as a 3-10-3 cEt gapmer, and is 16 nucleosides in length, wherein the central gap segment is comprised of ten 2'-deoxynucleosides and is flanked on both sides (in the 5' and 3' directions) by wings comprising 3 nucleosides each. Each nucleoside in the 5' wing segment and each nucleoside in the 3' wing segment has a cEt modification. The internucleoside linkages throughout the gapmer are phosphorothioate (P=S) linkages.

Treatment

Groups of Sprague-Dawley rats were placed on a fructose-fed diet for 12 weeks and then randomized, based on fed insulin and fed glucose levels, into one of three groups. Each group contained 10 rats. Two groups of rats were injected subcutaneously with 25 mg/kg of rat AGPAT5 ASO (ISIS 574933) or control oligonucleotide (ISIS 549144), administered weekly for 8 weeks. A control group of rats was injected with phosphate buffered saline (PBS) administered weekly for 8 weeks. Rats underwent IPGTT after 7 weeks of dosing. The animals were sacrificed one day after the last oligonucleotide injection.

AGPAT5 RNA Analysis

RNA was extracted from liver and fat tissues for real-time PCR analysis of AGPAT5, using rat AGPAT5 primer probe set (Life Technologies, Assay ID Rn01482872_ml).

The mRNA levels were normalized using Cyclophilin. As shown in Table 13, ISIS 574933 achieved significant reduction of murine AGPAT5 over the PBS control in both liver and fat tissues. Results are presented as percent inhibition of AGPAT5, relative to control.

TABLE 13

Percent inhibition of murine AGPAT5 mRNA by ISIS 574933 in Sprague-Dawley rats

| | % |
|---|---|
| Liver | 88 |
| Fat | 53 |

Effect on Glucose Tolerance

Glucose tolerance was measured via the intraperitoneal glucose tolerance test (IPGTT) at week 7. The rats were fasted overnight and then an intraperitoneal administration of 40% glucose at 2 g/kg was given. Blood glucose levels were measured before the glucose challenge and at different time points after challenge up to 120 min.

As presented in Table 14, in antisense oligonucleotide-treated rats, the increase in glucose levels during the IPGTT assay was substantially less than in the control. Therefore, antisense oligonucleotide treated rats had enhanced glucose clearance as compared to the control animals.

TABLE 14

Glucose tolerance as measured by IPGTT in Sprague-Dawley rats

| | Time | ISIS 549144 (control) | ISIS 574933 (AGPAT5 ASO) |
|---|---|---|---|
| Body weight | n/a | 558 | 500 |
| Glucose | 0 min | 83 | 86 |
| levels | 15 min | n/a | 419 |
| mg/kg) | 30 min | 496 | 416 |
| | 60 min | 506 | 262 |
| | 90 min | 426 | 194 |
| | 120 min | 355 | 154 |

Triglyceride Levels

Triglyceride levels were measured with the use of an automated clinical chemistry analyzer (Hitachi Olympus AU400e, Melville, N.Y.) (Nyblom, H. et al., Alcohol & Alcoholism 39: 336-339, 2004; Tietz N W (Ed): Clinical Guide to Laboratory Tests, 3rd ed. W. B. Saunders, Philadelphia, Pa., 1995). The results are presented in Table 15 and are expressed in mg/dL. Antisense inhibition of AGPAT5 resulted in reduction of plasma triglyceride levels compared to the PBS control.

TABLE 15

Plasma triglyceride levels (mg/dL) in Sprague-Dawley rats

| PBS | 465 |
|---|---|
| ISIS 549144 | 210 |
| ISIS 574933 | 112 |

Liver Function

To evaluate the effect of representative oligonucleotides on hepatic function, plasma concentrations of transaminases were measured using an automated clinical chemistry analyzer (Hitachi Olympus AU400e, Melville, N.Y.) (Nyblom, H. et al., Alcohol & Alcoholism 39: 336-339, 2004; Tietz N W (Ed): Clinical Guide to Laboratory Tests, 3rd ed. W. B. Saunders, Philadelphia, Pa., 1995). Plasma concentrations of ALT (alanine transaminase) and AST (aspartate transaminase) were measured and the results are presented in Table 16 expressed in IU/L. Antisense inhibition of AGPAT5 was considered tolerable in the rats, as demonstrated by their liver transaminase profile.

TABLE 16

ALT and AST levels (IU/L) of Sprague-Dawley rats

| | ALT | AST |
|---|---|---|
| PBS | 31 | 52 |
| ISIS 549144 | 46 | 65 |
| ISIS 574933 | 41 | 59 |

Example 6: Effect of an Oligomeric Compound Targeting Mouse AGPAT5 in DBA/2J Mice Fed a High Fat Diet ISIS 574933 (see Table 1) was further evaluated in DBA/2J mice (a strain prone to obesity and diabetes) fed a high fat diet. Mice received weekly i.p. injection of 20 mg/kg or 40 mg/kg of ISIS 574933 or 40 mg/kg of control antisense oligonucleotide ISIS 549144 while being fed a high fat diet. After 6 weeks of high fat diet feeding and 6 total doses of oligonucleotide, baseline levels of glucose were measured. Each treatment group consisted of 10 animals.

Three days after the final oligonucleotide dose was administered, insulin sensitivity was assessed by an insulin tolerance test (ITT). The mice were fasted for 5 hours before the ITT. Baseline blood glucose levels were measured before the insulin challenge. The mice were injected intraperitoneally (ip) with insulin (1 U/kg) and blood glucose measured at specific time points. The ability of the ip injected insulin to reduce glucose is an indicator of insulin sensitivity.

The results are presented in Table 17 as an average percent reduction in glucose from baseline for each treatment group.

TABLE 17

Insulin sensitivity as measured by ITT in DBA/2J mice

|  | Time | ISIS 574933 (40 mg/kg) | ISIS 574933 (20 mg/kg) | ISIS 549144 (40 mg/kg) |
|---|---|---|---|---|
| Body weight (grams) | n/a | 36.4 | 38.4 | 40.9 |

TABLE 17-continued

Insulin sensitivity as measured by ITT in DBA/2J mice

|  | Time | ISIS 574933 (40 mg/kg) | ISIS 574933 (20 mg/kg) | ISIS 549144 (40 mg/kg) |
|---|---|---|---|---|
| Glucose levels (% basal) | 0 min | 0 | 0 | 0 |
|  | 15 min | −19.6 | −16.3 | −6.6 |
|  | 30 min | −32.4 | −25.0 | −15.0 |
|  | 60 min | −28.3 | −20.8 | −9.4 |
|  | 120 min | −16.5 | −12.0 | −7.2 |

As presented in Table 17, in ISIS 574933 treated mice, the decrease in glucose levels during the ITT was substantially more than in control oligonucleotide ISIS 549144 treated mice after 6 weeks of treatment. Additionally, there was a dose-dependent reduction of glucose with the higher dose of ISIS 574933 (40 mg/kg) reducing glucose levels more than the lower dose of ISIS 574933 (20 mg/kg). Taken together, the data in Table 17 indicate that AGPAT5 antisense oligonucleotide treatment increased insulin sensitivity in a statistically significant and dose-dependent manner.

What is claimed is:

1. A method of reducing insulin, glucose, and/or free fatty acid levels in blood, triglyceride levels in the liver and/or the ratio of fat to body weight of an animal comprising administering a compound comprising an antisense oligonucleotide targeted to nucleic acid encoding human AGPAT5 wherein the level of insulin, glucose and/or free fatty acid in the blood, the level of triglycerides in the liver and/or the ratio of fat to body weight of the animal is/are reduced.

2. The method of claim 1, wherein the animal has elevated insulin, glucose and/or free fatty acid levels in its blood and/or elevated liver triglyceride levels.

3. The method of claim 1, wherein the animal is insulin resistant.

4. The method of claim 1, wherein muscle and/or liver cells of the animal have reduced glucose uptake and/or storage levels.

5. The method of claim 1, wherein the animal is a human.

6. The method of claim 1, wherein the animal has reduced glucose tolerance and/or glucose clearance.

7. The method of claim 1, wherein the animal's adipose cells have increased stored triglyceride hydrolysis levels.

8. The method of claim 1, wherein the compound reduces the level of AGPAT5 expression in the animal.

9. The method of claim 8, wherein the level of AGPAT5 expression in liver and/or adipose tissue of the animal is reduced by at least 50%.

10. The method of claim 8, wherein the level of AGPAT5 expression in liver and/or adipose tissue of the animal is reduced by at least 70%.

11. The method of claim 1, wherein the animal has obesity.

12. The method of claim 1, wherein the animal has type 2 diabetes.

13. The method of claim 1, wherein the animal has metabolic syndrome.

14. The method of claim 1, wherein the animal has non-alcoholic fatty liver disease (NAFLD).

* * * * *